US011098029B2

(12) United States Patent
Bogen et al.

(10) Patent No.: US 11,098,029 B2
(45) Date of Patent: Aug. 24, 2021

(54) 5-ALKYL PYRROLIDINE OREXIN RECEPTOR AGONISTS

(71) Applicant: Merck Sharp & Dohme Corp., Rahway, NJ (US)

(72) Inventors: Stephane L. Bogen, Somerset, NJ (US); Dane James Clausen, Rahway, NJ (US); Deodial Guy Guiadeen, Chesterfield, NJ (US); Michael T. Rudd, Collegeville, PA (US); Dexi Yang, Livingston, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/787,201

(22) Filed: Feb. 11, 2020

(65) Prior Publication Data

US 2020/0255403 A1 Aug. 13, 2020

Related U.S. Application Data

(60) Provisional application No. 62/949,672, filed on Dec. 18, 2019, provisional application No. 62/805,007, filed on Feb. 13, 2019.

(51) Int. Cl.
| | | |
|---|---|---|
| *C07D 401/14* | (2006.01) | |
| *C07D 207/16* | (2006.01) | |
| *C07D 403/12* | (2006.01) | |
| *C07D 409/12* | (2006.01) | |

(52) U.S. Cl.
CPC ......... *C07D 401/14* (2013.01); *C07D 207/16* (2013.01); *C07D 403/12* (2013.01); *C07D 409/12* (2013.01)

(58) Field of Classification Search
None
See application file for complete search history.

(56) References Cited

U.S. PATENT DOCUMENTS

| | | | |
|---|---|---|---|
| 8,030,495 B2 | 10/2011 | Coleman et al. | |
| 8,242,121 B2 | 8/2012 | Coleman et al. | |
| 8,357,709 B2 | 1/2013 | Coleman et al. | |
| 9,012,636 B2 | 4/2015 | Feng et al. | |
| 9,249,160 B2 | 2/2016 | Congreve et al. | |
| 9,527,807 B2 | 12/2016 | Fukumoto et al. | |
| 9,555,044 B2 | 1/2017 | Congreve et al. | |
| 9,850,237 B2 | 12/2017 | Congreve et al. | |
| 10,150,751 B2 | 12/2018 | Kuduk et al. | |
| 10,287,305 B2 | 5/2019 | Fujimoto et al. | |
| 10,316,028 B2 | 6/2019 | Congreve et al. | |
| 10,428,023 B2 | 10/2019 | Kajita et al. | |
| 10,508,083 B2 | 12/2019 | Fujimoto et al. | |
| 10,584,097 B2 | 3/2020 | Kajita et al. | |
| 2007/0270471 A1 | 11/2007 | Thewlis et al. | |
| 2011/0039857 A1 | 2/2011 | Aissaoui et al. | |
| 2017/0226137 A1 | 8/2017 | Fujimoto et al. | |
| 2019/0040010 A1 | 2/2019 | Kajita et al. | |
| 2019/0263843 A1 | 8/2019 | Fujimoto et al. | |
| 2020/0017444 A1 | 1/2020 | Kajita et al. | |
| 2020/0115399 A1 | 4/2020 | Fujimoto et al. | |

FOREIGN PATENT DOCUMENTS

| | | |
|---|---|---|
| EP | 3594202 A1 | 1/2020 |
| EP | 3594203 A1 | 1/2020 |
| EP | 3663281 A1 | 6/2020 |
| WO | 2017135306 A1 | 8/2017 |
| WO | 2018164191 A1 | 9/2018 |
| WO | 2018164192 A1 | 9/2018 |
| WO | 2019027003 A1 | 2/2019 |
| WO | 2019027058 A1 | 2/2019 |
| WO | 2019089991 A1 | 5/2019 |
| WO | 2020004536 A1 | 1/2020 |
| WO | 2020004537 A1 | 1/2020 |

OTHER PUBLICATIONS

International Search Report for PCT/US2020/017579 dated Apr. 20, 2020, 3 pages.
Written Opinion of the International Searching Authority for PCT/US2020/017579, dated Apr. 20, 2020, 5 pages.

*Primary Examiner* — Joseph R Kosack
(74) *Attorney, Agent, or Firm* — Dianne Pecoraro; John C. Todaro

(57) ABSTRACT

The present invention is directed to 5-alkyl pyrrolidine compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

12 Claims, No Drawings

5-ALKYL PYRROLIDINE OREXIN RECEPTOR AGONISTS

CROSS REFERENCE TO RELATED APPLICATIONS

This application claims priority under 35 U.S.C. § 119(e) from U.S. Ser. No. 62/805,007, filed Feb. 13, 2019, and claims priority under 35 U.S.C. § 119(e) from U.S. Ser. No. 62/949,672, filed Dec. 18, 2019.

BACKGROUND OF THE INVENTION

The orexins (hypocretins) comprise two neuropeptides produced in the hypothalamus: orexin A (OX-A) (a 33 amino acid peptide) and the orexin B (OX-B) (a 28 amino acid peptide) (Sakurai T. et al., Cell, 1998, 92, 573-585). Orexins regulate states of sleep and wakefulness opening potentially novel therapeutic approaches for narcolepsy, idiopathic hypersomnia, excessive daytime sleepiness, shift work disorder, obstructive sleep apnea and insomnia (Chemelli R. M. et al., Cell, 1999, 98, 437-451). Orexins are found to stimulate food consumption in rats suggesting a physiological role for these peptides as mediators in the central feedback mechanism that regulates feeding behavior (Sakurai T. et al., Cell, 1998, 92, 573-585).

Orexins have also been indicated as playing a role in arousal, emotion, energy homeostasis, reward, learning and memory (Peyron, et al., Journal Neurosci., 1998, 18(23): 9996-100150, Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is partially selective for OX-A and the orexin-2 receptor (OX2 or OX2R) is capable of binding OX-A as well as OX-B with similar affinity. The physiological actions in which orexins are presumed to participate are thought to be expressed via one or both of OX1 receptor and OX2 receptor as the two subtypes of orexin receptors.

SUMMARY OF THE INVENTION

The present invention is directed to 5-alkyl pyrrolidine compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

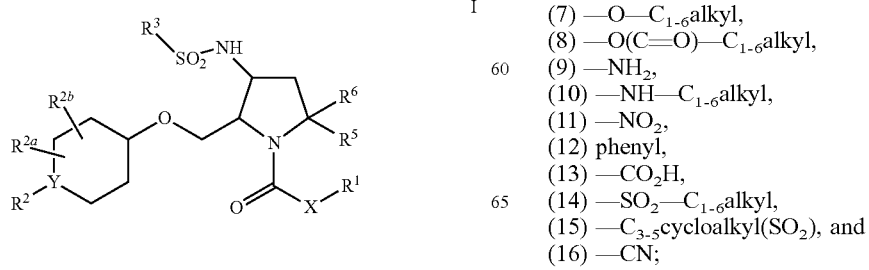

wherein:
X is —O— or —NH—, or X may be a direct bond to $R^1$;
Y is N or CH;
$R^1$ is selected from:
  (1) —$C_{1-6}$alkyl, where the alkyl is unsubstituted or substituted with one to six substituents independently selected from $R^4$, and
  (2) —$C_{3-6}$cycloalkyl, where the cycloalkyl is unsubstituted or substituted with one to six substituents independently selected from $R^4$;
$R^2$ is selected from:
  (1) hydrogen,
  (2) —$C_{1-6}$alkyl, where the alkyl is unsubstituted or substituted with one to six substituents independently selected from $R^4$,
  (3) —$C_{3-6}$cycloalkyl, where the cycloalkyl is unsubstituted or substituted with one to six substituents independently selected from $R^4$,
  (4) -phenyl, where the phenyl is unsubstituted or substituted with one to three substituents independently selected from $R^4$, and
  (5) -heteroaryl, where the heteroaryl is selected from: pyridyl, pyrimidinyl, and pyrazinyl, and the heteroaryl is unsubstituted or substituted with one to three substituents independently selected from $R^4$;
$R^{2a}$ and $R^{2b}$ are independently selected from:
  (1) hydrogen,
  (2) hydroxyl,
  (3) halogen, and
  (4) —$C_{1-6}$alkyl, where the alkyl is unsubstituted or substituted with one to six substituents independently selected from halogen;
$R^3$ is selected from:
  (1) —$C_{1-6}$alkyl, where the alkyl is unsubstituted or substituted with one to six substituents independently selected from $R^4$,
  (2) —$C_{3-6}$cycloalkyl, where the cycloalkyl is unsubstituted or substituted with one to six substituents independently selected from $R^4$,
  (3) -phenyl, where the phenyl is unsubstituted or substituted with one to three substituents independently selected from $R^4$,
  (4) —$NR^{10}R^{11}$, wherein $R^{10}$ and $R^{11}$ are independently selected from:
    (a) hydrogen, and
    (b) $C_{1-6}$alkyl, which is unsubstituted or substituted with one to six $R^4$;
$R^4$ is selected from:
  (1) hydroxyl,
  (2) halogen,
  (3) $C_{1-6}$alkyl, which is unsubstituted or substituted with one to six fluoro,
  (4) $C_{2-4}$alkenyl,
  (5) $C_{2-4}$alkynyl,
  (6) —$C_{3-6}$cycloalkyl,
  (7) —O—$C_{1-6}$alkyl,
  (8) —O(C=O)—$C_{1-6}$alkyl,
  (9) —$NH_2$,
  (10) —NH—$C_{1-6}$alkyl,
  (11) —$NO_2$,
  (12) phenyl,
  (13) —$CO_2H$,
  (14) —$SO_2$—$C_{1-6}$alkyl,
  (15) —$C_{3-5}$cycloalkyl($SO_2$), and
  (16) —CN;

$R^5$ and $R^6$ are independently selected from:
(1) hydrogen,
(2) $C_{1-6}$alkyl, where the alkyl is unsubstituted or substituted with one to six substituents independently selected from $R^4$, and
(3) —$C_{3-6}$cycloalkyl, where the cycloalkyl is unsubstituted or substituted with one to six substituents independently selected from $R^4$,
with the proviso that at least one of $R^5$ and $R^6$ is other than hydrogen,
or $R^5$ and $R^6$ are joined together with the carbon atoms to which they are attached to form a —$C_{3-6}$cycloalkyl ring, where the cycloalkyl is unsubstituted or substituted with one to six substituents independently selected from $R^4$;
or a pharmaceutically acceptable salt thereof.

An embodiment of the present invention includes compounds of the formula I:
wherein:
X is —O— or —NH—, or X may be a direct bond to $R^1$;
Y is N or CH;
$R^1$ is selected from:
(1) —$C_{1-6}$alkyl, where the alkyl is unsubstituted or substituted with one to six substituents independently selected from $R^4$, and
(2) —$C_{3-6}$cycloalkyl, where the cycloalkyl is unsubstituted or substituted with one to six substituents independently selected from $R^4$;
$R^2$ is selected from:
(1) hydrogen,
(2) —$C_{1-6}$alkyl, where the alkyl is unsubstituted or substituted with one to six substituents independently selected from $R^4$,
(3) —$C_{3-6}$cycloalkyl, where the cycloalkyl is unsubstituted or substituted with one to six substituents independently selected from $R^4$,
(4) -phenyl, where the phenyl is unsubstituted or substituted with one to three substituents independently selected from $R^4$, and
(5) -heteroaryl, where the heteroaryl is selected from: pyridyl, pyrimidinyl, and pyrazinyl, and the heteroaryl is unsubstituted or substituted with one to three substituents independently selected from $R^4$;
$R^{2a}$ and $R^{2b}$ are independently selected from:
(1) hydrogen,
(2) hydroxyl,
(3) halogen, and
(4) —$C_{1-6}$alkyl, where the alkyl is unsubstituted or substituted with one to six substituents independently selected from halogen;
$R^3$ is selected from:
(1) —$C_{1-6}$alkyl, where the alkyl is unsubstituted or substituted with one to six substituents independently selected from $R^4$,
(2) —$C_{3-6}$cycloalkyl, where the cycloalkyl is unsubstituted or substituted with one to six substituents independently selected from $R^4$,
(3) -phenyl, where the phenyl is unsubstituted or substituted with one to three substituents independently selected from $R^4$,
(4) —$NR^{10}R^{11}$, wherein $R^{10}$ and $R^{11}$ are independently selected from:
(a) hydrogen, and
(b) $C_{1-6}$alkyl, which is unsubstituted or substituted with one to six $R^4$;

$R^4$ is selected from:
(1) hydroxyl,
(2) halogen,
(3) $C_{1-6}$alkyl, which is unsubstituted or substituted with one to six fluoro,
(4) —$C_{3-6}$cycloalkyl,
(5) —O—$C_{1-6}$alkyl,
(6) —O(C=O)—$C_{1-6}$alkyl,
(7) —$NH_2$,
(8) —NH—$C_{1-6}$alkyl,
(9) —$NO_2$,
(10) phenyl,
(11) —$CO_2H$, and
(12) —CN;
$R^5$ and $R^6$ are independently selected from:
(1) hydrogen,
(2) $C_{1-6}$alkyl, where the alkyl is unsubstituted or substituted with one to six substituents independently selected from $R^4$, and
(3) —$C_{3-6}$cycloalkyl, where the cycloalkyl is unsubstituted or substituted with one to six substituents independently selected from $R^4$,
with the proviso that at least one of $R^5$ and $R^6$ is other than hydrogen,
or $R^5$ and $R^6$ are joined together with the carbon atoms to which they are attached to form a —$C_{3-6}$cycloalkyl ring, where the cycloalkyl is unsubstituted or substituted with one to six substituents independently selected from $R^4$;
or a pharmaceutically acceptable salt thereof.

An embodiment of the present invention includes compounds of the formula Ia:

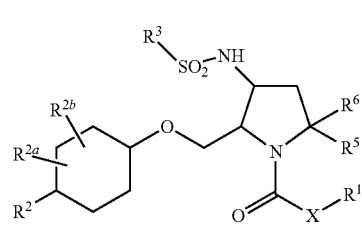

Ia wherein X, $R^1$, $R^2$, $R^{2a}$, $R^{2b}$, $R^3$, $R^5$ and $R^6$ are defined herein; or a pharmaceutically acceptable salt thereof.

An embodiment of the present invention includes compounds of the formula Ib:

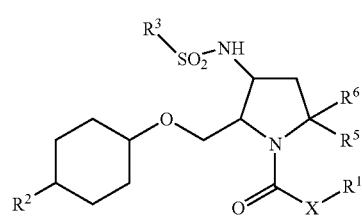

Ib wherein X, $R^1$, $R^2$, $R^3$, $R^5$ and $R^6$ are defined herein; or a pharmaceutically acceptable salt thereof.

An embodiment of the present invention includes compounds of the formula Ib':

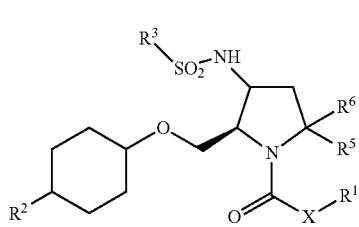
Ib' wherein X, $R^1$, $R^2$, $R^3$, $R^5$ and $R^6$ are defined herein; or a pharmaceutically acceptable salt thereof.

An embodiment of the present invention includes compounds of the formula Ib":

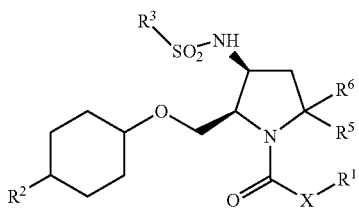
Ib"

wherein X, $R^1$, $R^2$, $R^3$, $R^5$ and $R^6$ are defined herein; or a pharmaceutically acceptable salt thereof.

An embodiment of the present invention includes compounds of the formula Ib''':

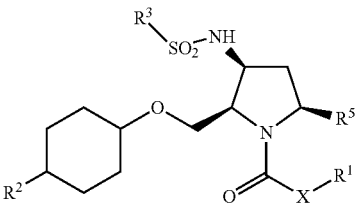
Ib''' wherein X, $R^1$, $R^2$, $R^3$ and $R^5$ are defined herein; or a pharmaceutically acceptable salt thereof.

An embodiment of the present invention includes compounds of the formula Ic:

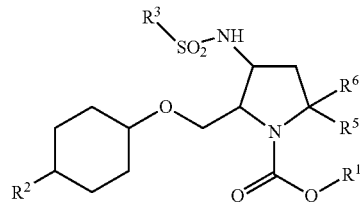
Ic wherein $R^1$, $R^2$, $R^3$, $R^5$ and $R^6$ are defined herein; or a pharmaceutically acceptable salt thereof.

An embodiment of the present invention includes compounds of the formula Ic':

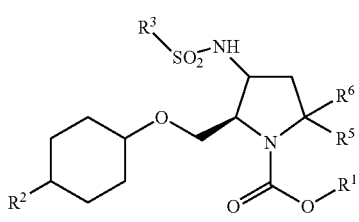
Ic' wherein $R^1$, $R^2$, $R^3$, $R^5$ and $R^6$ are defined herein; or a pharmaceutically acceptable salt thereof.

An embodiment of the present invention includes compounds of the formula Ic":

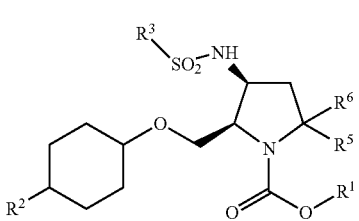
Ic"

wherein $R^1$, $R^2$, $R^3$, $R^5$ and $R^6$ are defined herein; or a pharmaceutically acceptable salt thereof.

An embodiment of the present invention includes compounds of the formula Ic''':

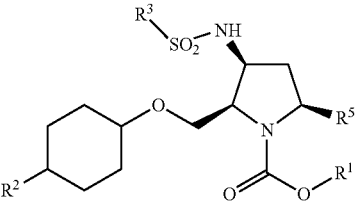
Ic''' wherein $R^1$, $R^2$, $R^3$ and $R^5$ are defined herein; or a pharmaceutically acceptable salt thereof.

An embodiment of the present invention includes compounds of the formula Id:

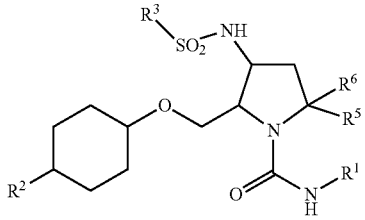
Id wherein $R^1$, $R^2$, $R^3$, $R^5$ and $R^6$ are defined herein; or a pharmaceutically acceptable salt thereof.

An embodiment of the present invention includes compounds of the formula Id':

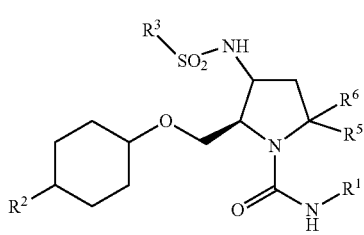

Id' wherein $R^1$, $R^2$, $R^3$, $R^5$ and $R^6$ are defined herein; or a pharmaceutically acceptable salt thereof.

An embodiment of the present invention includes compounds of the formula Id":

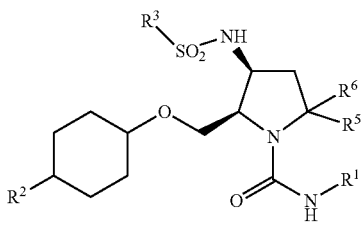

Id"

wherein $R^1$, $R^2$, $R^3$, $R^5$ and $R^6$ are defined herein; or a pharmaceutically acceptable salt thereof.

An embodiment of the present invention includes compounds of the formula Id''':

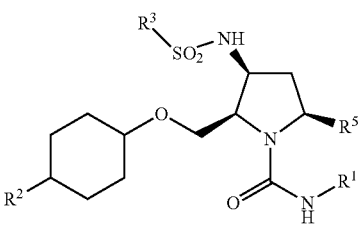

Id''' wherein $R^1$, $R^2$, $R^3$ and $R^5$ are defined herein; or a pharmaceutically acceptable salt thereof.

An embodiment of the present invention includes compounds of the formula Ie:

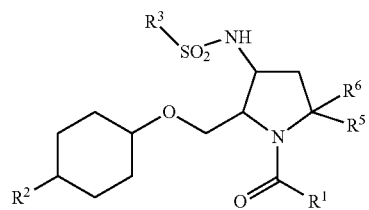

Ie wherein $R^1$, $R^2$, $R^3$, $R^5$ and $R^6$ are defined herein; or a pharmaceutically acceptable salt thereof.

An embodiment of the present invention includes compounds of the formula Ie':

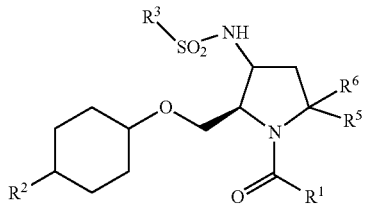

Ie' wherein $R^1$, $R^2$, $R^3$, $R^5$ and $R^6$ are defined herein; or a pharmaceutically acceptable salt thereof.

An embodiment of the present invention includes compounds of the formula Ie":

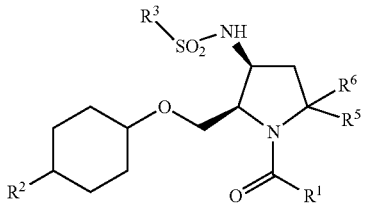

Ie"

wherein $R^1$, $R^2$, $R^3$, $R^5$ and $R^6$ are defined herein; or a pharmaceutically acceptable salt thereof.

An embodiment of the present invention includes compounds of the formula Ie''':

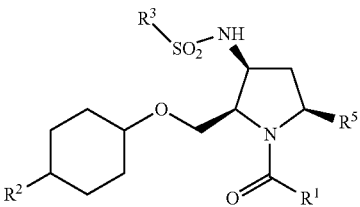

Ie''' wherein $R^1$, $R^2$, $R^3$ and $R^5$ are defined herein; or a pharmaceutically acceptable salt thereof.

An embodiment of the present invention includes compounds wherein X is —O—. An embodiment of the present invention includes compounds wherein X is —NH—. An embodiment of the present invention includes compounds wherein X is a direct bond to $R^1$.

An embodiment of the present invention includes compounds wherein Y is N. An embodiment of the present invention includes compounds wherein Y is CH.

An embodiment of the present invention includes compounds wherein $R^1$ is selected from:
(1) —$C_{1-6}$alkyl, which is unsubstituted or substituted with fluoro or —O(C═O)—$C_{1-6}$alkyl,
(2) —$C_{3-6}$cycloalkyl, and
(3) —$CH_2$—$C_{3-6}$cycloalkyl.

An embodiment of the present invention includes compounds wherein $R^1$ is selected from:
(1) methyl,
(2) ethyl,
(3) —$CH_2OH$, (4) —CH$_2$CF$_3$,
(5) —CH$_2$CHF$_2$,
(6) —CH(CH$_3$)$_2$,
(7) —CH$_2$CH$_2$CH$_2$F,
(8) cyclopropyl,
(9) —CH$_2$-cyclopropyl,
(10) —CH$_2$-cyclobutyl, and
(11) —CH$_2$O(C=O)CH$_3$.

An embodiment of the present invention includes compounds wherein R$^2$ is selected from:
(1) hydrogen,
(2) —C$_{1-6}$alkyl, where the alkyl is unsubstituted or substituted with one to three fluoro,
(3) phenyl, which is unsubstituted or substituted with one to three fluoro, or —C$_{1-6}$alkyl, where the alkyl is unsubstituted or substituted with one to three fluoro, and
(4) pyrimidinyl, which is unsubstituted or substituted with one to two fluoro, or —C$_{1-6}$alkyl, where the alkyl is unsubstituted or substituted with one to three fluoro.

An embodiment of the present invention includes compounds wherein R$^2$ is selected from:
(1) hydrogen,
(2) —CH$_2$(CH$_3$)$_2$,
(3) —CF$_3$,
(4) —CH$_2$CHF$_2$,
(5) —CH$_2$CF$_3$, and
(6) phenyl, which is unsubstituted or substituted with —CF$_3$, —CH$_2$CF$_3$, or one to three fluoro.

An embodiment of the present invention includes compounds wherein R$^2$ is selected from:
(1) hydrogen,
(2) —CH$_2$(CH$_3$)$_2$,
(3) —CF$_3$,
(4) —CH$_2$CHF$_2$,
(5) —CH$_2$CF$_3$,
(6) phenyl,
(7) phenyl-CF$_3$,
(8) phenyl-CH$_2$CF$_3$,
(9) fluorophenyl,
(10) difluorophenyl, and
(11) trifluorophenyl.

An embodiment of the present invention includes compounds wherein R$^{2a}$ is hydrogen and R$^{2b}$ is hydrogen. An embodiment of the present invention includes compounds wherein R$^{2a}$ is methyl and R$^{2b}$ is hydrogen. An embodiment of the present invention includes compounds wherein R$^{2a}$ is methyl and R$^{2b}$ is methyl. An embodiment of the present invention includes compounds wherein R$^{2a}$ is methyl and R$^{2b}$ is methyl, wherein R$^{2a}$ and R$^{2b}$ are attached to the same carbon atom. An embodiment of the present invention includes compounds wherein R$^{2a}$ is fluoro and R$^{2b}$ is fluoro, wherein R$^{2a}$ and R$^{2b}$ are attached to the same carbon atom. An embodiment of the present invention includes compounds wherein R$^{2a}$ is hydroxyl and R$^{2b}$ is hydrogen. An embodiment of the present invention includes compounds wherein R$^{2a}$ is fluoro and R$^{2b}$ is hydrogen.

An embodiment of the present invention includes compounds wherein R$^3$ is selected from:
(1) —C$_{1-6}$alkyl, where the alkyl is unsubstituted or substituted with one to three fluoro,
(2) —C$_{3-6}$cycloalkyl,
(3) —NH$_2$,
(4) —NH(C$_{1-6}$alkyl),
(5) —N(C$_{1-6}$alkyl)(C$_{1-6}$alkyl), and
(6) -phenyl.

An embodiment of the present invention includes compounds wherein R$^3$ is selected from:
(1) methyl,
(2) —CF$_3$,
(3) —CH$_2$F,
(4) ethyl,
(5) cyclopropyl,
(6) —CH(CH$_3$)$_2$,
(7) —NH(CH$_3$),
(8) —N(CH$_3$)$_2$, and
(9) -phenyl.

An embodiment of the present invention includes compounds wherein R$^5$ and R$^6$ are independently selected from:
(1) hydrogen,
(2) methyl,
(3) ethyl,
(4) —CHF$_2$,
(5) —CF$_3$,
(6) —CH$_2$OH,
(7) —CH$_2$OCH$_3$, and
(8) cyclopropyl,
with the proviso that at least one of R$^5$ and R$^6$ is other than hydrogen.

An embodiment of the present invention includes compounds wherein R$^5$ is methyl and R$^6$ is hydrogen. An embodiment of the present invention includes compounds wherein R$^5$ is ethyl and R$^6$ is hydrogen. An embodiment of the present invention includes compounds wherein R$^5$ is ethyl and R$^6$ is ethyl. An embodiment of the present invention includes compounds wherein R$^5$ and R$^6$ are joined together with the carbon atoms to which they are attached to form a cyclopropyl ring.

Certain embodiments of the present invention include a compound which is selected from the group consisting of the subject compounds of the Examples herein or a pharmaceutically acceptable salt thereof.

Certain embodiments of the present invention include a compound which is selected from:
(2R,3S,5R)—N-ethyl-2-(((4-isopropylcyclohexyl)oxy)methyl)-5-methyl-3-(methylsulfonamido)-pyrrolidine-1-carboxamide;
(2R,3S,5R)—N-ethyl-5-methyl-3-(methylsulfonamido)-2-(((4-(trifluoromethyl)-cyclohexyl)oxy)methyl)pyrrolidine-1-carboxamide;
methyl (2R,3S,5R)-2-(((4-isopropylcyclohexyl)oxy)methyl)-5-methyl-3-(methylsulfonamido)-pyrrolidine-1-carboxylate;
methyl (2R,3S,5R)-2-(((((1s,4S)-4-isopropylcyclohexyl)oxy)-methyl)-5-methyl-3-(methylsulfonamido)pyrrolidine-1-carboxylate;
isopropyl (2R,3S,5R)-2-(((4-isopropylcyclohexyl)oxy)methyl)-5-methyl-3-(methyl sulfonamido)pyrrolidine-1-carboxylate;
isopropyl (2R,3S,5R)-2-(((4-isopropylcyclohexyl)oxy)methyl)-5-methyl-3-((N-methylsulfamoyl)amino)pyrrolidine-1-carboxylate;
ethyl (2R,3S,5R)-2-(((4-isopropylcyclohexyl)oxy)methyl)-5-methyl-3-(methyl sulfonamido)pyrrolidine-1-carboxylate;
ethyl (2R,3S,5R)-3-((N,N-dimethylsulfamoyl)amino)-2-(((4-isopropylcyclohexyl)-oxy)methyl)-5-methylpyrrolidine-1-carboxylate;
2,2-difluoroethyl (2R,3S,5R)-2-(((4-isopropylcyclohexyl)oxy)methyl)-5-methyl-3-(methyl sulfonamido)pyrrolidine-1-carboxylate;

2-fluoroethyl (2R,3S,5R)-2-(((4-isopropylcyclohexyl)oxy)methyl)-5-methyl-3-(methyl sulfonamido)pyrrolidine-1-carboxylate;

methyl (2R,3S,5R)-3-((N,N-dimethylsulfamoyl)amino)-5-methyl-2-(((4-(trifluoromethyl)cyclohexyl)oxy)methyl)pyrrolidine-1-carboxylate;

methyl (2R,3S,5R)-5-methyl-3-(methylsulfonamido)-2-(((4-(2,2,2-trifluoroethyl)-cyclohexyl)oxy)methyl)pyrrolidine-1-carboxylate;

2,2-difluoroethyl (2R,3S,5R)-2-(((4-isopropylcyclohexyl)oxy)methyl)-5-methyl-3-((N-methyl sulfamoyl)amino)pyrrolidine-1-carboxylate;

2,2-difluoroethyl (2R,3S,5R)-3-((N,N-dimethylsulfamoyl)amino)-2-(((4-isopropylcyclohexyl)oxy)methyl)-5-methylpyrrolidine-1-carboxylate;

methyl (2R,3S,5R)-5-methyl-3-(methyl sulfonamido)-2-((((1s,4S)-4-phenylcyclohexyl)oxy)-methyl)pyrrolidine-1-carboxylate;

2,2-difluoroethyl (2R,3S,5R)-5-methyl-3-((N-methylsulfamoyl)amino)-2-((((1s,4S)-4-phenylcyclohexyl)oxy)methyl)pyrrolidine-1-carboxylate;

2,2-difluoroethyl (2R,3S,5R)-3-((N,N-dimethylsulfamoyl)amino)-5-methyl-2-((((1s,4S)-4-phenylcyclohexyl)oxy)methyl)pyrrolidine-1-carboxylate;

methyl (2R,3S,5R)-5-methyl-3-((N-methylsulfamoyl)amino)-2-((((1s,4S)-4-phenylcyclohexyl)-oxy)methyl)pyrrolidine-1-carboxylate;

methyl (2R,3S,5R)-5-methyl-3-((N-methylsulfamoyl)amino)-2-((((1s,4S)-4-phenylcyclohexyl)-oxy)methyl)pyrrolidine-1-carboxylate;

methyl (2R,3S,5R)-3-((N,N-dimethylsulfamoyl)amino)-5-methyl-2-((((1s,4S)-4-phenylcyclohexyl)oxy)methyl)pyrrolidine-1-carboxylate;

methyl (2R,3S,5R)-2-((((1r,4R)-4-(2,5-difluorophenyl)cyclohexyl)oxy)methyl)-5-methyl-3-(methyl sulfonamido)pyrrolidine-1-carboxylate;

methyl (2R,3S,5R)-2-((((1r,4R)-4-(2,5-difluorophenyl)cyclohexyl)oxy)methyl)-3-((N,N-dimethylsulfamoyl)amino)-5-methylpyrrolidine-1-carboxylate;

2,2-difluoroethyl (2R,3S,5R)-2-(((((1r,4R)-4-(2,5-difluorophenyl)-cyclohexyl)oxy)-methyl)-3-((N,N-dimethylsulfamoyl)amino)-5-methylpyrrolidine-1-carboxylate;

methyl (2R,3S,5R)-3-((N,N-dimethylsulfamoyl)amino)-2-((((1s,4S)-4-(2-fluorophenyl)cyclohexyl)oxy)methyl)-5-methylpyrrolidine-1-carboxylate;

methyl (2R,3S,5R)-2-((((1s,4S)-4-(3-fluorophenyl)cyclohexyl)oxy)methyl)-5-methyl-3-(methyl sulfonamido)pyrrolidine-1-carboxylate;

methyl (2R,3S,5R)-2-((((1s,4S)-4-(3-fluorophenyl)cyclohexyl)oxy)methyl)-5-methyl-3-((N-methyl sulfamoyl)amino)pyrrolidine-1-carboxylate;

methyl (2R,3S,5R)-3-((fluoromethyl)sulfonamido)-2-((((1s,4S)-4-(3-fluorophenyl)cyclohexyl)oxy)methyl)-5-methylpyrrolidine-1-carboxylate;

methyl (2R,3S,5R)-5-methyl-3-(methylsulfonamido)-2-((((1r,4R)-4-(2-(trifluoromethyl)phenyl)cyclohexyl)oxy)methyl)pyrrolidine-1-carboxylate;

methyl (2R,3S,5R)-5-methyl-3-(methylsulfonamido)-2-((((1r,4R)-4-(2,3,6-trifluorophenyl)cyclohexyl)oxy)methyl)pyrrolidine-1-carboxylate;

methyl (2R,3S,5R)-3-((fluoromethyl)sulfonamido)-5-methyl-2-((((1r,4R)-4-phenylcyclohexyl)oxy)methyl)pyrrolidine-1-carboxylate;

methyl (2R,3S,5R)-3-((N,N-dimethylsulfamoyl)amino)-2-((((1R,4S)-2-fluoro-4-phenylcyclohexyl)oxy)methyl)-5-methylpyrrolidine-1-carboxylate;

methyl (2R,3S,5R)-3-((N,N-dimethylsulfamoyl)amino)-2-((((1R,4S)-2-fluoro-4-(3-fluorophenyl)cyclohexyl)oxy)methyl)-5-methylpyrrolidine-1-carboxylate;

methyl (2R,3S,5R)-2-((((1s,4S)-4-(3,5-difluorophenyl)cyclohexyl)oxy)methyl)-3-((N,N-dimethylsulfamoyl)amino)-5-methylpyrrolidine-1-carboxylate;

methyl (2R,3S,5R)-2-(((2-methoxy-4-phenylcyclohexyl)oxy)methyl)-5-methyl-3-(methyl sulfonamido)pyrrolidine-1-carboxylate;

methyl (2R,3S,5R)-5-methyl-2-(((2-methyl-4-phenylcyclohexyl)oxy)methyl)-3-(methyl sulfonamido)pyrrolidine-1-carboxylate;

methyl (2R,3S,5R)-3-((N,N-dimethylsulfamoyl)amino)-2-(((((S)-3'-fluoro-2,3,4,5-tetrahydro-[1,1'-biphenyl]-4-yl)oxy)methyl)-5-methylpyrrolidine-1-carboxylate;

methyl (2R,3S,5R)-3-((N,N-dimethylsulfamoyl)amino)-2-((((1S)-4-(3-fluorophenyl)-3-hydroxycyclohexyl)oxy)methyl)-5-methylpyrrolidine-1-carboxylate;

methyl (2R,3S,5R)-3-((N,N-dimethylsulfamoyl)amino)-2-((((1s,4S)-4-(3-fluorophenyl)cyclohexyl)-oxy)methyl)-5-methylpyrrolidine-1-carboxylate;

isopropyl (2R,3S,5R)-5-methyl-3-((N-methylsulfamoyl)amino)-2-(((1-(pyrimidin-2-yl)piperidin-4-yl)oxy)methyl)pyrrolidine-1-carboxylate;

isopropyl (2R,3S,5R)-3-((N,N-dimethylsulfamoyl)amino)-2-(((1-(5-fluoropyrimidin-2-yl)piperidin-4-yl)oxy)methyl)-5-methylpyrrolidine-1-carboxylate;

methyl (CIS)-5-ethyl-3-(methylsulfonamido)-2-((((CIS)-4-phenylcyclohexyl)-oxy)methyl)-pyrrolidine-1-carboxylate;

methyl (CIS)-6-(methylsulfonamido)-5-((((CIS)-4-phenylcyclohexyl)oxy)methyl)-4-azaspiro[2.4]heptane-4-carboxylate;

methyl (CIS)-2,2-diethyl-4-(methylsulfonamido)-5-((((CIS)-4-phenylcyclohexyl)-oxy)methyl)-pyrrolidine-1-carboxylate;

methyl (2R,3S,5R)-5-ethyl-3-(methylsulfonamido)-2-((((CIS)-4-phenylcyclohexyl)-oxy)methyl)-pyrrolidine-1-carboxylate;

methyl (CIS)-5-cyclopropyl-3-(methylsulfonamido)-2-((((CIS)-4-phenylcyclohexyl)oxy)methyl)pyrrolidine-1-carboxylate;

methyl (2S,3R,5S)-5-ethyl-3-(methylsulfonamido)-2-((((CIS)-4-phenylcyclohexyl)oxy)methyl)-pyrrolidine-1-carboxylate;

methyl (2R,3S,5R)-5-ethyl-3-(methylsulfonamido)-2-((((CIS)-4-phenylcyclohexyl)oxy)methyl)-pyrrolidine-1-carboxylate;

methyl (CIS)-5-ethynyl-3-(methylsulfonamido)-2-((((CIS)-4-phenylcyclohexyl)oxy)methyl)-pyrrolidine-1-carboxylate;

methyl (CIS)-3-(methylsulfonamido)-2-((((CIS)-4-phenylcyclohexyl)oxy)methyl)-5-vinylpyrrolidine-1-carboxylate;

methyl (CIS)-5-(2-hydroxyethyl)-3-(methylsulfonamido)-2-((((CIS)-4-phenylcyclohexyl)oxy)methyl)pyrrolidine-1-carboxylate;

methyl (CIS)-5-(hydroxymethyl)-3-(methylsulfonamido)-2-((((CIS)-4-phenylcyclohexyl)oxy)-methyl)-pyrrolidine-1-carboxylate;

methyl (2R,3S,5S)-3-((N,N-dimethylsulfamoyl)amino)-2-((((CIS)-4-(3-fluorophenyl)cyclohexyl)oxy)methyl)-5-(methoxymethyl)pyrrolidine-1-carboxylate;

methyl (2R,3S,5S)-5-(cyanomethyl)-3-((N,N-dimethylsulfamoyl)amino)-2-((((CIS)-4-(3-fluorophenyl)cyclohexyl)oxy)methyl)pyrrolidine-1-carboxylate;

methyl (2R,3S,5R)-3-((N-(cyanomethyl)-N-methylsulfamoyl)amino)-2-((((1s,4S)-4-(3-fluorophenyl)cyclohexyl)oxy)methyl)-5-methylpyrrolidine-1-carboxylate;
methyl (2R,3S,5R)-3-((N-(2-cyanoethyl)-N-methylsulfamoyl)amino)-2-((((1s,4S)-4-(3-fluorophenyl)cyclohexyl)oxy)methyl)-5-methylpyrrolidine-1-carboxylate;
methyl (2R,3S,5R)-2-((((1s,4S)-4-(3-fluorophenyl)cyclohexyl)oxy)methyl)-3-((N-(2-methoxyethyl)-N-methylsulfamoyl)amino)-5-methylpyrrolidine-1-carboxylate;
methyl (2R,3S,5R)-2-((((1s,4S)-4-(3-fluorophenyl)cyclohexyl)oxy)methyl)-3-((N-(2-hydroxyethyl)-N-methylsulfamoyl)amino)-5-methylpyrrolidine-1-carboxylate;
methyl (2R,3S,5R)-2-((((1s,4S)-4-(3-fluorophenyl)cyclohexyl)oxy)methyl)-5-methyl-3-((N-methyl-N-(2-(methylsulfonyl)ethyl)sulfamoyl)amino)pyrrolidine-1-carboxylate;
methyl (2R,3S,5R)-3-((N-((1,1-dioxidothietan-3-yl)methyl)-N-methylsulfamoyl)-amino)-2-((((1s,4S)-4-(3-fluorophenyl)cyclohexyl)oxy)methyl)-5-methylpyrrolidine-1-carboxylate;
methyl (2R,3S,5R)-2-((((1s,4S)-4-(3-fluorophenyl)cyclohexyl)oxy)methyl)-5-methyl-3-((N-methyl-N-(2-(trifluoromethoxy)ethyl)sulfamoyl)amino)pyrrolidine-1-carboxylate;
methyl (2R,3S,5R)-3-((2,2-difluoroethyl)sulfonamido)-2-((((1s,4S)-4-(3-fluorophenyl)cyclohexyl)oxy)methyl)-5-methylpyrrolidine-1-carboxylate;
methyl (2R,3S,5R)-3-((N-(2-cyanoethyl)-N-methylsulfamoyl)amino)-2-((((1s,4S)-4-(3-fluorophenyl)cyclohexyl)oxy)methyl)-5-methylpyrrolidine-1-carboxylate;
methyl (2R,3S,5R)-3-((fluoromethyl)sulfonamido)-2-((((1s,4S)-4-(3-fluorophenyl)cyclohexyl)oxy)methyl)-5-methylpyrrolidine-1-carboxylate;
methyl (2R,3S,5R)-2-((((1s,4S)-4-(4-cyano-3-methylphenyl)cyclohexyl)oxy)-methyl)-3-((N,N-dimethylsulfamoyl)amino)-5-methylpyrrolidine-1-carboxylate;
methyl (2R,3S,5R)-2-((((1r,4R)-4-(4-cyano-3-methylphenyl)cyclohexyl)oxymethyl)-3-((N,N-dimethylsulfamoyl)amino)-5-methylpyrrolidine-1-carboxylate;
methyl (2R,3S,5R)-3-((N,N-dimethylsulfamoyl)amino)-2-((((1s,4S)-4-(2-ethylphenyl)cyclohexyl)oxy)methyl)-5-methylpyrrolidine-1-carboxylate;
methyl (2R,3S,5R)-3-((N,N-dimethylsulfamoyl)amino)-2-((((1r,4R)-4-(2-ethylphenyl)cyclohexyl)oxy)methyl)-5-methylpyrrolidine-1-carboxylate;
methyl (2R,3S,5R)-3-((N,N-dimethylsulfamoyl)amino)-2-((((1S,3R,4R)-4-(3-fluorophenyl)cyclohexyl-3,4-d2)oxy)methyl)-5-methylpyrrolidine-1-carboxylate;
methyl (2R,3S,5R)-3-((N,N-dimethylsulfamoyl)amino)-2-((((1S,3S,4S)-4-(3-fluorophenyl)cyclohexyl-3,4-d2)oxy)methyl)-5-methylpyrrolidine-1-carboxylate;
methyl (2R,3S,5R)-5-methyl-3-(methylsulfonamido)-2-((((1r,4R)-4-(pyrimidin-2-yl)cyclohexyl)oxy)methyl)pyrrolidine-1-carboxylate;
methyl (2R,3S,5R)-5-methyl-3-(methyl sulfonamido)-2-((((1s,4S)-4-(pyrimidin-2-yl)cyclohexyl)oxy)methyl)pyrrolidine-1-carboxylate;
methyl (2R,3S,5R)-2-((((1s,4S)-4-(3,5-difluorophenyl)cyclohexyl)oxy)methyl)-5-methyl-3-(methyl sulfonamido)pyrrolidine-1-carboxylate;
methyl (2R,3S,5R)-2-((((1r,4R)-4-(3,5-difluorophenyl)cyclohexyl)oxy)methyl)-5-methyl-3-(methylsulfonamido)pyrrolidine-1-carboxylate; and
methyl (2R,3S,5R)-2-((((1s,4S)-4-(3,4-difluorophenyl)cyclohexyl)oxy)methyl)-5-methyl-3-(methyl sulfonamido)pyrrolidine-1-carboxylate;
or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

The present invention is also directed to the use of the compounds disclosed herein as agonists of orexin receptor activity. The subject compounds and pharmaceutically acceptable salts thereof are useful in a method of agonizing orexin receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for agonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to agonize the orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R agonists may be readily determined without undue experimentation by methodology well known in the art. Both the OX1R and/or OX2R G-coupled protein receptors (GPCRs) couple through the Gaq signaling pathway, which ultimately promotes calcium mobilization via inositol triphosphate (IP3) production. The half-life of IP-3 is relatively short, being rapidly metabolized to inositol monophosphate (IP-1), which can be readily detected using a commercially available assay kit (IP-One; Cisbio; cat #621PAPEC) coupled with a cell line expressing the target receptor(s) of interest. The utility of the compounds in accordance with the present invention as orexin receptor OX1R and/or OX2R agonists may be determined utilizing this assay.

In a typical experiment, the OX1 and OX2 receptor agonist activity is determined in accordance with the following general experimental method. Chinese hamster ovary (CHO) cells expressing human OX1R and/or the human OX2R were grown in Iscove's modified DMEM containing glutaMAX®, 1% G418, 100 U/mL penicillin, 100 µg/mL streptomycin and 10% heat-inactivated qualified fetal bovine serum (FBS). The OX2R cells were seeded at 10,000 cells/well/50 L and the OX1R cells were seeded at 20,000 cells/well/50 µL into 384-well white tissue culture plates (Greiner; cat #781080). All cell/media reagents were from GIBCO-Invitrogen Corp. The seeded cell plate(s) were incubated at 37° C. with 5% $CO_2$ and 85% humidity for 20-24 hours. On the day of the assay, assay-ready compound plates were prepared using an acoustic liquid handler (ECHO; Labcyte), which dispensed sufficient volume of test compound stock (10 mM in DMSO) or 100% DMSO to prepare 10 point, ½-log dilutions in a final volume of 202.5 nL/well in all test wells of a 384-well diamond plate (Labcyte). Following completion of assay-ready plates, importantly, the next three steps were performed with minimal delay: 1) 20 µl of 1× stimulation buffer was added to the compound plate using a Multidrop Combi (small cassette, Thermo Fisher Scientific cat #24073290); 2) culture medium was removed from the cell plate using the Bluewasher plate washer (gentle spin; BlueCatBio); 3) 14 µl of compound/stimulation buffer mixture was added to the cell plate using a Bravo liquid handler (Agilent) prior to incubating cell plates at 37° C. with 5% $CO_2$ and 85% humidity for 1 or 2 hours (OX1R and OX2R, respectively). During this incubation, IP-one detection reagents were prepared (38:1:1 lysis buffer:D2:AB-cryptate reagents). Six L of mixed detection reagents were added to the cell plate using a Multidrop Combi (small cassette, Thermo Fisher Scientific cat #24073290) and incubated 60 minutes at room temperature in the dark. Fluorescence signal was detected using an Envision plate reader (Perkin Elmer) [LANCE/DELFIA Dual Enh (Em: APC 665; Ex: Cy5 620)].

For each compound, data were fit to a four parameter logistic fit (ActivityBase software) and the $EC_{50}$ was reported as the inflection point of the resulting curve. Percent effect for each test compound was determined as the percentage of sample raw value/mean max effect, where the mean max effect was derived from the mean raw value of 32 control wells per assay plate (using Orexin A (cat #003-30) at 1 µM for human OX1R and a reference compound at 1 uM with 100% activity previously established by comparison to Orexin A for human OX2R). The intrinsic orexin receptor agonist activity of a compound which may be used in the present invention may be determined by these assays.

All of the final compounds of the following examples had activity in agonizing the human orexin-2 receptor in the aforementioned IPOne assay with an EC50 of about 0.01 nM to 5000 nM. Additional data is provided in the following Examples. Such a result is indicative of the intrinsic activity of the compounds in use as agonists of orexin-1 receptor and/or the orexin-2 receptor. In general, one of ordinary skill in the art would appreciate that a substance is considered to effectively agonize the orexin receptor if it has an EC50 in the IPOne assay of less than about 50 µM, or more specifically less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of disorders associated with orexin receptors, including one or more of the following conditions or diseases: narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, wakefulness, nocturnal myoclonus, disturbances of consciousness, such as coma, REM sleep interruptions, jet-lag, excessive daytime sleepiness, shift workers' sleep disturbances, dyssomnias, sleep disorders, sleep disturbances, hypersomnia associated with depression, emotional/mood disorders, Alzheimer's disease or cognitive impairment, Parkinson's disease, Guillain-Barre syndrome, Kleine Levin syndrome, and sleep disorders which accompany aging; Alzheimer's sundowning; conditions associated with circadian rhythmicity as well as mental and physical disorders associated with travel across time zones and with rotating shift-work schedules; fibromyalgia; cardiac failure; diseases related to bone loss;

sepsis; syndromes which are manifested by non-restorative sleep and muscle pain or sleep apnea which is associated with respiratory disturbances during sleep; conditions which result from a diminished quality of sleep; and other diseases related to general orexin system dysfunction.

Thus, in certain embodiments the present invention may provide methods for: treating or controlling narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, disturbances of consciousness, REM sleep interruptions, jet-lag, shift workers' sleep disturbances, dyssomnias, night terror, insomnias associated with depression, emotional/mood disorders, Alzheimer's disease or cognitive impairment; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling insulin resistance syndrome; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling Guillain-Barre syndrome; treating or controlling Klein Levin syndrome; treating or controlling psychosis; treating or controlling dysthymic, mood, psychotic and anxiety disorders; treating side effects or complications due to anesthesia; reversal of anesthesia; reversal of anesthesia following surgery; treating or controlling depression, including major depression and major depression disorder; treating or controlling bipolar disorder; or treating, controlling, ameliorating or reducing the risk of schizophrenia, in a mammalian subject which comprises administering to the subject a compound of the present invention.

The compounds of the present invention may also potentially have utility in treating, preventing, ameliorating, controlling or reducing the risk of a variety of other disorders associated with orexin receptors, including one or more of the following conditions or diseases including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia; night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory diseases, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; treating or controlling Guillain-Barre syndrome; treating or controlling Klein Levin syndrome; treating or controlling psychosis; treating or controlling dysthymic, mood, psychotic and anxiety disorders; treating complications due to anesthesia; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize.

Generally, dosage levels of between 0.0001 to 100 mg/kg. of body weight daily are administered to the subject, e.g., humans, adolescent humans and elderly humans, to obtain effective agonism of orexin receptors. The dosage range will generally be about 0.5 mg to 10.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered once or multiple times during the day. The compounds may be administered upon awakening or otherwise in the morning, or during waking hours. For example, the compounds may be administered about 1 hour after awakening, about 30 minutes after awakening or immediately after awakening.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with compounds which are known in the art to be useful for treating or controlling narcolepsy, including e.g., methylphenidate, amphetamine, pemoline, phenelzine, protriptyline, gamma-hydroxybutyric acid, sodium oxybate, or other oxybate salts, modafinil, armodafinil, caffeine, and salts thereof, and combinations thereof, and the like, The compounds of the present invention may be administered in combination with compounds which are known in the art to be useful for preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, other orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARa agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARa agonists as described in WO 97/36579; (g) PPARδ agonists, such as those disclosed in WO97/28149; (h) PPAR α/δ agonists, such as muraglitazar, and the compounds disclosed in U.S. Pat. No. 6,414, 002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB 1 receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001, 836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those discribed in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) 3-hydroxy steroid dehydrogenase-1 inhibitors (P3-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871; WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373, 003, 5,387,595, 5,459,270, 5,494,926, 5,496,833, and 5,637, 699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors, such as verubecestat; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMPA agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, 03 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, orexin receptor antagonists, such as suvorexant, other orexin agonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DCM ($CH_2Cl_2$): dichloromethane; DCE: dichloroethane; DEAD: diethylazodicarboxylate; DIPEA: N,N-diisopropylethylamine; DMF: N,N-dimethylformamide; DMSO: dimethylsulfoxide; EDC: N-(3-Dimethylaminopropyl)-N'-ethylcarbodiimide; $Et_3N$: triethylamine; EtOAc: ethyl acetate; EtOH: ethanol; HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; THF: tetrahydrofuran; TFA: trifluoracetic acid; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE A 1-benzyl 2-methyl (5R)-5-methyl-3-oxopyrrolidine-1,2-dicarboxylate

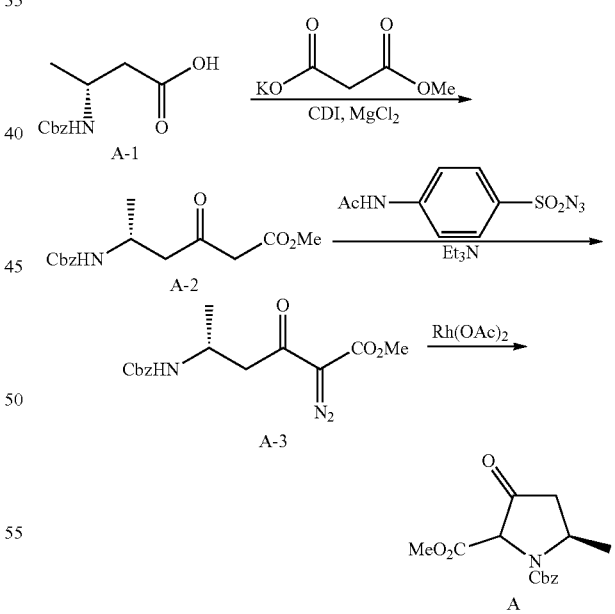

Step 1: methyl (R)-5-(((benzyloxy)carbonyl)amino)-3-oxohexanoate (A-2)

To a solution of (R)-3-(((benzyloxy)carbonyl)amino)butanoic acid (A-1) (6.25 g, 26.3 mmol) in anhydrous THF (100 mL) under $N_2$ was added di(1H-imidazol-1-yl)methanone (6.41 g, 39.5 mmol). After stirring at rt for 1 h, previously mixed MgCl₂ (4.64 mL, 52.7 mmol) and potassium 3-methoxy-3-oxopropanoate (8.23 g, 52.7 mmol) was added. The resulting mixture was stirred at rt for additional 18 h under N₂. The solvent was evaporated and the residue was dissolved in ethyl acetate (100 mL) and washed with water (100 mL), followed by brine (20 mL). The organic layer was dried over MgSO₄, filtered and concentrated in vacuo. The residue was purified by column chromatography (silica gel, 0-100% EtOAc in hexane) to afford methyl (R)-5-(((benzyloxy)carbonyl)amino)-3-oxohexanoate. LC-MS 294 (M+1).

Step 2: methyl (R)-5-(((benzyloxy)carbonyl)amino)-2-diazo-3-oxohexanoate (A-3)

To a solution of methyl (R)-5-(((benzyloxy)carbonyl)amino)-3-oxohexanoate (A-2) (6.2 g, 21.14 mmol) in DCM (200 mL) was added Et₃N (6.42 g, 63.4 mmol) and 4-acetamido-benzene-sulfonyl azide (5.08 g, 21.14 mmol) at rt under N₂. The reaction mixture was stirred for 12 h. LC-MS showed that the reaction was completed. The crude material was diluted with 200 mL of DCM, washed with 50 mL of H₂O. The organic phase was collected and dried (MgSO₄), concentrated and chromatographed over silica gel (0-100% Ethyl acetate in hexanes) to give the title compound methyl (R)-5-(((benzyloxy)carbonyl)amino)-2-diazo-3-oxohexanoate. LC-MS 320 (M+1).

Step 3: 1-benzyl 2-methyl (5R)-5-methyl-3-oxopyrrolidine-1,2-dicarboxylate (A)

To a solution of methyl (R)-5-(((benzyloxy)carbonyl)amino)-2-diazo-3-oxohexanoate (A-3) (2.0 g, 6.26 mmol) in toluene (50 mL) was added diacetoxyrhodium (0.138 g, 0.313 mmol) under N₂ at rt. The reaction mixture was degassed for 10 min, then was stirred at 80° C. for 2 h. LC-MS showed reaction completed. The reaction mixture was concentrated and chromatographed over silica gel (0-100% EtOAc in hexanes) to give the title compound 1-benzyl 2-methyl (5R)-5-methyl-3-oxopyrrolidine-1,2-dicarboxylate. LC-MS 292.28 (M+1).

INTERMEDIATE B

Benzyl (4aR,6R,7aS)-1-(4-methoxybenzyl)-6-methylhexahydro-5H-pyrrolo[3,2-d][1,2,3]oxathiazine-5-carboxylate 2,2-dioxide

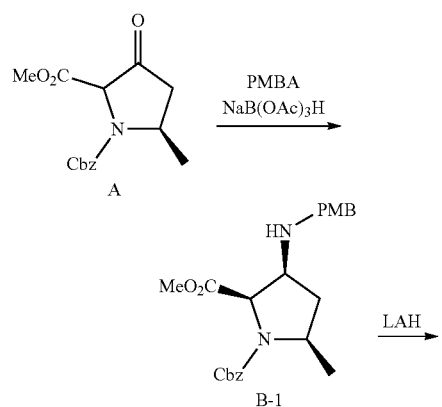

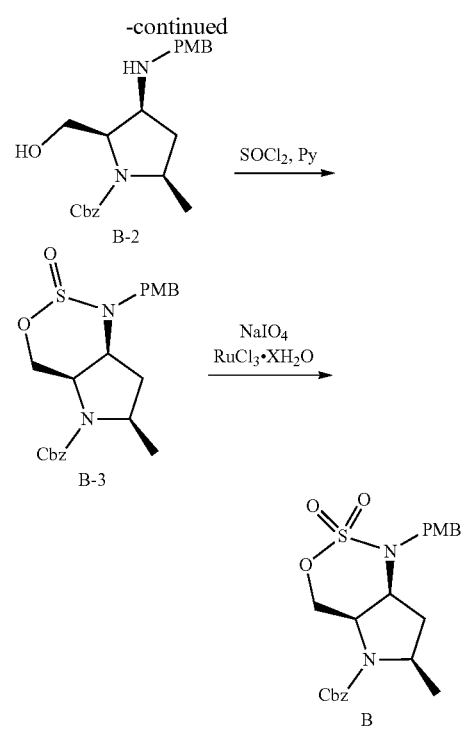

Step 1: methyl (R)-5-(((benzyloxy)carbonyl)amino)-3-oxohexanoate (B-1)7

To a solution of 1-benzyl 2-methyl (5R)-5-methyl-3-oxopyrrolidine-1,2-dicarboxylate (A) (5000 mg, 17.16 mmol) in DCM (100 mL) was added 4-methoxybenzylamine (2.467 mL, 18.88 mmol) and catalytic amount of acetic acid (0.049 mL, 0.858 mmol). The mixture was stirred at rt for 30 mins, then sodium triacetoxyborohydride (4.37 g, 20.6 mmol) was added to the mixture. The reaction was stirred at rt overnight. LC-MS showed completion of the reaction. The reaction was quenched with sat. aq. NaHCO₃ (50 mL), extracted with DCM (3×50 mL). The combined organic phases were dried over MgSO₄, filtered and concentrated. The residue was purified by column chromatography on silica gel (EtOAc in Hexane 0-100%) to afford the title compound 1-benzyl 2-methyl (5R)-3-((4-methoxybenzyl)amino)-5-methylpyrrolidine-1,2-dicarboxylate. LC-MS 413 (M+1).

Step 2: benzyl (2R,3S,5R)-2-(hydromethyl)-3-((4-methoxybenzyl)amino-5-methylpyrrolidine-1-carboxylate (B-2)

To a solution of 1-benzyl 2-methyl (5R)-3-((4-methoxybenzyl)amino)-5-methyl-pyrrolidine-1,2-dicarboxylate (B-1) (2000 mg, 4.85 mmol) in THF (50 mL) at −15° C. was added LiAlH₄ (5.82 mL, 5.82 mmol, 1M in THF) under N₂. The reaction was stirred at −15° C. for 15 min. LC-MS showed completion of the reaction. The reaction was quenched by sequential addition of 0.5 mL of H₂O, 0.5 mL of 1N NaOH and 1.5 mL of H₂O. After stirring for 0.5 h, the reaction mixture was filtered and the organic phase was collected, dried (MgSO₄), concentrated in vacuo and chromatographed over silica gel with 0-100% EtOAc in hexanes as eluent to give the title product benzyl (5R)-2-(hydroxymethyl)-3-((4-methoxybenzyl)amino)-5-methylpyrrolidine-1-carboxylate. LC-MS 385 (M+1).

Step 3: benzyl (4aR,6R,7aS)-1-(4-methoxybenzyl)-6-methylhexahydro-5H-pyrrolo[3,2-d][1,2,3]oxathiazine-5-carboxylate 2-oxide (B-3)

To a solution of benzyl (5R)-2-(hydroxymethyl)-3-((4-methoxybenzyl)amino)-5-methylpyrrolidine-1-carboxylate (B-2) (2320 mg, 6.03 mmol) in DCM (50 mL) was added pyridine (1432 mg, 18.10 mmol), followed by addition of sulfurous dichloride (861 mg, 7.24 mmol) in 10 mL of DCM via a syringe pump over 30 min at −78° C. (acetone in dry ice) under $N_2$. The reaction mixture was allowed to gradually rise to rt and stirred for 2 h. Then 50 mL MTBE were added and the mixture was filtered. The filtrate was dried over $K_2CO_3$, filtered and concentrated. The crude was purification by column chromatography (silica gel with EtOAc in hexanes, 0-100%) to give the title compound benzyl (4aR,6R,7aS)-1-(4-methoxybenzyl)-6-methylhexahydro-5H-pyrrolo[3,2-d][1,2,3]oxathiazine-5-carboxylate 2-oxide. LC-MS 431 (M+1).

Step 4: benzyl (4aR,6R,7aS)-1-(4-methoxybenzyl)-6-methylhexahydro-5H-pyrrolo[3,2-d][1,2,3]oxathiazine-5-carboxylate 2,2-dioxide (B)

To a solution of $RuCl_3$ (121 mg, 0.465 mmol) in 10 mL of $H_2O$ was added sodium periodate (1292 mg, 6.04 mmol) little by little until a yellow solution formed. Then 5 g of silica gel, as well as the rest of $NaIO_4$ were added sequentially to the reaction mixture, followed by addition of 20 mL of EtOAc. The resulting suspension was cooled to 0° C. and a solution of benzyl (4aR,6R,7aS)-1-(4-methoxybenzyl)-6-methylhexahydro-5H-pyrrolo[3,2-d][1,2,3]oxathiazine-5-carboxylate 2-oxide (B-3) (2000 mg, 4.65 mmol) in 10 mL of EtOAc was added dropwise. After the reaction mixture was stirred for 1 h at 0° C., LC-MS showed that the reaction was completed. The mixture was filtered using a 2-layered diatomaceous earth and silica gel pad, and eluted with 50 mL of EtOAc. The filtrate was concentrated in vacuo to give the title compound benzyl (4aR,6R,7aS)-1-(4-methoxybenzyl)-6-methylhexahydro-5H-pyrrolo[3,2-d][1,2,3]oxathiazine-5-carboxylate 2,2-dioxide. LC-MS 469 (M+1).

INTERMEDIATE C (2R,3S,5R)-2-((4-isopropylphenoxy)methyl)-N-(4-methoxybenzyl)-5-methylpyrrolidin-3-amine

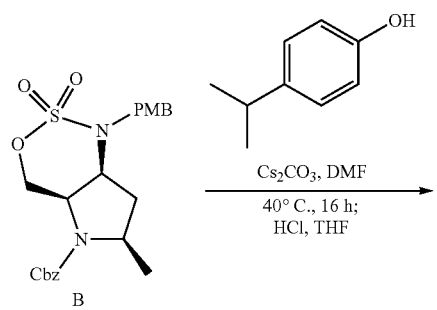

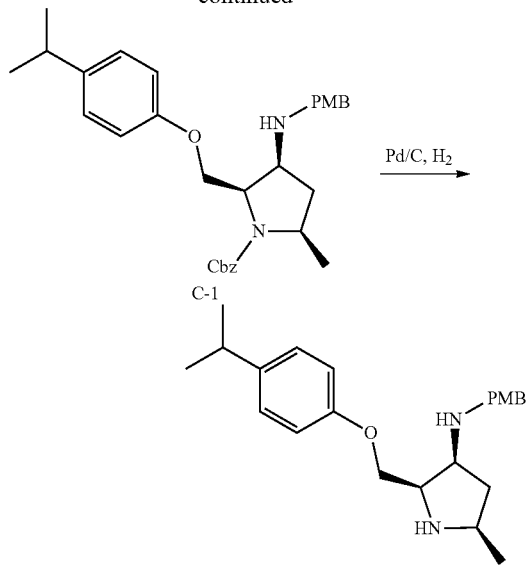

Step 1: benzyl (2R,3S,5R)-2-((4-isopropylphenoxy)methyl)-3-((4-methoxybenzyl)amino)-5-methylpyrrolidine-1-carboxylate (C-1)

To a solution of benzyl (4aR,6R,7aS)-1-(4-methoxybenzyl)-6-methylhexahydro-5H-pyrrolo[3,2-d][1,2,3]oxathiazine-5-carboxylate 2,2-dioxide (B) (2000 mg, 4.48 mmol) in DMF (20 mL) was added $Cs_2CO_3$ (2189 mg, 6.72 mmol) and 4-isopropylphenol (732 mg, 5.37 mmol) at rt under $N_2$. The reaction mixture was stirred at 40° C. for overnight. LC-MS showed reaction completed. The reaction mixture was filtered through a pad of diatomaceous earth. The organic phase was collected, concentrated and dissolved in 30 mL of THF, then was cooled to 0° C. 5 mL of 2N HCl was added. After stirring for 20 min, LC-MS showed only the desired product. The reaction mixture was diluted with 50 mL of EtOAc, then to the reaction mixture was added $K_2CO_3$ to neutralized the reaction mixture. The organic phase was collected, dried ($K_2CO_3$), concentrated and chromatographed over silica gel with 0-40% EtOAC in hexanes as eluent to give the title compound benzyl (2R,3S,5R)-2-((4-isopropylphenoxy)methyl)-3-((4-methoxybenzyl)amino)-5-methylpyrrolidine-1-carboxylate. LC-MS 503 (M+1).

Step 2: (2R,3S,5R)-2-((4-isopropylphenoxy)methyl)-N-(4-methoxybenzyl)-5-methylpyrrolidin-3-amine To a solution of benzyl (2R,3S,5R)-2-((4-isopropylphenoxy)methyl)-3-((4-methoxybenzyl)amino)-5-methylpyrrolidine-1-carboxylate (C-1) (2500 mg, 4.97 mmol) in THF (30.00 mL) was added palladium on carbon (5%, 1059 mg, 0.497 mmol). The reaction mixture was degassed and refilled with H2 three times. The reaction mixture was stirred at rt for 1 h. LC-MS showed reaction completed. The reaction mixture was filtered through a pad of diatomaceous earth. The filtrate was concentrated to give the title compound (2R,3S,5R)-2-((4-isopropylphenoxy)-methyl)-N-(4-methoxybenzyl)-5-methylpyrrolidin-3-amine. LC-MS 369 (M+1).

INTERMEDIATE D (2R,3S,5R)-2-((4-(trifluoromethyl)phenoxy)methyl)-N-(4-methoxybenzyl)-5-methylpyrrolidin-3-amine

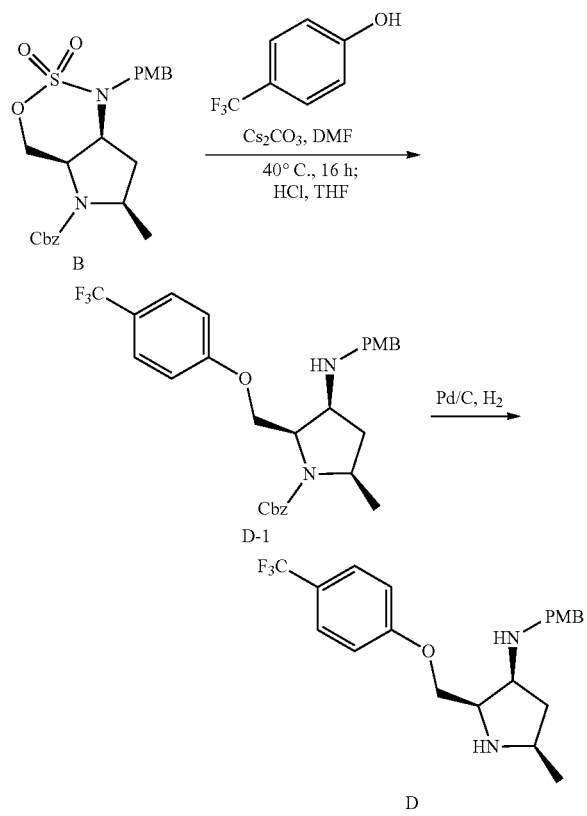

Step 1: benzyl (2R,3S,5R)-2-((4-(trifluoromethyl)phenoxy)methyl)-3-((4-methoxybenzyl)amino)-5-methylpyrrolidine-1-carboxylate (D-1)

To a solution of benzyl (4aR,6R,7aS)-1-(4-methoxybenzyl)-6-methylhexahydro-5H-pyrrolo[3,2-d][1,2,3]oxathiazine-5-carboxylate 2,2-dioxide (B) (200 mg, 0.448 mmol) in DMF (12 mL) was added $Cs_2CO_3$ (219 mg, 0.672 mmol) and 4-(trifluoromethyl)phenol (87 mg, 0.537 mmol) at rt under $N_2$. The reaction mixture was stirred at 40° C. overnight. LC-MS showed no starting material left. The reaction mixture was filtered through a pad of diatomaceous earth. The organic phase was collected, concentrated and dissolved in 30 mL of THF, then was cooled to 0° C. 5 mL of 2N HCl was added and the reaction mixture was stirred for 20 min, LC-MS showed only the desired product. The reaction mixture was diluted with 50 mL of EtOAc, then to the reaction mixture was added $K_2CO_3$ to neutralized the reaction mixture. The organic phase was collected, dried ($K_2CO_3$), concentrated and chromatographed over silica gel with 0-40% EtOAC in hexanes to give the title compound benzyl (2R,3S,5R)-2-((4-(trifluoromethyl)phenoxy)methyl)-3-((4-methoxybenzyl)amino)-5-methylpyrrolidine-1-carboxylate. LC-MS 529 (M+1).

Step 2: (2R,3S,5R)-2-((4-(trifluoromethyl)phenoxy)methyl)-N-(4-methoxybenzyl)-5-methylpyrrolidin-3-amine To a solution of benzyl (2R,3S,5R)-2-((4-(trifluoromethyl)phenoxy)methyl)-3-((4-methoxybenzyl)amino)-5-methylpyrrolidine-1-carboxylate (D-1) (150 mg, 0.284 mmol) in THF (4 mL) was added palladium on carbon (5%, 30 mg, 0.028 mmol). The reaction mixture was degassed and refilled with H2 from a balloon three times. The reaction mixture was stirred at rt for 3 h. LC-MS showed reaction completed. The reaction mixture was then filtered through a pad of diatomaceous earth. The filtrate was concentrated to give the title compound (2R,3S,5R)-2-((4-(trifluoromethyl)phenoxy)methyl)-N-(4-methoxybenzyl)-5-methylpyrrolidin-3-amine. LC-MS 395 (M+1).

INTERMEDIATE E (2R,3S,5R)-2-((4-(2,2,2-trifluoroethyl)phenoxy)methyl)-N-(4-methoxybenzyl)-5-methylpyrrolidin-3-amine

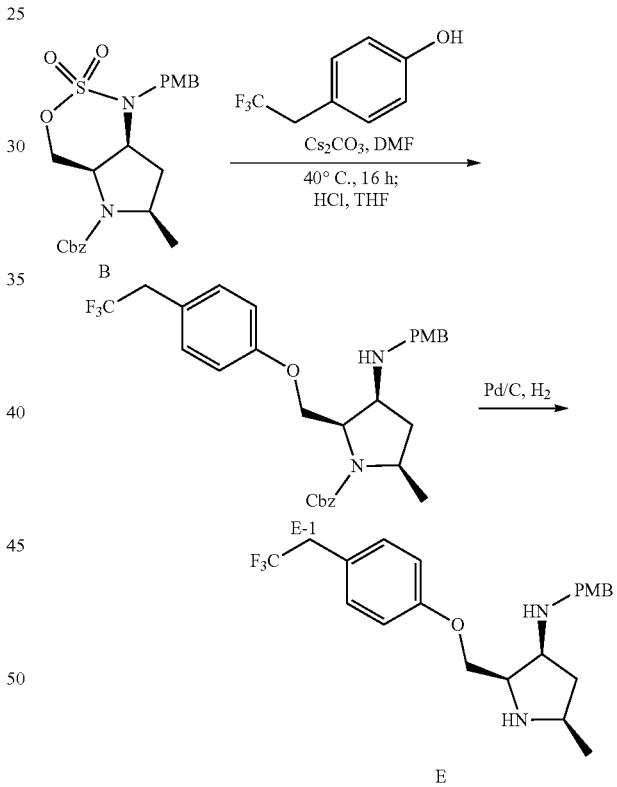

Step 1: benzyl (2R,3S,5R)-2-((4-(2,2,2-trifluoroethyl)phenoxy)methyl)-3-((4-methoxybenzyl)amino)-5-methylpyrrolidine-1-carboxylate (E-1)

To a solution of benzyl (4aR,6R,7aS)-1-(4-methoxybenzyl)-6-methylhexahydro-5H-pyrrolo[3,2-d][1,2,3]oxathiazine-5-carboxylate 2,2-dioxide (B) (400 mg, 0.896 mmol) in DMF (5 mL) was added $Cs_2CO_3$ (438 mg, 1.344 mmol) and 4-(2,2,2-trifluoroethyl)phenol (189 mg, 1.075 mmol) at rt under $N_2$. The reaction mixture was stirred at 40° C. for overnight. LC-MS showed no starting material left. The reaction mixture was filtered through a pad of diatomaceous earth. The organic phase was collected, concentrated and dissolved in 30 mL of THF, then was cooled to 0° C. 5 mL of 2N HCl was added and the reaction mixture, then the reaction was stirred for 20 min, LC-MS showed only the desired product. The reaction mixture was diluted with 50 mL of EtOAc, then to the reaction mixture was added K2CO3 to neutralized the reaction mixture. The organic phase was collected, dried (K2CO3), concentrated and chromatographed over silica gel with 0-40% EtOAC in hexanes to give the title compound benzyl (2R,3S,5R)-2-((4-(2,2,2-trifluoroethyl)phenoxy)-methyl)-3-((4-methoxybenzyl)amino)-5-methylpyrrolidine-1-carboxylate. LC-MS 543 (M+1).

Step 2: (2R,3S,5R)-2-((4-(2,2,2-trifluoroethyl))phenoxy)methyl)-N-(4-methoxybenzyl)-5-methylpyrrolidin-3-amine (E)

To a solution of benzyl (2R,3S,5R)-2-((4-(2,2,2-trifluoroethyl)phenoxy)methyl)-3-((4-methoxybenzyl)amino)-5-methylpyrrolidine-1-carboxylate (E-1) (220 mg, 0.405 mmol) in THF (4 mL) was added palladium on carbon (5%, 43 mg, 0.041 mmol). The reaction mixture was degassed and refilled with H2 three times. The reaction mixture was stirred at rt for 1 h. LC-MS showed SM disappeared. The reaction mixture was filtered through a pad of diatomaceous earth. The filtrate was concentrated to give the title compound (2R,3S,5R)-2-((4-(2,2,2-trifluoroethyl)-phenoxy)methyl)-N-(4-methoxybenzyl)-5-methylpyrrolidin-3-amine. LC-MS 409 (M+1).

INTERMEDIATE F 1-benzyl 2-methyl (5R)-3-(benzyloxy)-5-methylpyrrolidine-1,2-dicarboxylate

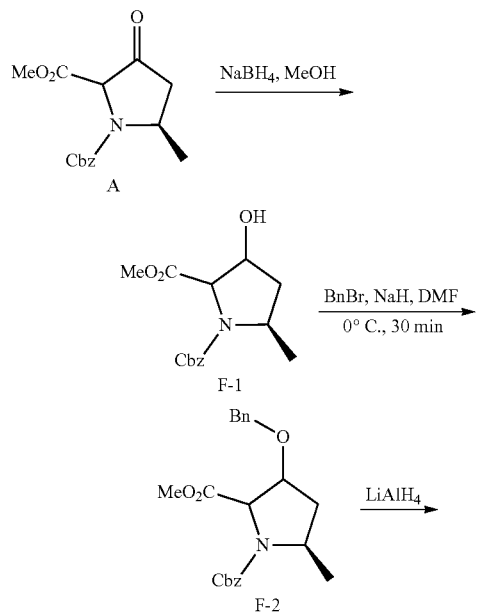

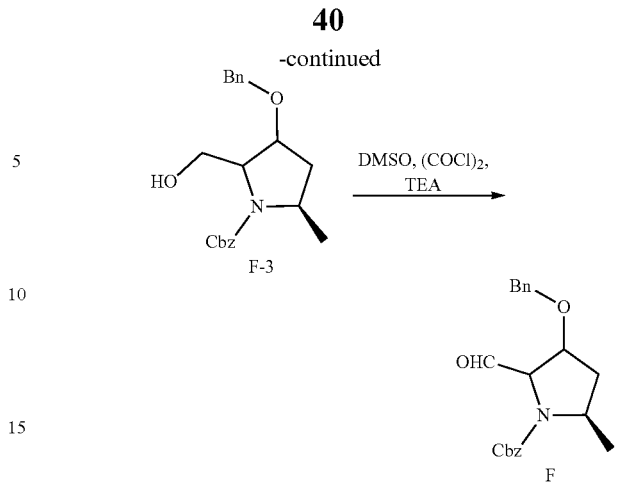

Step 1: 1-benzyl 2-methyl (5R)-3-hydroxy-5-methylpyrrolidine-1,2-dicarboxylate (F-1)

To a solution of 1-benzyl 2-methyl (5R)-5-methyl-3-oxopyrrolidine-1,2-dicarboxylate (A) (9.7 g, 33.3 mmol) in MeOH (20 mL) and THF (50 mL) was slowly added NaBH4 (1.0 g, 26.4 mmol) under N2 at 0° C. over a period of 15 min. The reaction mixture was stirred for 0.5 h. LC-MS showed reaction completed. The reaction was quenched by dropwise addition of 2N KHSO4 at 0° C. until pH<2. The mixture was extracted by 2 portions of 50 mL of EtOAc. The organic phases were combined, dried (MgSO4), concentrated and chromatographed over silica gel with 0-50% EtOAc in hexanes as eluent to give product 1-benzyl 2-methyl (5R)-3-hydroxy-5-methylpyrrolidine-1,2-dicarboxylate. LC-MS 294 (M+1).

Step 2: 1-benzyl 2-methyl (5R)-3-(benzyloxy)-5-methylpyrrolidine-1,2-dicarboxylate (F-2)

To a solution of 1-benzyl 2-methyl (5R)-3-hydroxy-5-methylpyrrolidine-1,2-dicarboxylate (F-1) (2000 mg, 6.82 mmol) and benzyl bromide (0.892 mL, 7.50 mmol) in DMF (30 mL) was added NaH (355 mg, 8.86 mmol) at 0° C. under N2. After stirring for 10 min, LC-MS showed reaction completed. The reaction mixture was quenched by addition of sat. aq. NH4Cl, then to the suspension was added 10 mL of EtOAc. After stirring for 30 min, the organic phase was separated, dried (MgSO4), concentrated and chromatographed over silica gel with 0-100% EtOAc in hexanes as eluent to give product 1-benzyl 2-methyl (5R)-3-(benzyloxy)-5-methylpyrrolidine-1,2-dicarboxylate (F-2). LC-MS 384 (M+1).

Step 3: benzyl (5R)-3-(benzyloxy)-2-(hydroxymethyl)-5-methylpyrrolidine-1-carboxylate (F-3)

To a solution of 1-benzyl 2-methyl (5R)-3-(benzyloxy)-5-methylpyrrolidine-1,2-dicarboxylate (F-2) (2000 mg, 5.22 mmol) in THF (30 mL) was added LiAlH4 (5.22 mL, 5.22 mmol) dropwise at −15° C. under N2. The reaction mixture was stirred for 5 min. LC-MS showed formation of the desired product. The reaction was quenched by adding 2 mL of H2O, 2 mL of 1N NaOH and 6 mL of H2O. After stirring for 0.5 h, the reaction mixture was filtered and the filtrate was collected, dried (MgSO4), concentrated and purified by chromatography on silica gel with 0-50% ethyl acetate in hexanes as eluent to give the desired product benzyl (5R)-

3-(benzyloxy)-2-(hydroxymethyl)-5-methylpyrrolidine-1-carboxylate (F-3). LC-MS 356 (M+1).

Step 4: benzyl (5R)-3-(benzyloxy)-2-formyl-5-methylpyrrolidine-1-carboxylate (F)

To a solution of oxalyl chloride (0.394 mL, 4.50 mmol) in DCM (30 mL) was added DMSO (0.639 mL, 9.00 mmol) in DCM (5 mL) at −78° C. under $N_2$. After addition finished, the reaction mixture was stirred for 5 min before addition of benzyl (5R)-3-(benzyloxy)-2-(hydroxymethyl)-5-methylpyrrolidine-1-carboxylate (F-3) (800 mg, 2.251 mmol) in 2 mL of DCM. The reaction was stirred for 30 min until no starting material left. A solution of $Et_3N$ (1.255 mL, 9.00 mmol) in 2 mL of DCM was added, then the reaction mixture was allowed to raise to rt, then the reaction was quenched by 2 mL of sat. aq. $NaHCO_3$. The organic phase was collected and dried ($MgSO_4$), filtered and the filtrate was concentrated to give the title compound benzyl (5R)-3-(benzyloxy)-2-formyl-5-methylpyrrolidine-1-carboxylate (F). LC-MS 354 (M+1).

INTERMEDIATE G (CIS)-4-phenylcyclohexanol

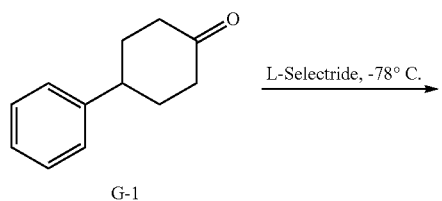

G-1

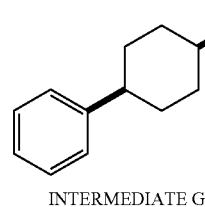

INTERMEDIATE G

To a mixture of 4-phenylcyclohexanone (10.50 g, 60.3 mmol) in THF (201 mL) at −78° C. was added L-Selectride (102 mL, 102 mmol) in THF over 20 min. The mixture stirred at −78° C. for 3 hours before warming to 0° C. and stirring for an additional 2 hours. The reaction was quenched with a saturated solution of $NH_4Cl$ (200 mL), extracted with EtOAc (250 mL×3), dried over $Na_2SO_4$, and concentrated. The residue was purified by column chromatography on silica (2% to 60% EtOAc/hexanes) to afford the title compound. MS: 199.9 (M+23).

INTERMEDIATE H ((CIS)-4-(chloromethoxy)cyclohexyl)benzene

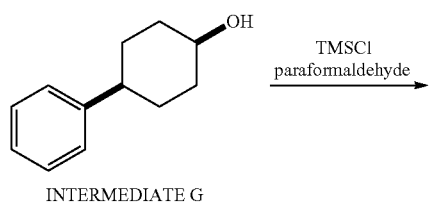

INTERMEDIATE G

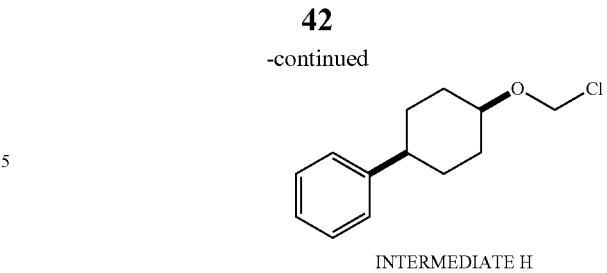

INTERMEDIATE H

To a mixture of (CIS)-4-phenylcyclohexanol (INTERMEDIATE G) (5.00 g, 28.4 mmol) in DCM (28.4 mL) at ambient temperature was added paraformaldehyde (0.937 g, 31.2 mmol) followed by the dropwise addition of TMS-Cl (10.88 mL, 85 mmol). The mixture was stirred for 2 hours before concentrating down, taking up in DCM (50 mL), drying over $Na_2SO_4$, and reconcentrating, and then placed under vacuum. The resulting residue was used directly without any further purification.

INTERMEDIATE I 2-(1-(4-fluorobenzamido)cyclopropyl)-7,8-dihydroquinolin-5-yl trifluoromethanesulfonate

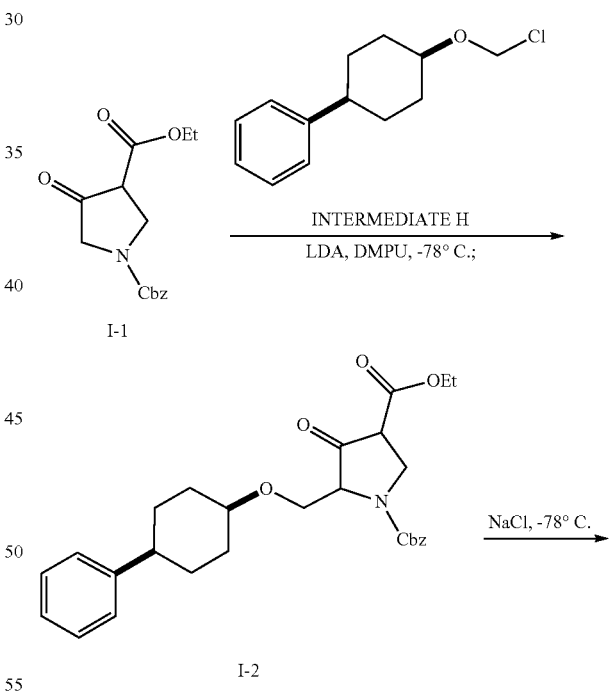

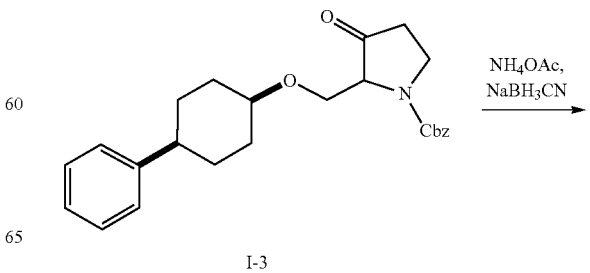

I-3

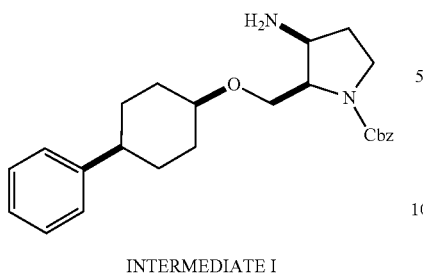

INTERMEDIATE I

Step 1: 1-benzyl 3-ethyl 4-oxo-5-((((1s,4s)-4-phenylcyclohexyl)oxy)methyl)pyrrolidine-1,3-dicarboxylate (C-2)

To a mixture of 1-benzyl 3-ethyl 4-oxopyrrolidine-1,3-dicarboxylate (I-1) (7.50 g, 25.7 mmol) in THF (129 mL)/DMPU (12.42 mL, 103 mmol) at −78° C. was added LDA (28.3 mL, 56.6 mmol) in THF dropwise. The mixture stirred for 15 min before adding ((CIS)-4-(chloromethoxy)cyclohexyl)benzene (INTERMEDIATE H) (6.36 g, 28.3 mmol) in THF (15 mL). The mixture stirred for another 20 min before quenching with a saturated solution of NH₄Cl (100 mL). The mixture was warmed to ambient temperature, extracted with EtOAc (3× @ 200 mL), dried over Na₂SO₄, and concentrated. The residue was purified by column chromatography on silica (2% to 100% EtOAc/hexanes) to afford the title compound. MS: 480.5 (M+1).

Step 2: benzyl 3-oxo-2-((((CIS)-4-phenylcyclohexyl)oxy)methyl)pyrrolidine-1-carboxylate (I-3)

To a mixture of 1-benzyl 3-ethyl 4-oxo-5-((((CIS)-4-phenylcyclohexyl)oxy)-methyl)pyrrolidine-1,3-dicarboxylate (I-2) (4.00 g, 8.34 mmol) in DMSO (25.3 mL) was added NaCl (0.975 g, 16.68 mmol) and H₂O (3.01 mL, 167 mmol). The mixture was heated to 130° C. and stirred for 2 hours before cooling to ambient temperature. The mixture was purified directly by column chromatography on C18 (5-95% MeCN/water with 0.05% TFA modifier) to afford the title compound. MS: 408.5 (M+1).

Step 3: benzyl (CIS)-3-amino-2-((((CIS)-4-phenylcyclohexyloxy)methyl)pyrrolidine-1-carboxylate (INTERMEDIATE I)

To a mixture of benzyl 3-oxo-2-((((CIS)-4-phenylcyclohexyl)oxy)methyl)-pyrrolidine-1-carboxylate (I-3) (6.00 g, 14.72 mmol) in Methanol (294 mL) at ambient temperature was added ammonium acetate (34.0 g, 442 mmol). The mixture stirred for 1 hour. NaCNBH₄ (0.925 g, 14.72 mmol) was added to the mixture for 16 more hours before it was concentrated. Take up in DCM (250 mL) and basify with a saturated solution of NaHCO₃ (250 mL). Extract with DCM (3×250 mL), dry over Na₂SO₄, and concentrate. The resulting residue was purified by column chromatography on C18 (5-95% MeCN/water with 0.05% TFA modifier) to afford the title compound. MS: 409.5 (M+1).

INTERMEDIATE J

N-((CIS)-2-((((CIS)-4-phenylcyclohexyl)oxy)methyl)pyrrolidin-3-yl)methanesulfonamide

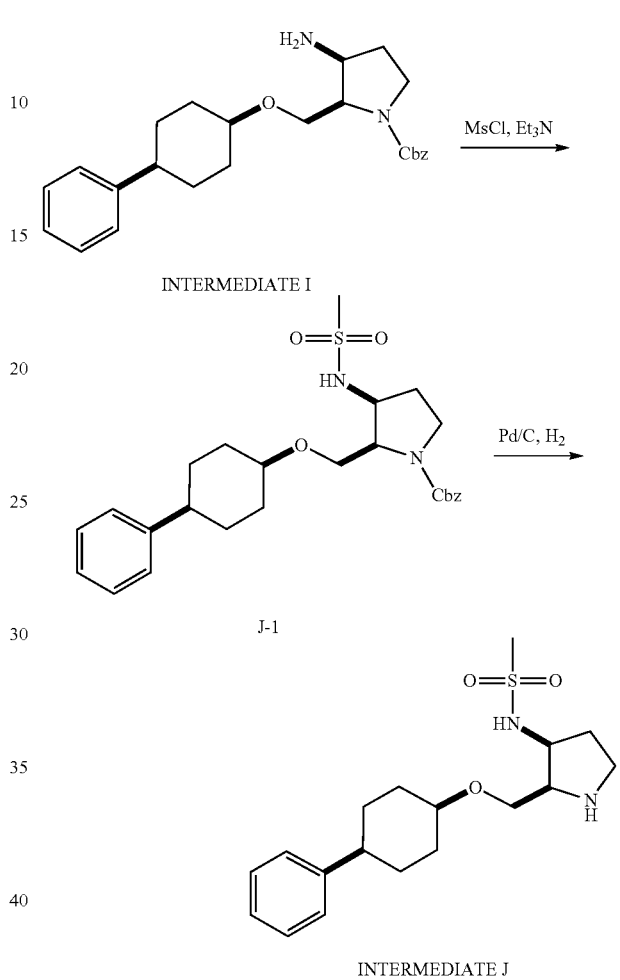

INTERMEDIATE J

Step 1: benzyl (CIS)-3-(methylsulfonamido)-2-((((CIS)-4-phenylcyclohexyl)oxy)methyl)-pyrrolidine-1-carboxylate (J-1)

To a mixture of benzyl 3-amino-2-((((CIS)-4-phenylcyclohexyl)oxy)methyl)pyrrolidine-1-carboxylate (INTERMEDIATE I) (1.00 g, 2.448 mmol) in DCM (12.24 mL) at ambient temperature was added TRIETHYLAMINE (0.682 mL, 4.90 mmol) and METHANESULFONYL CHLORIDE (0.229 mL, 2.94 mmol). The mixture stirred for 2 hours before quenching with a saturated solution of NaHCO₃ (25 mL). The mixture was extracted with EtOAc (3×25 mL), dried over Na₂SO₄, and concentrated. The residue was purified by column chromatography on silica (5% to 70% 3:1 EtOAc:EtOH/hexanes) to afford the title compound. MS: 487.4 (M+1).

Step 2: N-((CIS)-2-((((CIS)-4-phenylcyclohexyl)oxy)methyl)pyrrolidin-3-yl)methanesulfonamide (INTERMEDIATE J)

To a mixture benzyl (CIS)-3-(methylsulfonamido)-2-((((CIS)-4-phenylcyclohexyl)oxy)methyl)pyrrolidine-1-carboxylate (J-1) (756 mg, 1.554 mmol) in MeOH (10.400 mL) at ambient temperature was added Pd/C (165 mg, 0.155 mmol). A balloon of H2 was added (vacuum purge 3×) and the mixture stirred for 2 hours. The resulting mixture was filtered through a pad of diatomaceous earth and the filtrate was concentrated to afford the title compound. MS: 353.3 (M+1).

INTERMEDIATE K

N-((CIS)-1-benzyl-5-oxo-2-(((((CIS)-4-phenylcyclohexyl)oxy)methyl)pyrrolidin-3-yl)methanesulfonamide

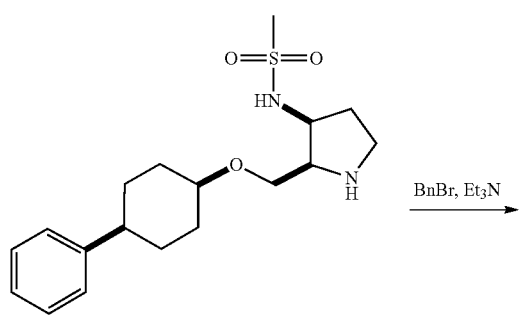

INTERMEDIATE J

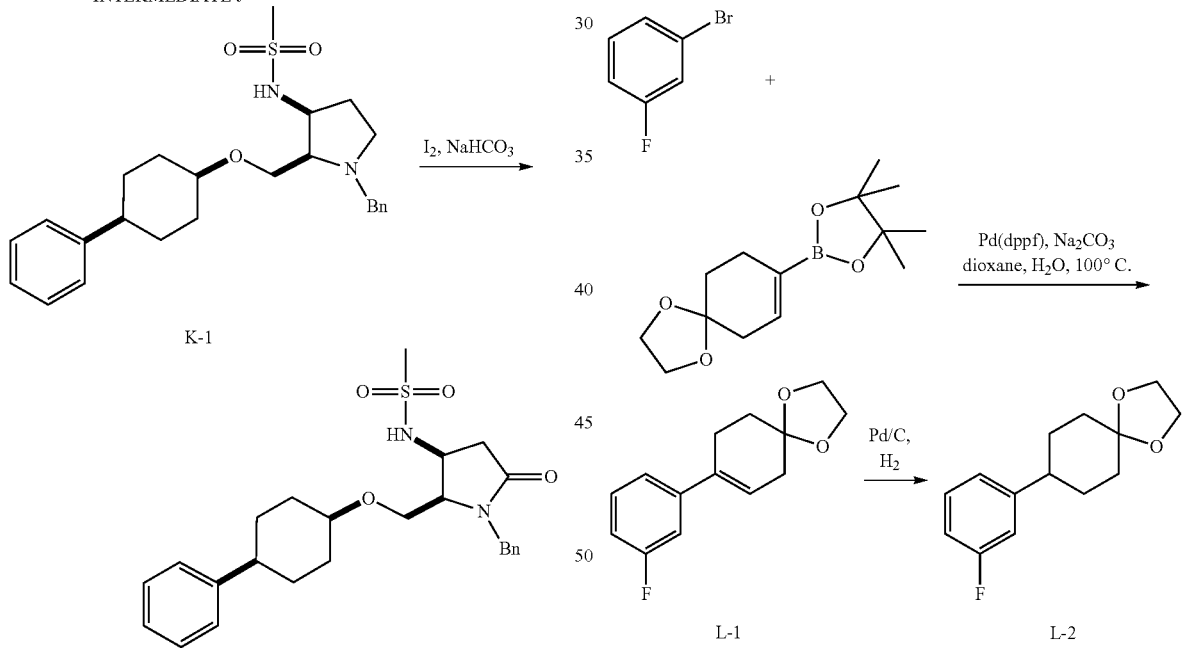

K-1

INTERMEDIATE K

Step 1: N-((CIS)-1-benzyl-2-(((((CIS)-4-phenylcyclohexyl)oxy)methyl)pyrrolidin-3-yl)methanesulfonamide (K-1)

To a mixture of N-((CIS)-2-(((((CIS)-4-phenylcyclohexyl)oxy)methyl)pyrrolidin-3-yl)methanesulfonamide (INTERMEDIATE J) (325 mg, 0.922 mmol) in DMF (2794 µl) at ambient temperature was added TRIETHYLAMINE (257 µl, 1.844 mmol) and BENZYL BROMIDE (132 µl, 1.106 mmol). The mixture was stirred for 2 hours before it was acidified with a few drops of AcOH. The mixture was purified directly by column chromatography on C18 (5-95% MeCN/water with 0.05% TFA modifier) to afford the title compound. MS: 443.5 (M+1).

Step 2: N-((CIS)-1-benzyl-5-oxo-2-(((((CIS)-4-phenylcyclohexyl)oxy)methyl)pyrrolidin-3-yl)methanesulfonamide (INTERMEDIATE K)

To a mixture of N-((CIS)-1-benzyl-2-(((((CIS)-4-phenylcyclohexyl)oxy)methyl)pyrrolidin-3-yl)methanesulfonamide (K-1) (400 mg, 0.719 mmol) in THF (20.5 mL) was added sodium bicarbonate (604 mg, 7.19 mmol) dissolved in water (8.20 mL) and I2 (1368 mg, 5.39 mmol). The mixture was stirred for 6 hours before it was diluted with DCM (50 mL) and quenched with a saturated solution of NaS2O3 (25 mL), extracted with DCM (3×50 mL), dried over Na2SO4, and concentrated. The resulting residue was purified by column chromatography on C18 (5-95% MeCN/water with 0.05% TFA modifier) to afford the title compound. MS: 457.5 (M+1).

INTERMEDIATE L (1s,4s)-4-(3-fluorophenyl)cyclohexan-1-ol

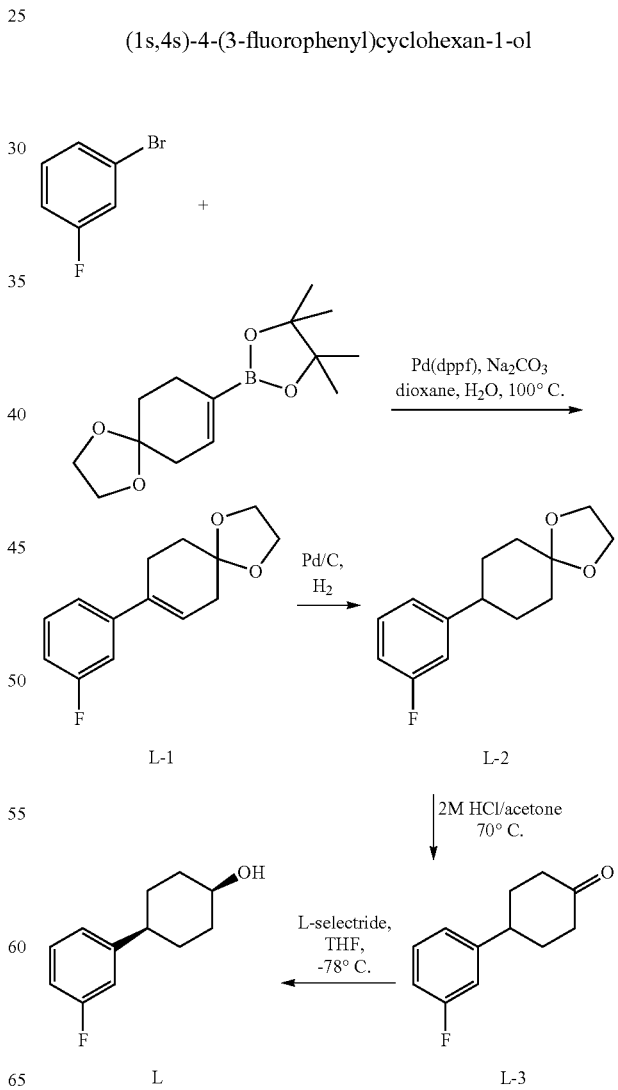

Step 1: 8-(3-fluorophenyl)-1,4-dioxaspiro[4.5]dec-7-ene (L-1)

A suspension of 1-bromo-3-fluorobenzene (2.4 g, 13.71 mmol), 1,1'-bis(diphenylphosphino)-ferrocene-palladium (ii)dichloride dichloromethane complex (2.240 g, 2.74 mmol), sodium carbonate (4.36 g, 41.1 mmol) and 4,4,5,5-tetramethyl-2-(1,4-dioxaspiro[4.5]dec-7-en-8-yl)-1,3,2-dioxaborolane (4.38 g, 16.46 mmol) in DME (54 ml) and $H_2O$ (18 ml) was degassed for 10 mins. The reaction mixture was sealed and heated at 100° C. for overnight. LC-MS indicated reaction was completed. The reaction mixture was cooled down to rt, then was diluted with 70 mL of EtOAc. The organic phase was collected and the aqueous layer was extracted with 2×20 ml of EtOAc. The combined organic phase was dried over $MgSO_4$, concentrated, and the residue was purified by ISCO (silica gel, 120 g, eluent with 0~10% EtOAc in hexane) to give the title compound 8-(3-fluorophenyl)-1,4-dioxaspiro[4.5]dec-7-ene. (L-1). LC-MS 235 (M+1).

Step 2: 8-(3-fluorophenyl)-1,4-dioxaspiro[4.5]decane (L-2)

To a solution of 8-(3-fluorophenyl)-1,4-dioxaspiro[4.5]dec-7-ene (L-1) (3.17 g, 13.53 mmol) in MeOH (60 ml) was added 10% Pd on C (1.152 g, 1.083 mmol). The reaction mixture was stirred under a $H_2$ balloon for overnight. LC-MS indicated reaction completion. The reaction mixture was filtered through a celite pad and the filtrate was concentrated to give the title compound 8-(3-fluorophenyl)-1,4-dioxaspiro[4.5]decane. (L-2). LC-MS 237 (M+1).

Step 3: 4-(3-fluorophenyl)cyclohexan-1-one (L-3)

To a solution of 8-(3-fluorophenyl)-1,4-dioxaspiro[4.5]decane (L-2) (3.18 g, 13.46 mmol) in acetone (35 ml) was added 2M HCl in water (16.82 ml, 33.6 mmol). The reaction mixture was heated at 70° C. for 3 hrs. LC-MS indicated reaction completed. The reaction was concentrated to remove acetone. The residue was extracted with 3 portions of 30 ml of EtOAc, dried over $MgSO_4$, concentrated to give a yellow oil. The residue was purified by ISCO (silica gel, 80 g, eluent with 0~12% EtOAc in hexane) to give the title compound 4-(3-fluorophenyl)cyclohexan-1-one. (L-3). LC-MS 193 (M+1).

Step 4: (1s,4s)-4-(3-fluorophenyl)cyclohexan-1-ol (L)

To a solution of 4-(3-fluorophenyl)cyclohexan-1-one (L-3) (1.99 g, 10.35 mmol) in THF (35 ml) at −78° C. under nitrogen was added L-Selectride (1.0 M in THF, 15.53 ml, 15.53 mmol) dropwise. The mixture was stirred at −78° C. for 20 mins. LC-MS indicated completion. The reaction mixture was quenched with water followed by MeOH, 1N NaOH and H2O2 solution. It was stirred at rt for 10 mins, then it was extracted with EtOAc (30 mL×3), dried over $MgSO_4$, and concentrated to leave colorless oil. The residue was purified by Isco (Loaded onto a 80 g column, eluent with 0~20% EtOAc in hexane, the peak was collected at 16% EtOAc in hexane) to give the title compound (1s,4s)-4-(3-fluorophenyl)cyclohexan-1-ol ((L). LC-MS 236 (M+1).

INTERMEDIATE M, N, O (1s,4s)-4-(2,5-difluorophenyl)cyclohexan-1-ol (M), (1s,4s)-4-(2,3,6-trifluorophenyl)-cyclohexan-1-ol (N), (1s,4s)-4-(2-(trifluoromethyl)phenyl)cyclohexan-1-ol (O) and (1s,4s)-4-(2-fluorophenyl)cyclohexan-1-ol (P)

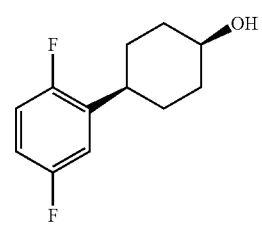

M

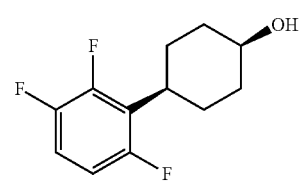

N

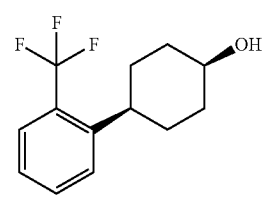

O

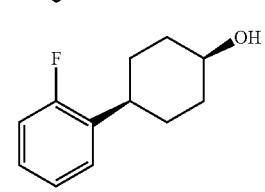

P

Each the intermediate compounds were prepared by following the same procedure as intermediate H using commercially available 2-bromo-1,4-difluorobenzene, 1-bromo-2,3,5-trifluorobenzene and 1-bromo-2-(trifluoromethyl)benzene and 1-bromo-2-fluorobenzene.

INTERMEDIATE Q (4S)-2-fluoro-4-(3-fluorophenyl)cyclohexan-1-one (Q)

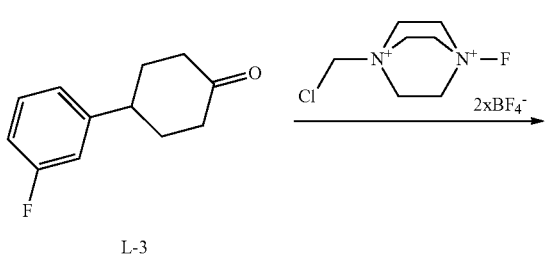

-continued

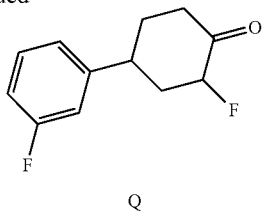

Q

To a solution of 4-(3-fluorophenyl)cyclohexan-1-one (L-3) (400 mg, 2.081 mmol) in acetonitrile (10 ml) was added 1-chloromethyl-4-fluoro-1,4-diazoniabicyclo[2.2.2]octane bis(tetrafluoroborate) (737 mg, 2.081 mmol) and the reaction mixture was heated under reflux for 6 h until KI starch paper showed consumption of the fluorinating reagent. The reaction was stopped and the solvent removed under reduced pressure. The crude reaction mixture was dissolved in $CH_2Cl_2$ (10 ml) and the insoluble material was filtered off. The solution was washed with saturated aqueous $NaHCO_3$, dried over $Na_2SO_4$ and the solvent was concentrated in vacuo. The crude was chromatographed over silica gel (ISCO, 24 g, EtOAc in hexanes 0-80%) to give the desired product 2-fluoro-4-(3-fluorophenyl)cyclohexan-1-one (Q). LC-MS 211 (M+H+).

INTERMEDIATE R benzyl (2R,3S,5R)-3-((N,N-dimethylsulfamoyl)(4-methoxybenzyl)amino)-5-methyl-2-(((triethyl silyl)oxy)methyl)pyrrolidine-1-carboxylate (R)

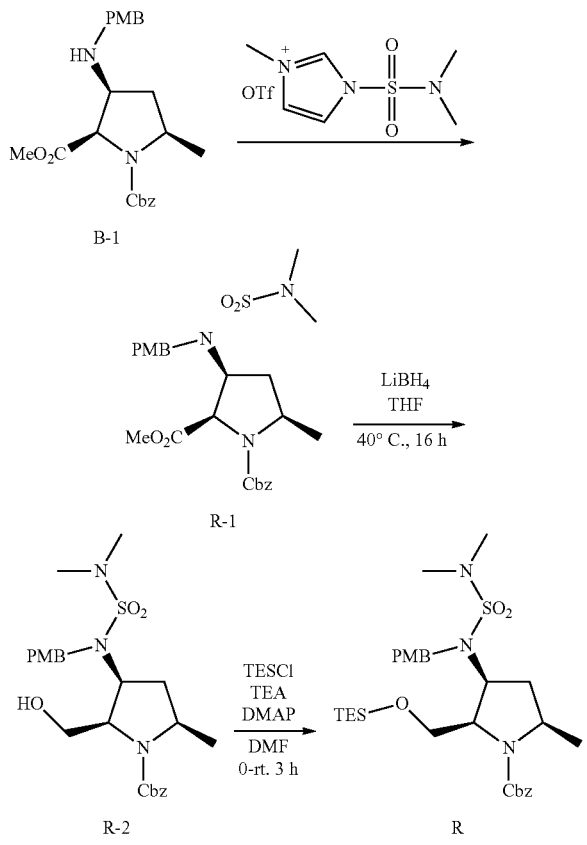

Step 1: 1-benzyl 2-methyl (2R,3S,5R)-3-((N,N-dimethylsulfamoyl)(4-methoxybenzyl)amino)-5-methylpyrrolidine-1,2-dicarboxylate (R-1

Into a 2000-mL 4-necked round-bottom flask, was placed DCM (450 ml), 1-benzyl 2-methyl (5R)-3-((4-methoxybenzyl)amino)-5-methylpyrrolidine-1,2-dicarboxylate (150 g, 1 eq) and 1-(N,N-dimethylsulfamoyl)-3-methyl-1H-imidazol-3-ium trifluoromethanesulfonate (370 g, 3 equiv), The resulting solution was stirred for 3 d at 80° C. in an oil bath. The reaction progress was monitored by LCMS. The reaction mixture was cooled to room temperature and concentrated. The residue was applied onto a silica gel column with ethyl acetate/petroleum ether (1/5-1/4) to give the desired product benzyl (2R,3S,5R)-3-((N,N-dimethylsulfamoyl)(4-methoxybenzyl)amino)-5-methyl-2-(((triethylsilyl)oxy)methyl)pyrrolidine-1-carboxylate (R).

Step 2: benzyl (2R,3S,5R)-3-((N,N-dimethylsulfamoyl)(4-methoxybenzyl)amino)-2-(hydroxymethyl)-5-methylpyrrolidine-1-carboxylate (R-2)

Into a 2000-mL 3-necked round-bottom flask purged and maintained with an inert atmosphere of nitrogen, was placed a solution of 1-benzyl 2-methyl (2R,3S,5R)-3-((N,N-dimethylsulfamoyl)(4-methoxybenzyl)amino)-5-methylpyrrolidine-1,2-dicarboxylate (R-1) (40 g, 80 mmol) in THF (400 ml). This was followed by the addition of LiBH4 (7 g, 315 mmol) with stirring at 0° C. The resulting solution was stirred at 40° C. for 16 h. The reaction was then quenched by the addition of water/ice. The resulting solution was extracted with 3×500 ml of EA and the organic layers combined and dried over $Na_2SO_4$ and concentrated to give the desired product benzyl (2R,3S,5R)-3-((N,N-dimethylsulfamoyl)(4-methoxybenzyl)amino)-2-(hydroxymethyl)-5-methylpyrrolidine-1-carboxylate. (ESI, m/z): (M+Na)+: 514

Step 3: benzyl (2R,3S,5R)-3-((N,N-dimethylsulfamoyl)(4-methoxybenzyl)amino)-5-methyl-2-(((triethylsilyl)oxy)methyl)pyrrolidine-1-carboxylate (R)

Into a 1000-mL 3-necked round-bottom flask purged and maintained with an inert atmosphere of nitrogen, was placed a solution of benzyl (2R,3S,5R)-3-((N,N-dimethylsulfamoyl)(4-methoxybenzyl)amino)-2-(hydroxymethyl)-5-methylpyrrolidine-1-carboxylate (34 g, 69 mmol) in DMF (340 ml) was added TEA (8.36 g, 83 mmol) at r.t under $N_2$. Then add DMAP (1.68 g, 14 mmol) to the system. This was followed by the addition of TESCl (12.5 g, 83 mmol) dropwise with stirring at 0° C. The resulting solution was stirred at 25° C. for 3 h. The reaction was then quenched by the addition of water/ice. The resulting solution was extracted with 2×300 mL of EA. The organic layer was washed with 200 mL of brine and the organic layers combined and dried over $Na_2SO_4$ and concentrated. The residue was applied onto a silica gel column with petroleum ether/ethyl acetate (15/1) to give the desired product benzyl (2R,3S,5R)-3-((N,N-dimethylsulfamoyl)(4-methoxybenzyl)amino)-5-methyl-2-(((triethyl silyl)oxy)methyl)pyrrolidine-1-carboxylate. (ESI, m/z): (M+Na)+: 606.

INTERMEDIATE S AND T

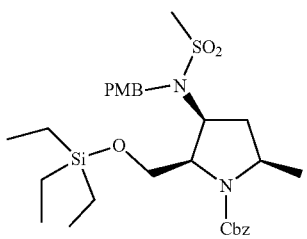

S

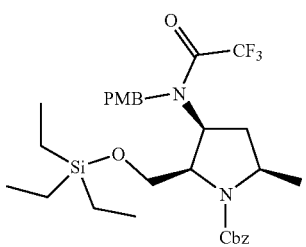

T

Benzyl (2R,3S,5R)-3-(N-(4-methoxybenzyl)methylsulfonamido)-5-methyl-2-(((triethylsilyl)oxy)methyl)pyrrolidine-1-carboxylate (S) and benzyl (2R,3S,5R)-5-methyl-2-(((triethyl silyl)oxy)methyl)-3-(2,2,2-trifluoro-N-(4-methoxybenzyl)acetamido)pyrrolidine-1-carboxylate (T) were prepared according to the same procedure provided in Intermediate R by substituting the appropriate methylsulfonyl chloride or trifluoroacetic anhydride.

INTERMEDIATE U tert-butyl (CIS)-3-(N-(4-methoxybenzyl)methylsulfonamido)-5-oxo-2-((((CIS)-4-phenylcyclohexyl)oxy)methyl)pyrrolidine-1-carboxylate

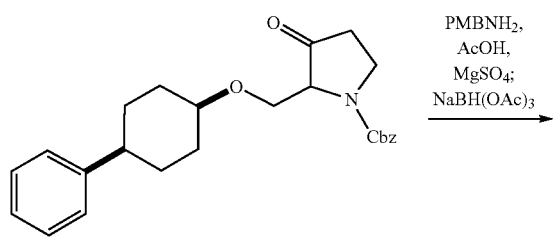

I-3

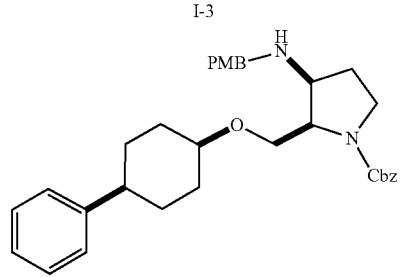

U-1

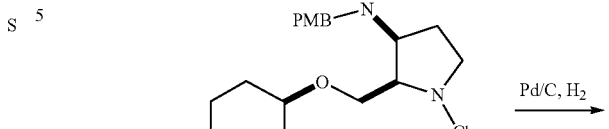

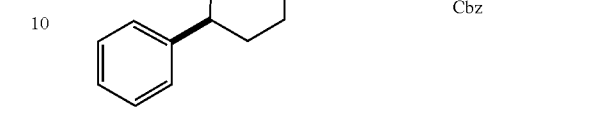

U-2

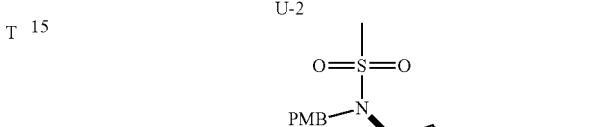

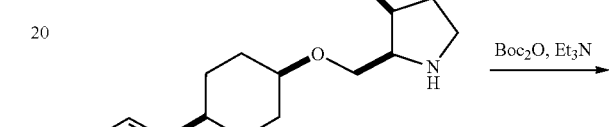

U-3

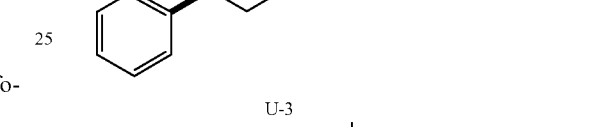

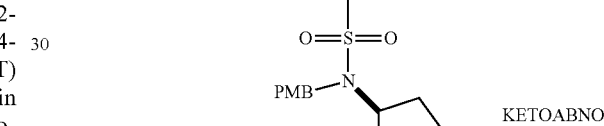

U-4

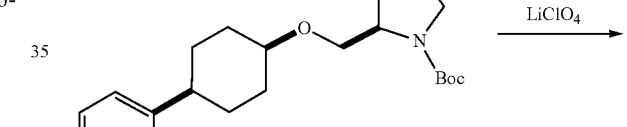

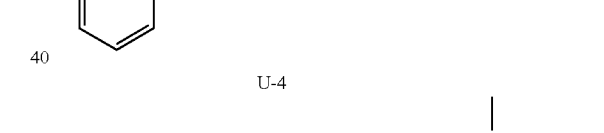

INTERMEDIATE U

Step 1: benzyl (CIS)-3-((4-methoxybenzyl)amino)-2-((((CIS)-4-phenylcyclohexyl)oxy)methyl)-pyrrolidine-1-carboxylate (U-1)

To a mixture of benzyl 3-oxo-2-((((CIS)-4-phenylcyclohexyl)oxy)methyl)pyrrolidine-1-carboxylate (I-3) (10.00 g, 24.54 mmol) in DCM (100 ml) at ambient temperature was added 4-METHOXYBENZYLAMINE (4.81 ml, 36.8 mmol), ACETIC ACID (0.070 ml, 1.227 mmol), and MgSO₄ (5.91 g, 49.1 mmol). The mixture stirred for 3 hours before adding SODIUM TRIACETOXYBOROHYDRIDE (5.72 g, 27.0 mmol) and continuing stirring overnight. The reaction was quenched with a saturated solution of NaHCO$_3$ (100 mL), extracted with DCM (3× @100 mL), dried over Na$_2$SO$_4$, and concentrated. The residue was purified by column chromatography on silica (2% to 90% 3:1 EtOAc:EtOH/hexanes) to afford the title compound. MS: 529.4 (M+1).

Step 2: benzyl (CIS)-3-(N-(4-methoxybenzyl)methylsulfonamido)-2-((((CIS)-4-phenylcyclohexyl)oxy)methyl)pyrrolidine-1-carboxylate (U-2)

To a mixture of 1-METHYLIMIDAZOLE (226 μl, 2.84 mmol) in DMF (1433 μl) at 0° C. was added METHANESULFONYL CHLORIDE (221 μl, 2.84 mmol) dropwise. The mixture stirred for 20 min before adding benzyl (CIS)-3-((4-methoxybenzyl)amino)-2-((((CIS)-4-phenylcyclohexyl)oxy)methyl)pyrrolidine-1-carboxylate (U-1) (250 mg, 0.473 mmol) and TRIETHYLAMINE (395 μl, 2.84 mmol) in DMF (1433 μl) dropwise. The mixture was allowed to warm to ambient temperature and stirred for 2 hours. The reaction was quenched with a saturated solution of NaHCO$_3$ (10 mL), extracted with DCM (3× @ 10 mL), dried over Na$_2$SO$_4$, and concentrated. The residue was purified by column chromatography on silica (2% to 90% 3:1 EtOAc:EtOH/hexanes) to afford the title compound. MS: 607.4 (M+1).

Step 3: N-(4-methoxybenzyl)-N-((CIS)-2-((((CIS)-4-phenylcyclohexyl)oxy)methyl)pyrrolidin-3-yl)methanesulfonamide (U-3)

To a mixture of benzyl (CIS)-3-(N-(4-methoxybenzyl)methylsulfonamido)-2-((((CIS)-4-phenylcyclohexyl)oxy)methyl)pyrrolidine-1-carboxylate (U-2) (130 mg, 0.214 mmol) in MeOH (2142 μl) at ambient temperature was added Pd/C (22.80 mg, 0.021 mmol). A hydrogen balloon was added (vacuum purge 3×) and the reaction was allowed to stir overnight. The mixture was filtered through a pad of diatomaceous earth and the filtrate was concentrated to give the title compound. MS: 473.4 (M+1).

Step 4: tert-butyl (CIS)-3-(N-(4-methoxybenzyl)methylsulfonamido)-2-((((CIS)-4-phenylcyclohexyl)oxy)methyl)pyrrolidine-1-carboxylate (U-4)

To a mixture of N-(4-methoxybenzyl)-N-((CIS)-2-((((CIS)-4-phenylcyclohexyl)oxy)methyl)pyrrolidin-3-yl)methanesulfonamide (U-3) (1.90 g, 4.02 mmol) in DCM (20.10 ml) at ambient temperature was added BOC2O (1.120 ml, 4.82 mmol) and TRIETHYLAMINE (1.121 ml, 8.04 mmol). The mixture was stirred for 2 hours before quenching with a saturated solution of NaHCO$_3$ (20 mL), extracting with DCM (3× @ 30 mL), dried over Na$_2$SO$_4$, and concentrated. The residue was purified by column chromatography on silica (2% to 70% 3:1 EtOAc:EtOH/hexanes) to afford the title compound. MS: 573.4 (M+1).

Step 5: tert-butyl (CIS)-3-(N-(4-methoxybenzyl)methylsulfonamido)-5-oxo-2-((((CIS)-4-phenylcyclohexyl)oxy)methyl)pyrrolidine-1-carboxylate (INTERMEDIATE U)

To a solution of tert-butyl (CIS)-3-(N-(4-methoxybenzyl)methylsulfonamido)-2-((((CIS)-4-phenylcyclohexyl)oxy)methyl)pyrrolidine-1-carboxylate (U-4) (100 mg, 0.175 mmol) in MeCN (2000 μl) and Water (200 μl) was added KETOABNO (16.15 mg, 0.105 mmol) under ambient atmosphere and a constant Potential of 2.5 V was applied resulting in an initial current of 12.2 mA. The working electrode is RVC and the cathode was the IKA platinum plated electrode. Amount of LiClO4 was adjusted to be approximately 0.1M. Reaction stopped after 7 hours, Reaction worked up by partitioning between EtOAc and sat NaHCO$_3$, phases separated, organic phase dried with MgSO$_4$ and concentrated under vacuum. The residue was purified by column chromatography on silica (20% to 70% MTBE/hexanes) to afford the title compound.

INTERMEDIATE V tert-butyl (CIS)-3-(N-(4-methoxybenzyl)methylsulfonamido)-5-oxo-2-((((CIS)-4-phenylcyclohexyl)oxy)methyl)pyrrolidine-1-carboxylate

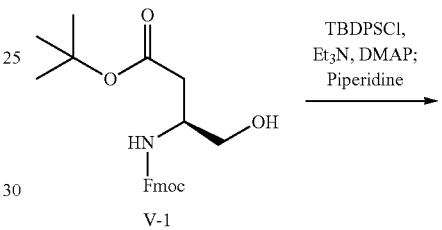

V-1

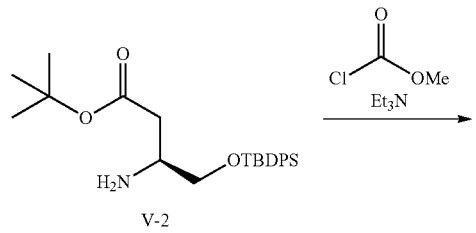

V-2

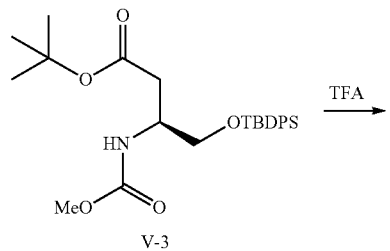

V-3

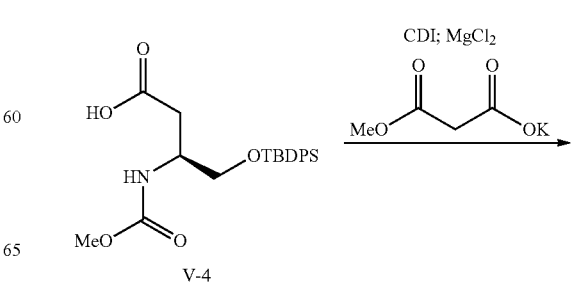

V-4

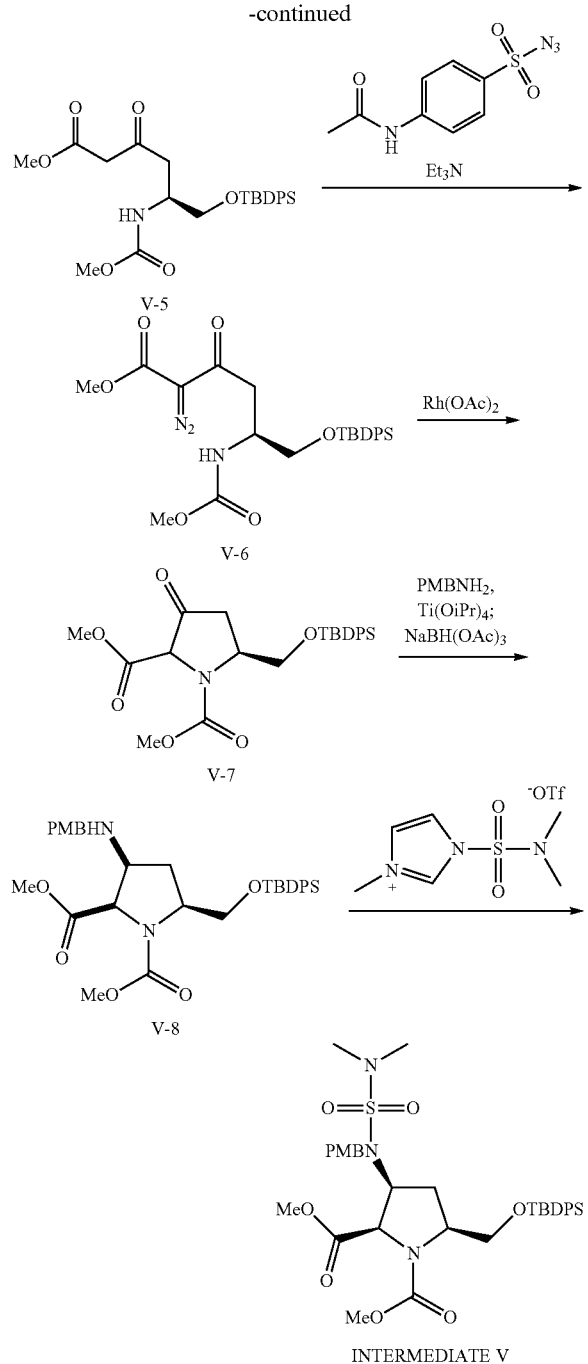

drying over Na$_2$SO$_4$, and concentrating. The residue was purified by column chromatography on silica (2% to 60% EtOAc/hexanes) to afford the title compound. MS: 414.5 (M+1).

Step 2: tert-butyl (S)-4-((tert-butyldiphenylsilyl)oxy)-3-((methoxycarbonyl)amino)butanoate (V-3)

To a mixture of tert-butyl (S)-3-amino-4-((tert-butyldiphenylsilyl)oxy)butanoate (V-2) (5.15 g, 12.45 mmol) in DCM (37.7 ml) at ambient temperature was added TRIETHYLAMINE (3.47 ml, 24.90 mmol) and METHYL CHLOROFORMATE (1.157 ml, 14.94 mmol). The mixture stirred for 16 hour before quenching with a saturated solution of NaHCO$_3$ (50 mL), extracting with DCM (3×@ 50 mL), drying over Na$_2$SO$_4$, and concentrating. The residue was purified by column chromatography on silica (1% to 40% EtOAc/hexanes) to afford the title compound. MS: 472.5 (M+1).

Step 3: (S)-4-((tert-butyldiphenylsilyl)oxy)-3-((methoxycarbonyl)amino)butanoic acid (V-4)

To a mixture of tert-butyl (S)-4-((tert-butyldiphenylsilyl)oxy)-3-((methoxycarbonyl)amino)butanoate (V-3) (5.50 g, 11.66 mmol) in DCM (23.32 ml) at ambient temperature was added TFA (8.98 ml, 117 mmol). The mixture stirred for 4 hours before diluting with EtOAc (150 mL) and quenching with a saturated solution on NaHCO$_3$ (150 mL), extract with EtOAc (3× @ 150 mL), dried over Na$_2$SO$_4$, and concentrated. The residue was purified by column chromatography on C18 (5-95% MeCN/water with 0.05% TFA modifier) to afford the title compound. MS: 416.4 (M+1).

Step 4: methyl (S)-6-((tert-butyldiphenylsilyl)oxy)-5-((methoxycarbonyl)amino)-3-oxohexanoate (V-5)

To a mixture of (S)-4-((tert-butyldiphenylsilyl)oxy)-3-((methoxycarbonyl)amino)butanoic acid (V-4) (2.50 g, 6.02 mmol) in THF (20.05 ml) at ambient temperature was added CDI (1.463 g, 9.02 mmol). The mixture stirred for 1 hour before adding potassium 3-methoxy-3-oxopropanoate (1.879 g, 12.03 mmol) and magnesium chloride (1.145 g, 12.03 mmol). The mixture was allowed to stir for 20 hours before quenching with a saturated solution of NaHCO$_3$ (50 mL), extracting with EtOAc (3× @ 50 mL), drying over Na$_2$SO$_4$ and concentrating. The residue was purified by column chromatography on silica (2% to 75% 3:1 EtOAc:EtOH/hexanes) to afford the title compound. MS: 472.4 (M+1).

Step 5: methyl (S)-6-((tert-butyldiphenylsilyl)oxy)-2-diazo-5-((methoxycarbonyl)amino)-3-oxohexanoate (V-6)

To a mixture of methyl (S)-6-((tert-butyldiphenylsilyl)oxy)-5-((methoxycarbonyl)amino)-3-oxohexanoate (V-5) (1.75 g, 3.71 mmol) in DCM (18.55 ml) at ambient temperature was added 4-acetamidobenzenesulfonyl azide (0.891 g, 3.71 mmol) and TRIETHYLAMINE (1.552 ml, 11.13 mmol). The mixture stirred for 2 hours before diluting with water (20 mL), extracting with DCM (3× @ 20 mL), drying over Na$_2$SO$_4$ and concentrating. The residue was purified by column chromatography on silica (2% to 50% EtOAc/hexanes) to afford the title compound. MS: 498.4 (M+1).

Step 1: tert-butyl (S)-3-amino-4-((tert-butyldiphenylsilyl)oxy)butanoate (V-2)

To a mixture of tert-butyl (S)-3-((((9H-fluoren-9-yl)methoxy)carbonyl)amino)-4-hydroxybutanoate (V-1) (5.00 g, 12.58 mmol) in DCM (15.72 ml) at ambient temperature was added TBDPS-Cl (3.55 ml, 13.84 mmol), TRIETHYLAMINE (2.279 ml, 16.35 mmol), and DMAP (0.154 g, 1.258 mmol). The mixture was heated to 40° C. for 3 hours before cooling back to ambient temperature and adding PIPERIDINE (3.74 ml, 37.7 mmol). The mixture stirred for another 1 hour before quenching with a saturated solution of NaHCO$_3$ (50 mL), extracting with DCM (3× @ 50 mL),

Step 6: dimethyl (5S)-5-(((tert-butyldiphenylsilyl) oxy)methyl)-3-oxopyrrolidine-1,2-dicarboxylate (V-7)

To a mixture of methyl (S)-6-((tert-butyldiphenylsilyl) oxy)-2-diazo-5-((methoxycarbonyl)amino)-3-oxohexanoate (V-6) (1.80 g, 3.62 mmol) in Toluene (18.09 ml) at ambient temperature was added RHODIUM(II) ACETATE DIMER (0.080 g, 0.181 mmol) and the mixture was heated to 80° C. and stirred for 20 min. The mixture was cooled and concentrated. The residue was purified by column chromatography on silica (2% to 80% EtOAc/hexanes) to afford the title compound. MS: 470.4 (M+1).

Step 7: dimethyl (2R,3S,5S)-5-(((tert-butyldiphenylsilyl)oxy)methyl)-3-((4-methoxybenzyl)amino)pyrrolidine-1,2-dicarboxylate (V-8)

To a mixture of dimethyl (5S)-5-(((tert-butyldiphenylsilyl)oxy)methyl)-3-oxopyrrolidine-1,2-dicarboxylate (V-7) (1.55 g, 3.30 mmol) in Tetrahydrofuran (22.00 ml) at 0° C. was added (4-methoxyphenyl)methanamine (0.517 ml, 3.96 mmol) followed by TITANIUM(IV) ISOPROPOXIDE (0.967 ml, 3.30 mmol) dropwise. The mixture was warmed to ambient temperature and stirred for 5 hours. To the mixture was added SODIUM TRIACETOXYBOROHYDRIDE (2.099 g, 9.90 mmol) and stirred for 20 hours. Add SODIUM TRIACETOXYBOROHYDRIDE (2.099 g, 9.90 mmol) and stir for another 24 hours. The reaction was diluted with EtOAc (100 mL) and quenched with a saturated solution of NaHCO$_3$ (100 mL). Extract with EtOAc (3× @ 100 mL), dry over Na$_2$SO$_4$, and concentrate. The residue was purified by column chromatography on silica (2% to 75% 3:1 EtOAc:EtOH/hexanes) to afford the title compound. MS: 591.6 (M+1).

Step 8: dimethyl (2R,3S,5S)-5-(((tert-butyldiphenylsilyl)oxy)methyl)-3-((N,N-dimethylsulfamoyl)(4-methoxybenzyl)amino)pyrrolidine-1,2-dicarboxylate (INTERMEDIATE V)

To a mixture of dimethyl (2R,3S,5S)-5-(((tert-butyldiphenylsilyl)oxy)methyl)-3-((4-methoxybenzyl)amino)pyrrolidine-1,2-dicarboxylate (V-8) (1650 mg, 2.79 mmol) in MeCN (3990 µl) at ambient temperature was added 1-(N,N-dimethylsulfamoyl)-3-methyl-1H-imidazol-3-ium trifluoromethanesulfonate (2843 mg, 8.38 mmol). The mixture was warmed to 80° C. and stirred for 3 days. The mixture was cooled and purified directly by column chromatography on C18 (5-95% MeCN/water with 0.05% TFA modifier) to afford the title compound. MS: 698.6 (M+1).

INTERMEDIATE W methyl (2R,3S,5R)-3-amino-2-(((((1s,4S)-4-(3-fluorophenyl)cyclohexyl)oxy)methyl)-5-methylpyrrolidine-1-carboxylate (W)

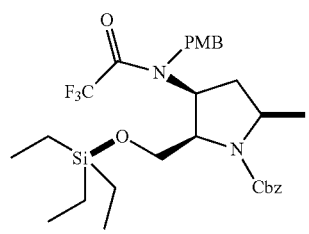

INTERMEDIATE T

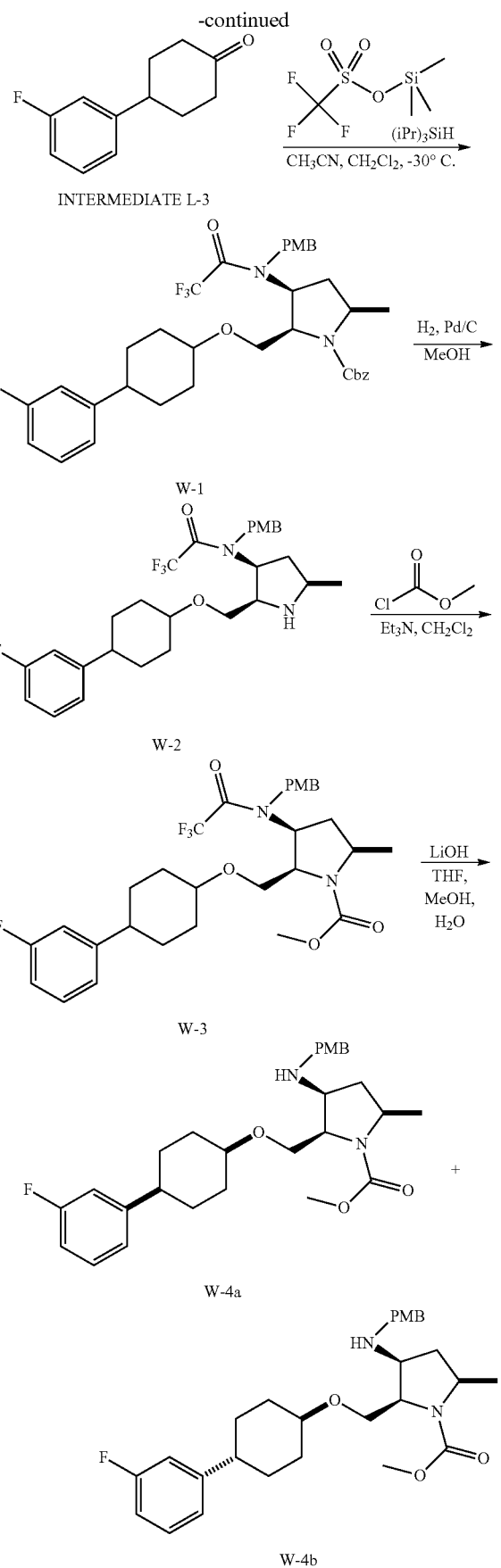

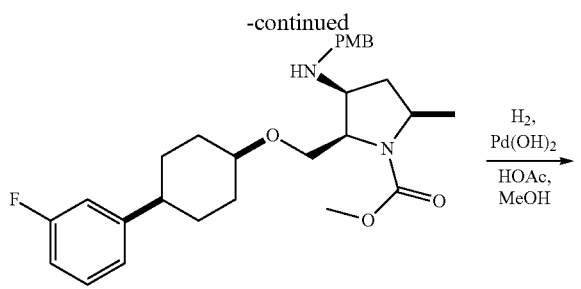

Step 1: benzyl (2R,3S,5R)-2-(((4-(3-fluorophenyl)cyclohexyl)oxy)methyl)-5-methyl-3-(2,2,2-trifluoro-N-(4-methoxybenzyl)acetamido)pyrrolidine-1-carboxylate (W-1)

To a stirred solution of benzyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (T) (400 mg, 0.673 mmol) and 4-(3-fluorophenyl)cyclohexan-1-one (L-3) (155 mg, 0.807 mmol) in acetonitrile (8000 µl) cooled in a acetonitrile/dry ice bath (−30° C.) was added triisopropylsilane (276 µl, 1.345 mmol). Trimethylsilyl trifluoromethanesulfonate (TMS-OTf) (122 µl, 0.673 mmol) as a solution in CH$_2$Cl$_2$ (1000 µl) was then added to above mixture dropwise under N$_2$ at −30° C. The resulting mixture was stirred at −30° C. for 30 min. The cold bath was then replaced with an ice bath. After stirring for 1 hr at −0° C., the reaction was quenched with aqueous sodium hydrogen carbonate (saturated, 30 mL) and brine (10 ml) to facilitate layer separation. The mixture was then extracted with ethyl acetate (3×50 mL). The combined organic fractions were washed with brine (saturated, 30 mL), dried (Na$_2$SO$_4$), filtered and the solvent was evaporated under reduced pressure. The residue was purified by column chromatography on 40 g ISCO silica gel column, eluting with 0 to 30% EtOAc/isohexane. The desired fractions were combined and concentrated under reduced pressure to afford the title compound. MS: 656.0 (M+1).

Step 2: 2,2,2-trifluoro-N-((2R,3S,5R)-2-(((4-(3-fluorophenyl)cyclohexyl)oxy)methyl)-5-methylpyrrolidin-3-yl)-N-(4-methoxybenzyl)acetamide (W-2)

To a stirred solution of benzyl (2R,3S,5R)-2-(((4-(3-fluorophenyl)cyclohexyl)oxy)methyl)-5-methyl-3-(2,2,2-trifluoro-N-(4-methoxybenzyl)acetamido)pyrrolidine-1-carboxylate (547 mg, 0.833 mmol) (W-1) and palladium on carbon (17.73 mg, 0.167 mmol) in MeOH (10 ml) under a Hydrogen balloon. After 1 hr, the reaction was completed with formation of the desired product. The mixture was filtered through a diatomaceous earth cake, washing with methanol. The combined filtrates were concentrated under reduced pressure to the title compound. MS: 522.0 (M+1).

Step 3: methyl (2R,3S,5R)-2-(((4-(3-fluorophenyl)cyclohexyl)oxy)methyl)-5-methyl-3-(2,2,2-trifluoro-N-(4-methoxybenzyl)acetamido)pyrrolidine-1-carboxylate (W-3)

Methyl chloroformate (0.116 ml, 1.498 mmol) was added to a stirred and cooled in an ice bath mixture of 2,2,2-trifluoro-N-((2R,3S,5R)-2-(((4-(3-fluorophenyl)cyclohexyl)oxy)methyl)-5-methylpyrrolidin-3-yl)-N-(4-methoxybenzyl)acetamide (435 mg, 0.832 mmol) (W-2) and triethylamine (0.348 ml, 2.497 mmol) in dichloromethane (10 ml). The mixture was stirred at room temperature for 30 min. The reaction mixture was directly purified by column chromatography on 80 g ISCO silica gel column, eluting with 0 to 50% EtOAc/isohexane. The desired fractions were combined and concentrated under reduced pressure to give the title compound. MS: 580.1 (M+1)

Step 4: methyl (2R,3S,5R)-2-((((1s,4S)-4-(3-fluorophenyl)cyclohexyl)oxy)methyl)-3-((4-methoxybenzyl)amino)-5-methylpyrrolidine-1-carboxylate (W-4)

To a stirred solution of methyl (2R,3S,5R)-2-(((4-(3-fluorophenyl)cyclohexyl)oxy)methyl)-5-methyl-3-(2,2,2-trifluoro-N-(4-methoxybenzyl)acetamido)pyrrolidine-1-carboxylate (W-3) (353 mg, 0.608 mmol) in THF (4000 µl)/MeOH (2000 Cl)/H2O (2000 µl) was added LiOH (87 mg, 3.65 mmol). The mixture was heated to 50° C. After 1 hr, the SM was fully consumed. Removed most of solvent under reduce pressure. The residue was added water (100 mL) and extracted with ethyl acetate (3×75 mL). The combined organic fractions were washed with brine (saturated, 30 mL), dried (Na$_2$SO$_4$), filtered and the solvent was evaporated under reduced pressure. The residue was purified on a reverse preparative HPLC using C18 column and eluting with 5 to 75% water in acetonitrile+0.05% TFA in 15 min method. Two isomers were mostly separated. The desired fractions were combined and concentrated under reduced pressure to give title compound W-4a and W-4b. MS: 484.0 (M+H)

Step 5: methyl (2R,3S,5R)-3-amino-2-((((1s,4S)-4-(3-fluorophenyl)cyclohexyl)oxy)methyl)-5-methylpyrrolidine-1-carboxylate (INTERMEDIATE W)

To a stirred solution of methyl (2R,3S,5R)-2-((((1s,4S)-4-(3-fluorophenyl)cyclohexyl)oxy)-methyl)-3-((4-methoxybenzyl)amino)-5-methylpyrrolidine-1-carboxylate (W-4a) (228 mg, 0.470 mmol) in MeOH (10 ml) was added acetic acid (0.027 ml, 0.470 mmol) followed by Pd(OH)$_2$ (66.1 mg, 0.094 mmol). The mixture was stirred at 25° C. under a hydrogen balloon. After 3 hr, the mixture was filtered, washing with methanol. The combined filtrates were concentrated under reduced pressure. The residue was purified by ISCO preparative reverse phase HPLC (40 g C18 column), eluting with 10 to 100% water in acetonitrile with 0.05% TFA. The desired fractions of cis isomer were combined and concentrated to the title compound. MS: 364.0 (M+H).

INTERMEDIATE X

Methyl (2R,3S,5R)-3-((N,N-dimethylsulfamoyl)(4-methoxybenzyl)amino)-5-methyl-2-(((4-(((trifluoromethyl)sulfonyl)oxy)cyclohex-3-en-1-yl)oxy)methyl)pyrrolidine-1-carboxylate

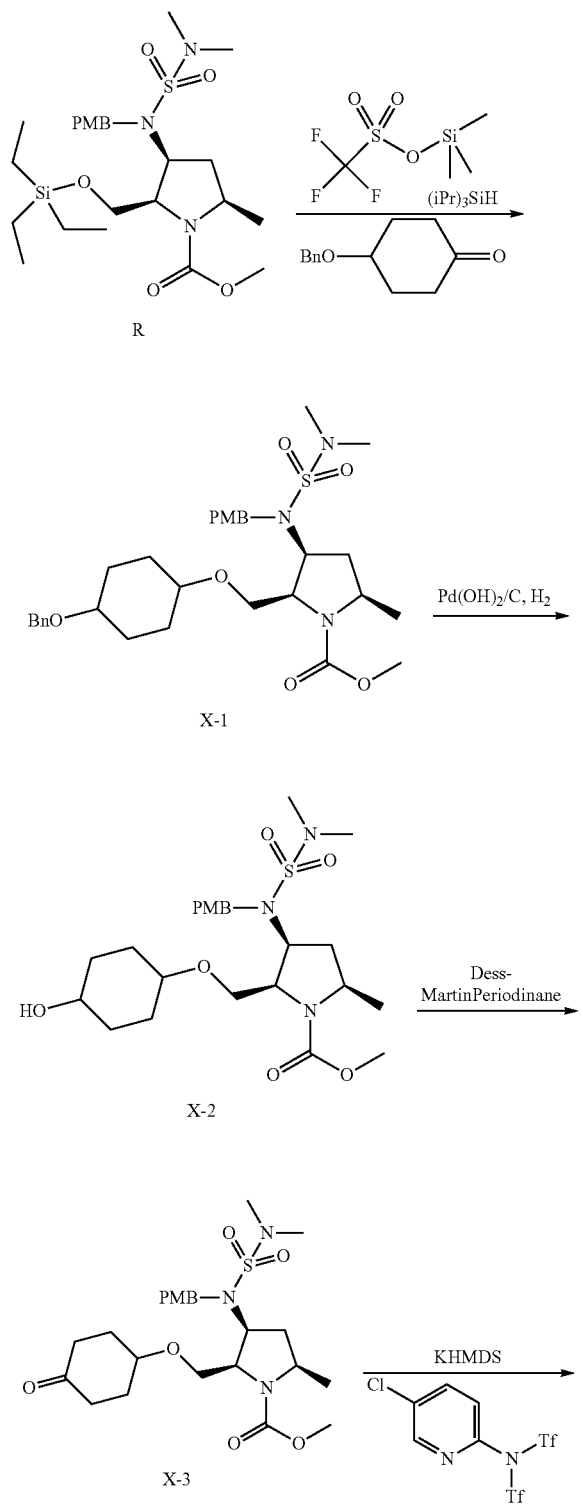

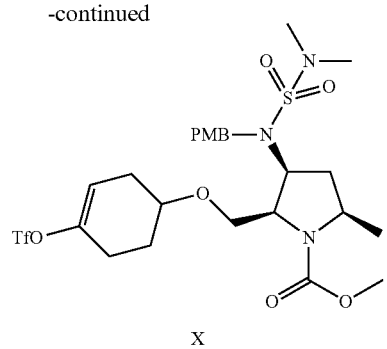

Step 1: Methyl (2R,3S,5R)-2-(((4-(benzyloxy)cyclohexyl)oxy)methyl)-3-((N,N-dimethylsulfamoyl)(4-methoxybenzyl)amino)-5-methylpyrrolidine-1-carboxylate (X-1)

A solution of methyl (2R,3S,5R)-3-((N,N-dimethylsulfamoyl)(4-methoxybenzyl)-amino)-5-methyl-2-(((triethylsilyl)oxy)methyl)pyrrolidine-1-carboxylate (R) (2.44 g, 4.61 mmol), 4-(benzyloxy)cyclohexan-1-one (1.223 g, 5.99 mmol) and TRIISOPROPYLSILANE (1.887 ml, 9.21 mmol) at −35° C. in DCM (4.61 ml)/Acetonitrile (41.5 ml) under $N_2$ was treated with trimethylsilyl trifluoromethanesulfonate (0.834 ml, 4.61 mmol) via a syringe (glass) and needle and the mixture stirred at −35° C. for 3 h (temp up to −20 C). The reaction was quenched with Sat. Aq $NaHCO_3$ and diluted with EtOAc. After warming to rt the layers were separated (need some brine) and the aq layer washed EtOAc. The combined organics was dried ($MgSO_4$), filtered and concentrated under reduced pressure to afford the crude. The crude was purified by silica gel chromatography, on the Combiflash NextGEn 300+ with ELDS on an 80 g column, eluting with a gradient of ethyl acetate:ethanol (3:1)/hexanes—0:100 to 20:80 to afford the title compound (cis/trans). MS: m/z=604.4 (M+1).

Step 2: Methyl (2R,3S,5R)-3-((N,N-dimethylsulfamoyl)(4-methoxybenzyl)amino)-2-(((4-hydroxycyclohexyl)oxy)methyl)-5-methylpyrrolidine-1-carboxylate (X-2)

In a round bottom flask containing a solution of methyl (2R,3S,5R)-2-(((4-(benzyloxy)cyclohexyl)oxy)methyl)-3-((N,N-dimethylsulfamoyl)(4-methoxybenzyl)amino)-5-methylpyrrolidine-1-carboxylate (Intermediate X-1), 2.58 g, 4.27 mmol in MeOH (85 ml) was added PdOH2 (0.600 g, 0.855 mmol) and the flask sealed. The flask was purged, and the mixture stirred under a Hydrogen atmosphere (Balloon) for 10 h. The mixture was diluted with MeOH and filtered through diatomaceous earth. The filtrate was concentrated under reduced pressure to afford the crude as a blackish solid. The crude was purified on the CombiFlash NextGEn 300+ with ELDS on a silica gel 80 g column, eluting with a gradient of ethyl acetate; ethanol (3:1)/hexane 0:100% to 60:40% to give the title compound (mixture of diastereomers). MS: m/z=514.3 (M+1).

Step 3: Methyl (2R,3S,5R)-3-((N,N-dimethylsulfamoyl)(4-methoxybenzyl)amino)-5-methyl-2-(((4-oxocyclohexyl)oxy)methyl)pyrrolidine-1-carboxylate (X-3)

A solution of methyl (2R,3S,5R)-3-((N,N-dimethylsulfamoyl)(4-methoxybenzyl)-amino)-2-(((4-hydroxycyclohexyl)oxy)methyl)-5-methylpyrrolidine-1-carboxylate (Intermediate X-2) 1000 mg, 1.947 mmol, in DCM (9734 μl) at 0° C. was treated with Dess-Martin Periodinane (1651 mg, 3.89 mmol) in 3 portions and the mixture stirred at 0° C. for 15 min then at 25° C. for another 4.5 h. At 0° C. the mixture was quenched with Sat. Aq. NaHCO₃ and diluted with DCM. The layers were separated and the aq layer washed with DCM. The combined organics was washed with brine, filtered and concentrated under reduced pressure to afford the crude. The crude was purified on the CombiFlash NextGEn 300+ with ELSD on a silica gel 40 g column, eluting with a gradient of ethyl acetate; ethanol (3:1)/hexane 0:100% to 50:50% to give the title compound as a white sticky solid. MS: m/z=512.3 (M+1).

Step 3: Methyl (2R,3S,5R)-3-((N,N-dimethylsulfamoyl)(4-methoxybenzyl)amino)-5-methyl-2-(((4-(((trifluoromethyl)sulfonyl)oxy)cyclohex-3-en-1-yl)oxy)methyl)pyrrolidine-1-carboxylate (Intermediate X)

A suspension of methyl (2R,3S,5R)-3-((N,N-dimethylsulfamoyl)(4-methoxybenzyl)amino)-5-methyl-2-(((4-oxocyclohexyl)oxy)methyl)pyrrolidine-1-carboxylate (Intermediate X-3) 844 mg, 1.650 mmol in THF (8248 μl) at 25° C. was treated with 2-[N,N-BIS(TRIFLUOROMETHANESULFONYL)AMINO]-5-CHLOROPYRIDINE (713 mg, 1.815 mmol) and the mixture cool to −78° C. POTASSIUM BIS(TRIMETHYLSILYL)AMIDE (2145 μl, 2.145 mmol) (1 M in THF) was then added via a Hamilton syringe and needle dropwise and the mixture stirred at −78° C. for 2 h. At −78° C. the reaction was quenched with Sat. Aq. NaHCO₃. The mixture was diluted with EtOAc and the layers separated. The aq layer was washed with EtOAc and the combined organics washed with brine, dried, filtered and concentrated under reduced pressure to afford the crude. The crude was purified on the CombiFlash NextGEn 300+ with ELSD on a silica gel 24 g column, eluting with a gradient of ethyl acetate:ethanol (3:1)/hexane 0:100% to 60:45% to give the title compound (Intermediate X). LC-MS: m/z=644.3 (M+1).

EXAMPLE 1

(2R,3S,5R)—N-ethyl-2-(((4-isopropylcyclohexyl)oxy)methyl)-5-methyl-3-(methylsulfonamido)-pyrrolidine-1-carboxamide

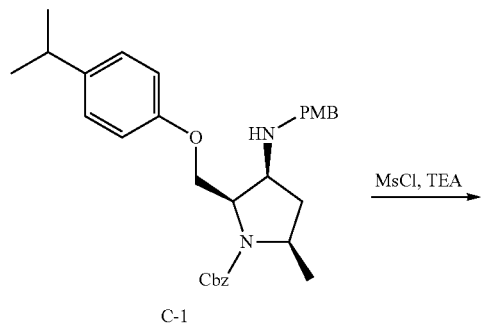

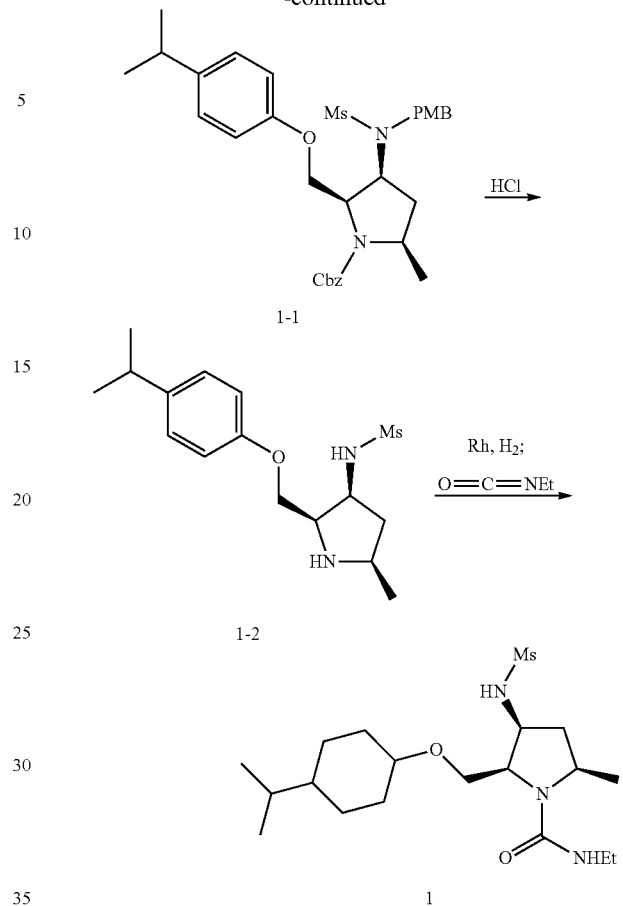

Step 1: benzyl (2R,3S,5R)-2-((4-isopropylphenoxy)methyl)-3-(N-(4-methoxybenzyl)-methylsulfonamido)-5-methylpyrrolidine-1-carboxylate (1-1)

To a solution of benzyl (2R,3S,5R)-2-((4-isopropylphenoxy)methyl)-3-((4-methoxy-benzyl)-amino)-5-methylpyrrolidine-1-carboxylate (C-1) (500 mg, 0.995 mmol) in 30 mL of THF was added Et₃N (0.416 mL, 2.98 mmol) followed by addition of MsCl (0.093 mL, 1.194 mmol) at 0° C. under N₂. The resulting mixture was stirred at 0° C. for 1 hr, then warmed up to rt and stirred for 2 hr. LC-MS showed completion of the reaction. The reaction mixture was filtered and the filtrate was washed with 5 mL of H₂O, extracted with DCM (2×20 mL). The combined organic phases were dried over MgSO₄, filtered, and the filtrate was concentrated in vacuo. The residue was purified by column chromatography on silica gel with 0-30% EtOAc in hexanes as eluent to afford the title compound benzyl (2R,3S,5R)-2-((4-isopropylphenoxy)-methyl)-3-(N-(4-methoxybenzyl)-methyl sulfonamido)-5-methylpyrrolidine-1-carboxylate. LC-MS 581 (M+1).

Step 2: N-((2R,3S,5R)-2-((4-isopropylphenoxy)methyl)-5-methylpyrrolidin-3-yl)methanesulfonamide (1-2)

A solution of benzyl (2R,3S,5R)-2-((4-isopropylphenoxy)methyl)-3-(N-(4-methoxybenzyl)-methylsulfonamido)-5-methylpyrrolidine-1-carboxylate (30 mg, 0.052 mmol) was dissolved in 4 mL of 4N HCl in dioxane. The reaction mixture was sealed in a microwave tube and stirred to 80° C. for 8 h. The reaction mixture was concentrated and the crude was purified by column chromatography (C18, 10-100% acetonitrile in $H_2O$) to give the title compound N-((2R,3S,5R)-2-((4-isopropylphenoxy)methyl)-5-methylpyrrolidin-3-yl)methanesulfonamide. LC-MS 327 (M+1).

Step 3: (2R,3S,5R)—N-ethyl-2-(((4-isopropylcyclohexyl)oxy)methyl)-5-methyl-3-(methyl sulfonamido)pyrrolidine-1-carboxamide (1)

To a solution of N-((2R,3S,5R)-2-((4-isopropylphenoxy)methyl)-5-methylpyrrolidin-3-yl)methanesulfonamide (1-2) (8 mg, 0.025 mmol) dissolved in MeOH (5 mL) was added rhodium on alumina (5%, 5.04 mg, 2.451 μmol), followed by a few drops of acetic acid. The reaction mixture was degassed and refilled with H2 from balloon for 3 times, then was stirred at rt for 2 h. LC-MS showed reaction completed. The reaction mixture was filtered through a pad of diatomaceous earth and the filtrate was concentrated and dissolved in DCM (5 mL). To the reaction mixture was added TEA (0.019 mL, 0.138 mmol), followed by addition of isocyanatoethane (7.84 mg, 0.110 mmol) at 0° C. under $N_2$. The reaction mixture was stirred at rt for 30 min. LC-MS showed reaction completed. The reaction was quenched by addition of a few drops of methanol and the reaction mixture was filtered through a silica gel pad. The filtrate was concentrated in vacuo, followed by column chromatography (C18, 10-100% acetonitrile in $H_2O$) to give the title compound. LC-MS 404 (M+1).

EXAMPLE 2

(2R,3S,5R)—N-ethyl-5-methyl-3-(methylsulfonamido)-2-(((4-(trifluoromethyl)-cyclohexyl)oxy)methyl)pyrrolidine-1-carboxamide

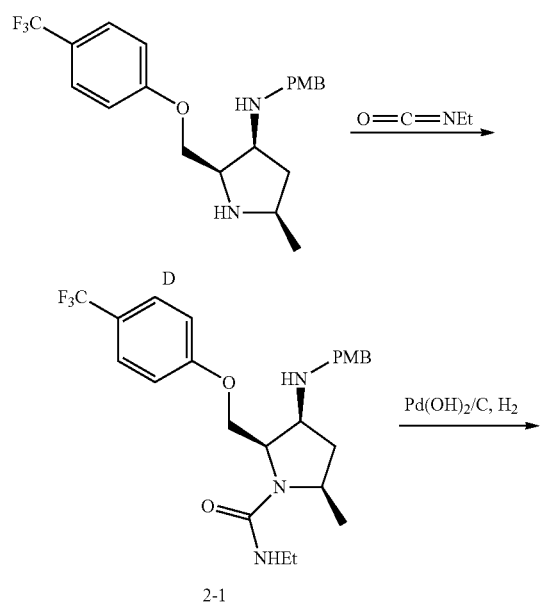

Step 1: (2R,3S,5R)—N-ethyl-3-((4-methoxybenzyl)amino)-5-methyl-2-((4-(trifluoromethyl)phenoxy)methyl)pyrrolidine-1-carboxamide (2-1)

To a solution of (2R,3S,5R)—N-(4-methoxybenzyl)-5-methyl-2-((4-(trifluoromethyl)-phenoxy)methyl)pyrrolidin-3-amine (D) (34 mg, 0.086 mmol) in DCM (1.0 mL) at 0° C. was added $Et_3N$ (0.036 mL, 0.259 mmol), followed by ethyl isocyanate (7.85 μl, 0.099 mmol). The reaction mixture was stirred at 0° C. under $N_2$ for 30 mins. LC-MS showed no starting material left. The reaction mixture was concentrated in vacuo and the residue was purified by prep TLC on on silica gel with 5% MeOH/DCM as eluent to give the title compound (2R,3S,5R)—N-ethyl-3-((4-methoxybenzyl)amino)-5-methyl-2-((4-(trifluoromethyl)phenoxy)methyl)pyrrolidine-1-carboxamide. LC-MS: 466.3 (M+1).

Step 2: (2R,3S,5R)-3-amino-N-ethyl-5-methyl-2-((4-(trifluoromethyl)phenoxy)methyl)-pyrrolidine-1-carboxamide (2-2)

To a solution of (2R,3S,5R)—N-ethyl-3-((4-methoxybenzyl)amino)-5-methyl-2-((4-(trifluoromethyl)phenoxy)methyl)pyrrolidine-1-carboxamide (2-1) (39 mg, 0.084 mmol) in 1 mL of MeOH was added dihydroxypalladium on carbon (5%, 23.53 mg, 0.034 mmol) followed by addition of 3 drops of conc. aq. HCl. The reaction mixture was degassed and refilled with $H_2$, 3 times, then was stirred under H2 at rt for overnight. LC-MS showed the reaction was completed.

The reaction mixture was filtered through a pad of diatomaceous earth. The filtrate was neutralized with TEA, then was concentrated in vacuo and the residue was purified by prep silica gel TLC with 5% 7N NH₃ in MeOH/DCM to provide the title compound (2R,3S,5R)-3-amino-N-ethyl-5-methyl-2-((4-(trifluoromethyl)phenoxy)methyl)pyrrolidine-1-carboxamide (2-2). LC-MS: 346.2 (M+1).

Step 3: (2R,3S,5R)—N-ethyl-5-methyl-3-(methylsulfonamido)-2-((4-(trifluoromethyl)phenoxy)-methyl)pyrrolidine-1-carboxamide (2-3)

To a solution of (2R,3S,5R)-3-amino-N-ethyl-5-methyl-2-((4-(trifluoromethyl)phenoxy)-methyl)pyrrolidine-1-carboxamide (2-2) (29 mg, 0.084 mmol) in 1 mL of DCM was added TEA (0.035 mL, 0.252 mmol) followed by addition of Ms-Cl (8.51 µl, 0.109 mmol) at 0° C. under N₂.

After stirring for 20 mins, LC-MS showed reaction completed. The reaction mixture was concentrated in vacuo and the residue was purified by column chromatography on C18 with 10-100% acetonitrile in H₂O as eluent to provide the title compound (2R,3S,5R)—N-ethyl-5-methyl-3-(methyl sulfonamido)-2-((4-(trifluoromethyl)phenoxy)-methyl)pyrrolidine-1-carboxamide (2-3). MS: 424.6 (M+1).

Step 4: (2R,3S,5R)—N-ethyl-5-methyl-3-(methylsulfonamido)-2-(((4-(trifluoromethyl)cyclohexyl)-oxy)methyl)pyrrolidine-1-carboxamide (2)

To a solution of (2R,3S,5R)—N-ethyl-5-methyl-3-(methylsulfonamido)-2-((4-(trifluoro-methyl)phenoxy)methyl)pyrrolidine-1-carboxamide (2-3) (33 mg, 0.078 mmol) in 1.2 mL of MeOH was added rhodium on alumina (5%, 48.1 mg, 0.023 mmol) followed by 3 drops of acetic acid. The reaction mixture was degassed and refilled with H2 three times, then stirred under hydrogen balloon at rt for overnight. LC-MS indicated reaction was completed. The reaction mixture was filtered through a pad of diatomaceous earth and the filtrate was concentrated in vacuo to afford the title compound (2R,3S,5R)—N-ethyl-5-methyl-3-(methyl sulfonamido)-2-(((4-(trifluoromethyl)-cyclohexyl)oxy)methyl)pyrrolidine-1-carboxamide (2). MS: 430.2 (M+1).

EXAMPLES 3 AND 4 methyl (2R,3S,5R)-2-(((4-isopropylcyclohexyl)oxy)methyl)-5-methyl-3-(methyl sulfonamido)-pyrrolidine-1-carboxylate and methyl (2R,3S,5R)-2-((((1s,4S)-4-isopropylcyclohexyl)oxy)-methyl)-5-methyl-3-(methylsulfonamido)pyrrolidine-1-carboxylate

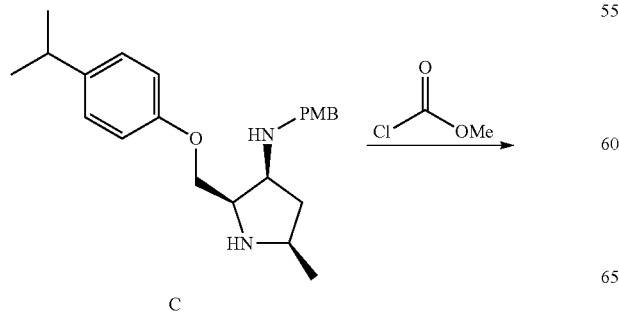

C

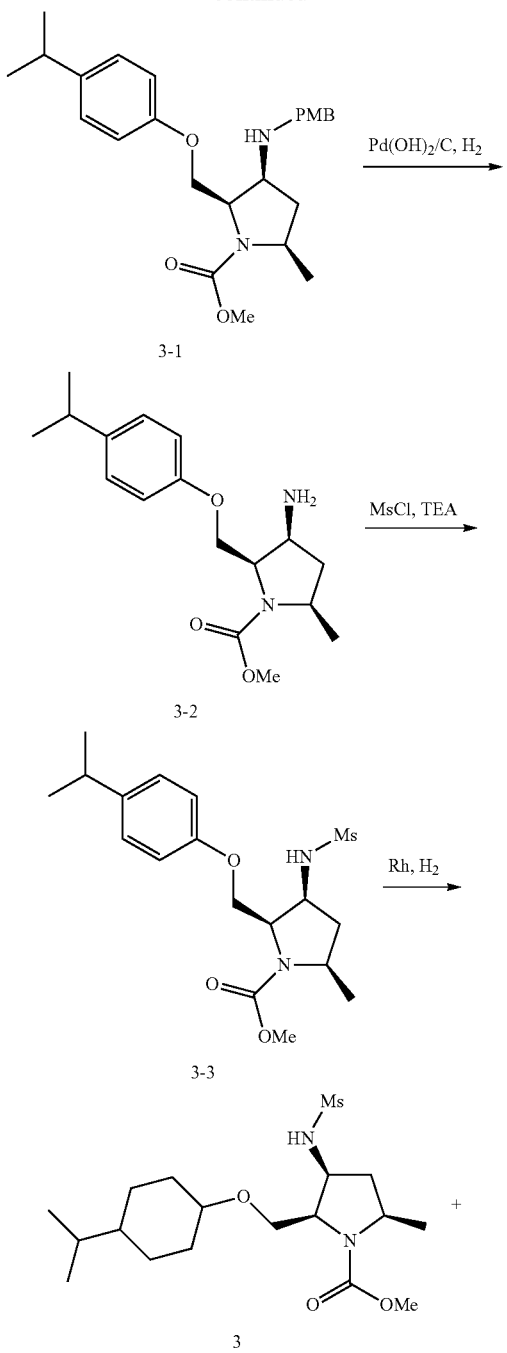

3-1

3-2

3-3

3

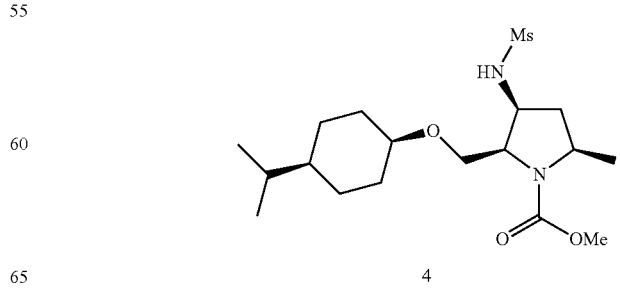

4

Step 1: methyl (2R,3S,5R)-2-((4-isopropylphenoxy)methyl)-3-((4-methoxybenzyl)amino)-5-methylpyrrolidine-1-carboxylate (3-1)

To a solution of (2R,3S,5R)-2-((4-isopropylphenoxy)methyl)-N-(4-methoxybenzyl)-5-methylpyrrolidin-3-amine (C) (1.2 g, 3.26 mmol) dissolved in DCM (50 mL) was added Et$_3$N (0.908 mL, 6.51 mmol), followed by addition of methyl carbonochloridate (369 mg, 3.91 mmol) at 0° C. under N$_2$. The reaction mixture was stirred at rt for 30 min. LC-MS showed no starting material remained. The reaction mixture was quenched by addition of a few drops of methanol, and the reaction mixture was concentrated in vacuo. The crude material was purified by column chromatography on silica gel with 0-50% EtOAc in hexanes as eluent to give the title compound methyl (2R,3S,5R)-2-((4-isopropylphenoxy)methyl)-3-((4-methoxybenzyl)amino)-5-methylpyrrolidine-1-carboxylate (3-1). LC-MS 427 (M+1).

Step 2: methyl (2R,3S,5R)-3-amino-2-((4-isopropylphenoxy)methyl)-5-methylpyrrolidine-1-carboxylate (3-2)

To a solution of methyl (2R,3S,5R)-2-((4-isopropylphenoxy)methyl)-3-((4-methoxy-benzyl)amino)-5-methylpyrrolidine-1-carboxylate (3-1) (1.3 g, 3.05 mmol) in MeOH (50 mL) was added dihydroxypalladium on carbon (5%, 856 mg, 0.305 mmol) and a few drops of aq. HCl. The reaction mixture was degassed and refilled with H2 with balloon for 3 times. The reaction mixture was stirred at rt for 2 h. LC-MS showed no starting material remained. The reaction mixture was filtered through a pad of diatomaceous earth and the filtrate was neutralized by Et$_3$N, then concentrated and chromatographed via column chromatography on C18 with 10-100% acetonitrile in H$_2$O as eluent to give the title compound methyl (2R,3S,5R)-3-amino-2-((4-isopropylphenoxy)methyl)-5-methylpyrrolidine-1-carboxylate. LC-MS 307 (M+1).

Step 3: methyl (2R,3S,5R)-2-((4-isopropylphenoxy)methyl)-5-methyl-3-(methylsulfonamido)-pyrrolidine-1-carboxylate (3-3)

To a solution of methyl (2R,3S,5R)-3-amino-2-((4-isopropylphenoxy)methyl)-5-methylpyrrolidine-1-carboxylate (3-2) (450 mg, 1.469 mmol) in DCM (5 mL) was added Et$_3$N (0.614 mL, 4.41 mmol), followed by addition of Ms-Cl (0.137 mL, 1.762 mmol) at 0° C. under N$_2$. After stirring for 30 min. LC-MS showed reaction completed. To the reaction mixture was added a few drops of methanol, then the reaction mixture was concentrated in vacuo. The crude material was purified by column chromatography on C18 with 10-100% acetonitrile in H$_2$O as eluent to give the tittle compound methyl (2R,3S,5R)-2-((4-isopropylphenoxy)methyl)-5-methyl-3-((methyl sulfonamido)pyrrolidine-1-carboxylate (3-3). LC-MS 385 (M+1).

Step 4: EXAMPLE 3: methyl (2R,3S,5R)-2-(((4-isopropylcyclohexyl)oxy)methyl)-5-methyl-3-(methyl sulfonamido)pyrrolidine-1-carboxylate and EXAMPLE 4: methyl (2R,3S,5R)-2-((((1s,4S)-4-isopropylcyclohexyl)oxy)methyl)-5-methyl-3-(methyl sulfonamido)pyrrolidine-1-carboxylate To a solution of methyl (5R)-2-((4-isopropylphenoxy)methyl)-5-methyl-3-(methyl-sulfonamido)pyrrolidine-1-carboxylate (3-3) (250 mg, 0.650 mmol) in MeOH (5 mL) was added rhodium on alumia (5%, 134 mg, 0.065 mmol) and a few drops of acetic acid. The reaction mixture was degassed three times, then hydrogenated with balloon. After stirring for overnight, LC-MS showed reaction was completed. The reaction mixture was filtered through a pad of diatomaceous earth and the filtrate was concentrated to give the title product methyl (2R,3S,5R)-2-(((4-isopropylcyclohexyl)oxy)methyl)-5-methyl-3-(methyl sulfonamido)pyrrolidine-1-carboxylate (3).

The crude material was further purified by column chromatography to title compound methyl (2R,3S,5R)-2-(((((1s,4S)-4-isopropylcyclohexyl)oxy)methyl)-5-methyl-3-(methylsulfonamido)-pyrrolidine-1-carboxylate (4). LC-MS 391 (M+1).

The following compounds were prepared according to the general procedure provided in Examples 1-4, and procedures herein, by substituting the appropriate alkyl carbonochloridate and sulfamoyl chloride. The starting materials are either prepared as described in the intermediates section, commercially available, or may be prepared from commercially available reagents using conventional reactions well known in the art.

| Example Number | Structure | Name | Exact Mass [M + H]$^+$ |
|---|---|---|---|
| 5 | 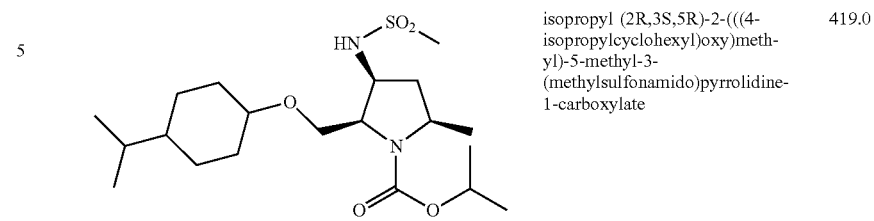<br>(from Intermediate C) | isopropyl (2R,3S,5R)-2-(((4-isopropylcyclohexyl)oxy)methyl)-5-methyl-3-(methylsulfonamido)pyrrolidine-1-carboxylate | 419.0 |

| Example Number | Structure | Name | Exact Mass [M + H]+ |
|---|---|---|---|
| 6 | (from Intermediate C) | isopropyl (2R,3S,5R)-2-(((4-isopropylcyclohexyl)oxy)methyl)-5-methyl-3-((N-methylsulfamoyl)amino)pyrrolidine-1-carboxylate | 434.1 |
| 7 | (from Intermediate C) | ethyl (2R,3S,5R)-2-(((4-isopropylcyclohexyl)oxy)methyl)-5-methyl-3-(methylsulfonamido)pyrrolidine-1-carboxylate | 405.0 |
| 8 | (from Intermediate C) | ethyl (2R,3S,5R)-3-((N,N-dimethylsulfamoyl)amino)-2-(((4-isopropylcyclohexyl)oxy)methyl)-5-methylpyrrolidine-1-carboxylate | 434.2 |
| 9 | (from Intermediate C) | 2,2-difluoroethyl (2R,3S,5R)-2-(((4-isopropylcyclohexyl)oxy)methyl)-5-methyl-3-(methylsulfonamido)pyrrolidine-1-carboxylate | 441.1 |
| 10 | (from Intermediate C) | 2-fluoroethyl (2R,3S,5R)-2-(((4-isopropylcyclohexyl)oxy)methyl)-5-methyl-3-(methylsulfonamido)pyrrolidine-1-carboxylate | 423.2 |

-continued

| Example Number | Structure | Name | Exact Mass [M + H]+ |
|---|---|---|---|
| 11 | (from Intermediate D) | methyl (2R,3S,5R)-3-((N,N-dimethylsulfamoyl)amino)-5-methyl-2-(((4-(trifluoromethyl)cyclohexyl)oxy)methyl)pyrrolidine-1-carboxylate | 446.1 |
| 12 | (from Intermediate E) | methyl (2R,3S,5R)-5-methyl-3-(methylsulfonamido)-2-(((4-(2,2,2-trifluoroethyl)cyclohexyl)oxy)methyl)pyrrolidine-1-carboxylate | 431.2 |
| 13 | (from Intermediate C) | 2,2-difluoroethyl (2R,3S,5R)-2-(((4-isopropylcyclohexyl)oxy)methyl)-5-methyl-3-((N-methylsulfamoyl)amino)pyrrolidine-1-carboxylate | 456.2 |
| 14 | (from Intermediate C) | 2,2-difluoroethyl (2R,3S,5R)-3-((N,N-dimethylsulfamoyl)amino)-2-(((4-isopropylcyclohexyl)oxy)methyl)-5-methylpyrrolidine-1-carboxylate | 470.3 |

EXAMPLE 15 methyl (2R,3S,5R)-5-methyl-3-(methyl sulfonamido)-2-((((1s,4S)-4-phenylcyclohexyl)oxy)-methyl) pyrrolidine-1-carboxylate

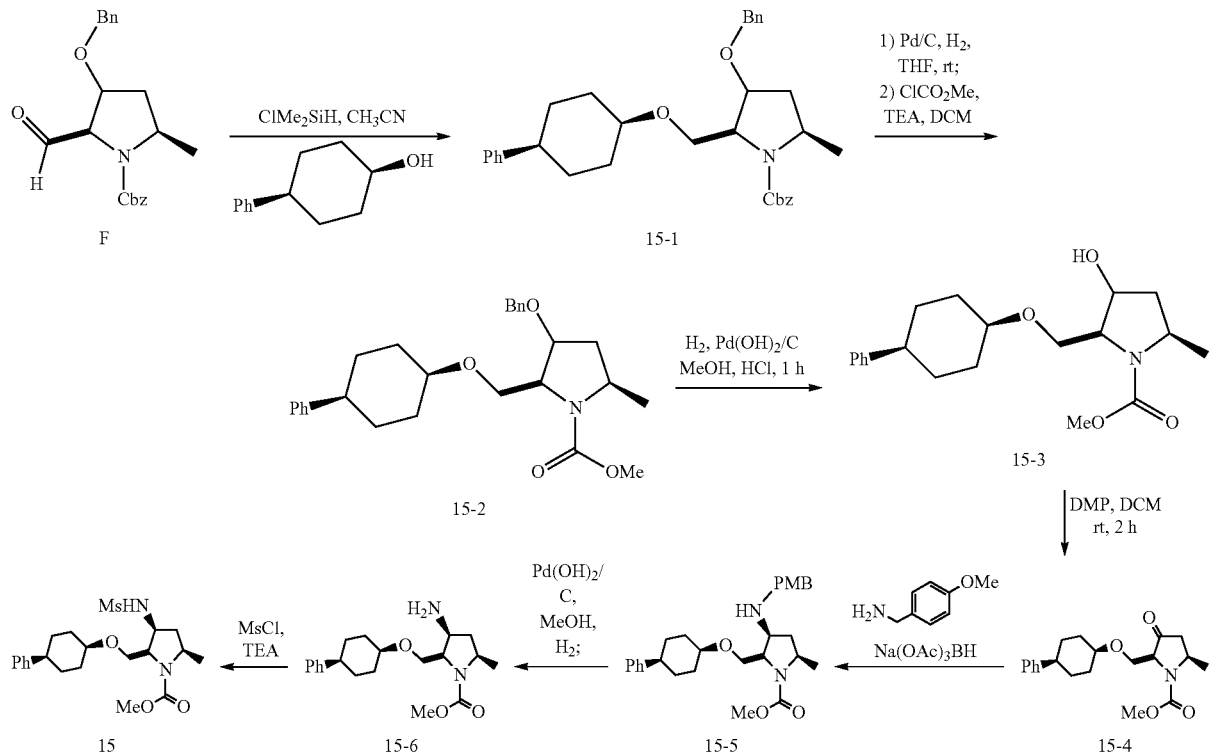

1: benzyl (2S,5R)-3-(benzyloxy)-5-methyl-2-((((1s, 4R)-4-phenylcyclohexyl)oxy)methyl)-pyrrolidine-1-carboxylate (15-1)

To a solution of benzyl (5R)-3-(benzyloxy)-2-formyl-5-methylpyrrolidine-1-carboxylate (F) (400 mg, 1.132 mmol) and (1s,4s)-4-phenylcyclohexan-1-ol (299 mg, 1.698 mmol) in 2 mL of acetonitrile was added chlorodimethylsilane (161 mg, 1.698 mmol) at 0° C. under $N_2$. The reaction mixture was raised to rt and stirred for 8 h. LC-MS showed formation of the desired product. The reaction was quenched by sat. aq. NaHCO$_3$, and the mixture was diluted with 5 mL of DCM, derived by MgSO$_4$, filtered, and the filtrate was concentrated in vacuo. The crude product was purified by column chromatography on C18 with 10-100% acetonitrile in H$_2$O as eluent to give the title compound benzyl (2S,5R)-3-(benzyloxy)-5-methyl-2-((((1S,4R)-4-phenylcyclohexyl)oxy) methyl)-pyrrolidine-1-carboxylate (15-1). LC-MS 514 (M+1).

Step 2: methyl (2S,5R)-3-(benzyloxy)-5-methyl-2-((((1S,4R)-4-phenylcyclohexyl)oxy)methyl)-pyrrolidine-1-carboxylate (15-2)

To a solution of benzyl (2S,5R)-3-(benzyloxy)-5-methyl-2-((((1S,4R)-4-phenylcyclohexyl)oxy)methyl)pyrrolidine-1-carboxylate (15-1) (210 mg, 0.409 mmol) in THF (10 mL) was added palladium on carbon (5%, 87 mg, 0.041 mmol).

The reaction mixture was degassed and refilled with H2 three times from a balloon. The reaction mixture was stirred at rt for 30 min.

LC-MS showed reaction completed. The reaction mixture was filtered through a pad of diatomaceous earth and the filtrate was concentrated to give the crude product (2S,5R)-3-(benzyloxy)-5-methyl-2-((((1S,4R)-4-phenylcyclohexyl) oxy)methyl)pyrrolidine. LC-MS 380 (M+1). The crude product was dissolved in DCM (5 mL), followed by addition of Et$_3$N (0.044 mL, 0.316 mmol) and chloromethylformate (17.93 mg, 0.190 mmol) at 0° C. under $N_2$. The reaction mixture was stirred for 20 min. LC-MS showed reaction completed. The reaction mixture was quenched by methanol, then was concentrated in vacuo. The crude was chromatographed over silica gel with 0-50% EtOAc in hexanes as eluent to give the title compound methyl (2S,5R)-3-(benzyloxy)-5-methyl-2-((((1S,4R)-4-phenylcyclohexyl) oxy)methyl)pyrrolidine-1-carboxylate (15-2). LC-MS 438 (M+1).

Step 3: methyl (2S,5R)-3-hydroxy-5-methyl-2-((((1s,4R)-4-phenylcyclohexyl)oxy)methyl)-pyrrolidine-1-carboxylate (15-3)

A solution of methyl (2S,5R)-3-(benzyloxy)-5-methyl-2-((((1S,4R)-4-phenylcyclohexyl)-oxy)methyl)pyrrolidine-1-carboxylate (15-2) (45 mg, 0.103 mmol) was dissolved in methanol (5 mL), followed by addition of dihydroxypalladium on carbon (5%, 28.9 mg, 10.28 μmol). The reaction mixture was degassed and refilled with H2 for 3 times, then stirred at rt for 2 h. LC-MS showed reaction was complete. The reaction mixture was filtered through a pad of diatomaceous earth and the filtrate was concentrated in vacuo. The crude was chromatographed over silica gel on C18 with 10-100% acetonitrile in H₂O to give the title compound methyl (2S,5R)-3-hydroxy-5-methyl-2-((((1s,4R)-4-phenyl-cyclohexyl)oxy)methyl)pyrrolidine-1-carboxylate (15-3). LC-MS 348 (M+1).

Step 4: methyl (2S,5R)-5-methyl-3-oxo-2-(((((1S,4R)-4-phenylcyclohexyl)oxy)methyl)-pyrrolidine-1-carboxylate (15-4)

A solution of methyl (2S,5R)-3-hydroxy-5-methyl-2-((((1s,4R)-4-phenylcyclohexyl)oxy)-methyl)pyrrolidine-1-carboxylate (15-3) (30 mg, 0.086 mmol) was dissolved in DCM (5 mL), followed by addition of Dess-MartinPeriodinane (36.6 mg, 0.086 mmol) at 0° C. under N₂. The reaction mixture was stirred for 2 h. LC-MS showed reaction was complete. The reaction mixture was washed with sat. aq. NaHCO₃, then was dried (MgSO₄) and concentrated in vacuo. The crude material was chromatographed over silica gel and eluted with 10-100% acetonitrile in H₂O to give the title compound methyl (2S,5R)-5-methyl-3-oxo-2-((((1s,4R)-4-phenylcyclohexyl)-oxy)-methyl)pyrrolidine-1-carboxylate (15-4). LC-MS 346 (M+1).

Step 5: methyl (2R,3S,5R)-3-((4-methoxybenzyl)amino)-5-methyl-2-((((1s,4S)-4-phenylcyclohexyl)oxy)methyl)pyrrolidine-1-carboxylate (15-5)

To a solution of methyl (2S,5R)-5-methyl-3-oxo-2-(((((1S,4R)-4-phenylcyclohexyl)oxy)-methyl)pyrrolidine-1-carboxylate (15-4) (20 mg, 0.058 mmol) in DCM (10 mL) was added (4-methoxyphenyl)methanamine (8.74 mg, 0.064 mmol) and catalytic amount of acetic acid (0.166 μl, 2.89 μmol). The mixture was stirred at rt for 30 mins, then sodium triacetoxyborohydride (14.72 mg, 0.069 mmol) was added to the mixture. The reaction was stirred at rt for overnight. LCMS showed completion of the reaction. The reaction was quenched with saturated NaHCO₃ solution (10 mL), extracted with DCM (3×5 mL). The combined organic phases were dried over MgSO₄, filtered and concentrated. The residue was purified by column chromatography on silica gel with 0-100% EtOAc in hexanes as eluent to afford the title compound methyl (2R,3S,5R)-3-((4-methoxybenzyl)amino)-5-methyl-2-((((1s,4S)-4-phenylcyclohexyl)oxy)-methyl)pyrrolidine-1-carboxylate (15-5). LCMS 467 (M+1).

Step 6: methyl (2R,3S,5R)-3-amino-5-methyl-2-((((1s,4S)-4-phenylcyclohexyl)oxy)methyl)-pyrrolidine-1-carboxylate (15-6)

A solution of methyl (2R,3S,5R)-3-((4-methoxybenzyl)amino)-5-methyl-2-((((1s,4S)-4-phenylcyclohexyl)oxy)methyl)pyrrolidine-1-carboxylate (15-5) (18 mg, 0.039 mmol) was dissolved in MeOH (10 mL), followed by addition of dihydroxypalladium on carbon (5%, 10.83 mg, 3.86 mol). The reaction mixture was degassed and refilled with H2 for 3 times with balloon. The reaction mixture was stirred at rt for 30 min. LC-MS showed reaction was completed. The reaction mixture was filtered through a pad of diatomaceous earth and the filtrate was concentrated and chromatographed over over C18 with 10-100% acetonitrile in H₂O) to give the title compound methyl (2R,3S,5R)-3-amino-5-methyl-2-(((4-phenylcyclohexyl)oxy)methyl)pyrrolidine-1-carboxylate (15-6). LC-MS 347 (M+1).

Step 7: methyl (2R,3S,5R)-5-methyl-3-(methyl sulfonamido)-2-((((1s,4S)-4-phenylcyclohexyl)-oxy)methyl)pyrrolidine-1-carboxylate (15)

To a solution of methyl (2R,3S,5R)-3-amino-5-methyl-2-((((1s,4S)-4-phenylcyclohexyl)-oxy)methyl)pyrrolidine-1-carboxylate (15-6) (10 mg, 0.029 mmol) in DCM (5 mL) was added Et₃N (0.012 mL, 0.087 mmol), followed by addition of Ms-Cl (2.70 μl, 0.035 mmol) at 0° C. under N₂.

After stirring for 30 min. LC-MS showed reaction was completed. To the reaction mixture was added a few drops of methanol, then the reaction mixture was concentrated in vacuo. The crude was purified by column chromatography over C18 with 10-100% acetonitrile in H₂O to give the title compound methyl (2R,3S,5R)-5-methyl-3-(methyl sulfonamido)-2-((((1s,4S)-4-phenylcyclohexyl)oxy)methyl)pyrrolidine-1-carboxylate (15). LC-MS 425 (M+1); ¹H NMR (500 MHz, Methanol-d4) δ 7.26 (m, 4H), 7.15 (m, 1H), 4.14 (s, 1H), 3.99 (dt, J=12.0, 7.7 Hz, 1H), 3.95-3.82 (m, 1H), 3.79-3.65 (m, 5H), 3.03 (s, 3H), 2.58 (ddd, J=12.2, 8.9, 3.3 Hz, 1H), 2.45 (dt, J=12.1, 7.3 Hz, 1H), 2.20-2.04 (m, 2H), 2.04-1.75 (m, 3H), 1.72-1.51 (m, 4H), 1.41 (d, J=6.0 Hz, 3H).

EXAMPLE 16

2,2-difluoroethyl (2R,3S,5R)-5-methyl-3-((N-methylsulfamoyl)amino)-2-((((s,4S)-4-phenylcyclohexyl)oxy)methyl)pyrrolidine-1-carboxylate

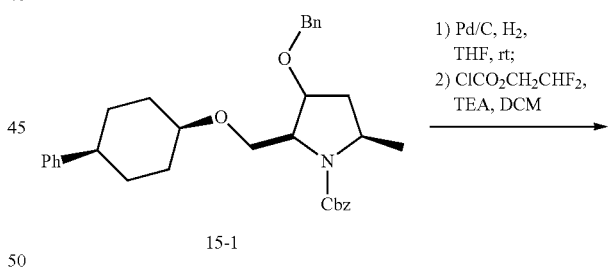

15-1

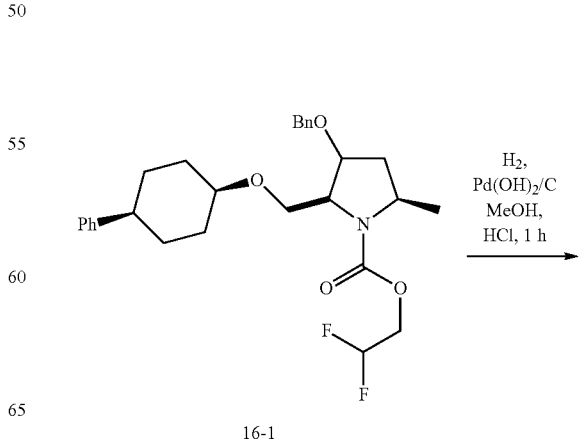

16-1

-continued

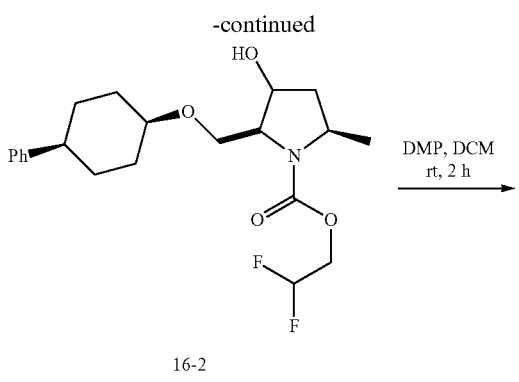

16-2

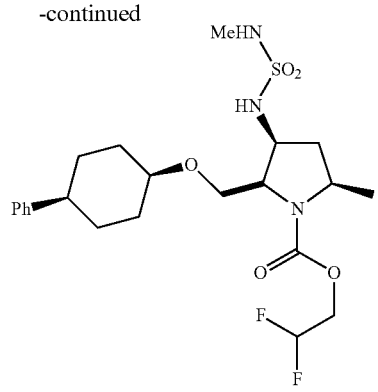

16

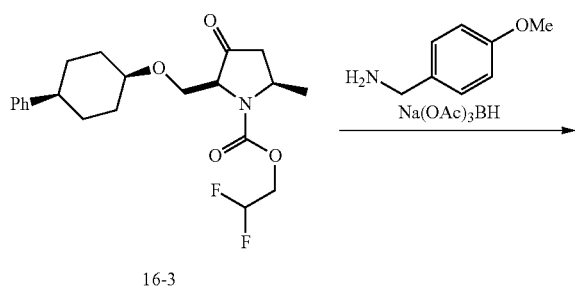

16-3

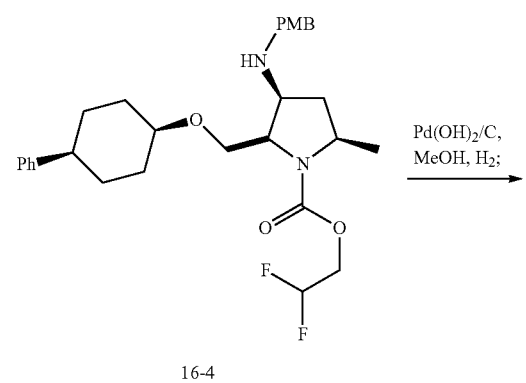

16-4

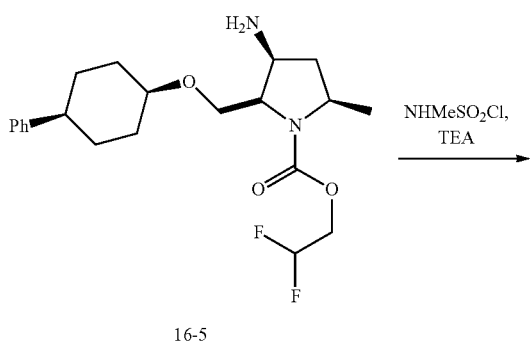

16-5

Step 1: 2,2-difluoroethyl (2S,5R)-3-(benzyloxy)-5-methyl-2-((((1s,4R)-4-phenylcyclohexyl)oxy)-methyl)pyrrolidine-1-carboxylate (16-1)

To a solution of benzyl (2S,5R)-3-(benzyloxy)-5-methyl-2-((((1s,4R)-4-phenylcyclohexyl)-oxy)-methyl)pyrrolidine-1-carboxylate (15-1) (160 mg, 0.311 mmol) in THF (10 ml) was added palladium on carbon (5%, 66 mg, 0.031 mmol). The reaction mixture was degassed and refilled with H2 from a balloon. The reaction mixture was stirred at rt for 30 min. LC-MS shown reaction completed. The reaction mixture was filtered through a celite pad and the filtrate was concentrated to give the crude product (2S,5R)-3-(benzyloxy)-5-methyl-2-((((1s,4R)-4-phenylcyclohexyl)oxy)-methyl)pyrrolidine. LC-MS 380 (M+1).

The crude product (2S,5R)-3-(benzyloxy)-5-methyl-2-((((1s,4R)-4-phenylcyclohexyl)-oxy)methyl)pyrrolidine was dissolved in CH$_2$Cl$_2$ (5 ml), followed by addition of Et$_3$N (0.081 ml, 0.58 mmol) and 2,2-difluoroethyl carbonochloridate (50.3 mg, 0.348 mmol) at 0° C. under N$_2$. The reaction mixture was stirred for 20 min. LC-MS shown reaction completed. The reaction mixture was quenched by methanol, then was concentrated in vacuo. The crude was chromatographed over silic gel with 0-50% EtOAc in hexanes as eluent to give the title compound 2,2-difluoroethyl (2S,5R)-3-(benzyloxy)-5-methyl-2-((((1s,4R)-4-phenylcyclohexyl)oxy)-methyl)pyrrolidine-1-carboxylate (16-1). LC-MS 488 (M+1).

Step 2: 2,2-difluoroethyl (2S,5R)-3-hydroxy-5-methyl-2-((((1s,4R)-4-phenylcyclohexyl)oxy)-methyl)pyrrolidine-1-carboxylate (16-2)

A solution of 2,2-difluoroethyl (2S,5R)-3-(benzyloxy)-5-methyl-2-((((1s,4R)-4-phenylcyclohexyl)oxy)-methyl)pyrrolidine-1-carboxylate (16-1) (120 mg, 0.246 mmol) was dissolved in methanol (10 ml), followed by addition of dihydroxypalladium on carbon (5%, 69.1 mg, 0.025 mmol). The reaction mixture was degassed and refilled with H2 for 3 times, then stirred at rt for 2 h. LC-MS shown reaction completed. The reaction mixture was filtered through a celite pad and the filtrate was concentrated in vacuo. The crude was chromatographed over silic gel on C18 with 10-100% acetonitrile in H$_2$O to give the title compound 2,2-difluoroethyl (2S,5R)-3-hydroxy-5-methyl-2-((((1s,4R)-4-phenylcyclohexyl)oxy)-methyl)pyrrolidine-1-carboxylate (16-2). LC-MS 398 (M+1).

Step 3: 2,2-difluoroethyl (2S,5R)-5-methyl-3-oxo-2-((((1s,4R)-4-phenylcyclohexyl)oxy)methyl)-pyrrolidine-1-carboxylate (16-3)

A solution of 2,2-difluoroethyl (2S,5R)-3-hydroxy-5-methyl-2-((((1s,4R)-4-phenylcyclohexyl)oxy)-methyl)pyrrolidine-1-carboxylate (16-2) (80 mg, 0.201 mmol) was dissolved in CH$_2$Cl$_2$ (5 ml), followed by addition of Dess-MartinPeriodinane (85 mg, 0.201 mmol) at 0° C. under N$_2$. The reaction mixture was stirred for 2 h. LC-MS shown reaction completed. The reaction mixture was washed with sat. aq. NaHCO$_3$, then was dried (MgSO$_4$) and concentrated in vacuo. The crude was chromatographed over silic gel and eluted with 10-100% acetonitrile in H$_2$O to give the title compound 2,2-difluoroethyl (2S,5R)-5-methyl-3-oxo-2-((((1s,4R)-4-phenylcyclohexyl)oxy)methyl)-pyrrolidine-1-carboxylate (16-3). LC-MS 396 (M+1).

Step 4: 2,2-difluoroethyl (2R,3S,5R)-3-((4-methoxybenzyl)amino)-5-methyl-2-((((1s,4S)-4-phenylcyclohexyl)oxy)methyl)pyrrolidine-1-carboxylate (16-4)

To a solution of 2,2-difluoroethyl (2S,5R)-5-methyl-3-oxo-2-((((1s,4R)-4-phenylcyclohexyl)oxy)methyl)-pyrrolidine-1-carboxylate (16-3) (55 mg, 0.139 mmol) in DCM (10 ml) was added (4-methoxyphenyl)methanamine (20.99 mg, 0.153 mmol) and catalytic amount of acetic acid (0.398 μl, 6.95 μmol). The mixture was stirred at rt for 30 mins, then sodium triacetoxyborohydride (35.4 mg, 0.167 mmol) was added to the mixture. The reaction was stirred at rt for overnight. LCMS shown completion of the reaction. The reaction was quenched with saturated NaHCO$_3$ solution (10 ml), extracted with CH$_2$Cl$_2$ (3×5 ml). The combined organic phases were dried over MgSO$_4$, filtered and concentrated. The residue was purified by column chromatography on silica gel with 0-100% EtOAc in hexanes as eluent to afford the title compound 2,2-difluoroethyl (2R,3S,5R)-3-((4-methoxybenzyl)amino)-5-methyl-2-((((1s,4S)-4-phenylcyclohexyl)oxy)methyl)pyrrolidine-1-carboxylate (16-4). LCMS 517 (M+1).

Step 5: 2,2-difluoroethyl (2R,3S,5R)-3-amino-5-methyl-2-((((1s,4S)-4-phenylcyclohexyl)oxy)-methyl)pyrrolidine-1-carboxylate (16-5)

A solution of 2,2-difluoroethyl (2R,3S,5R)-3-((4-methoxybenzyl)amino)-5-methyl-2-((((1s,4S)-4-phenylcyclohexyl)oxy)methyl)pyrrolidine-1-carboxylate (16-4) (18 mg, 0.035 mmol) was dissolved in MeOH (10 ml), followed by addition of dihydroxypalladium on carbon (5%, 9.8 mg, 3.48 μmol). The reaction mixture was degassed and refilled with H2 for with balloon. The reaction mixture was stirred at rt for 30 min. LC-MS shown reaction completed. The reaction mixture was filtered through a syringe filter and the filtrate was concentrated and chromatographed over over C18 with 10-100% acetonitrile in H$_2$O) to give the title compound 2,2-difluoroethyl (2R,3S,5R)-3-amino-5-methyl-2-((((1s,4S)-4-phenylcyclohexyl)oxy)-methyl)pyrrolidine-1-carboxylate (16-5). LC-MS 397 (M+1).

Step 6: 2,2-difluoroethyl (2R,3S,5R)-5-methyl-3-((N-methylsulfamoyl)amino)-2-((((1s,4S)-4-phenylcyclohexyl)oxy)methyl)pyrrolidine-1-carboxylate (16)

To a solution of 2,2-difluoroethyl (2R,3S,5R)-3-amino-5-methyl-2-((((1s,4S)-4-phenylcyclohexyl)oxy)-methyl)pyrrolidine-1-carboxylate (16-5) (10 mg, 0.025 mmol) in CH$_2$Cl$_2$ (5 ml) was added Et$_3$N (0.011 ml, 0.076 mmol), followed by addition of methylsulfamoyl chloride (3.92 mg, 0.030 mmol) at 0° C. under N$_2$. After stirring for 30 min. LC-MS shown reaction completed. To the reaction mixture was added a few drops of methanol, then the reaction mixture was concentrated in vacuo. The crude was purified by column chromatography over C18 with 10-100% acetonitrile in H$_2$O to give the title compound 2,2-difluoroethyl (2R,3S,5R)-5-methyl-3-((N-methyl sulfamoyl) amino)-2-((((1s,4S)-4-phenylcyclohexyl)oxy)methyl)pyrrolidine-1-carboxylate (16). LC-MS 490.1 (M+1); $^1$H NMR (500 MHz, Methanol-d4) δ 7.30 (dt, J=11.8, 7.3 Hz, 4H), 7.08 (tt, J=6.4, 1.7 Hz, 1H), 6.07 (t, J=55.0 Hz, 1H), 4.33 (dt, J=30.0, 15.6 Hz, 2H), 4.23 (dt, J=7.2, 3.3 Hz, 1H), 4.11 (m, 1H), 3.87 (dt, J=11.9, 7.7 Hz, 2H), 3.75-3.60 (m, 3H), 3.39 (s, 1H), 3.17 (p, J=1.6 Hz, 19H), 2.80 (s, 3H), 2.59 (tt, J=12.2, 3.3 Hz, 1H), 2.48 (dd, J=10.2, 4.1 Hz, 1H), 2.12 (ddt, J=19.8, 14.0, 2.8 Hz, 2H), 1.98-1.74 (m, 3H), 1.69-1.55 (m, 4H), 1.43 (d, J=6.0 Hz, 3H).

EXAMPLE 17

2,2-difluoroethyl (2R,3S,5R)-3-((N,N-dimethylsulfamoyl)amino)-5-methyl-2-((((1s,4S)-4-phenylcyclohexyl)oxy)methyl)pyrrolidine-1-carboxylate

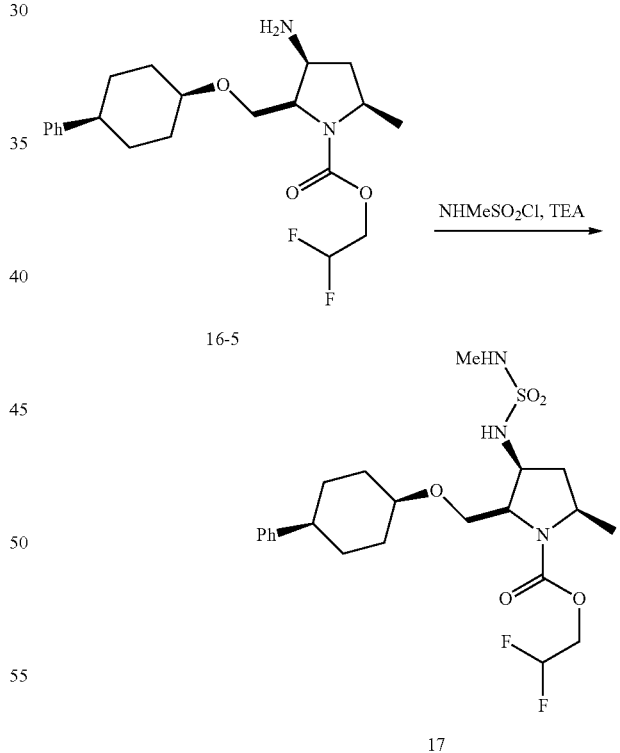

To a solution of 2,2-difluoroethyl (2R,3S,5R)-3-amino-5-methyl-2-((((1s,4S)-4-phenylcyclohexyl)oxy)-methyl)pyrrolidine-1-carboxylate (16-5) (9 mg, 0.023 mmol) in CH$_2$Cl$_2$ (5 ml) was added Et$_3$N (0.010 ml, 0.068 mmol), followed by addition of dimethylsulfamoyl chloride (3.66 μl, 0.034 mmol) at 0° C. under N$_2$. After stirring for 48 h, LC-MS shown reaction completed. To the reaction mixture was added a few drops of methanol, then the reaction mixture was concentrated in vacuo. The crude was purified by column chromatography over C18 with 10-100% acetonitrile in H$_2$O to give the title compound 2,2-difluoroethyl (2R,3S,5R)-3-((N,N-dimethylsulfamoyl)amino)-5-methyl-2-((((1s,4S)-4-phenylcyclohexyl)oxy)methyl)-pyrrolidine-1-carboxylate (17). LC-MS 504.2 (M+1); $^1$H NMR (500 MHz, Chloroform-d) δ 7.25 (dt, J=11.8, 7.3 Hz, 4H), 7.15 (tt, J=6.4, 1.7 Hz, 1H), 6.08 (t, J=55.0 Hz, 1H), 4.33 (dt, J=30.0, 15.6 Hz, 2H), 4.17 (dt, J=7.2, 3.3 Hz, 1H), 3.95 (dt, J=11.9, 7.7 Hz, 2H), 3.82-3.67 (m, 3H), 3.61 (s, 1H), 3.33 (p, J=1.6 Hz, 19H), 2.81 (s, 6H), 2.58 (tt, J=12.2, 3.3 Hz, 1H), 2.46 (dd, J=10.2, 4.1 Hz, 1H), 2.12 (ddt, J=19.8, 14.0, 2.8 Hz, 2H), 1.96 (s, 1H), 1.93-1.74 (m, 3H), 1.71-1.56 (m, 4H), 1.43 (d, J=6.0 Hz, 3H).

EXAMPLE 18 methyl (2R,3S, R)-5-methyl-3-((N-methylsulfamoyl)amino)-2-((((1s,4S)-4-phenylcyclohexyl)-oxy)methyl)pyrrolidine-1-carboxylate

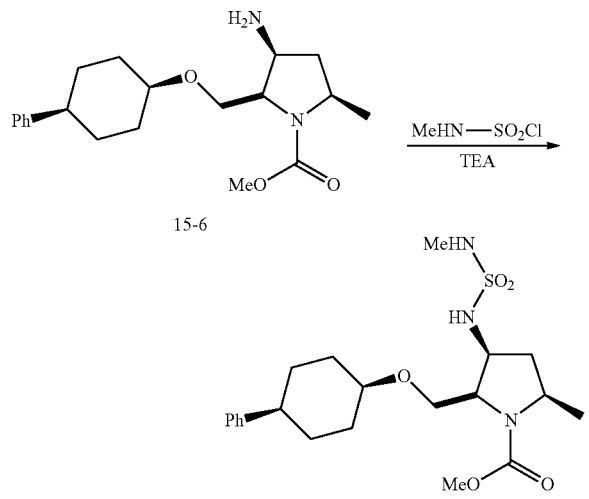

methyl (2R,3S,5R)-5-methyl-3-((N-methylsulfamoyl)amino)-2-((((1s,4S)-4-phenylcyclohexyl)-oxy)methyl)pyrrolidine-1-carboxylate (18)

To a solution of methyl (2R,3S,5R)-3-amino-5-methyl-2-((((1s,4S)-4-phenylcyclohexyl)-oxy)methyl)pyrrolidine-1-carboxylate (15-6) (12 mg, 0.035 mmol) in CH$_2$Cl$_2$ (5 ml) was added Et$_3$N (0.014 ml, 0.104 mmol), followed by addition of methylsulfamoyl chloride (6.73 mg, 0.052 mmol) at 0° C. under N$_2$. After stirring for 30 min. LC-MS shown reaction completed. To the reaction mixture was added a few drops of methanol, then the reaction mixture was concentrated in vacuo. The crude was purified by column chromatography over C18 with 10-100% acetonitrile in H$_2$O to give the title compound methyl (2R,3S,5R)-5-methyl-3-((N-methyl-sulfamoyl)amino)-2-((((1s,4S)-4-phenylcyclohexyl)-oxy)methyl)pyrrolidine-1-carboxylate (18). LC-MS 440.1 (M+1); $^1$H NMR (500 MHz, Chloroform-d) δ 7.29-7.21 (m, 4H), 7.15 (t, J=6.8 Hz, 1H), 4.17 (s, 1H), 3.84 (ddd, J=12.3, 8.9, 6.6 Hz, 2H), 3.70 (d, J=15.8 Hz, 6H), 3.60-3.48 (m, 1H), 3.36-3.29 (m, 4H), 2.65 (s, 3H), 2.58 (ddd, J=15.4, 7.8, 3.2 Hz, 1H), 2.46 (dt, J=14.2, 7.0 Hz, 1H), 2.11 (dd, J=25.5, 14.0 Hz, 2H), 1.96-1.75 (m, 3H), 1.63 (q, J=14.5, 13.5 Hz, 4H), 1.40 (d, J=5.9 Hz, 3H), 1.31 (s, 1H).

EXAMPLE 19 methyl (2R,3S,5R)-3-((N,N-dimethylsulfamoyl)amino)-5-methyl-2-((((s,4S)-4-phenylcyclohexyl)-oxy)methyl)pyrrolidine-1-carboxylate

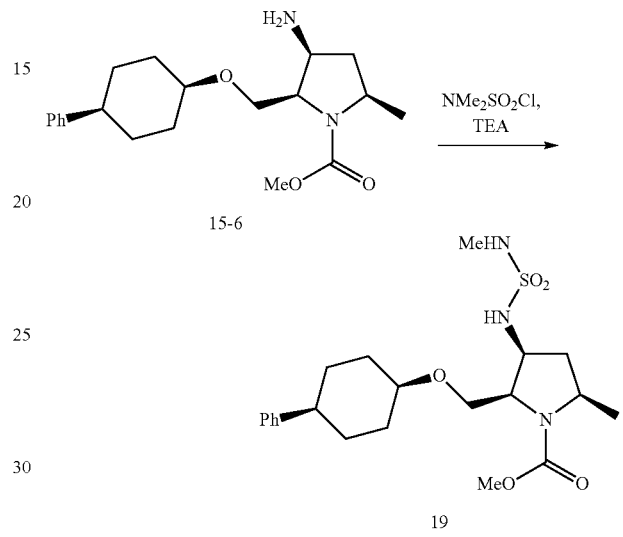

methyl (2R,3S,5R)-3-((N,N-dimethylsulfamoyl)amino)-5-methyl-2-((((1s,4S)-4-phenylcyclohexyl)-oxy)methyl)pyrrolidine-1-carboxylate (19)

To a solution of methyl (2R,3S,5R)-3-amino-5-methyl-2-((((1s,4S)-4-phenylcyclohexyl)-oxy)methyl)pyrrolidine-1-carboxylate (15-6) (12 mg, 0.029 mmol) in CH$_2$Cl$_2$ (5 ml) was added Et$_3$N (0.014 ml, 0.104 mmol), followed by addition of dimethylsulfamoyl chloride (5.58 µl, 0.052 mmol) at 0° C. under N$_2$. After stirring for 48 h, LC-MS shown reaction completed. To the reaction mixture was added a few drops of methanol, then the reaction mixture was concentrated in vacuo. The crude was purified by column chromatography over C18 with 10-100% acetonitrile in H$_2$O to give the title methyl (2R,3S,5R)-3-((N,N-dimethylsulfamoyl)amino)-5-methyl-2-((((1s,4S)-4-phenyl-cyclohexyl)oxy)methyl)pyrrolidine-1-carboxylate (19). LC-MS 454.2 (M+1); $^1$H NMR (500 MHz, Chloroform-d) δ 7.31-7.20 (m, 4H), 7.15 (t, J=6.9 Hz, 1H), 4.87 (s, 8H), 4.22-4.11 (m, 1H), 3.88 (ddt, J=35.1, 9.2, 7.2 Hz, 2H), 3.70 (d, J=15.3 Hz, 6H), 3.33 (s, 6H), 2.81 (s, 6H), 2.58 (tt, J=12.2, 3.1 Hz, 1H), 2.45 (dt, J=12.3, 7.4 Hz, 1H), 2.10 (ddt, J=25.4, 14.0, 6.9 Hz, 2H), 1.97-1.74 (m, 3H), 1.63 (q, J=15.4, 12.5 Hz, 4H), 1.40 (d, J=6.0 Hz, 3H), 1.31 (s, 1H).

The following compounds were prepared according to the general procedure provided in Examples 1-15, and procedures herein, by substituting the appropriate alkyl carbonochloridate, methylsulfamoyl chloride and dimethylsulfamoyl chloride. The starting materials are either prepared as described in the intermediates section, commercially available, or may be prepared from commercially available reagents using conventional reactions well known in the art.

| Example Number | Structure | Name | Exact Mass [M + H]+ |
|---|---|---|---|
| 20 | Chiral 2R,3S,5R from M | methyl (2R,3S,5R)-2-((((1r,4R)-4-(2,5-difluorophenyl)cyclohexyl)oxy)methyl)-5-methyl-3-(methylsulfonamido)pyrrolidine-1-carboxylate | 461.2 |
| 21 | 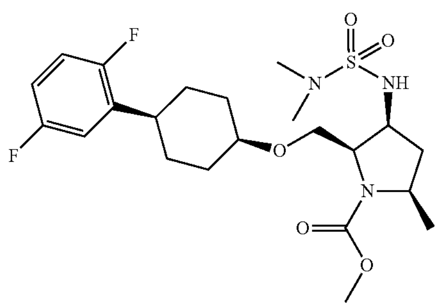 [SMILES: COC(=O)N1[C@H](C)C[C@H](NS(=O)(=O)N(C)C)[C@@H]1CO[C@H]1CC[C@@H](c2cc(F)ccc2F)CC1] | methyl (2R,3S,5R)-2-((((1R,4R)-4-(2,5-difluorophenyl)cyclohexyl)oxy)methyl)-3-((N,N-dimethylsulfamoyl)amino)-5-methylpyrrolidine-1-carboxylate | 490.1 |
| 22 | Chiral 2R,3S,5R from M | 2,2-difluoroethyl (2R,3S,5R)-2-((((1r,4R)-4-(2,5-difluorophenyl)cyclohexyl)oxy)methyl)-3-((N,N-dimethylsulfamoyl)amino)-5-methylpyrrolidine-1-carboxylate | 540.2 |
| 23 | Chiral 2R,3S,5R from P | methyl (2R,3S,5R)-3-((N,N-dimethylsulfamoyl)amino)-2-((((1s,4S)-4-(2-fluorophenyl)cyclohexyl)oxy)methyl-5-methylpyrrolidine-1-carboxylate | 472.2 |

-continued

| Example Number | Structure | Name | Exact Mass [M + H]⁺ |
|---|---|---|---|
| 24 | Chiral 2R,3S,5R from L | methyl (2R,3S,5R)-2-((((1s,4S)-4-(3-fluorophenyl)cyclohexyl)oxy)methyl)-5-methyl-3-(methylsulfonamido)pyrrolidine-1-carboxylate | 443.2 |
| 25 | Chiral 2R,3S,5R from L | methyl (2R,3S,5R)-2-((((1s,4S)-4-(3-fluorophenyl)cyclohexyl)oxy)methyl)-5-methyl-3-((N-methylsulfamoyl)amino)pyrrolidine-1-carboxylate | 458.2 |
| 26 | Chiral 2R,3S,5R from L | methyl (2R,3S,5R)-3-((fluoromethyl)sulfonamido)-2-((((1s,4S)-4-(3-fluorophenyl)cyclohexyl)oxy)methyl)-5-methylpyrrolidine-1-carboxylate | 461.2 |
| 27 | Chiral 2R,3S,5R from O | methyl (2R,3S,5R)-5-methyl-3-(methylsulfonamido)-2-((((1r,4R)-4-(2-(trifluoromethyl)phenyl)cyclohexyl)oxy)methyl)pyrrolidine-1-carboxylate | 493.2 |

-continued

| Example Number | Structure | Name | Exact Mass [M + H]+ |
|---|---|---|---|
| 28 | Chiral 2R,3S,5R from N | methyl (2R,3S,5R)-5-methyl-3-(methylsulfonamido)-2-((((1r,4R)-4-(2,3,6-trifluorophenyl)cyclohexyl)oxy)methyl)pyrrolidine-1-carboxylate | 479.1 |
| 29 | Chiral 2R,3S,5R from F | methyl (2R,3S,5R)-3-((fluoromethyl)sulfonamido)-5-methyl-2-((((1r,4R)-4-phenylcyclohexyl)oxy)methyl)pyrrolidine-1-carboxylate | 443.3 | methyl (2R,3S,5R)-3-((N,N-dimethylsulfamoyl)amino)-2-((((1R,4S)-2-fluoro-4-phenylcyclohexyl)oxy)methyl)-5-methylpyrrolidine-1-carboxylate (30)

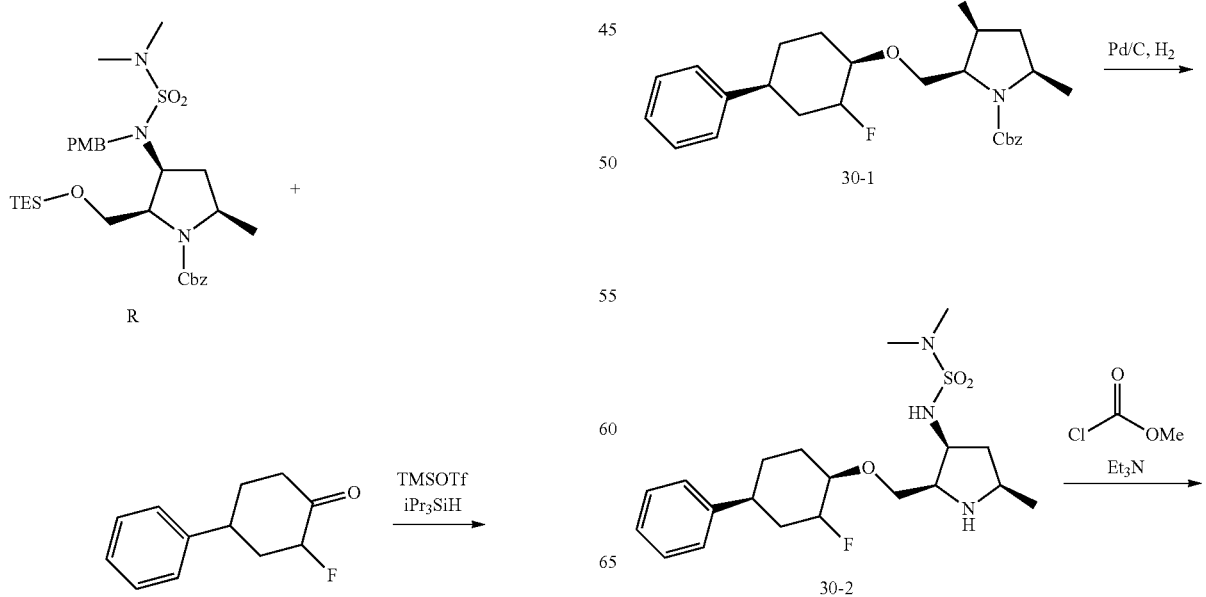

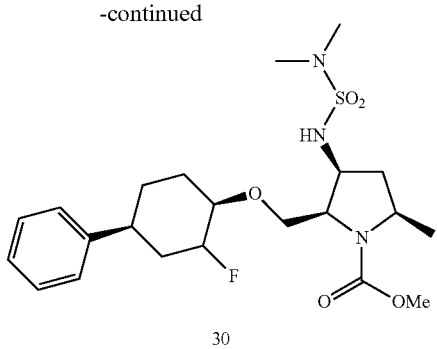

30

Step 1: benzyl (2R,3S,5R)-3-((N,N-dimethylsulfamoyl)amino)-2-((((1R,4S)-2-fluoro-4-phenylcyclohexyl)oxy)methyl)-5-methylpyrrolidine-1-carboxylate (30-1)

To a solution of benzyl (5R)-3-((N,N-dimethylsulfamoyl)(4-methoxybenzyl)amino)-5-methyl-2-(((triethyl silyl)oxy)methyl)pyrrolidine-1-carboxylate (R) (300 mg, 0.495 mmol), 2-fluoro-4-phenylcyclohexan-1-one (143 mg, 0.743 mmol) in acetonitrile (20 ml) was added triisopropylsilane (157 mg, 0.99 mmol) and trimethylsilyl trifluoromethanesulfonate (132 mg, 0.594 mmol) at −20° C. under $N_2$. The reaction mixture was raised to 0° C. and stirred for overnight. LC-MS shown formation of desired product. The reaction was quenched by addition of 1 ml of sat. aq. NaHCO3, and the mixture was diluted with 10 ml of EtOAc, dried by $MgSO_4$, filtered and concentrated in vacuo. The crude product was purified by column chromatography (Gilson, C18, 10-100% acetonitrile in $H_2O$) to give the product benzyl (5R)-3-((N,N-dimethylsulfamoyl)amino)-2-(((2-fluoro-4-phenylcyclohexyl)oxy)methyl)-5-methylpyrrolidine-1-carboxylate (30-1). LC-MS is 548.2 (M+H+).

Step 2: (2R,3S,5R)-3-((N,N-dimethylsulfamoyl)amino)-2-((((1R,4S)-2-fluoro-4-phenylcyclohexyl)oxy)methyl)-5-methylpyrrolidine (30-2)

To a solution of benzyl (2R,3S,5R)-3-((N,N-dimethylsulfamoyl)amino)-2-(((2-fluoro-4-phenylcyclohexyl)oxy)methyl)-5-methylpyrrolidine-1-carboxylate (30-1) (130 mg, 0.237 mmol) dissolved in THF (2.00 ml) was added palladium on carbon (25.3 mg, 0.237 mmol), degassed and refilled with H2 from a balloon. The reaction mixture was stirred for 1 h. LC-MS shown Cbz removed. The reaction mixture was filtered through a celite pad and the filtrate was concentrated to give the desired product (2R,3S,5R)-3-((N,N-dimethylsulfamoyl)amino)-2-((((1R,4S)-2-fluoro-4-phenylcyclohexyl)oxy)methyl)-5-methylpyrrolidine (30-2). The crude was pure enough for direct use in the following step. LC-MS is 414.2 (M+H+).

Step 3: methyl (2R,3S,5R)-3-((N,N-dimethylsulfamoyl)amino)-2-((((1R,4S)-2-fluoro-4-phenylcyclohexyl)oxy)methyl)-5-methylpyrrolidine-1-carboxylate (30)

To a solution of (2R,3S,5R)-3-((N,N-dimethylsulfamoyl)amino)-2-((((1R,4S)-2-fluoro-4-phenylcyclohexyl)oxy)methyl)-5-methylpyrrolidine (91 mg, 0.22 mmol) dissolved in $CH_2Cl_2$ (10 ml), was added TEA (0.066 ml, 0.475 mmol) and methyl carbonochloridate (33.6 mg, 0.356 mmol). After stirring for 1 h, LC-MS shown formation of the desired product. To the reaction mixture was added a few drops of MeOH, then the reaction mixture was concentrated and chromatographed over Gilson (10-100% EtOAc Acetonitrile in $H_2O$) to give the desired products methyl (2R,3S,5R)-3-((N,N-dimethylsulfamoyl)amino)-2-((((1R,4S)-2-fluoro-4-phenylcyclo-hexyl)oxy)methyl)-5-methylpyrrolidine-1-carboxylate and diastereomers (30). LC-MS 472.2.

The following compounds were prepared according to the general procedure provided in Examples 30, and procedures herein, by using different arylcyclohexanones. The starting materials are either prepared as described in the intermediates section (intermediate Q), or commercially available 4-(3,5-difluorophenyl)cyclohexan-1-one as described in Example 32.

| | | |
|---|---|---|
| 31 | 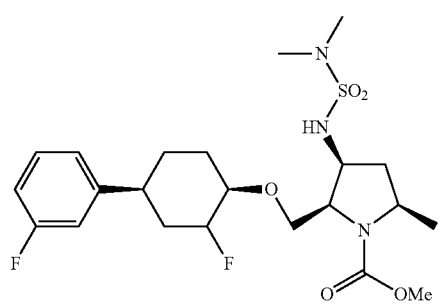<br>Chiral 2R,3S,5R<br>from Q | methyl (2R,3S,5R)-3-((N,N-dimethylsulfamoyl)amino)-2-((((1R,4S)-2-fluoro-4-(3-fluorophenyl)cyclohexyl)oxy)methyl)-5-methylpyrrolidine-1-carboxylate     490.2 |

| | | | |
|---|---|---|---|
| 32 | 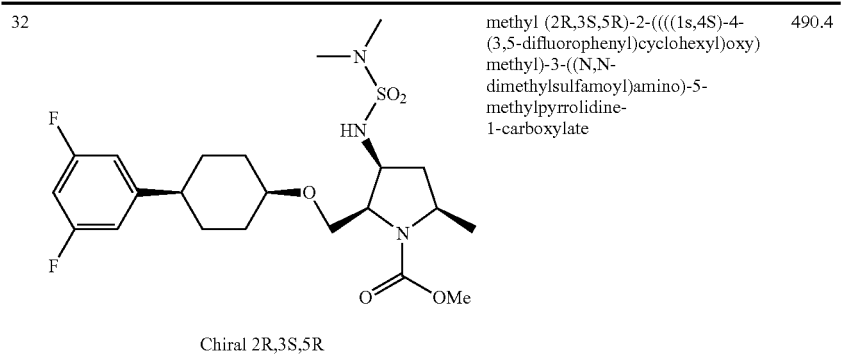  Chiral 2R,3S,5R | methyl (2R,3S,5R)-2-((((1s,4S)-4-(3,5-difluorophenyl)cyclohexyl)oxy)methyl)-3-((N,N-dimethylsulfamoyl)amino)-5-methylpyrrolidine-1-carboxylate | 490.4 |

EXAMPLE 33 methyl (2R,3S,5R)-2-(((2-methoxy-4-phenylcyclohexyl)oxy)methyl)-5-methyl-3-(methyl sulfonamido)pyrrolidine-1-carboxylate (33)

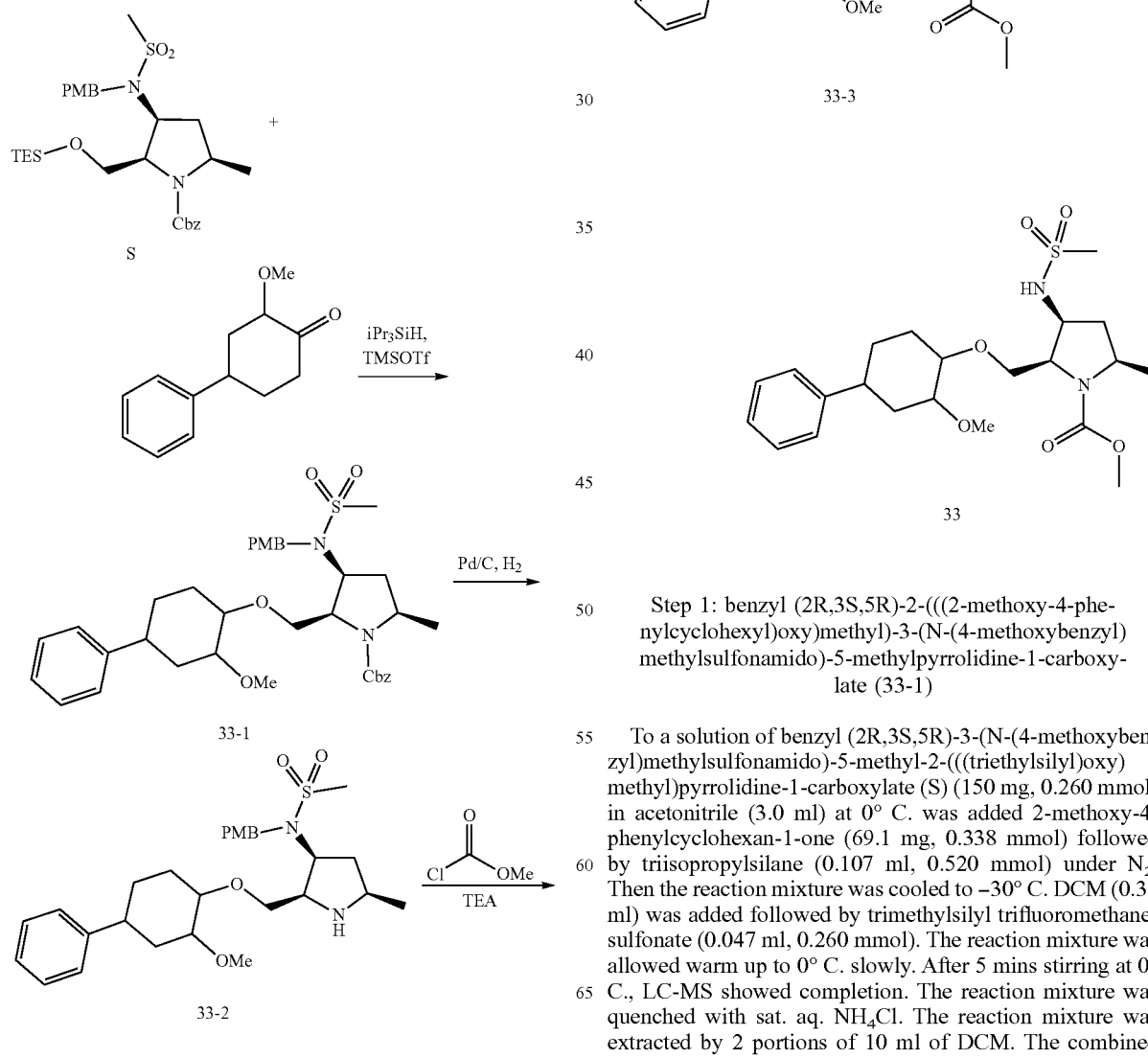

Step 1: benzyl (2R,3S,5R)-2-(((2-methoxy-4-phenylcyclohexyl)oxy)methyl)-3-(N-(4-methoxybenzyl)methylsulfonamido)-5-methylpyrrolidine-1-carboxylate (33-1)

To a solution of benzyl (2R,3S,5R)-3-(N-(4-methoxybenzyl)methylsulfonamido)-5-methyl-2-(((triethylsilyl)oxy)methyl)pyrrolidine-1-carboxylate (S) (150 mg, 0.260 mmol) in acetonitrile (3.0 ml) at 0° C. was added 2-methoxy-4-phenylcyclohexan-1-one (69.1 mg, 0.338 mmol) followed by triisopropylsilane (0.107 ml, 0.520 mmol) under $N_2$. Then the reaction mixture was cooled to −30° C. DCM (0.35 ml) was added followed by trimethylsilyl trifluoromethanesulfonate (0.047 ml, 0.260 mmol). The reaction mixture was allowed warm up to 0° C. slowly. After 5 mins stirring at 0° C., LC-MS showed completion. The reaction mixture was quenched with sat. aq. $NH_4Cl$. The reaction mixture was extracted by 2 portions of 10 ml of DCM. The combined organic phase was collected and concentrated to leave colorless oil. The residue was purified by prep silica gel TLC eluent with 3% MeOH/DCM to give the title compound benzyl (2R,3S,5R)-2-(((2-methoxy-4-phenylcyclohexyl)oxy)methyl)-3-(N-(4-methoxybenzyl)methylsulfonamido)-5-methylpyrrolidine-1-carboxylate (33-1). LC-MS 651 (M+1).

Step 2: N-((2R,3S,5R)-2-(((2-methoxy-4-phenylcyclohexyl)oxy)methyl)-5-methylpyrrolidin-3-yl)-N-(4-methoxybenzyl)methanesulfonamide (33-2)

To a solution of benzyl (2R,3S,5R)-2-(((2-methoxy-4-phenylcyclohexyl)oxy)methyl)-3-(N-(4-methoxybenzyl)methylsulfonamido)-5-methylpyrrolidine-1-carboxylate (33-1) (125 mg, 0.192 mmol) in THF (2.5 ml) was added 10% palladium on carbon (20.44 mg, 0.019 mmol). The reaction mixture was degassed and refilled with H2 from balloon for three times. The reaction mixture was stirred at rt under hydrogen balloon for 55 mins, LC-MS showed completion. The reaction mixture was filtered through a celite pad. The filtrate was concentrated to leave yellow oil. The residue was purified by prep silica gel TLC eluent with 4% 7N NH$_3$ in MeOH/DCM to give the title compound N-((2R,3S,5R)-2-(((2-methoxy-4-phenylcyclohexyl)oxy)methyl)-5-methylpyrrolidin-3-yl)-N-(4-methoxybenzyl)methanesulfonamide (33-2). LC-MS 517 (M+1).

Step 3: methyl (2R,3S,5R)-2-(((2-methoxy-4-phenylcyclohexyl)oxy)methyl)-3-(N-(4-methoxybenzyl)methylsulfonamido)-5-methylpyrrolidine-1-carboxylate (33-3)

To a solution of N-((2R,3S,5R)-2-(((2-methoxy-4-phenylcyclohexyl)oxy)methyl)-5-methylpyrrolidin-3-yl)-N-(4-methoxybenzyl)methanesulfonamide (33-2) (59 mg, 0.114 mmol) in DCM (1.5 ml) at 0° C. was added Et$_3$N (0.048 ml, 0.343 mmol) followed by methyl carbonochloridate (11 µl, 0.148 mmol) under N$_2$. The reaction mixture was stirred at 0° C. for 20 mins. LC-MS showed completion. The reaction mixture was concentrated to leave colorless film. The residue was purified by prep silica gel TLC eluent with 4% MeOH/DCM to give the title compound methyl (2R,3S,5R)-2-(((2-methoxy-4-phenylcyclohexyl)oxy)methyl)-3-(N-(4-methoxybenzyl)methylsulfonamido)-5-methylpyrrolidine-1-carboxylate (33-3). LC-MS 575 (M+1).

Step 4: methyl (2R,3S,5R)-2-(((2-methoxy-4-phenylcyclohexyl)oxy)methyl)-5-methyl-3-(methyl sulfonamido)pyrrolidine-1-carboxylate (33)

To a solution of methyl (2R,3S,5R)-2-(((2-methoxy-4-phenylcyclohexyl)oxy)methyl)-3-(N-(4-methoxybenzyl)methylsulfonamido)-5-methylpyrrolidine-1-carboxylate (33-3) (55 mg, 0.096 mmol) in DCM (1.5 ml) was added MsOH (37 µl, 0.574 mmol) at rt under N2. The reaction mixture was stirred at rt for 20 mins, LC-MS showed completion. The reaction mixture was concentrated to leave colorless film. The residue was purified by Gilson to give the title compound methyl (2R,3S,5R)-2-(((2-methoxy-4-phenylcyclohexyl)oxy)methyl)-5-methyl-3-(methylsulfonamido)-pyrrolidine-1-carboxylate (33). LC-MS 455 (M+1).

EXAMPLE 34 methyl (2R,3S,5R)-5-methyl-2-(((2-methyl-4-phenylcyclohexyl)oxy)methyl)-3-(methyl sulfonamido)pyrrolidine-1-carboxylate (34)

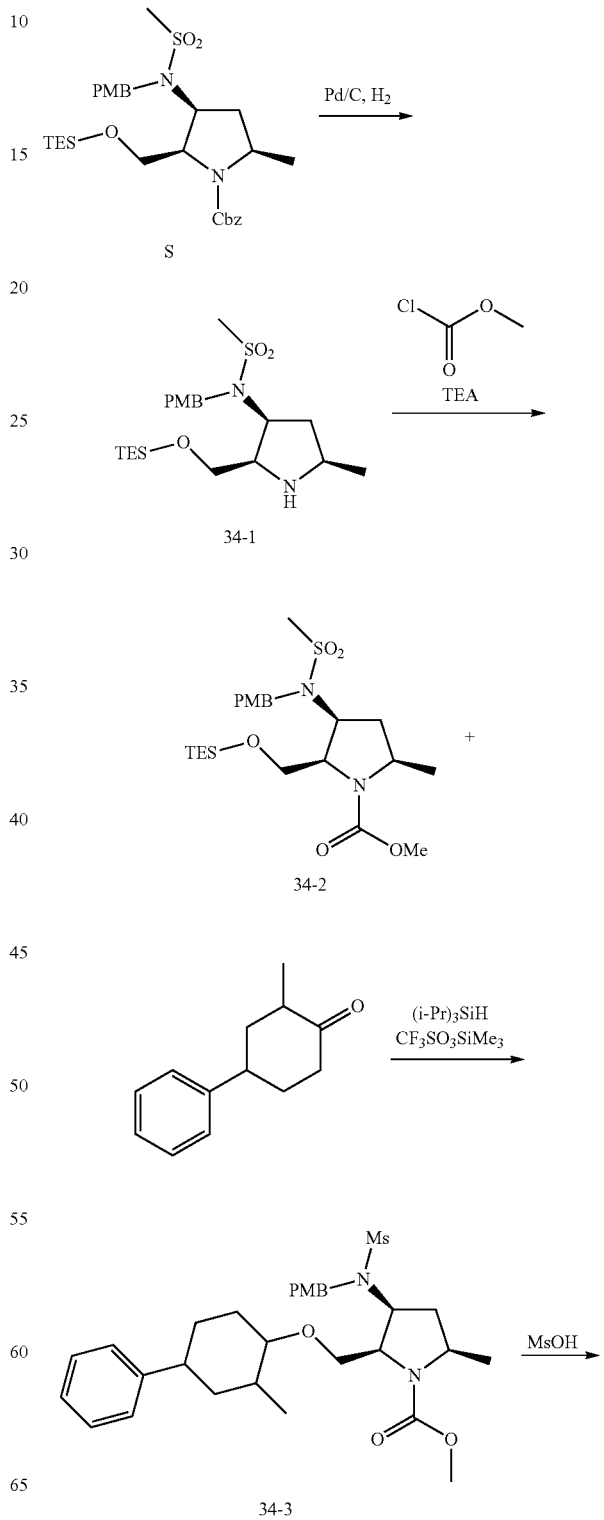

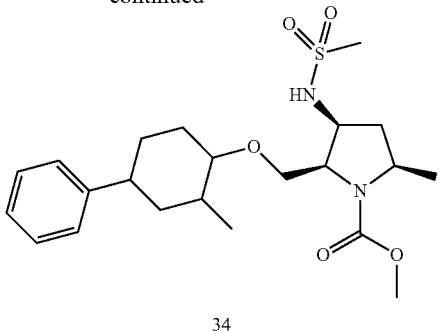

34

Step 1: N-(4-methoxybenzyl)-N-((2R,3S,5R)-5-methyl-2-(((triethylsilyl)oxy)methyl)pyrrolidin-3-yl)methanesulfonamide (34-1)

To a solution of benzyl (2R,3S,5R)-3-(N-(4-methoxybenzyl)methylsulfonamido)-5-methyl-2-(((triethylsilyl)oxy)methyl)pyrrolidine-1-carboxylate (S) (620 mg, 1.075 mmol) in THF (12 ml) was added 10% palladium on carbon (114 mg, 0.107 mmol). The reaction mixture was degassed and refilled with H2 from balloon for three times. The reaction mixture was stirred at rt under hydrogen balloon for 1 hr, LC-MS showed completion. The reaction mixture was filtered through a celite pad. The filtrate was concentrated to give the title compound N-(4-methoxybenzyl)-N-((2R,3S,5R)-5-methyl-2-(((triethylsilyl)oxy)methyl)pyrrolidin-3-yl)methanesulfonamide (34-1). LC-MS 444 (M+1).

Step 2: methyl (2R,3S,5R)-3-(N-(4-methoxybenzyl)methylsulfonamido)-5-methyl-2 (((triethyl silyl)oxy)methyl)pyrrolidine-1-carboxylate (34-2)

To a solution of N-(4-methoxybenzyl)-N-((2R,3S,5R)-5-methyl-2-(((triethylsilyl)oxy)-methyl)pyrrolidin-3-yl)methanesulfonamide (34-1) (450 mg, 1.017 mmol) in DCM (10 ml) at 0° C. was added Et3N (0.425 ml, 3.05 mmol) followed by methyl chloroformate (0.102 ml, 1.321 mmol) under $N_2$. The reaction mixture was stirred at 0° C. for 50 mins. LC-MS showed completion. The reaction mixture was concentrated to leave yellow oil. The residue was purified by prep silica gel TLC eluent with 1% MeOH/DCM to give the title compound methyl (2R,3S,5R)-3-(N-(4-methoxybenzyl)methylsulfonamido)-5-methyl-2-(((triethyl silyl)oxy)-methyl)pyrrolidine-1-carboxylate (34-2). LC-MS 501 (M+1).

Step 3: methyl (2R,3S,5R)-3-(N-(4-methoxybenzyl)methylsulfonamido)-5-methyl-2-(((2-methyl-4-phenylcyclohexyl)oxy)methyl)pyrrolidine-1-carboxylate (34-3)

To a solution of methyl (2R,3S,5R)-3-(N-(4-methoxybenzyl)methylsulfonamido)-5-methyl-2-(((triethylsilyl)oxy)methyl)pyrrolidine-1-carboxylate (34-2) (110 mg, 0.220 mmol) in Acetonitrile (1.5 ml) and DCM (1.5 ml) at 0° C. was added 2-methyl-4-phenylcyclohexan-1-one (62.0 mg, 0.330 mmol) followed by triisopropylsilane (0.090 ml, 0.439 mmol) under $N_2$. Then the reaction mixture was cooled to −30° C. Trimethylsilyl trifluoromethanesulfonate (0.040 ml, 0.220 mmol) was added. The reaction mixture was allowed warm up to 0° C. slowly. After 1.5 hrs stirring at 0° C., LC-MS showed the major was desired product formation. The reaction mixture was quenched with sat. aq. NaHCO3. The reaction mixture was extracted by 2 portions of 10 ml of DCM. The combined organic phase was collected and concentrated to leave colorless oil. The residue was purified by prep silica gel TLC eluent with 3% MeOH/DCM to give the title compound methyl (2R,3S,5R)-3-(N-(4-methoxybenzyl)methylsulfonamido)-5-methyl-2-(((2-methyl-4-phenylcyclohexyl)oxy)methyl)pyrrolidine-1-carboxylate (34-3). LC-MS 559 (M+1).

Step 4: methyl (2R,3S,5R)-5-methyl-2-(((2-methyl-4-phenylcyclohexyl)oxy)methyl)-3-(methyl sulfonamido)pyrrolidine-1-carboxylate (34)

To a solution of methyl (2R,3S,5R)-3-(N-(4-methoxybenzyl)methylsulfonamido)-5-methyl-2-(((2-methyl-4-phenylcyclohexyl)oxy)methyl)pyrrolidine-1-carboxylate (34-3) (108 mg, 0.193 mmol) in DCM (2.0 ml) was added MsOH (75 μl, 1.160 mmol) at rt under $N_2$. The reaction mixture was stirred at rt started for 25 mins, LC-MS showed completion. The reaction mixture was concentrated to leave light brown film. The residue was purified by Gilson to give the title compound methyl (2R,3S,5R)-5-methyl-2-(((2-methyl-4-phenylcyclohexyl)oxy)methyl)-3-(methyl sulfonamido)pyrrolidine-1-carboxylate (34). LC-MS 439 (M+1).

EXAMPLE 35 AND 36 methyl (2R,3S,5R)-3-((N,N-dimethylsulfamoyl)amino)-2-((((S)-3'-fluoro-2,3,4,5-tetrahydro-[1,1'-biphenyl]-4-yl)oxy)methyl)-5-methylpyrrolidine-1-carboxylate (35) methyl (2R,3S,5R)-3-((N,N-dimethylsulfamoyl)amino)-2-((((1S)-4-(3-fluorophenyl)-3-hydroxycyclohexyl)oxy)methyl)-5-methylpyrrolidine-1-carboxylate (36)

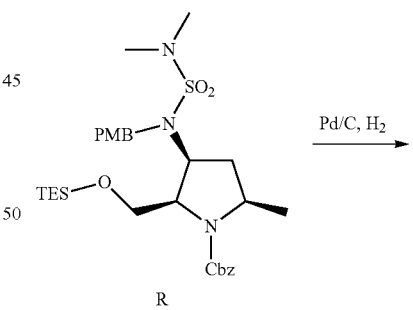

R

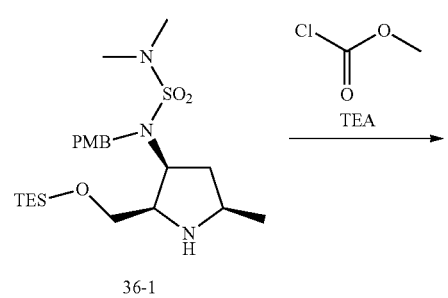

36-1

99
-continued
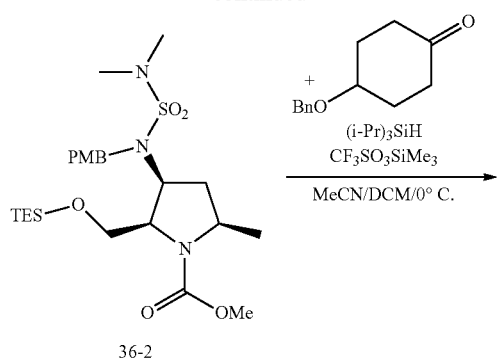
36-2
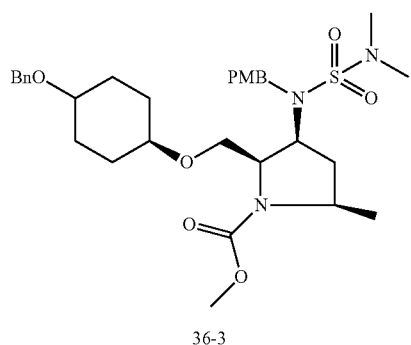
36-3
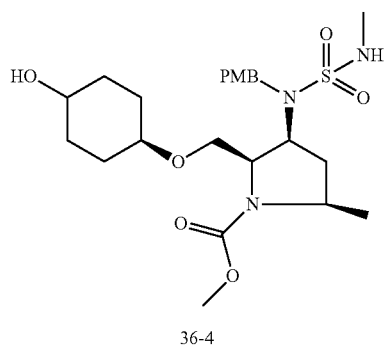
36-4
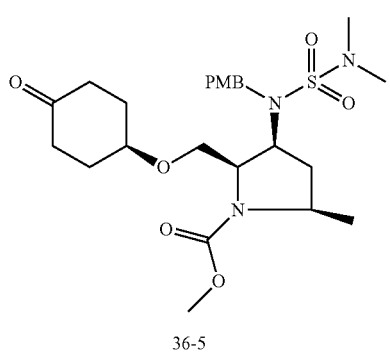
36-5
100
-continued
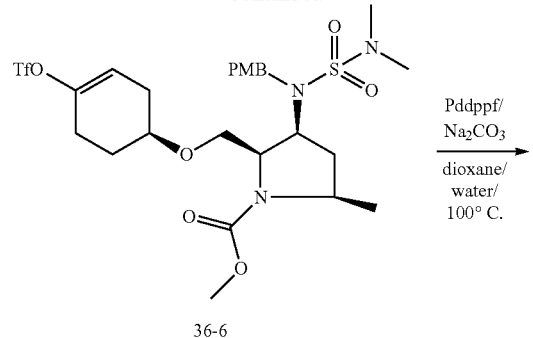
36-6
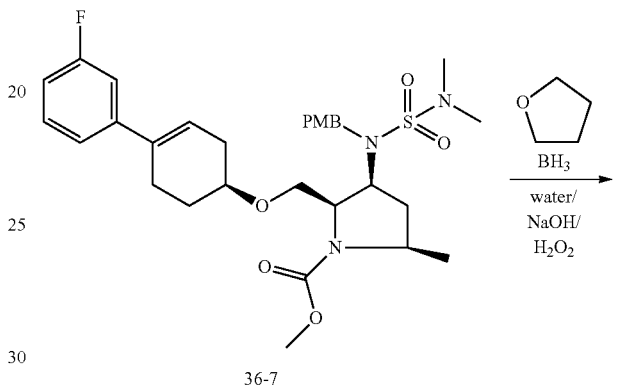
36-7
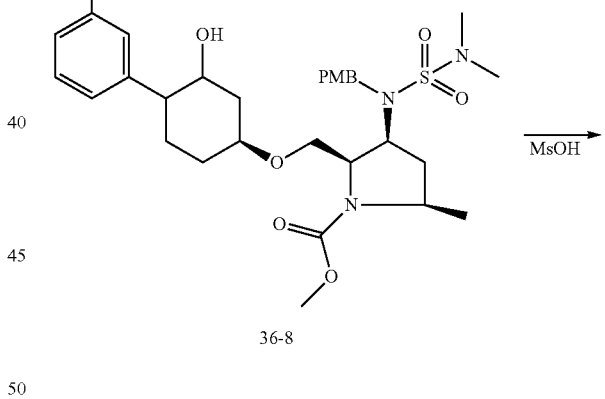
36-8
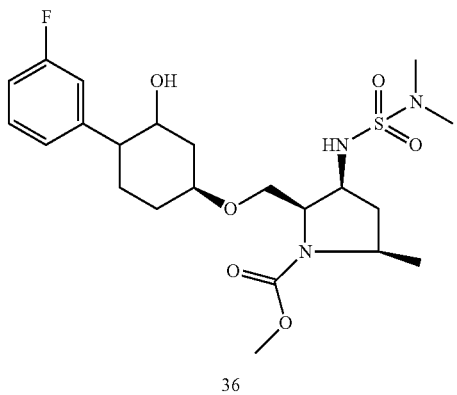
36

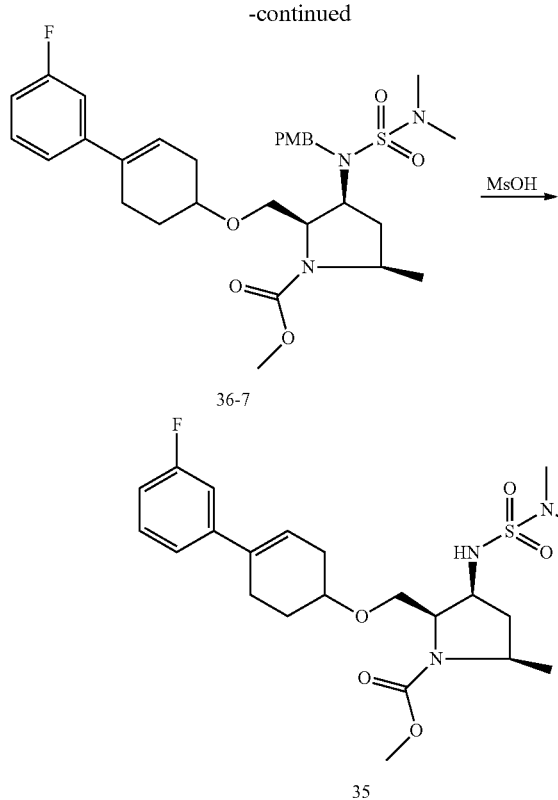

36-7

35

Step 1: N-(4-methoxybenzyl)-N-((2R,3S,5R)-5-methyl-2-(((triethylsilyl)oxy)methyl)pyrrolidin-3-yl)-N,N-dimethylsulfonamide (36-1)

To a solution of benzyl (2R,3S,5R)-3-((N,N-dimethylsulfamoyl)(4-methoxybenzyl)amino)-5-methyl-2-(((triethyl silyl)oxy)methyl)pyrrolidine-1-carboxylate (C) (2.0 g, 3.30 mmol) in THF (30 ml) was added 10% palladium on carbon (351 mg, 0.330 mmol). The reaction mixture was degassed and refilled with H2 from balloon for three times. The reaction mixture was stirred at rt under hydrogen balloon for 100 mins. LC-MS showed completion. The reaction mixture was filtered through a celite pad. The filtrate was concentrated to give the title compound N-(4-methoxybenzyl)-N-((2R,3S,5R)-5-methyl-2-(((triethyl silyl)oxy)methyl)pyrrolidin-3-yl)-N,N-dimethylsulfonamide (36-1). LC-MS 473 (M+1).

Step 2: methyl (2R,3S,5R)-3-((N,N-dimethylsulfamoyl)(4-methoxybenzyl)amino)-5-methyl-2-(((triethyl silyl)oxy)methyl)pyrrolidine-1-carboxylate (36-2)

To a solution of N-(4-methoxybenzyl)-N-((2R,3S,5R)-5-methyl-2 (((triethylsilyl)oxy)methyl)pyrrolidin-3-yl)-N,N-dimethylsulfonamide (36-1) (1.55 g, 3.29 mmol) in DCM (24 ml) at 0° C. was added Et$_3$N (1.374 ml, 9.86 mmol) followed by methyl chloroformate (0.331 ml, 4.27 mmol) under N$_2$. The reaction mixture was stirred at 0° C. for 20 mins and then warmed up to rt and stirred at rt for 2 hrs. LC-MS showed completion. The reaction mixture was quenched with water. Separated the organic layer, dried with MgSO$_4$, concentrated to leave yellow oil. The residue was purified by prep silica gel TLC eluent with 3% MeOH/DCM t to give the title compound methyl (2R,3S,5R)-3-((N,N-dimethylsulfamoyl)(4-methoxybenzyl)amino)-5-methyl-2-(((triethylsilyl)oxy)methyl)pyrrolidine-1-carboxylate (36-2). LC-MS 530 (M+1).

Step 3: methyl (2R,3S,5R)-2-(((4-(benzyloxy)cyclohexyl)oxy)methyl)-3-((N,N-dimethyl-sulfamoyl)(4-methoxybenzyl)amino)-5-methylpyrrolidine-1-carboxylate (36-3)

To a solution of methyl (2R,3S,5R)-3-((N,N-dimethylsulfamoyl)(4-methoxybenzyl)amino)-5-methyl-2-(((triethyl silyl)oxy)methyl)pyrrolidine-1-carboxylate (36-2) (3.32 g, 6.27 mmol) in Acetonitrile (48 ml) at 0° C. was added 4-(benzyloxy)cyclohexan-1-one (1.92 g, 9.40 mmol) followed by triisopropylsilane (2.57 ml, 12.53 mmol) under N2. Then the reaction mixture was cooled to −30° C., trimethylsilyl trifluoromethanesulfonate (1.134 ml, 6.27 mmol) was added. It was continued to stir at −30° C. for 4 hrs. LC-MS showed almost completion. The reaction mixture was quenched with sat. aq. NaHCO$_3$. The reaction mixture was extracted by 2 portions of 10 ml of DCM. The combined organic phase was collected and concentrated to leave yellow oil. The residue was purified by ISCO (Loaded onto a 80 g column, eluent with 0~55% EtOAc/hexane, the peak was collected at 50% EtOAc/hexane) to give the title compound methyl (2R,3S,5R)-2-(((4-(benzyloxy)cyclohexyl)oxy)methyl)-3-((N,N-dimethylsulfamoyl)(4-methoxybenzyl)amino)-5-methylpyrrolidine-1-carboxylate (36-3). LC-MS 604 (M+1).

Step 4: methyl (2R,3S,5R)-3-((N,N-dimethylsulfamoyl)(4-methoxybenzyl)amino)-2-(((4-hydroxycyclohexyl)oxy)methyl)-5-methylpyrrolidine-1-carboxylate (36-4)

To a solution of methyl (2R,3S,5R)-2-(((4-(benzyloxy)cyclohexyl)oxy)methyl)-3-((N,N-dimethylsulfamoyl)(4-methoxybenzyl)amino)-5-methylpyrrolidine-1-carboxylate (36-3) (3.65 g, 6.05 mmol) in MeOH (45 ml) was added PALLADIUM HYDROXIDE ON CARBON (20%, 1.486 g, 2.116 mmol). The reaction mixture was degassed and refilled with H2 from balloon for three times. The reaction mixture was stirred at rt under hydrogen balloon overnight. LC-MS showed completion. The reaction mixture was filtered through a celite pad. The filtrate was concentrated to give the title compound methyl (2R,3S,5R)-3-((N,N-dimethylsulfamoyl)(4-methoxybenzyl)amino)-2-(((4-hydroxycyclohexyl)oxy)methyl)-5-methylpyrrolidine-1-carboxylate & methyl (2R,3S,5R)-3-((N,N-dimethylsulfamoyl)amino)-2-(((4-hydroxycyclohexyl)oxy)methyl)-5-methylpyrrolidine-1-carboxylate (36-4). LC-MS 514 (M+1).

Step 5: methyl (2R,3S,5R)-3-((N,N-dimethylsulfamoyl)(4-methoxybenzyl)amino)-5-methyl-2-(((4-oxocyclohexyl)oxy)methyl)pyrrolidine-1-carboxylate (36-5)

To a solution of methyl (2R,3S,5R)-3-((N,N-dimethylsulfamoyl)(4-methoxybenzyl)-amino)-2-(((4-hydroxycyclohexyl)oxy)methyl)-5-methylpyrrolidine-1-carboxylate and methyl (2R,3S,5R)-3-((N,N-dimethylsulfamoyl)amino)-2-(((4-hydroxycyclohexyl)oxy)methyl)-5-methylpyrrolidine-1-carboxylate (36-4) (3.08 g, 6.00 mmol) in DCM (50 ml) at 0° C. was added DESS-MARTIN PERIODINANE (5.09 g, 11.99 mmol). The reaction mixture was stirred at 0° C. for 30 mins and then let it warm up to rt slowly and stirred at rt overnight. LC-MS showed completion. The reaction mixture was washed with sat. NaHCO₃. The organic layer was dried with MgSO₄, concentrated to leave yellow oil. The residue was purified by ISCO (Loaded onto a 80 g column, eluent with 0~6% MeOH/DCM, the peak was collected at 6% MeOH/DCM) to give the title compound methyl (2R, 3S,5R)-3-((N,N-dimethylsulfamoyl)(4-methoxybenzyl) amino)-5-methyl-2-(((4-oxocyclohexyl)oxy)methyl)-pyrrolidine-1-carboxylate (36-5). LC-MS 512 (M+1).

Step 6: methyl (2R,3S,5R)-3-((N,N-dimethylsulfamoyl)(4-methoxybenzyl)amino)-5-methyl-2-((((S)-4-(((trifluoromethyl)sulfonyl)oxy)cyclohex-3-en-1-yl)oxy)methyl)pyrrolidine-1-carboxylate (36-6)

To a mixture of methyl (2R,3S,5R)-3-((N,N-dimethylsulfamoyl)(4-methoxybenzyl)-amino)-5-methyl-2-(((4-oxocyclohexyl)oxy)methyl)pyrrolidine-1-carboxylate (36-5) (2.94 g, 5.75 mmol) and N-(5-chloropyridin-2-yl)-1,1,1-trifluoro-N-((trifluoromethyl)-sulfonyl)methanesulfonamide (2.93 g, 7.47 mmol) in 55 ml of THF at −78° C. was added POTASSIUM BIS(TRIMETHYLSILYL)AMIDE (1.0 M in THF, 8.62 ml, 8.62 mmol). The reaction mixture was stirred at −78° C. under nitrogen for 4 hrs. LC-MS showed the major was desired product. The reaction was quenched with sat. NaHCO₃ at −78° C. Let it stirring at rt for 30 mins. Extracted with EtOAc (×3). The organic layer was dried with MgSO₄, concentrated to leave brown oil. The residue was purified by prep silica gel TLC eluent with 3% MeOH/DCM to give the title compound methyl (2R,3S,5R)-3-((N,N-dimethylsulfamoyl)(4-methoxybenzyl)-amino)-5-methyl-2-((((S)-4-(((trifluoromethyl)sulfonyl)oxy)cyclohex-3-en-1-yl)oxy)methyl)-pyrrolidine 1-carboxylate (36-6). LC-MS 644 (M+1).

Step 7: methyl (2R,3S,5R)-3-((N,N-dimethylsulfamoyl)(4-methoxybenzyl)amino)-2-((((S)-3'-fluoro-2,3,4,5-tetrahydro-[1,1'-biphenyl]-4-yl)oxy)methyl)-5-methylpyrrolidine-1-carboxylate (36-7)

A suspension of methyl (2R,3S,5R)-3-((N,N-dimethylsulfamoyl)(4-methoxy-benzyl)amino)-5-methyl-2-((((S)-4-(((trifluoromethyl)sulfonyl)oxy)cyclohex-3-en-1-yl)oxy)methyl)pyrrolidine-1-carboxylate (36-6) (53 mg, 0.082 mmol), 1,1'-BIS(DIPHENYL-PHOSPHINO)FERROCENE-PALLADIUM(II)DICHLORIDE DICHLOROMETHANE COMPLEX (13.45 mg, 0.016 mmol), SODIUM CARBONATE (26.2 mg, 0.247 mmol) and (3-fluorophenyl)boronic acid (13.82 mg, 0.099 mmol) in Dioxane (1 ml) and Water (0.5 ml) was bubbled with nitrogen for 5 min. The reaction mixture was sealed in the reaction vial and heated at 100° C. overnight. LC-MS showed completion. The reaction mixture was purified by prep silica gel TLC eluent with 2% MeOH/DCM to give the title compound methyl (2R,3S,5R)-3-((N,N-dimethylsulfamoyl)(4-methoxybenzyl)amino)-2-((((S)-3'-fluoro-2,3,4,5-tetrahydro-[1,1'-biphenyl]-4-yl)oxy)methyl)-5-methylpyrrolidine-1-carboxylate (36-7). LC-MS 590 (M+1).

Step 8: methyl (2R,3S,5R)-3-((N,N-dimethylsulfamoyl)amino)-2-((((S)-3'-fluoro-2,3,4,5-tetrahydro-[1,1'-biphenyl]-4-yl)oxy)methyl)-5-methylpyrrolidine-1-carboxylate (35)

To a solution of methyl (2R,3S,5R)-3-((N,N-dimethylsulfamoyl)(4-methoxy-benzyl)amino)-2-((((S)-3'-fluoro-2,3,4,5-tetrahydro-[1,1'-biphenyl]-4-yl)oxy)methyl)-5-methylpyrrolidine-1-carboxylate (36-7) (7 mg, 0.012 mmol) in DCM (0.5 ml) was added MsOH (3.85 µl, 0.059 mmol) at rt under N2. The reaction mixture was stirred at rt for 1.5 hrs, LC-MS showed ~70% desired product was formed. The reaction mixture was concentrated to leave colorless film. The residue was purified by Gilson to give the title compound methyl (2R,3S,5R)-3-((N,N-dimethylsulfamoyl)amino)-2-((((S)-3'-fluoro-2,3,4,5-tetrahydro-[1,1'-biphenyl]-4-yl)oxy)methyl)-5-methylpyrrolidine-1-carboxylate (35). LC-MS 470 (M+1).

Step 9: methyl (2R,3S,5R)-3-((N,N-dimethylsulfamoyl)(4-methoxybenzyl)amino)-2-((((1S)-4-(3-fluorophenyl)-3-hydroxycyclohexyl)oxy)methyl)-5-methylpyrrolidine-1-carboxylate (36-8)

To a solution of methyl (2R,3S,5R)-3-((N,N-dimethylsulfamoyl)(4-methoxybenzyl)amino)-2-((((S)-3'-fluoro-2,3,4,5-tetrahydro-[1,1'-biphenyl]-4-yl)oxy)methyl)-5-methylpyrrolidine-1-carboxylate (36-7) (35 mg, 0.059 mmol) in THF (1.5 ml) at 0° C. was added BORANE-THF COMPLEX (1.0 M in THF, 0.237 ml, 0.237 mmol). The reaction mixture was warmed up to rt and stirred at rt under nitrogen for 3 days. LC-MS showed the major was desired product. The reaction was cooled down in the ice bath again, and then water (21.38 µl, 1.186 mmol) was added followed by 3N NaOH (0.064 ml, 0.192 mmol) and H₂O₂ solution (30% in water, 0.064 ml, 0.734 mmol). The resulting reaction mixture was warmed up to rt and stirred at rt for another 2.5 hrs. Then the reaction mixture was quenched with brine, extracted with EtOAc twice. The organic layer was washed with water, dried with MgSO₄, concentrated to leave colorless film. The residue was purified by prep silica gel TLC eluent with 3% MeOH/DCM to give the title compound methyl (2R,3S,5R)-3-((N,N-dimethylsulfamoyl)(4-methoxybenzyl)amino)-2-((((1S)-4-(3-fluorophenyl)-3-hydroxycyclohexyl)oxy)methyl)-5-methylpyrrolidine-1-carboxylate (36-8). LC-MS 608 (M+1).

Step 10: methyl (2R,3S,5R)-3-((N,N-dimethylsulfamoyl)amino)-2-((((1S)-4-(3-fluorophenyl)-3-hydroxycyclohexyl)oxy)methyl)-5-methylpyrrolidine-1-carboxylate (36)

To a solution of methyl (2R,3S,5R)-3-((N,N-dimethylsulfamoyl)(4-methoxy-benzyl)amino)-2-((((1S)-4-(3-fluorophenyl)-3-hydroxycyclohexyl)oxy)methyl)-5-methylpyrrolidine-1-carboxylate (36-8) (10 mg, 0.016 mmol) in DCM (0.5 ml) was added MsOH (7.48 µl, 0.115 mmol) at rt under N2. The reaction mixture was stirred at rt for 5 mins, LC-MS showed completion. The reaction mixture was concentrated to leave colorless film. The residue was purified by Gilson to give the title compound methyl (2R,3S,5R)-3-((N,N-dimethyl-sulfamoyl)amino)-2-((((1S)-4-(3-fluorophenyl)-3-hydroxycyclohexyl)oxy)methyl)-5-methylpyrrolidine-1-carboxylate (36). LC-MS 488 (M+1).

EXAMPLE 37 methyl (2R,3S,5R)-3-((N,N-dimethylsulfamoyl)amino)-2-((((1s,4S)-4-(3-fluorophenyl)cyclohexyl)oxy)methyl)-5-methylpyrrolidine-1-carboxylate

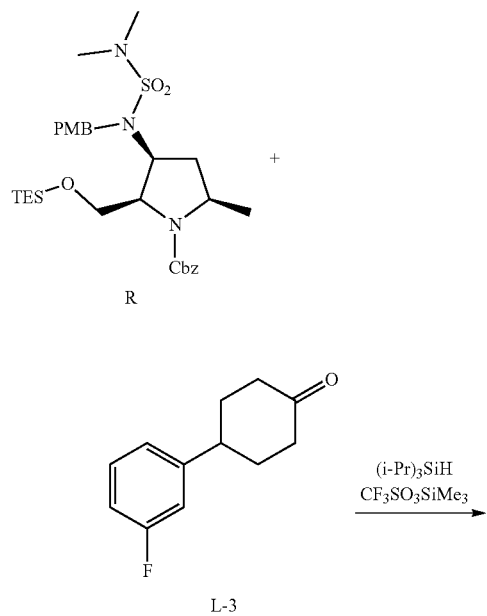

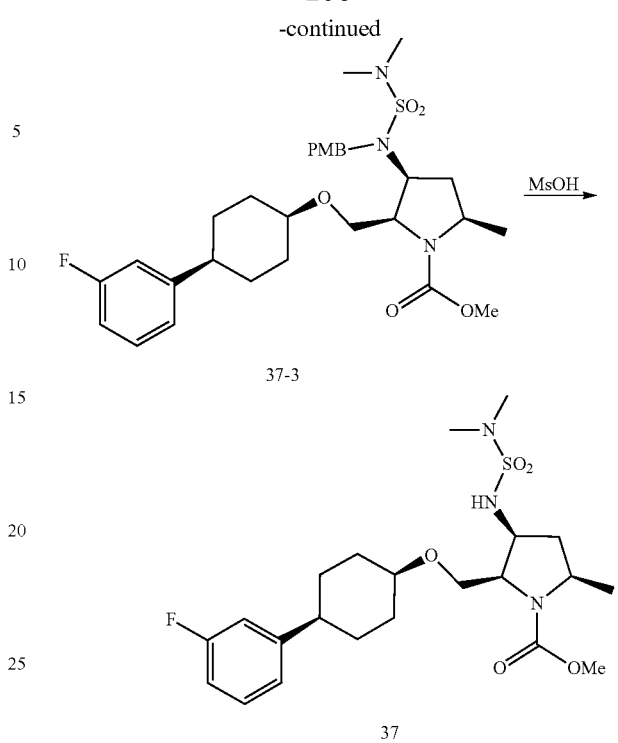

Step 1: benzyl (2R,3S,5R)-3-((N,N-dimethylsulfamoyl)(4-methoxybenzyl)amino)-2-((((1s,4S)-4-(3-fluorophenyl)cyclohexyl)oxy)methyl)-5-methylpyrrolidine-1-carboxylate (37-1)

To a solution of benzyl (2R,3S,5R)-3-((N,N-dimethylsulfamoyl)(4-methoxybenzyl)-amino)-5-methyl-2-(((triethylsilyl)oxy)methyl)pyrrolidine-1-carboxylate (Intermediate R, 175 mg, 0.289 mmol) in acetonitrile (4.0 ml) at 0° C. was added 4-(3-fluorophenyl)cyclohexan-1-one (Intermediate L-3, 72.2 mg, 0.375 mmol) followed by triisopropylsilane (0.118 ml, 0.578 mmol) under $N_2$. The reaction mixture was then cooled to −30° C. A solution of trimethylsilyl trifluoromethanesulfonate (0.052 ml, 0.289 mmol) in 0.5 ml of DCM was added. The reaction mixture was allowed to warm up to 0° C. slowly. After stirring for another 1 h, the reaction mixture was quenched with sat. aq. NH4Cl. The reaction mixture was extracted with 2 portions of 10 ml of DCM. The combined organic phase was collected and concentrated to give a colorless oil. The residue was purified by prep silica gel TLC eluent with 2% MeOH/DCM to provide the desired product. LC-MS 668.4 (M+1).

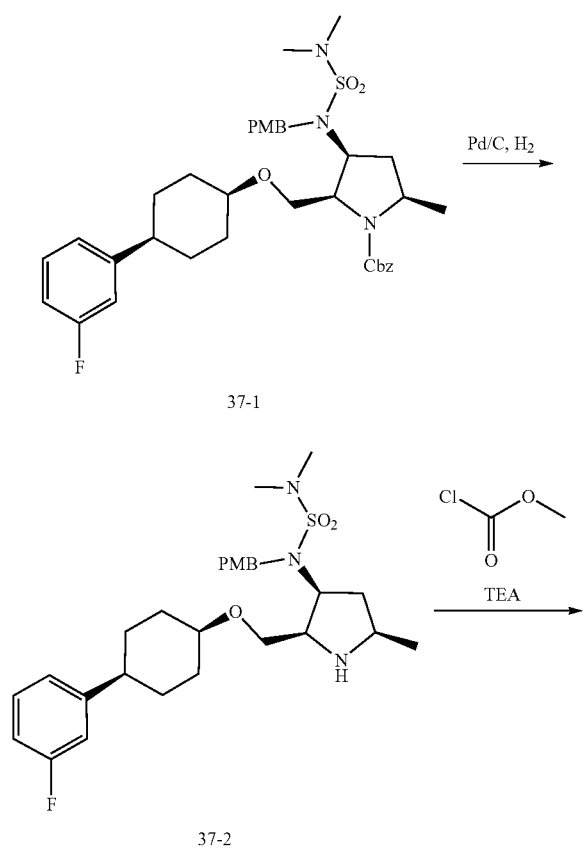

Step 2: (2R,3S,5R)-3-((N,N-dimethylsulfamoyl)(4-methoxybenzyl)amino)-2-((((1s,4S)-4-(3-fluorophenyl)cyclohexyl)oxy)methyl)-5-methylpyrrolidine (37-2)

To a solution of benzyl (2R,3S,5R)-3-((N,N-dimethylsulfamoyl)(4-methoxybenzyl)-amino)-2-((((1s,4S)-4-(3-fluorophenyl)cyclohexyl)oxy)methyl)-5-methylpyrrolidine-1-carboxylate (37-1, 1.23 g, 1.842 mmol) in THF (25 ml) was added 10% palladium on carbon (196 mg, 0.184 mmol). The reaction mixture was degassed and refilled with H2 from balloon for three times. The reaction mixture was stirred at rt under hydrogen balloon for 1 h, and the reaction mixture was filtered through a celite pad. The filtrate was concentrated to afford crude desired product. LC-MS 534.4 (M+1).

Step 3: methyl (2R,3S,5R)-3-((N,N-dimethylsulfamoyl)(4-methoxybenzyl)amino)-2-((((1s,4S)-4-(3-fluorophenyl)cyclohexyl)oxy)methyl)-5-methylpyrrolidine-1-carboxylate (37-3)

To a solution of (2R,3S,5R)-3-((N,N-dimethylsulfamoyl)(4-methoxybenzyl)-amino)-2-((((1s,4S)-4-(3-fluorophenyl)cyclohexyl)oxy)methyl)-5-methylpyrrolidine (37-2, 972 mg, 1.821 mmol) in CH$_2$Cl$_2$ (15 ml) at 0° C. was added Et$_3$N (0.762 ml, 5.46 mmol) followed by methyl carbonochloridate (0.183 ml, 2.368 mmol) under N$_2$. The reaction mixture was stirred at 0° C. for 1 h, then stopped and concentrated. The residue was purified by prep silica gel TLC eluent with 4% MeOH/DCM to provide the title compound (37-3). LC-MS 592.3 (M+1).

Step 4: methyl (2R,3S,5R)-3-((N,N-dimethylsulfamoyl)amino)-2-((((1s,4S)-4-(3-fluorophenyl)-cyclohexyl)oxy)methyl)-5-methylpyrrolidine-1-carboxylate (37)

To a solution of methyl (2R,3S,5R)-3-((N,N-dimethylsulfamoyl)(4-methoxybenzyl)-amino)-2-((((1s,4S)-4-(3-fluorophenyl)cyclohexyl)oxy)methyl)-5-methylpyrrolidine-1-carboxylate (37-3, 950 mg, 1.605 mmol) in CH$_2$Cl$_2$ (16 ml) was added MsOH (1.251 ml, 19.27 mmol) at rt under N$_2$. The reaction mixture was stirred at rt 15 min, then the reaction was stopped and concentrated. The residue was purified by Gilson (C18, 10-100% acetonitrile in H$_2$O) to provide the title compound methyl (2R,3S,5R)-3-((N,N-dimethylsulfamoyl)amino)-2-((((1s,4S)-4-(3-fluorophenyl)cyclohexyl)oxy)methyl)-5-methylpyrrolidine-1-carboxylate (37). LC-MS 472.4 (M+1). $^1$H NMR (500 MHz, Methanol-d4) δ 7.27 (q, J=7.9 Hz, 1H), 7.06 (d, J=7.7 Hz, 1H), 6.97 (d, J=10.5 Hz, 1H), 6.93-6.85 (m, 1H), 4.16 (s, 1H), 3.87 (m, 1H), 3.82 (m, 1H), 3.72 (m. 3H), 3.69 (s, 3H), 2.81 (s, 6H), 2.63 (m, 1H), 2.45 (dt, J=12.2, 7.4 Hz, 1H), 2.12 (m, 2H), 1.82 (m, 3H), 1.68 (m, 2H), 1.62 (m, 2H), 1.39 (d, J=5.9 Hz, 3H).

EXAMPLE 38 isopropyl (2R,3S,5R)-5-methyl-3-((N-methylsulfamoyl)amino)-2-(((1-(pyrimidin-2-yl)piperidin-4-yl)oxy)methyl)pyrrolidine-1-carboxylate (38)

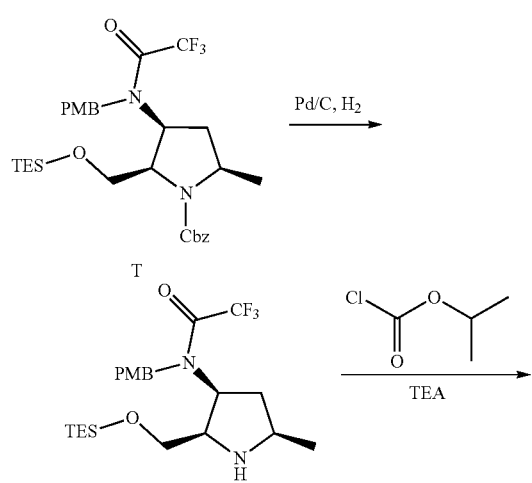

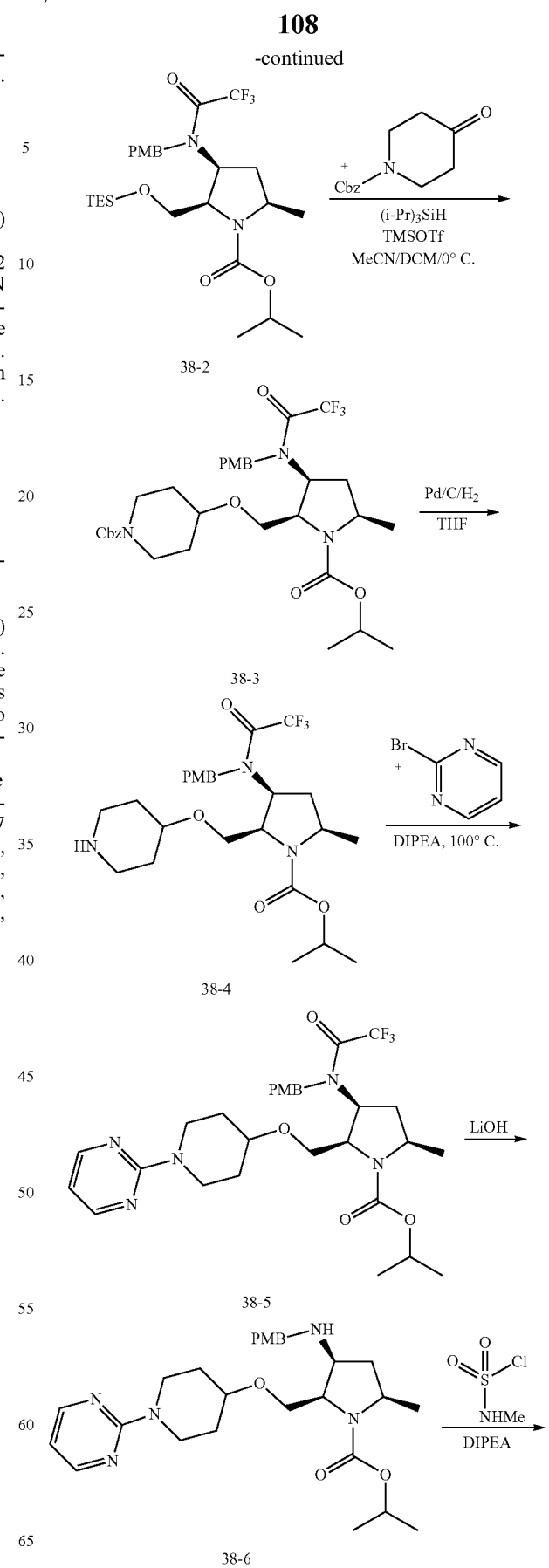

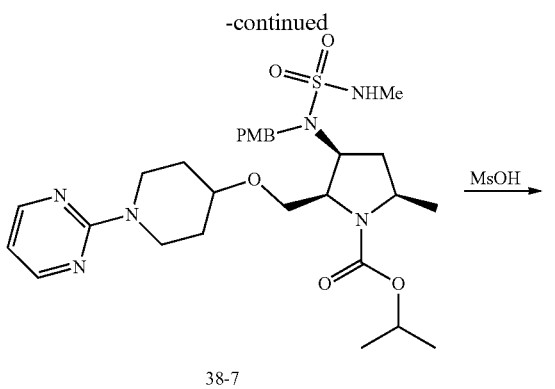

38-7

38

Step 1: 2,2,2-trifluoro-N-(4-methoxybenzyl)-N-((2R,3S,5R)-5-methyl-2-(((triethyl silyl)oxy)methyl) pyrrolidin-3-yl)acetamide (38-1)

To a solution of benzyl (2R,3S,5R)-5-methyl-2-(((triethylsilyl)oxy)methyl)-3-(2,2,2-trifluoro-N-(4-methoxybenzyl) acetamido)pyrrolidine-1-carboxylate (T) (400 mg, 0.673 mmol) in THF (10 ml) was added Pd on C (71.6 mg, 0.067 mmol) at rt under $N_2$. The reaction mixture was degassed and refilled with H2 (1.356 mg, 0.673 mmol) for 3 times. The reaction mixture was left stirring at rt for 30 min. LC-MS shown starting material disappeared and desired product formed. The reaction mixture was filtered through a celite pad. The crude product was concentrated to give 2,2,2-trifluoro-N-(4-methoxybenzyl)-N-((2R,3S,5R)-5-methyl-2-(((triethylsilyl)oxy)methyl)-pyrrolidin-3-yl)acetamide (38-1). Since LC-MS shown it to be sufficiently pure, it was used in the next step without further purification. LC-MS 462.

Step 2: isopropyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (38-2)

To a solution of 2,2,2-trifluoro-N-(4-methoxybenzyl)-N-((2R,3S,5R)-5-methyl-2-(((triethylsilyl)oxy)methyl)pyrrolidin-3-yl)acetamide (38-1) (260 mg, 0.564 mmol) in $CH_2Cl_2$ (10 ml) was added TEA (0.157 ml, 1.129 mmol) and isopropyl carbonochloridate (83 mg, 0.677 mmol) at 0° C. under $N_2$. The reaction mixture was stirred at rt for 30 min. LC-MS shown starting material disappeared. To the reaction mixture was added a few drops of methanol, then the reaction mixture was washed with 2 ml of sat. aq. $NaHCO_3$. The organic phase was collected, dried ($MgSO_4$) and concentrated and the crude product was chromatographed over silica gel (ISCO 12 g, 0-40% EtOAc in hexanes) to give the desired product isopropyl (2R,3S,5R)-5-methyl-2-(((triethylsilyl)oxy)methyl)-3-(2,2,2-trifluoro-N-(4-methoxybenzyl) acetamido)pyrrolidine-1-carboxylate (38-2). LC-MS 548.

Step 3: benzyl 4-(((2R,3S,5R)-1-(isopropoxycarbonyl)-5-methyl-3-(2,2,2-trifluoro-N-(4-methoxybenzyl)acetamido)pyrrolidin-2-yl)methoxy)piperidine-1-carboxylate (38-3)

To a solution of isopropyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (38-2) (240 mg, 0.439 mmol) in acetonitrile (5 ml) was added benzyl 4-oxopiperidine-1-carboxylate (133 mg, 0.571 mmol) and triisopropylsilane (139 mg, 0.878 mmol) at 0° C. under $N_2$. When cooling to −20° C., the reaction mixture turned cloudy. Up to 0.5 ml of DCM was added and the solution turned clear. A solution of trimethylsilyl trifluoromethanesulfonate (98 mg, 0.439 mmol) in 0.2 ml of DCM was added dropwise. The reaction mixture was allowed to slowly raise to rt. After 10 min, LCMS shown formation of the desired product. The reaction mixture was allowed to stir for 30 min, then to the reaction was added 0.5 ml of sat. aq. $NaHCO_3$. The reaction mixture was extracted by 2 portions of 10 ml of EtOAc. The combined organic phase was collected and concentrated. The crude was chromatographed over silic gel (ISCO, 12 g, EtOAc in hexanes 0-60%) to give the desired product benzyl 4-(((2R,3S,5R)-1-(isopropoxycarbonyl)-5-methyl-3-(2,2,2-trifluoro-N-(4-methoxybenzyl)acetamido) pyrrolidin-2-yl)methoxy)piperidine-1-carboxylate (38-3). LC-MS 650.

Step 4: isopropyl (2R,3S,5R)-5-methyl-2-((piperidin-4-yloxy)methyl)-3-(2,2,2-trifluoro-N-(4-methoxybenzyl)acetamido)pyrrolidine-1-carboxylate (38-4)

A solution of benzyl 4-(((2R,3S,5R)-1-(isopropoxycarbonyl)-5-methyl-3-(2,2,2-trifluoro-N-(4-methoxybenzyl)acetamido)pyrrolidin-2-yl)methoxy)piperidine-1-carboxylate (38-3) (230 mg, 0.354 mmol) in THF (10 ml) was added Pd on Carbon (0.354 mg, 0.354 mmol), then was degassed and refilled with H2 three times with a balloon. The reaction mixture was stirred at rt for 30 min. LC-MS shown starting material disappeared. The reaction mixture was filtered through a celite pad and the filtrate was concentrated directly to give the crude product isopropyl (2R,3S,5R)-5-methyl-2-((piperidin-4-yloxy)methyl)-3-(2,2,2-trifluoro-N-(4-methoxybenzyl)-acetamido)pyrrolidine-1-carboxylate (38-4). LC-MS 516. It is pure enough and used directly in the next step.

Step 5: isopropyl (2R,3S,5R)-5-methyl-2-(((1-(pyrimidin-2-yl)piperidin-4-yl)oxy)methyl)-3-(2,2,2-trifluoro-N-(4-methoxybenzyl)acetamido)pyrrolidine-1-carboxylate (38-5)

A solution of isopropyl (2R,3S,5R)-5-methyl-2-((piperidin-4-yloxy)methyl)-3-(2,2,2-trifluoro-N-(4-methoxybenzyl)acetamido)pyrrolidine-1-carboxylate (38-4) (50 mg, 0.097 mmol) in Dioxane (5 ml) was added 2-bromopyrimidine (30.8 mg, 0.194 mmol) and N-ethyl-N-isopropylpropan-2-amine (62.7 mg, 0.485 mmol) was heated to 100° C. for 8 h. LC-MS shown formation of the desired product. The reaction mixture was concentrated and chromatographed over C18 (10-100% Acetonitrile in $H_2O$) to give the desired product isopropyl (2R,3S,5R)-5-methyl-2-(((1-(pyrimidin- 2-yl)piperidin-4-yl)oxy)methyl)-3-(2,2,2-trifluoro-N-(4-methoxybenzyl)acetamido)-pyrrolidine-1-carboxylate (38-5). LC-MS 594.

Step 6: isopropyl (2R,3S,5R)-3-((4-methoxybenzyl)amino)-5-methyl-2-(((1-(pyrimidin-2-yl)piperidin-4-yl)oxy)methyl)pyrrolidine-1-carboxylate (38-6)

To solution of isopropyl (2R,3S,5R)-5-methyl-2-(((1-(pyrimidin-2-yl)piperidin-4-yl)oxy)methyl)-3-(2,2,2-trifluoro-N-(4-methoxybenzyl)acetamido)pyrrolidine-1-carboxylate (38-5) (35 mg, 0.059 mmol) in THF (5 ml) was added 2M LiOH solution 1 ml, and another 1 ml of MeOH was added to get a clear solution. The reaction mixture was heated at 50° C. for 2 h. LC-MS shown SM disappeared. The reaction mixture was extracted by 2 portions of 10 ml of EtOAc. The combined organic phases were dried (MgSO$_4$), concentrated and chromatographed over C18 (10-100% acetonitrile in H$_2$O) to give the desired product isopropyl (2R,3S,5R)-3-((4-methoxybenzyl)amino)-5-methyl-2-(((1-(pyrimidin-2-yl)piperidin-4-yl)oxy)methyl)pyrrolidine-1-carboxylate (38-6). LC-MS 498.

Step 7: isopropyl (2R,3S,5R)-3-((4-methoxybenzyl)(N-methyl sulfamoyl)amino)-5-methyl-2-(((1-(pyrimidin-2-yl)piperidin-4-yl)oxy)methyl)pyrrolidine-1-carboxylate (38-7)

A solution of isopropyl (2R,3S,5R)-3-((4-methoxybenzyl)amino)-5-methyl-2-(((1-(pyrimidin-2-yl)piperidin-4-yl)oxy)methyl)pyrrolidine-1-carboxylate (38-6) (25 mg, 0.050 mmol) was dissolved in CH$_2$Cl$_2$ (10 ml), followed by addition of methylsulfamoyl chloride (19.53 mg, 0.151 mmol) at rt under N$_2$. The reaction mixture was stirred at 0° C. for 10 min, followed by addition of N-ethyl-N-isopropylpropan-2-amine (26.0 mg, 0.201 mmol). LC-MS shown SM disappeared and the desired product formed. The reaction completed after 30 min. To the reaction mixture was added sat. aq. NaHCO$_3$, then the organic phase was collected, dried (MgSO$_4$), concentrated and chromatographed over silica gel (ISCO, 12 g, 0-80% EtOAc in hexanes) to give the desired product isopropyl (2R,3S,5R)-3-((4-methoxybenzyl)(N-methylsulfamoyl)amino)-5-methyl-2-(((1-(pyrimidin-2-yl)piperidin-4-yl)oxy)methyl)pyrrolidine-1-carboxylate (38-7). LC-MS 591.

Step 8: isopropyl (2R,3S,5R)-5-methyl-3-((N-methylsulfamoyl)amino)-2-(((1-(pyrimidin-2-yl)piperidin-4-yl)oxy)methyl)pyrrolidine-1-carboxylate (38)

To a solution of isopropyl (2R,3S,5R)-3-((4-methoxybenzyl)(N-methylsulfamoyl)amino)-5-methyl-2-(((1-(pyrimidin-2-yl)piperidin-4-yl)oxy)methyl)pyrrolidine-1-carboxylate (38-7) (21 mg, 0.036 mmol) in CH$_2$Cl$_2$ (2 ml) was added MsOH (0.012 ml, 0.178 mmol) at rt under N$_2$. The reaction mixture was stirred for 0.5 h. LC-MS shown no SM left. The reaction mixture was diluted with 5 ml of DCM, washed with sat. aq. NaHCO$_3$, dried (MgSO$_4$), concentrated, then was dissolved in 2 ml of DMF, chromatographed via Gilson (C18, 10-100% acetonitrile in H$_2$O) to give the desired product isopropyl (2R,3S,5R)-5-methyl-3-((N-methylsulfamoyl)amino)-2-(((1-(pyrimidin-2-yl)piperidin-4-yl)oxy)methyl)pyrrolidine-1-carboxylate (38). LC-MS 471.

EXAMPLE 39 isopropyl (2R,3S,5R)-3-((N,N-dimethylsulfamoyl)amino)-2-(((1-(5-fluoropyrimidin-2-yl)piperidin-4-yl)oxy)methyl)-5-methylpyrrolidine-1-carboxylate (39)

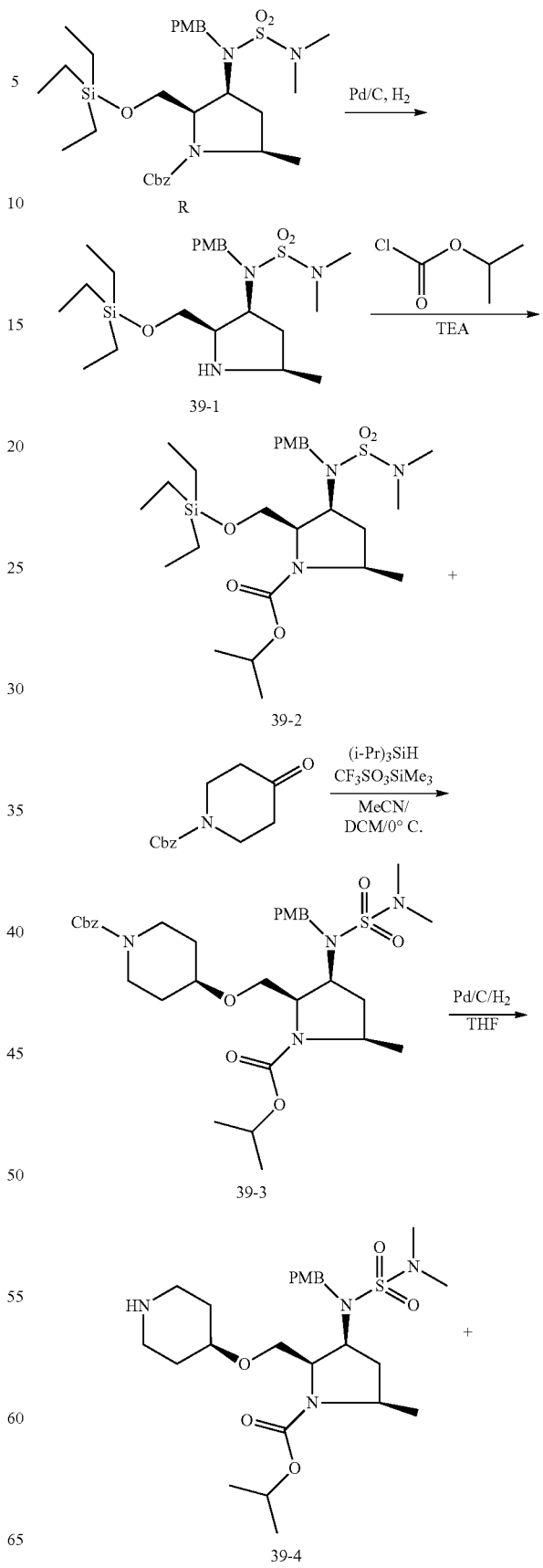

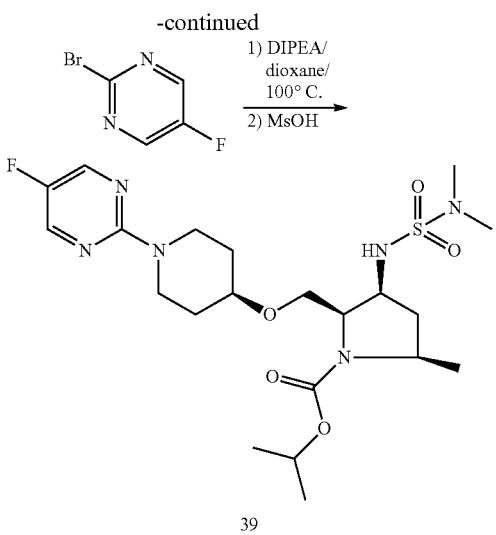

39

Step 1: isopropyl (2R,3S,5R)-3-((N,N-dimethylsulfamoyl)(4-methoxybenzyl)amino)-5-methyl-2-(((triethylsilyl)oxy)methyl)pyrrolidine-1-carboxylate (39-1)

To a solution of (2R,3S,5R)-3-((N,N-dimethylsulfamoyl)(4-methoxybenzyl)amino)-5-methyl-2-(((triethylsilyl)oxy)methyl)pyrrolidine (36-1) (600 mg, 1.272 mmol) in $CH_2Cl_2$ (12 ml) at 0° C. was added $Et_3N$ (0.532 ml, 3.82 mmol) followed by isopropyl carbonochloridate (1.0 M in toluene, 1.653 ml, 1.653 mmol) under $N_2$. The reaction mixture was stirred at 0° C. for 70 mins. LC-MS indicated almost completion. The reaction mixture was concentrated to leave yellow oil. The residue was purified by prep silica gel TLC eluent with 1% MeOH/DCM to give the title compound isopropyl (2R,3S,5R)-3-((N,N-dimethylsulfamoyl)(4-methoxybenzyl)amino)-5-methyl-2-(((triethylsilyl)oxy)methyl)pyrrolidine-1-carboxylate. (39-2). LC-MS 558 (M+1).

Step 2: benzyl 4-(((2R,3S,5R)-3-((N,N-dimethylsulfamoyl)(4-methoxybenzyl)amino)-1-(isopropoxycarbonyl)-5-methylpyrrolidin-2-yl)methoxy)piperidine-1-carboxylate (39-3)

To a solution of isopropyl (2R,3S,5R)-3-((N,N-dimethylsulfamoyl)(4-methoxybenzyl)-amino)-5-methyl-2-(((triethyl silyl)oxy)methyl)pyrrolidine-1-carboxylate (39-2) (65 mg, 0.117 mmol) in acetonitrile (0.8 ml) and DCM (0.8 ml) at 0° C. was added benzyl 4-oxopiperidine-1-carboxylate (43.5 mg, 0.186 mmol) followed by triisopropylsilane (0.048 ml, 0.233 mmol) under $N_2$. After 5 mins stirring at 0° C., trimethylsilyl trifluoromethanesulfonate (0.021 ml, 0.117 mmol) was added. After 6 hrs stirring at 0° C., LC-MS indicated almost completion. The reaction mixture was quenched with sat. aq. $NaHCO_3$, extracted by 2 portions of 10 ml of DCM. The combined organic phase was collected and concentrated to leave colorless oil. The residue was purified by prep silica gel TLC eluent with 3% MeOH/DCM to give the title compound benzyl 4-(((2R,3S,5R)-3-((N,N-dimethylsulfamoyl)(4-methoxybenzyl)amino)-1-(isopropoxycarbonyl)-5-methylpyrrolidin-2-yl)methoxy)piperidine-1-carboxylate. (39-3). LC-MS 661 (M+1).

Step 3: isopropyl (2R,3S,5R)-3-((N,N-dimethylsulfamoyl)(4-methoxybenzyl)amino)-5-methyl-2-((piperidin-4-yloxy)methyl)pyrrolidine-1-carboxylate (39-4)

To a solution of benzyl 4-(((2R,3S,5R)-3-((N,N-dimethylsulfamoyl)amino)-1-(isopropoxy-carbonyl)-5-methylpyrrolidin-2-yl)methoxy)piperidine-1-carboxylate (39-3) (13 mg, 0.024 mmol) in THF (1.0 ml) was added 10% palladium on carbon (3.84 mg, 3.61 μmol). The reaction mixture was degassed and refilled with H2 from balloon for three times. The reaction mixture was stirred at rt under hydrogen balloon for 1.5 hrs. LC-MS indicated completion. The reaction mixture was filtered through a celite pad. The filtrate was concentrated to give the title compound isopropyl (2R,3S,5R)-3-((N,N-dimethylsulfamoyl)amino)-5-methyl-2-((piperidin-4-yloxy)methyl)pyrrolidine-1-carboxylate. (39-4). LC-MS 527 (M+1).

Step 4: isopropyl (2R,3S,5R)-3-((N,N-dimethylsulfamoyl)amino)-2-(((1-(5-fluoropyrimidin-2-yl)piperidin-4-yl)oxy)methyl)-5-methylpyrrolidine-1-carboxylate (39)

To a solution of isopropyl (2R,3S,5R)-3-((N,N-dimethylsulfamoyl)amino)-5-methyl-2-((piperidin-4-yloxy)methyl)pyrrolidine-1-carboxylate (39-4) (10 mg, 0.025 mmol) and 2-bromo-5-fluoropyrimidine (6.97 mg, 0.039 mmol) in 1,4-dioxane (0.5 ml) was added DIPEA (13 μl, 0.074 mmol). The reaction mixture was sealed in the reaction vial and heated at 100° C. overnight. LC-MS indicated completion. The reaction mixture was concentrated to leave brown oil. The residue was dissolved in DCM (0.25 ml). MsOH (0.024 ml, 0.369 mmol) was added. The reaction mixture was stirred at rt for 10 mins. LC-MS indicated completion. The reaction mixture was concentrated to leave brown oil. The residue was purified by Gilson (the peak was collected at −13.5 mins) to give the title compound isopropyl (2R,3S,5R)-3-((N,N-dimethylsulfamoyl)amino)-2-(((1-(5-fluoropyrimidin-2-yl)piperidin-4-yl)oxy)methyl)-5-methylpyrrolidine-1-carboxylate. (39). LC-MS 503 (M+1).

EXAMPLES 40 AND 41 methyl (CIS)-5-ethyl-3-(methyl sulfonamido)-2-(((((CIS)-4-phenylcyclohexyl)oxy)methyl)-pyrrolidine-1-carboxylate and methyl (CIS)-6-(methyl sulfonamido)-5-(((((CIS)-4-phenylcyclohexyl)oxy)methyl)-4-azaspiro[2.4]heptane-4-carboxylate

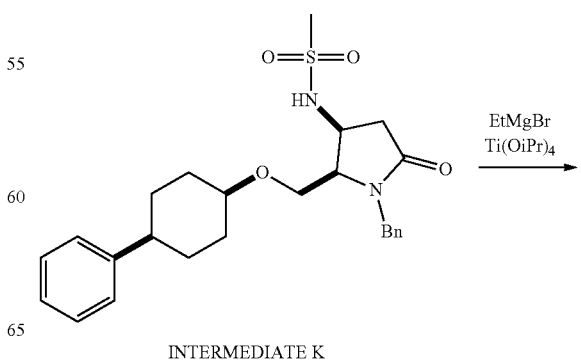

INTERMEDIATE K

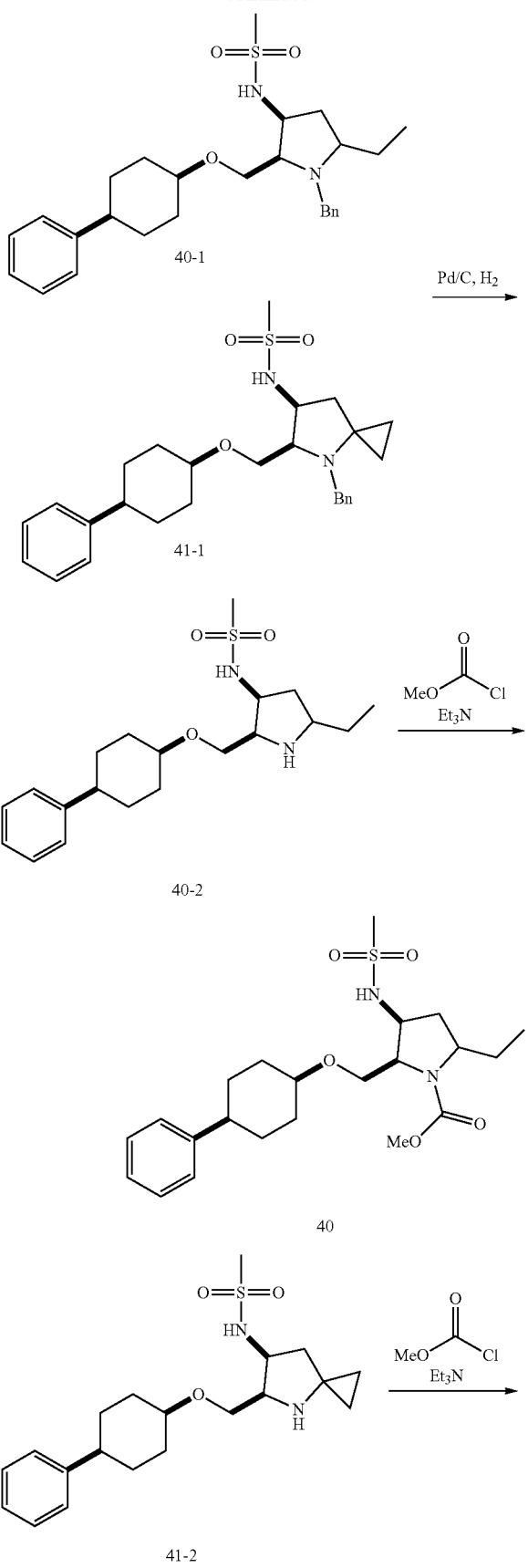
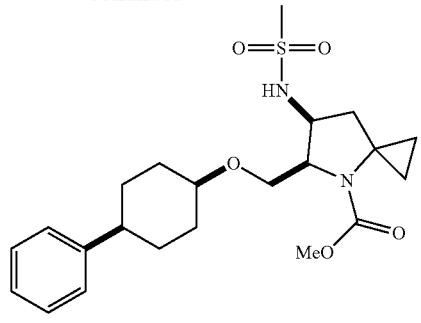

Step 1: N-((CIS)-1-benzyl-5-ethyl-2-((((CIS)-4-phenylcyclohexyl)oxy)methyl)pyrrolidin-3-yl)methanesulfonamide (40-1) and N-((CIS)-4-benzyl-5-((((CIS)-4-phenylcyclohexyl)oxy)methyl)-4-azaspiro[2.4]heptan-6-yl)methanesulfonamide (41-1)

To a mixture of N-((CIS)-1-benzyl-5-oxo-2-((((CIS)-4-phenylcyclohexyl)oxy)methyl)-pyrrolidin-3-yl)methanesulfonamide (INTERMEDIATE K) (150 mg, 0.329 mmol) in Tetrahydrofuran (2190 µl) at −78° C. was added titanium (IV) isopropoxide (289 µl, 0.986 mmol). After stirring for 10 min, add ethylmagnesium bromide (657 µl, 1.971 mmol). The mixture was stirred for 30 min before warming to ambient temperature. After 1 hour at ambient temperature was added titanium(IV) isopropoxide (289 µl, 0.986 mmol) followed by ethylmagnesium bromide (657 µl, 1.971 mmol). After another 2 hours added ethylmagnesium bromide (657 µl, 1.971 mmol). After another 2 hours the mixture was quenched with a sat'd solution of $NH_4Cl$ (15 mL), taken up in EtOAc (15 mL), filtered through a pad of diatomaceous earth, extracted with EtOAc (3× @ 15 mL), dried over $Na_2SO_4$, and concentrated. The residue was purified by column chromatography on C18 (5-95% MeCN/water with 0.05% TFA modifier) to afford a mixture of both the title compounds. 40-1 MS: 471.4 (M+1). 41-1 MS: 469.5 (M+1).

Step 2: N-((CIS)-5-ethyl-2-((((CIS)-4-phenylcyclohexyl)oxy)methyl)pyrrolidin-3-yl)methanesulfonamide (40-2) and N-((CIS)-5-((((CIS)-4-phenylcyclohexyl)oxy)methyl)-4-azaspiro[2.4]heptan-6-yl)methanesulfonamide (41-2)

To a mixture of N-((CIS)-1-benzyl-5-ethyl-2-((((CIS)-4-phenylcyclohexyl)oxy)methyl)-pyrrolidin-3-yl)methanesulfonamide (40-1) and N-((CIS)-4-benzyl-5-((((CIS)-4-phenylcyclohexyl)-oxy)methyl)-4-azaspiro[2.4]heptan-6-yl)methanesulfonamide (41-1) (60 mg, 0.128 mmol) in Methanol (1216 µl)/AcOH (64.0 µl) was added Pd/C (13.62 mg, 0.013 mmol). A H2 balloon was added (vacuum purge 3×) and the mixture was stirred for 2 hours. The resulting solution was filtered through a pad of diatomaceous earth and the filtrate was concentrated. The mixture was purified by mass triggered reverse phase HPLC (MeCN/water with 0.1% TFA modifier) to afford both title compounds separately. 40-2 MS: 381.4 (M+1). 41-2 MS: 379.4 (M+1).

Step 3: methyl (CIS)-5-ethyl-3-(methylsulfonamido)-2-((((CIS)-4-phenylcyclohexyl)oxy)-methyl)pyrrolidine-1-carboxylate (40)

To a mixture of N-((CIS)-5-ethyl-2-((((CIS)-4-phenylcyclohexyl)oxy)methyl)-pyrrolidin-3-yl)methanesulfonamide (40-2) (4 mg, 10.51 µmol) in DCM (105 µl) at ambient temperature was added triethylamine (5.86 µl, 0.042 mmol) and methyl chloroformate (1.628 µl, 0.021 mmol). The mixture was stirred for 30 min before being quenched with a few drops of H₂O.

The mixture was concentrated. The residue was purified by mass triggered reverse phase HPLC (MeCN/water with 0.1% TFA modifier) to afford the title compound. MS: 439.2 (M+1).

Step 4: methyl (CIS)-6-(methylsulfonamido)-5-(((((CIS)-4-phenylcyclohexyl)oxy)methyl)-4-azaspiro[2.4]heptane-4-carboxylate (41)

To a mixture of N-((CIS)-5-(((((CIS)-4-phenylcyclohexyl)oxy)methyl)-4-azaspiro[2.4]heptan-6-yl)methanesulfonamide (41-2) (5 mg, 0.013 mmol) in DCM (132 µl) at ambient temperature was added triethylamine (7.36 µl, 0.053 mmol) and methyl chloroformate (2.046 µl, 0.026 mmol). The mixture was stirred for 30 min before being quenched with a few drops of H₂O. The mixture was concentrated, and the residue was purified by mass triggered reverse phase HPLC (MeCN/water with 0.1% TFA modifier) to afford the title compound. MS: 437.1 (M+1).

EXAMPLE 42 methyl (CIS)-2,2-diethyl-4-(methyl sulfonamido)-5-(((((CIS)-4-phenylcyclohexyl)oxy)methyl)-pyrrolidine-1-carboxylate

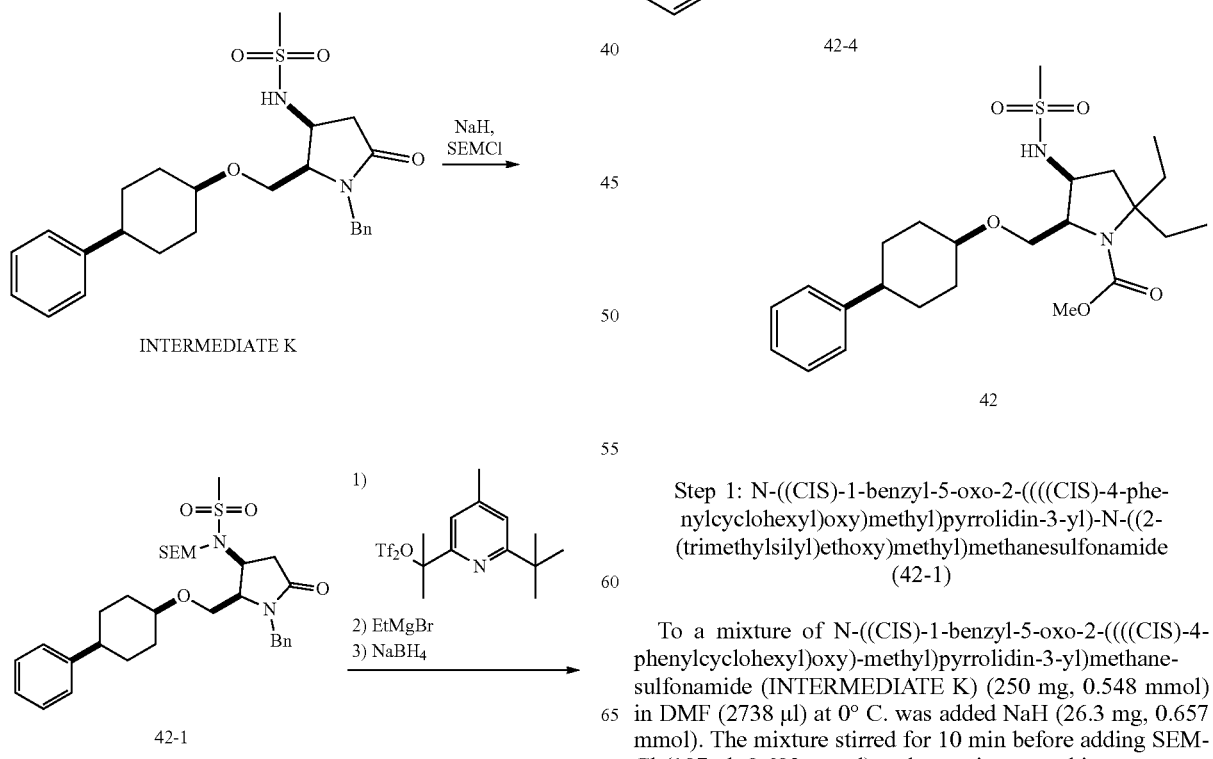

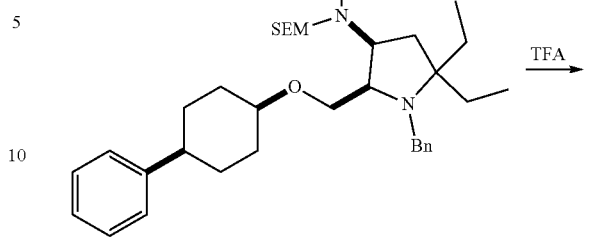

Step 1: N-((CIS)-1-benzyl-5-oxo-2-(((((CIS)-4-phenylcyclohexyl)oxy)methyl)pyrrolidin-3-yl)-N-((2-(trimethylsilyl)ethoxy)methyl)methanesulfonamide (42-1)

To a mixture of N-((CIS)-1-benzyl-5-oxo-2-(((((CIS)-4-phenylcyclohexyl)oxy)-methyl)pyrrolidin-3-yl)methanesulfonamide (INTERMEDIATE K) (250 mg, 0.548 mmol) in DMF (2738 µl) at 0° C. was added NaH (26.3 mg, 0.657 mmol). The mixture stirred for 10 min before adding SEM-Cl (107 µl, 0.602 mmol) and warming to ambient temperature. After 2 hours the reaction was quenched with H₂O (10 mL), extract with EtOAc (3× @ 10 mL), dry over Na₂SO₄, and concentrate. The residue was purified by column chromatography on silica (2% to 50% 3:1 EtOAc:EtOH/hexanes) to afford the title compound. MS: 587.5 (M+1).

Step 2: N-((CIS)-1-benzyl-5,5-diethyl-2-(((((CIS)-4-phenylcyclohexyl)oxy)methyl)pyrrolidin-3-yl)-N-((2-(trimethylsilyl)ethoxy)methyl)methanesulfonamide (42-2)

To a mixture N-((CIS)-1-benzyl-5-oxo-2-(((((CIS)-4-phenylcyclohexyl)oxy)methyl)-pyrrolidin-3-yl)-N-((2-(trimethylsilyl)ethoxy)methyl)methanesulfonamide (42-1) (50 mg, 0.085 mmol) in DCM (501 µl) at −78° C. was added 2,6-di-tert-butyl-4-methylpyridine (20.99 mg, 0.102 mmol) followed by TriflicAnhydride (102 µl, 0.102 mmol) in DCM. The reaction was stirred for 45 min before adding ethylmagnesium bromide (28.4 µl, 0.085 mmol) in Et₂O before slowly warming to ambient temperature over 1 hour. Next, NaBH₄ (9.67 mg, 0.256 mmol) was added along 1.0 mL DCM and 0.5 mL MeOH and the mixture stirred for 2 hours. The resulting mixture was concentrated, and the residue was purified by column chromatography on C18 (5-95% MeCN/water with 0.05% TFA modifier) to afford the title compound. MS: 629.4 (M+1).

Step 3: N-((CIS)-1-benzyl-5,5-diethyl-2-(((((CIS)-4-phenylcyclohexyl)oxy)methyl)pyrrolidin-3-yl)methanesulfonamide (42-3)

To a mixture of N-((CIS)-1-benzyl-5,5-diethyl-2-(((((CIS)-4-phenylcyclohexyl)-oxy)methyl)pyrrolidin-3-yl)-N-((2-(trimethylsilyl)ethoxy)methyl)methanesulfonamide (42-2) (35 mg, 0.056 mmol) in DCM (556 µl) was added TFA (86 µl, 1.113 mmol). The mixture was stirred for 16 hours. The mixture was concentrated and placed under vacuum. The residue was taken up in Dioxane (185 µl) at ambient temperature and added 4.0 M HCl (278 µl, 1.113 mmol) in Dioxane. The mixture was heated to 50° C. and stirred for 4 hours. The resulting mixture was concentrated and placed under vacuum to afford the title compound. MS: 499.4 (M+1).

Step 4: N-((CIS)-5,5-diethyl-2-(((((CIS)-4-phenylcyclohexyl)oxy)methyl)pyrrolidin-3-yl)methanesulfonamide (42-4)

To a mixture of N-((CIS)-1-benzyl-5,5-diethyl-2-(((((CIS)-4-phenylcyclohexyl)oxy)-methyl)pyrrolidin-3-yl)methanesulfonamide (42-3) (25 mg, 0.050 mmol) in MeOH (501 µl) was added Pd/C (5.33 mg, 5.01 µmol). A hydrogen balloon was added (vacuum purge 3×) and the reaction was stirred overnight. The resulting residue was filtered through a pad of diatomaceous earth and the resulting filtrate was concentrated to the title compound. MS: 409.4 (M+1).

Step 5: methyl (CIS)-2,2-diethyl-4-(methylsulfonamido)-5-(((((CIS)-4-phenylcyclohexyl)oxy)methyl) pyrrolidine-1-carboxylate (22)

To a mixture of N-((CIS)-5,5-diethyl-2-(((((CIS)-4-phenylcyclohexyl)oxy)methyl)-pyrrolidin-3-yl)methanesulfonamide (42-4) (15 mg, 0.037 mmol) in DCM (367 µl) at ambient temperature was added triethylamine (10.23 µl, 0.073 mmol) and methyl chloroformate (4.27 µl, 0.055 mmol). The reaction was stirred for 24 hours. Methyl chloroformate (4.27 µl, 0.055 mmol), triethylamine (10.23 µl, 0.073 mmol), and DMAP (0.224 mg, 1.836 µmol) were added. The mixture was stirred for another 24 hours, and the reaction was concentrated. The residue was purified by mass triggered reverse phase HPLC (MeCN/water with 0.1% TFA modifier) to afford the title compound. MS: 467.3 (M+1).

EXAMPLE 43

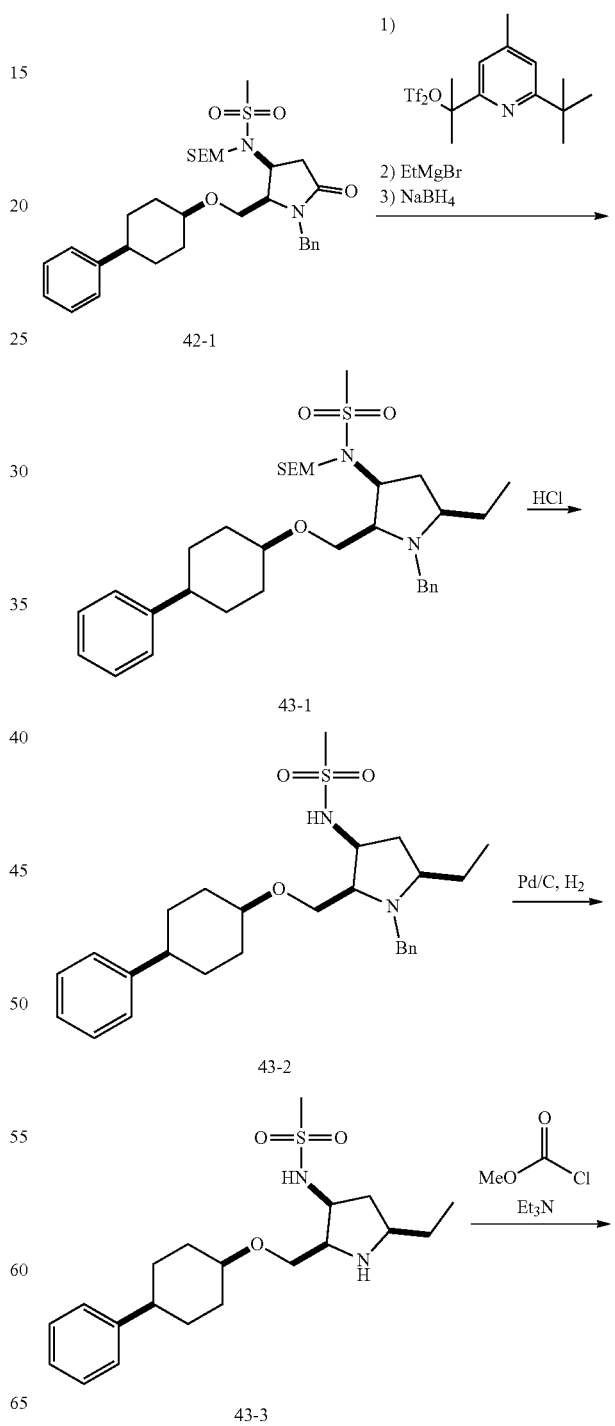

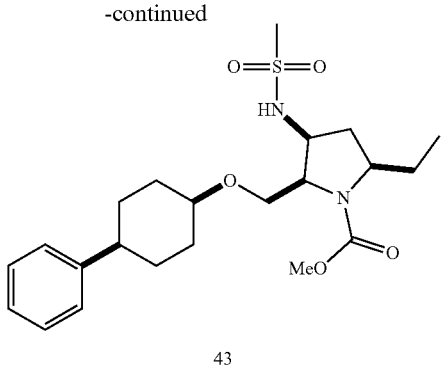

43 methyl (2R,3S,5R)-5-ethyl-3-(methylsulfonamido)-2-((((CIS)-4-phenylcyclohexyl)oxy)methyl)-pyrrolidine-1-carboxylate Step 1: N-((2R,3S)-1-benzyl-5-ethyl-2-((((CIS)-4-phenylcyclohexyl)oxy)methyl)pyrrolidin-3-yl)-N-((2-(trimethylsilyl)ethoxy)methyl)methanesulfonamide (racemic) (43-1)

To a mixture of N-((CIS)-1-benzyl-5-oxo-2-((((CIS)-4-phenylcyclohexyl)oxy)methyl)-pyrrolidin-3-yl)-N-((2-(trimethylsilyl)ethoxy)methyl)methanesulfonamide (42-1) (250 mg, 0.426 mmol) in DCM (4260 µl) at −78° C. was added 2,6-di-tert-butyl-4-methylpyridine (105 mg, 0.511 mmol) followed by Triflic Anhydride (511 µl, 0.511 mmol) in DCM. The reaction mixture was warmed to 0° C. and stirred for one hour. The reaction was cooled back to −78° C. and ethylmagnesium bromide (142 µl, 0.426 mmol) in Et₂O was added before slowly warming to ambient temperature over 1 hour. Next, NaBH₄ (48.3 mg, 1.278 mmol) was added with 1.0 mL DCM and 0.5 mL MeOH and the mixture was stirred for 2 hours. The resulting mixture was concentrated, and the residue was purified by column chromatography on C18 (5-95% MeCN/water with 0.05% TFA modifier) to afford the title compound. MS: 601.5 (M+1).

Step 2: N-((2R,3S,5R)-1-benzyl-5-ethyl-2-((((CIS)-4-phenylcyclohexyl)oxy)methyl)pyrrolidin-3-yl)-N-((2-(trimethylsilyl)ethoxy)methyl)methanesulfonamide (racemic) (43-2)

To a mixture of N-((2R,3S)-1-benzyl-5-ethyl-2-((((CIS)-4-phenylcyclohexyl)oxy)-methyl)pyrrolidin-3-yl)-N-((2-(trimethylsilyl)ethoxy)methyl)methanesulfonamide (racemic) (43-1) (115 mg, 0.183 mmol) in Dioxane (609 µl) at ambient temperature was added 4.0 M HCl (914 µl, 3.66 mmol) in dioxanes. The mixture was heated to 50° C. and stirred for 8 hours. The resulting mixture was concentrated and placed under vacuum. The residue was purified by reverse phase HPLC (MeCN/water with 0.1% TFA modifier) to afford the title compound. MS: 471.3 (M+1).

Step 3: N-((2R,3S,5R)-5-ethyl-2-((((CIS)-4-phenylcyclohexyl)oxy)methyl)pyrrolidin-3-yl)methanesulfonamide (racemic) (43-3)

To a mixture of N-((2R,3S,5R)-1-benzyl-5-ethyl-2-((((CIS)-4-phenylcyclohexyl)-oxy)methyl)pyrrolidin-3-yl)-N-((2-(trimethylsilyl)ethoxy)methyl)methanesulfonamide (racemic) (43-2) (50.0 mg, 0.106 mmol) in MeOH (1062 µl) was added Pd/C (11.31 mg, 10.62 µmol). A hydrogen balloon was added (vacuum purge 3×) and the reaction was stirred 8 h. The resulting residue was filtered through a pad of diatomaceous earth and the resulting filtrate was concentrated to the title compound. MS: 381.2 (M+1).

Step 4: methyl (2R,3S,5R)-5-ethyl-3-(methylsulfonamido)-2-((((CIS)-4-phenylcyclohexyl)-oxy)methyl)pyrrolidine-1-carboxylate (racemic) (43)

To a mixture of N-((2R,3S,5R)-5-ethyl-2-((((CIS)-4-phenylcyclohexyl)oxy)-methyl)pyrrolidin-3-yl)methanesulfonamide (racemic) (43-3) (40 mg, 0.098 mmol) in DCM (979 µl) at ambient temperature was added triethylamine (40.9 µl, 0.294 mmol) and methyl chloroformate (11.37 µl, 0.147 mmol). The reaction was stirred for 2 hours before being concentrated. The residue was purified by reverse phase HPLC (MeCN/water with 0.1% TFA modifier) to afford the title compound. MS: 439.4 (M+1). $^1$H NMR (500 MHz, Chloroform-d) δ 7.32 (t, J=7.5 Hz, 2H), 7.28-7.15 (m, 3H), 5.52 (d, J=78.8 Hz, 1H), 4.96 (brs, 1H), 4.24 (d, J=42.4 Hz, 1H), 4.05 (brs, 1H), 3.81-3.59 (m, 6H), 3.02 (s, 3H), 2.62-2.50 (m, 2H), 2.25 (brs, 1H), 2.11-2.01 (m, 2H), 1.85 (brs, 1H), 1.81-1.69 (m, 4H), 1.69-1.53 (m, 2H), 1.47 (brs, 1H), 0.90 (t, J=7.5 Hz, 3H).

The following compound was prepared according to the general procedure provided in Examples 1-21, and procedures herein, by substituting the appropriate alkyl carbonochloridate and sulfamoyl chloride. The starting materials are either prepared as described in the intermediates section, commercially available, or may be prepared from commercially available reagents using conventional reactions well known in the art.

| Example Number | Structure | Name | Exact Mass [M + H]⁺ |
|---|---|---|---|
| 44 | 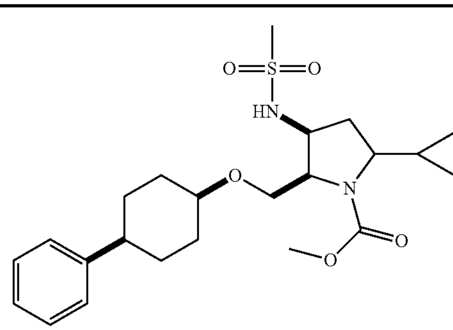 | methyl (CIS)-5-cyclopropyl-3-(methylsulfonamido)-2-((((CIS)-4-phenylcyclohexyl)oxy)methyl)pyrrolidine-1-carboxylate | 451.0 |

EXAMPLE 45 and EXAMPLE 46 methyl (2S,3R,5S)-5-ethyl-3-(methylsulfonamido)-2-(((((CIS)-4-phenylcyclohexyl)oxy)methyl)-pyrrolidine-1-carboxylate and methyl (2R,3S,5R)-5-ethyl-3-(methylsulfonamido)-2-(((((CIS)-4-phenylcyclohexyl)oxy)methyl)pyrrolidine-1-carboxylate

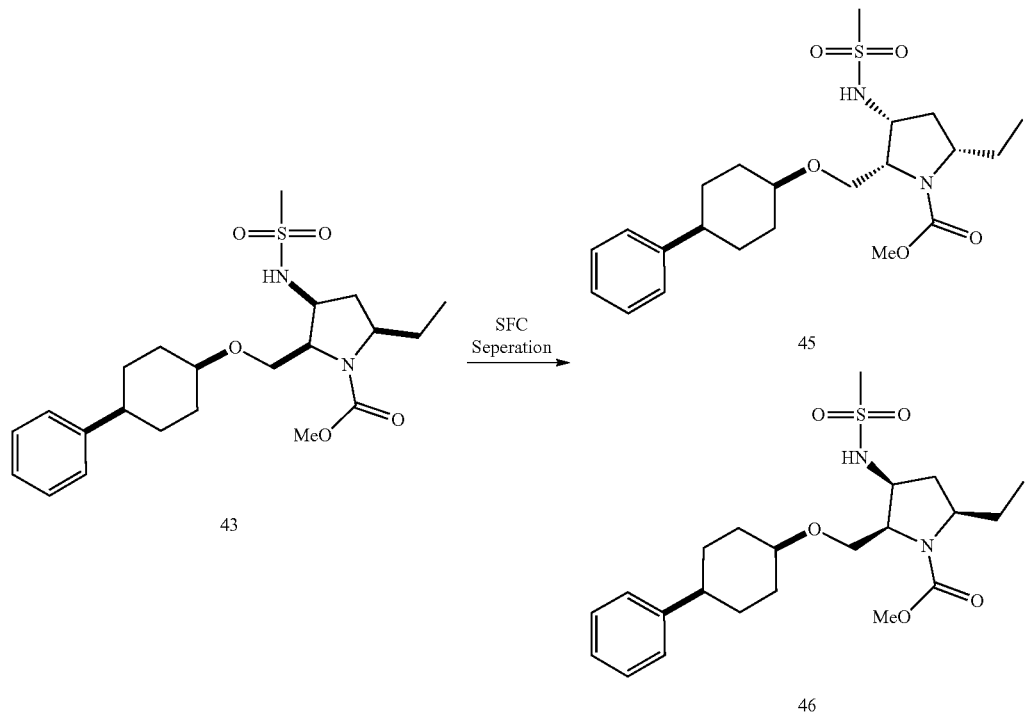 [SMILES: CC[C@@H]1C[C@H](NS(C)(=O)=O)[C@H](CO[C@H]2CC[C@@H](c3ccccc3)CC2)N1C(=O)OC ; CC[C@@H]1C[C@H](NS(C)(=O)=O)[C@H](CO[C@H]2CC[C@@H](c3ccccc3)CC2)N1C(=O)OC ; CC[C@H]1C[C@@H](NS(C)(=O)=O)[C@@H](CO[C@H]2CC[C@@H](c3ccccc3)CC2)N1C(=O)OC]

A mixture of methyl (2R,3S,5R)-5-ethyl-3-(methylsulfonamido)-2-(((((CIS)-4-phenylcyclohexyl)oxy)methyl)pyrrolidine-1-carboxylate (racemic) (23) was subjected to SFC purification, OJ-H, 21×250 mm, 15% (MeOH) to obtain two chiral isomers: methyl (2S,3R,5S)-5-ethyl-3-(methylsulfonamido)-2-(((((CIS)-4-phenylcyclohexyl)oxy)methyl)pyrrolidine-1-carboxylate (25, peak 1): MS: 439.2. $^1$H NMR (500 MHz, Chloroform-d) δ 7.32 (t, J=7.6 Hz, 2H), 7.27-7.18 (m, 3H), 5.54 (d, J=77.8 Hz, 1H), 4.23 (d, J=44.0 Hz, 1H), 4.13-3.96 (m, 1H), 3.72 (d, J=10.6 Hz, 6H), 3.01 (s, 3H), 2.62-2.48 (m, 2H), 2.27 (brs, 1H), 2.07 (d, J=14.5 Hz, 2H), 1.84 (brs, 1H), 1.81-1.69 (m, 4H), 1.69-1.55 (m, 2H), 1.55-1.39 (m, 1H), 0.91 (q, J=7.9, 7.5 Hz, 3H). methyl (2R,3S,5R)-5-ethyl-3-(methylsulfonamido)-2-(((((CIS)-4-phenylcyclohexyl)oxy)methyl)-pyrrolidine-1-carboxylate (26, peak 2): MS: 439.2. $^1$H NMR (500 MHz, Chloroform-d) δ 7.32 (t, J=7.5 Hz, 1H), 7.27-7.18 (m, 3H), 5.55 (d, J=77.3 Hz, 1H), 4.23 (d, J=40.7 Hz, 1H), 4.09-4.00 (m, 1H), 3.72 (d, J=10.6 Hz, 6H), 3.01 (s, 3H), 2.63-2.49 (m, 2H), 2.27 (brs, 1H), 2.07 (d, J=14.3 Hz, 2H), 1.84 (brs, 1H), 1.80-1.69 (m, 4H), 1.69-1.53 (m, 2H), 1.53-1.40 (m, 1H), 0.90 (t, J=7.4 Hz, 3H).

EXAMPLE 47 methyl (CIS)-5-ethynyl-3-(methylsulfonamido)-2-(((((CIS)-4-phenylcyclohexyl)oxy)methyl)-pyrrolidine-1-carboxylate

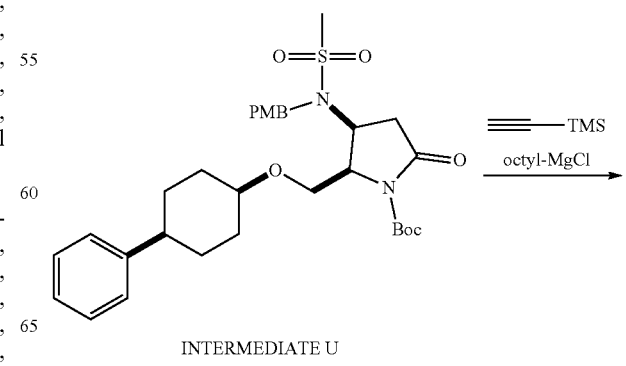

INTERMEDIATE U

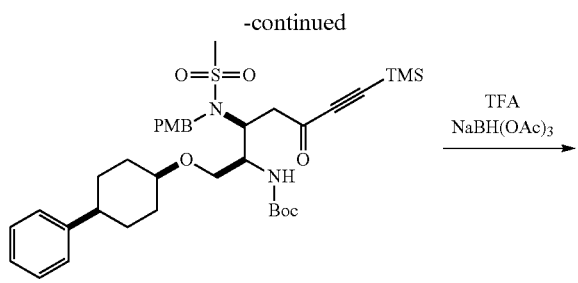

47-1

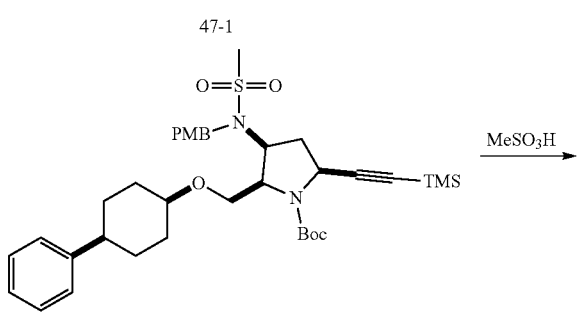

47-2

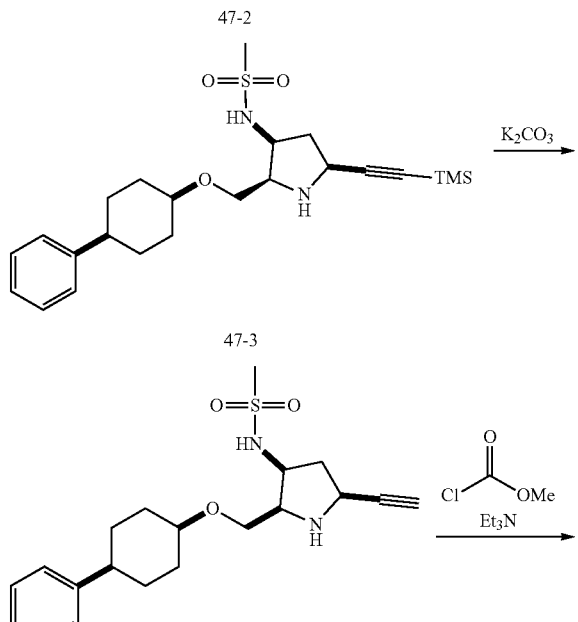

47-3

47-4

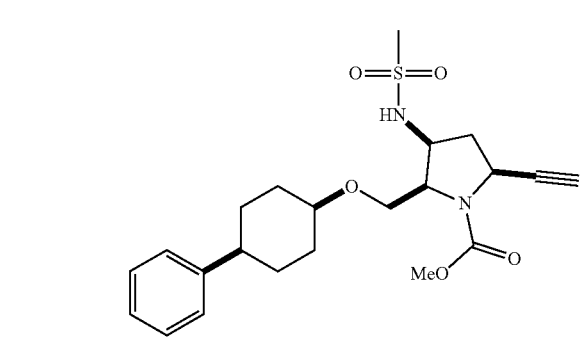

47

Step 1: tert-butyl ((CIS)-3-(N-(4-methoxybenzyl) methylsulfonamido)-5-oxo-1-(((CIS)-4-phenylcyclohexyl)oxy)-7-(trimethylsilyl)hept-6-yn-2-yl)carbamate (47-1)

To a mixture of ethynyltrimethylsilane (803 µl, 5.79 mmol) in THF (7243 µl) at 0° C. was added 2.0 M octylmagnesium chloride in THF (2173 µl, 4.35 mmol). The reaction stirred for 1 hour. In a separate flask combine tert-butyl (CIS)-3-(N-(4-methoxybenzyl)methylsulfonamido)-5-oxo-2-((((CIS)-4-phenylcyclohexyl)oxy)methyl) pyrrolidine-1-carboxylate (INTERMEDIATE U) (850 mg, 1.449 mmol) with THF (7243 µl) and cool to −10° C. Add 1 equiv. Grignard reagent to the flask containing the lactam. After 1 hour, add another 1 equiv. of Grignard reagent and stir for another 30 min. Quench the reaction with a saturated solution of NH4Cl (5 mL) and warm to ambient temperature. The reaction mixture was extracted with EtOAc (3× @ 5 mL), dried over Na2SO4, and concentrated. The residue was purified by column chromatography on silica (2% to 70% 3:1 EtOAc:EtOH/hexanes) to afford the title compound. MS: 685.5 (M+1).

Step 2: tert-butyl (CIS)-3-(N-(4-methoxybenzyl) methylsulfonamido)-2-((((CIS)-4-phenylcyclohexyl) oxy)methyl)-5-((trimethyl silyl)ethynyl)pyrrolidine-1-carboxylate (47-2)

To a mixture of tert-butyl ((CIS)-3-(N-(4-methoxybenzyl) methylsulfonamido)-5-oxo-1-(((CIS)-4-phenylcyclohexyl) oxy)-7-(trimethylsilyl)hept-6-yn-2-yl)carbamate (47-1) (560 mg, 0.818 mmol) in EtOAc (5450 µl) at 0° C. was added SODIUM TRIACETOXYBOROHYDRIDE (260 mg, 1.226 mmol) followed by TFA (252 µl, 3.27 mmol) dropwise. After 4 hours, add SODIUM TRIACETOXYBOROHYDRIDE (260 mg, 1.226 mmol) and TFA (252 µl, 3.27 mmol). The mixture stirred overnight before adding SODIUM TRIACETOXYBOROHYDRIDE (260 mg, 1.226 mmol) and TFA (252 µl, 3.27 mmol) reaction was stirred overnight. The mixture was quenched with a saturated solution of NaHCO3 (10 mL), extracted with EtOAc (3× @ 10 mL), dried over Na2SO4, and concentrated. The residue was purified by column chromatography on silica (2% to 70% 3:1 EtOAc:EtOH/hexanes) to afford the title compound. MS: 691.3 (M+23).

Step 3: N-((CIS)-2-((((CIS)-4-phenylcyclohexyl) oxy)methyl)-5-((trimethylsilyl)ethynyl)pyrrolidin-3-yl)methanesulfonamide (47-3)

To a mixture of tert-butyl (CIS)-3-(N-(4-methoxybenzyl) methylsulfonamido)-2-((((CIS)-4-phenylcyclohexyl)oxy) methyl)-5-((trimethylsilyl)ethynyl)pyrrolidine-1-carboxylate (27-2) (422 mg, 0.631 mmol) in DCM (4206 µl) at ambient temperature was added METHANESULFONIC ACID (410 µl, 6.31 mmol) dropwise. The mixture stirred for 2 hours before quenching with a saturated solution of NaHCO3 (5 mL), extracting with EtOAc (3× @ 5 mL), dried over Na2SO4, and concentrated to afford the title compound. MS: 449.2 (M+1).

Step 4: N-((CIS)-5-ethynyl-2-((((CIS)-4-phenylcyclohexyl)oxy)methyl)pyrrolidin-3-yl)methanesulfonamide (47-4)

To a mixture of N-((CIS)-2-((((CIS)-4-phenylcyclohexyl) oxy)methyl)-5-((trimethylsilyl)-ethynyl)pyrrolidin-3-yl)

methanesulfonamide (47-3) (283 mg, 0.631 mmol) in MeOH (4205 μl) at ambient temperature was added K2CO3 (174 mg, 1.261 mmol). The mixture stirred for 2 hours before filtering off the solids and concentrating to afford the title compound. MS: 377.4 (M+1).

Step 5: methyl (CIS)-5-ethynyl-3-(methylsulfonamido)-2-((((CIS)-4-phenylcyclohexyl)oxy)methyl)-pyrrolidine-1-carboxylate (47)

To a mixture of N-((CIS)-5-ethynyl-2-((((CIS)-4-phenylcyclohexyl)oxy)methyl)pyrrolidin-3-yl)methanesulfonamide (47-4) (237.0 mg, 0.629 mmol) in DCM (4196 μl) was added METHYL CHLOROFORMATE (63.4 μl, 0.818 mmol) and TRIETHYLAMINE (175 μl, 1.259 mmol). The mixture stirred for 1 hour before concentrating. The residue was purified by column chromatography on C18 (5-95% MeCN/water with 0.05% TFA modifier) to afford the title compound. MS: 435.3 (M+1). 1H NMR (500 MHz, Chloroform-d) δ 7.33-7.29 (m, 2H), 7.28-7.24 (m, 2H), 7.20 (t, J=7.1 Hz, 1H), 5.80-5.48 (m, 1H), 4.45 (s, 1H), 4.26-4.03 (m, 2H), 3.78 (d, J=6.3 Hz, 3H), 3.73 (s, 1H), 3.02 (s, 3H), 2.70 (dt, J=12.4, 7.6 Hz, 1H), 2.63-2.51 (m, 2H), 2.46-2.34 (m, 1H), 2.26 (s, 1H), 2.19-2.00 (m, 2H), 1.89-1.68 (m, 4H), 1.60 (dt, J=27.0, 12.9 Hz, 2H).

EXAMPLE 48 methyl (CIS)-3-(methylsulfonamido)-2-((((CIS)-4-phenylcyclohexyl)oxy)methyl)-5-vinylpyrrolidine-1-carboxylate (48)

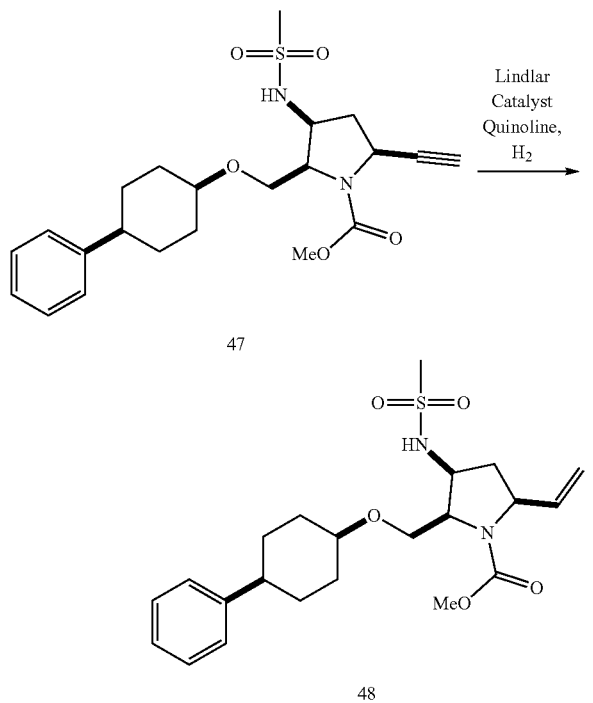

To a mixture of methyl (CIS)-5-ethynyl-3-(methylsulfonamido)-2-((((CIS)-4-phenylcyclohexyl)oxy)methyl)pyrrolidine-1-carboxylate (47) (25 mg, 0.058 mmol) in Methanol (575 μl) at ambient temperature was added QUINOLINE (13.63 μl, 0.115 mmol) and Lindlar Catalyst (6.12 mg, 2.88 μmol). A balloon of H2 was added (vacuum purge 3×) and the mixture stirred for 3 hours. The mixture was filtered through a pad of celite and concentrated. The residue was purified by column chromatography on C18 (5-95% MeCN/water with 0.05% TFA modifier) to afford the title compound. MS: 437.4 (M+1). 1H NMR (500 MHz, Chloroform-d) δ 7.32 (t, J=7.5 Hz, 2H), 7.25 (d, J=7.1 Hz, 2H), 7.21 (t, J=7.2 Hz, 1H), 5.91-5.81 (m, 1H), 5.57-5.02 (m, 4H), 4.31-4.15 (m, 2H), 4.14-4.01 (m, 1H), 3.88-3.76 (m, 2H), 3.72 (s, 3H), 3.02 (s, 3H), 2.59 (dt, J=15.2, 7.9 Hz, 2H), 2.07 (d, J=14.8 Hz, 2H), 2.01 (d, J=10.2 Hz, 1H), 1.83-1.68 (m, 3H), 1.68-1.52 (m, 2H).

EXAMPLE 49 methyl (CIS)-5-(2-hydroxyethyl)-3-(methylsulfonamido)-2-((((CIS)-4-phenylcyclohexyl)oxy)methyl)pyrrolidine-1-carboxylate

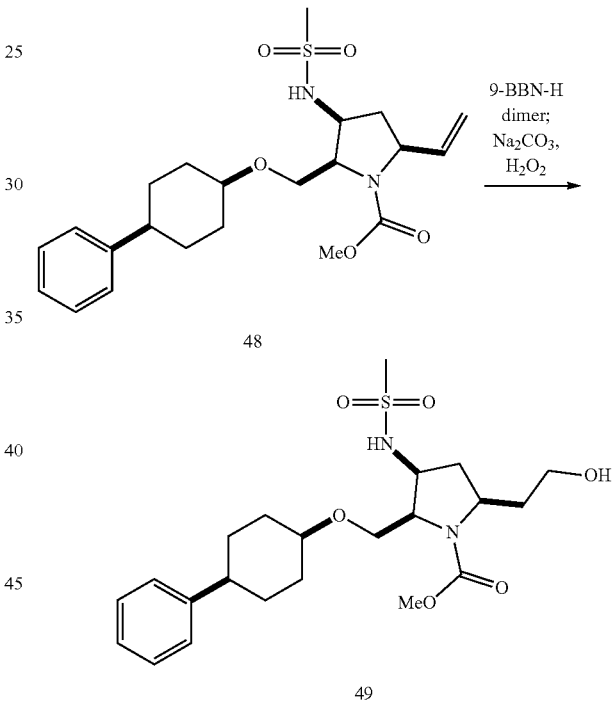

To a mixture of methyl (CIS)-3-(methylsulfonamido)-2-((((CIS)-4-phenylcyclohexyl)oxy)methyl)-5-vinylpyrrolidine-1-carboxylate (48) (10 mg, 0.023 mmol) in THF (229 μl) at ambient temperature was added 9-BBNDimer (8.32 mg, 0.034 mmol). The mixture was heated to 50° C. for one hour before cooling to 0° C. To the mixture was added SODIUM CARBONATE (45.8 μl, 0.092 mmol) and 30% H2O2 (8.02 μl, 0.092 mmol). The mixture stirred for 2 hours before purifying directly using column chromatography on C18 (5-95% MeCN/water with 0.05% TFA modifier) to afford the title compound. MS: 455.4 (M+1). 1H NMR (500 MHz, Chloroform-d) δ 7.32 (t, J=7.6 Hz, 2H), 7.22 (dd, J=16.2, 7.6 Hz, 3H), 5.38 (s, 1H), 4.27 (s, 1H), 4.14-4.01 (m, 2H), 3.75 (s, 3H), 3.72 (d, J=13.9 Hz, 4H), 3.01 (s, 3H), 2.61 (dt, J=15.7, 8.0 Hz, 2H), 2.07 (s, 3H), 1.88 (s, 2H), 1.82-1.55 (m, 8H).

EXAMPLE 50 methyl (CIS)-5-(hydroxymethyl)-3-(methylsulfonamido)-2-((((CIS)-4-phenylcyclohexyl)oxy)-methyl)pyrrolidine-1-carboxylate

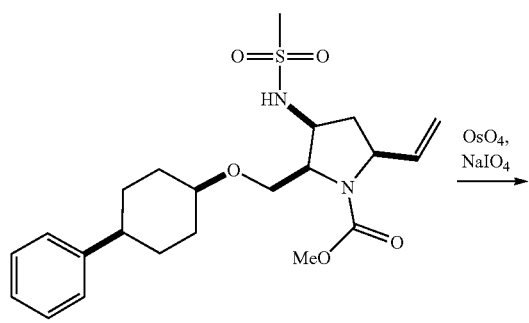

48

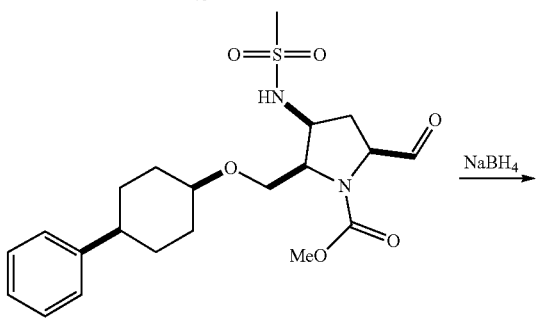

50-1

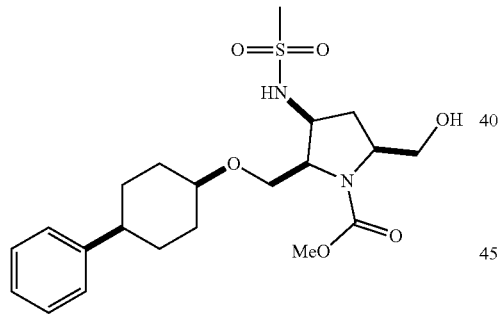

50

Step 1: methyl (CIS)-5-formyl-3-(methyl sulfonamido)-2-((((CIS)-4-phenylcyclohexyl)oxy)-methyl)pyrrolidine-1-carboxylate (50-1)

To a mixture of methyl (CIS)-3-(methyl sulfonamido)-2-((((CIS)-4-phenylcyclohexyl)oxy)-methyl)-5-vinylpyrrolidine-1-carboxylate (48) (110 mg, 0.252 mmol) in THF (13.4 mL)/Water (3.35 mL) at ambient temperature was added SODIUM PERIODATE (269 mg, 1.260 mmol) and 2.5% OSMIUM TETROXIDE (0.051 mL, 5.04 μmol) in water. The mixture was allowed to stir overnight before quenching with a saturated solution of sodium thiosulfate (15 mL), NaHCO$_3$ (15 mL), extracting with DCM (3× @ 15 mL), drying over Na2SO4, and concentrating to afford the title compound. MS: 439.2 (M+1).

Step 2: methyl (CIS)-5-(hydroxymethyl)-3-(methylsulfonamido)-2-((((CIS)-4-phenylcyclohexyl)oxy)methyl)pyrrolidine-1-carboxylate (50)

To a mixture of methyl (CIS)-5-formyl-3-(methyl sulfonamido)-2-((((CIS)-4-phenylcyclo-hexyl)oxy)methyl)pyrrolidine-1-carboxylate (50-1) (110.0 mg, 0.251 mmol) in MeOH (2508 μl) at ambient temperature was added NaBH4 (9.49 mg, 0.251 mmol). The mixture stirred for overnight before adding a few drops of 2.0 M HCl. The resulting mixture was purified directly by column chromatography on C18 (5-95% MeCN/water with 0.05% TFA modifier) to afford the title compound. MS: 441.4 (M+1). 1H NMR (500 MHz, Chloroform-d) δ 7.33 (t, J=7.6 Hz, 2H), 7.27-7.19 (m, 3H), 5.64-5.50 (m, 1H), 5.27 (s, 1H), 4.78-4.63 (m, 1H), 4.46 (s, 1H), 4.30-3.97 (m, 3H), 3.89 (d, J=10.3 Hz, 1H), 3.85-3.64 (m, 5H), 3.02 (s, 3H), 2.60 (t, J=11.2 Hz, 1H), 2.48 (s, 1H), 2.14-1.96 (m, 3H), 1.85-1.55 (m, 6H).

EXAMPLE 51 methyl (2R,3S,5S)-3-((N,N-dimethylsulfamoyl)amino)-2-((((CIS)-4-(3-fluorophenyl)cyclohexyl)-oxy)methyl)-5-(methoxymethyl)pyrrolidine-1-carboxylate (51)

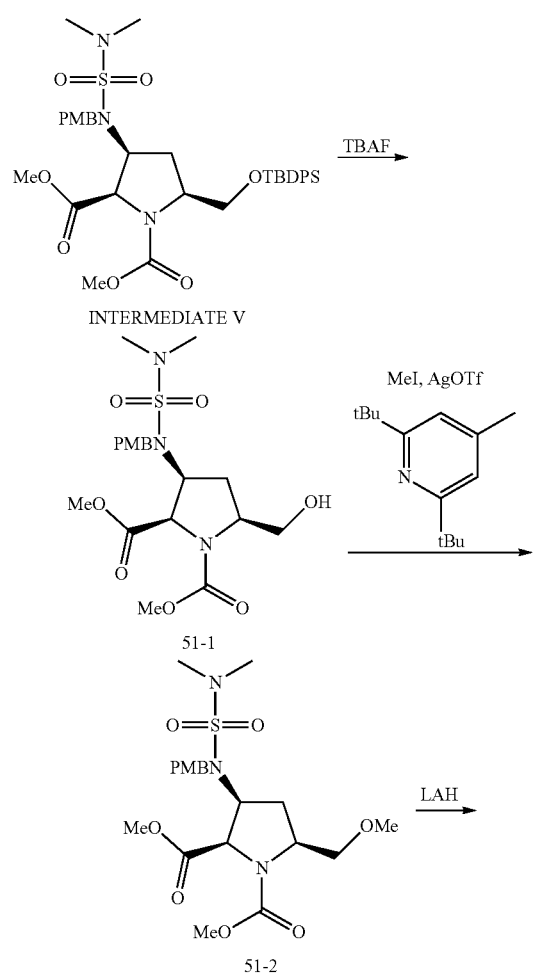

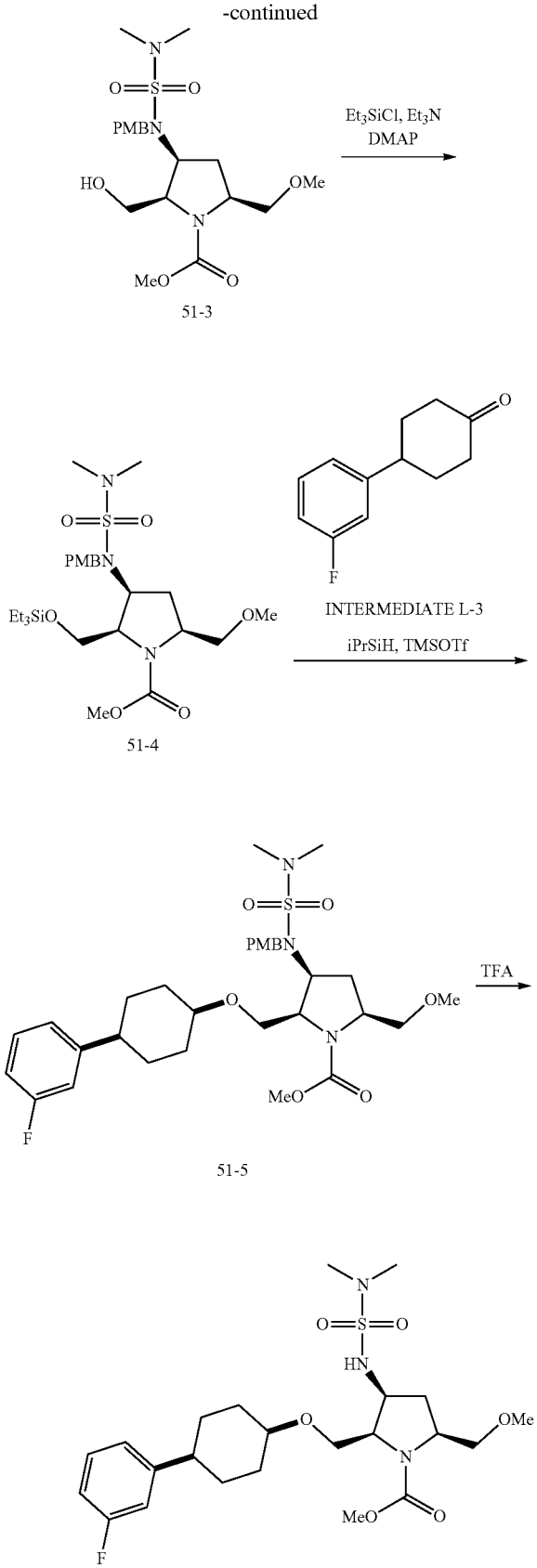

Step 1: dimethyl (2R,3S,5S)-3-((N,N-dimethylsulfamoyl)(4-methoxybenzyl)amino)-5-(hydroxymethyl)pyrrolidine-1,2-dicarboxylate (51-1)

To a mixture of dimethyl (2R,3S,5S)-5-(((tert-butyldiphenylsilyl)oxy)methyl)-3-((N,N-dimethylsulfamoyl)(4-methoxybenzyl)amino)pyrrolidine-1,2-dicarboxylate (INTERMEDIATE V) (175 mg, 0.251 mmol) in THF (501 μl) at ambient temperature was added 1.0 MTBAF (501 μl, 0.501 mmol) in THF. The mixture stirred for 4 hours before concentrating. The residue was purified by column chromatography on silica (1% to 80% 3:1 EtOAc:EtOH/hexanes) to afford the title compound. MS: 460.4 (M+1).

Step 2: dimethyl (2R,3S,5S)-3-((N,N-dimethylsulfamoyl)(4-methoxybenzyl)amino)-5-(methoxymethyl)pyrrolidine-1,2-dicarboxylate (51-2)

To a mixture of dimethyl (2R,3S,5S)-3-((N,N-dimethyl sulfamoyl)(4-methoxybenzyl)amino)-5-(hydroxymethyl)pyrrolidine-1,2-dicarboxylate (51-1) (100 mg, 0.218 mmol) in DCM (1088 μl) at 0° C. was added IODOMETHANE (21.77 μl, 0.348 mmol), 2,6-di-tert-butyl-4-methylpyridine (89 mg, 0.435 mmol), and SILVER TRIFLUOROMETHANESULFONATE (89 mg, 0.348 mmol). The mixture was allowed to warm to ambient temperature and stirred overnight. The resulting mixture was filtered through a pad of celite and concentrated. The residue was purified by column chromatography on silica (2% to 75% EtOAc/hexanes) to afford the title compound. MS: 474.3 (M+1).

Step 3: methyl (2R,3S,5S)-3-((N,N-dimethylsulfamoyl)(4-methoxybenzyl)amino)-2-(hydroxymethyl)-5-(methoxymethyl)pyrrolidine-1-carboxylate (51-3)

To a mixture of dimethyl (2R,3S,5S)-3-((N,N-dimethyl sulfamoyl)(4-methoxybenzyl)-amino)-5-(methoxymethyl)pyrrolidine-1,2-dicarboxylate (51-2) (70 mg, 0.148 mmol) in THF (2956 μl) at −20° C. was added 1.0 M LAH (148 μl, 0.148 mmol) in THF. The mixture stirred for 20 min before quenching with solid Na2SO4-10H2O. After stirring for 20 min, the mixture was filtered through a pad of celite and concentrated to afford the title compound. MS: 446.4 (M+1).

Step 4: methyl (2R,3S,5S)-3-((N,N-dimethylsulfamoyl)(4-methoxybenzyl)amino)-5-(methoxymethyl)-2-((((triethylsilyl)oxy)methyl)pyrrolidine-1-carboxylate (51-4)

To a mixture of methyl (2R,3S,5S)-3-((N,N-dimethyl sulfamoyl)(4-methoxybenzyl)-amino)-2-(hydroxymethyl)-5-(methoxymethyl)pyrrolidine-1-carboxylate (51-3) (65 mg, 0.146 mmol) in DCM (729 μl) at ambient temperature was added TRIETHYLAMINE (30.5 μl, 0.219 mmol), DMAP (1.782 mg, 0.015 mmol), and chlorotriethylsilane (29.4 μl, 0.175 mmol). The mixture stirred overnight before concentrating. The residue was purified by column chromatography on silica (1% to 50% EtOAc/hexanes) to afford the title compound.

Step 5: methyl (2R,3S,5S)-3-((N,N-dimethylsulfamoyl)(4-methoxybenzyl)amino)-2-((((CIS)-4-(3-fluorophenyl)cyclohexyl)oxy)methyl)-5-(methoxymethyl)pyrrolidine-1-carboxylate (51-5)

To a mixture of methyl (2R,3S,5S)-3-((N,N-dimethyl sulfamoyl)(4-methoxybenzyl)amino)-5-(methoxymethyl)-

2-(((triethylsilyl)oxy)methyl)pyrrolidine-1-carboxylate (51-4) (45 mg, 0.080 mmol) in Acetonitrile (2412 μl)/DCM (268 μl) at ambient temperature was added 4-(3-fluorophenyl)cyclohexan-1-one (INTERMEDIATE L-3) (30.9 mg, 0.161 mmol) and triisopropylsilane (32.9 μl, 0.161 mmol). The mixture was cooled to −30° C. and TRIMETHYLSILYL TRIFLUOROMETHANESULFONATE (14.53 μl, 0.080 mmol) was added dropwise. The mixture was warmed to 0° C. and stirred for 10 min before quenching with a saturated solution of NaHCO₃ (10 mL), extract with DCM (3× @ 10 mL), dry over Na2SO4, and concentrate.

The residue was purified by column chromatography on silica (0% to 50% EtOAc/hexanes) to afford the title compound. MS: 622.5 (M+1).

Step 6: methyl (2R,3S,5S)-3-((N,N-dimethylsulfamoyl)amino)-2-((((CIS)-4-(3-fluorophenyl)cyclohexyl)oxy)methyl)-5-(methoxymethyl)pyrrolidine-1-carboxylate (51)

To a mixture of methyl (2R,3S,5S)-3-((N,N-dimethylsulfamoyl)(4-methoxybenzyl)-amino)-2-((((CIS)-4-(3-fluorophenyl)cyclohexyl)oxy)methyl)-5-(methoxymethyl)pyrrolidine-1-carboxylate (51-5) (30 mg, 0.048 mmol) in DCM (241 μl) at ambient temperature was added TFA (37.2 μl, 0.482 mmol). The mixture stirred for 2 hours before concentrating. The residue was purified by column chromatography on C18 (5-95% MeCN/water with 0.05% TFA modifier) to afford the title compound. MS: 502.5 (M+1). 1H NMR (500 MHz, Chloroform-d) δ 7.27-7.22 (m, 1H), 7.04 (d, J=7.7 Hz, 1H), 6.97 (d, J=10.3 Hz, 1H), 6.94-6.85 (m, 1H), 5.50 (s, 1H), 4.24 (s, 1H), 4.04-3.95 (m, 1H), 3.92 (s, 1H), 3.79-72 (m, 5H), 3.70 (s, 1H), 3.47 (s, 1H), 3.35 (s, 3H), 2.83 (s, 6H), 2.62-2.48 (m, 2H), 2.12-1.94 (m, 5H), 1.79-1.69 (m, 3H), 1.66-1.53 (m, 2H).

EXAMPLE 52 methyl (2R,3S,5S)-5-(cyanomethyl)-3-((N,N-dimethylsulfamoyl)amino)-2-((((CIS)-4-(3-fluorophenyl)cyclohexyl)oxy)methyl)pyrrolidine-1-carboxylate (52)

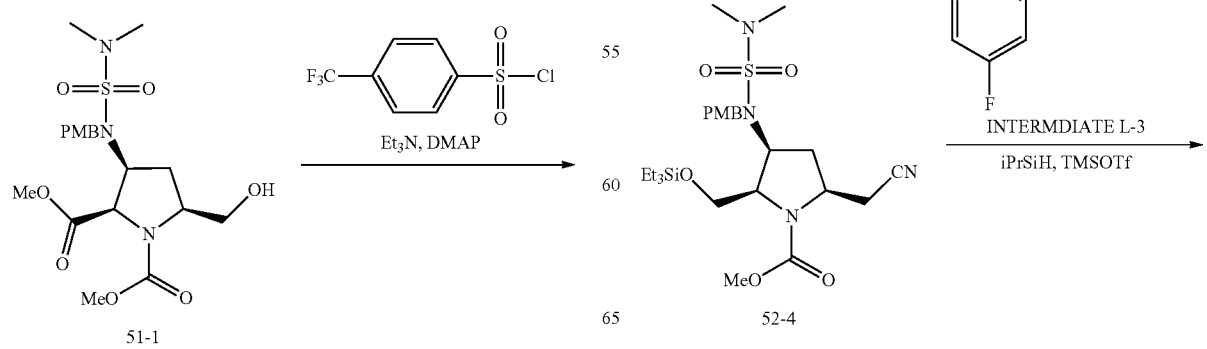

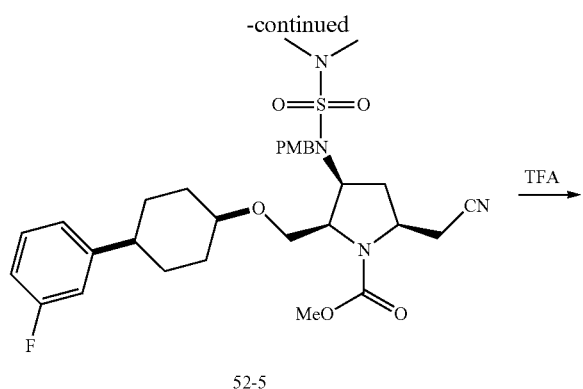

52-5

52

Step 1: dimethyl (2R,3S,5S)-3-((N,N-dimethylsulfamoyl)(4-methoxybenzyl)amino)-5-((((4-(trifluoromethyl)phenyl)sulfonyl)oxy)methyl)pyrrolidine-1,2-dicarboxylate (52-1)

To a mixture of dimethyl (2R,3S,5S)-3-((N,N-dimethylsulfamoyl)(4-methoxybenzyl)amino)-5-(hydroxymethyl)pyrrolidine-1,2-dicarboxylate (51-1) (125 mg, 0.272 mmol) in DCM (1360 µl) at ambient temperature was added 4-(trifluoromethyl)benzenesulfonyl chloride (87 mg, 0.354 mmol), Et₃N (56.9 µl, 0.408 mmol), and DMAP (3.32 mg, 0.027 mmol). The mixture stirred for 4 hours before concentrating. The residue was purified by column chromatography on silica (1% to 60% 3:1 EtOAc:EtOH/hexanes) to afford the title compound. MS: 668.5 (M+1).

Step 2: dimethyl (2R,3S,5S)-5-(cyanomethyl)-3-((N,N-dimethylsulfamoyl)(4-methoxybenzyl)amino)pyrrolidine-1,2-dicarboxylate (52-2)

To a mixture of dimethyl (2R,3S,5S)-3-((N,N-dimethylsulfamoyl)(4-methoxybenzyl)-amino)-5-((((4-(trifluoromethyl)phenyl)sulfonyl)oxy)methyl)pyrrolidine-1,2-dicarboxylate (52-1) (160 mg, 0.240 mmol) in DMSO (479 µl) at ambient temperature was added POTASSIUM CYANIDE (23.41 mg, 0.359 mmol). The reaction was heated to 60° C. and stirred for 16 hours. After cooling the reaction mixture was purified directly by column chromatography on silica (2% to 80% 3:1 EtOAc:EtOH/hexanes) to afford the title compound. MS: 469.4 (M+1).

Step 3: methyl (2R,3S,5S)-5-(cyanomethyl)-3-((N,N-dimethylsulfamoyl)(4-methoxybenzyl)amino)-2-(hydroxymethyl)pyrrolidine-1-carboxylate (52-3)

To a mixture of dimethyl (2R,3S,5S)-5-(cyanomethyl)-3-((N,N-dimethylsulfamoyl)(4-methoxybenzyl)amino)pyrrolidine-1,2-dicarboxylate (52-2) (60.0 mg, 0.128 mmol) in THF (1281 µl) at ambient temperature was added LiBH4 (5.58 mg, 0.256 mmol). The mixture was heated to 50° C. and stirred for 5 hours before cooling, quenching with H2O (5 mL), extracting with DCM (4× @10 mL), dried over Na₂SO₄, and concentrated to afford the title compound. MS: 463.4 (M+23).

Step 4: methyl (2R,3S,5S)-5-(cyanomethyl)-3-((N,N-dimethylsulfamoyl)(4-methoxybenzyl)amino)-2-((((triethyl silyl)oxy)methyl)pyrrolidine-1-carboxylate (52-4)

To a mixture of methyl (2R,3S,5S)-5-(cyanomethyl)-3-((N,N-dimethylsulfamoyl)(4-methoxybenzyl)amino)-2-(hydroxymethyl)pyrrolidine-1-carboxylate (52-3) (56 mg, 0.127 mmol) in DCM (636 µl) at ambient temperature was added TRIETHYLAMINE (26.6 µl, 0.191 mmol), DMAP (1.553 mg, 0.013 mmol), and chlorotriethylsilane (25.6 µl, 0.153 mmol). The mixture stirred overnight before concentrating. The residue was purified by column chromatography on silica (1% to 50% EtOAc/hexanes) to afford the title compound.

Step 5: methyl (2R,3S,5S)-5-(cyanomethyl)-3-((N,N-dimethylsulfamoyl)(4-methoxybenzyl)amino)-2-(((((CIS)-4-(3-fluorophenyl)cyclohexyl)oxy)methyl)pyrrolidine-1-carboxylate (52-5)

To a mixture of methyl (2R,3S,5S)-5-(cyanomethyl)-3-((N,N-dimethylsulfamoyl)(4-methoxybenzyl)amino)-2-(((triethylsilyl)oxy)methyl)pyrrolidine-1-carboxylate (52-4) (50 mg, 0.090 mmol) in Acetonitrile (2704 µl)/DCM (300 µl) at ambient temperature was added 4-(3-fluorophenyl)cyclohexan-1-one (INTERMEDIATE L-3) (34.7 mg, 0.180 mmol) and triisopropylsilane (36.9 µl, 0.180 mmol). The mixture was cooled to −30° C. and TRIMETHYLSILYL TRIFLUOROMETHANESULFONATE (16.29 µl, 0.090 mmol) was added dropwise. The mixture was warmed to 0° C. and stirred for 10 min before quenching with a saturated solution of NaHCO₃ (10 mL), extract with DCM (3× @ 10 mL), dry over Na₂SO₄, and concentrate. The residue was purified by column chromatography on silica (0% to 50% EtOAc/hexanes) to afford the title compound. MS: 617.6 (M+1).

Step 6: methyl (2R,3S,5S)-5-(cyanomethyl)-3-((N,N-dimethylsulfamoyl)amino)-2-(((((CIS)-4-(3-fluorophenyl)cyclohexyl)oxy)methyl)pyrrolidine-1-carboxylate (52)

To a mixture of methyl (2R,3S,5S)-5-(cyanomethyl)-3-((N,N-dimethylsulfamoyl)(4-methoxybenzyl)amino)-2-(((((CIS)-4-(3-fluorophenyl)cyclohexyl)oxy)methyl)pyrrolidine-1-carboxylate (52-5) (43 mg, 0.070 mmol) in DCM (349 µl) at ambient temperature was added TFA (53.7 µl, 0.697 mmol). The mixture stirred for 2 hours before concentrating. The residue was purified by column chromatography on C18 (5-95% MeCN/water with 0.05% TFA modifier) to afford the title compound. MS: 497.4 (M+1). 1H NMR (500 MHz, Chloroform-d) δ 7.26 (d, J=7.7 Hz, 1H), 7.03 (d, J=7.7 Hz, 1H), 6.96 (d, J=10.3 Hz, 1H), 6.90 (t, J=8.2 Hz, 1H), 5.37 (d, J=8.6 Hz, 1H), 4.37-4.18 (m, 2H), 4.10-3.95 (m, 2H), 3.85 (dd, J=10.2, 2.1 Hz, 1H), 3.89-3.66 (m, 4H), 3.08 (d, J=16.9 Hz, 1H), 2.96 (d, J=12.1 Hz, 1H), 2.84 (s, 6H), 2.78-2.55 (m, 2H), 2.19-1.85 (m, 4H), 1.82-1.60 (m, 5H).

EXAMPLE 53

Methyl (2R,3S,5R)-3-((N-(cyanomethyl)-N-methyl-sulfamoyl)amino)-2-((((1s,4S)-4-(3-fluorophenyl)cyclohexyl)oxy)methyl)-5-methylpyrrolidine-1-carboxylate (53)

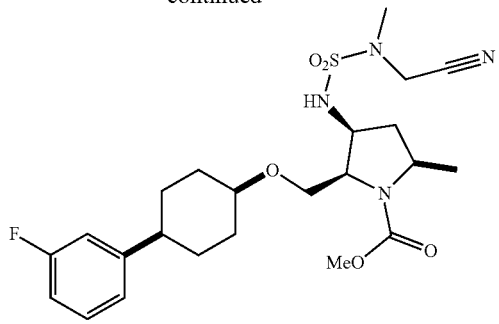

53

Step 1: methyl (2R,3S,5R)-2-((((1s,4S)-4-(3-fluorophenyl)cyclohexyl)oxy)methyl)-3-((fluorosulfonyl)amino)-5-methylpyrrolidine-1-carboxylate (53-1)

Methyl (2R,3S,5R)-3-amino-2-((((1s,4S)-4-(3-fluorophenyl)cyclohexyl)oxy)methyl)-5-methylpyrrolidine-1-carboxylate (W) (176 mg, 0.381 mmol) in acetonitrile (5 ml) at 0° C. was added triethylamine (0.175 ml, 1.256 mmol) followed by 1-(fluorosulfonyl)-2,3-dimethyl-1H-imidazol-3-ium methanesulfonate (231 mg, 0.842 mmol) all at once. The reactions were stirred at 0° C. for 15 min, then slowly allowed to warm to rt. After 2 hrs, conversion to the desired product was completed. The reaction was concentrated under reduced pressure and used directly on next step. MS: 446.4 (M+H)

Step 2: methyl (2R,3S,5R)-3-((N-(cyanomethyl)-N-methylsulfamoyl)amino)-2-((((1s,4S)-4-(3-fluorophenyl)cyclohexyl)oxy)methyl)-5-methylpyrrolidine-1-carboxylate (53)

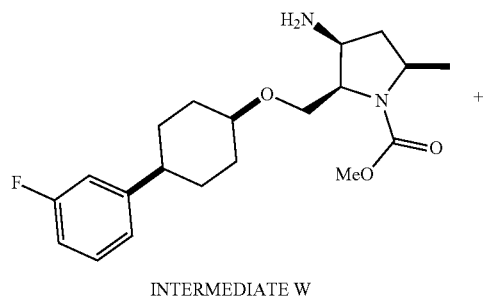

INTERMEDIATE W

To a solution of methyl (2R,3S,5R)-2-((((1s,4S)-4-(3-fluorophenyl)cyclohexyl)oxy)methyl)-3-((fluorosulfonyl)amino)-5-methylpyrrolidine-1-carboxylate (53-1) (24 mg, 0.054 mmol) in 700 ul of acetonitrile was added triethylamine (18 mg, 0.178 mmol) followed by 2-(methylamino)-acetonitrile (9.13 mg, 0.130 mmol). The mixture was stirred at room temperature overnight. After removing the solvent under reduced pressure, the residue was purified by ISCO preparative reverse phase HPLC, eluting with 10 to 100% water in acetonitrile with 0.05% TFA. The desired fractions were combined and concentrated to the title compound. MS: 497.37 (M+H). $^1$H NMR (500 MHz, DMSO-d6): δ 7.32 (q, J=7.3 Hz, 1H), 7.05 (d, J=7.6 Hz, 1H), 6.98 (t, J=8.1 Hz, 2H), 4.31 (s, 2H), 3.98 (s, 1H), 3.71 (dd, J=11.2, 6.6 Hz, 2H), 3.57 (d, J=13.4 Hz, 2H), 2.81 (s, 3H), 2.62-2.57 (m, 1H), 2.54 (m, 3H), 2.31-2.24 (m, J=12.2, 7.2 Hz, 1H), 2.01 (d, J=13.7 Hz, 1H), 1.93 (d, J=13.6 Hz, 1H), 1.85-1.61 (m, 3H), 1.51-1.45 (m, 5H), 1.26 (d, J=5.8 Hz, 4H).

The following compounds were prepared according to the general procedure provided in Examples 1-53, and procedures herein, by substituting with the appropriate amine after conversion into the sulfamoyl fluoride. The starting materials are either prepared as described in the intermediates section, commercially available, or may be prepared from commercially available reagents using conventional reactions well known in the art.

| Example Number | Structure | Name | Exact Mass [M + H]+ |
|---|---|---|---|
| 54 | 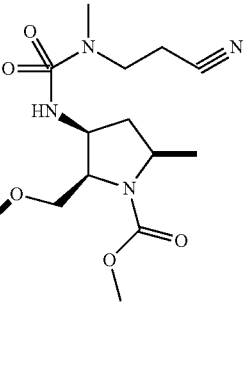 | methyl (2R,3S,5R)-3-((N-(2-cyanoethyl)-N-methylsulfamoyl)amino)-2-((((1s,4S)-4-(3-fluorophenyl)cyclohexyl)oxy)methyl)-5-methylpyrrolidine-1-carboxylate | 511.4 |
| 55 | 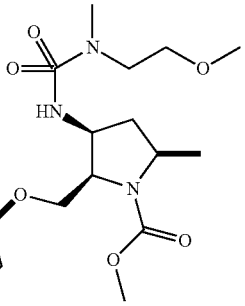 | methyl (2R,3S,5R)-2-((((1s,4S)-4-(3-fluorophenyl)cyclohexyl)oxy)methyl)-3-((N-(2-methoxyethyl)-N-methylsulfamoyl)amino)-5-methylpyrrolidine-1-carboxylate | 516.4 |
| 56 | 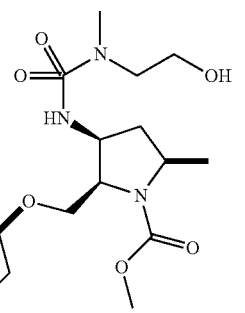 | methyl (2R,3S,5R)-2-((((1s,4S)-4-(3-fluorophenyl)cyclohexyl)oxy)methyl)-3-((N-(2-hydroxyethyl)-N-methylsulfamoyl)amino)-5-methylpyrrolidine-1-carboxylate | 502.4 |

-continued

| Example Number | Structure | Name | Exact Mass [M + H]+ |
|---|---|---|---|
| 57 | 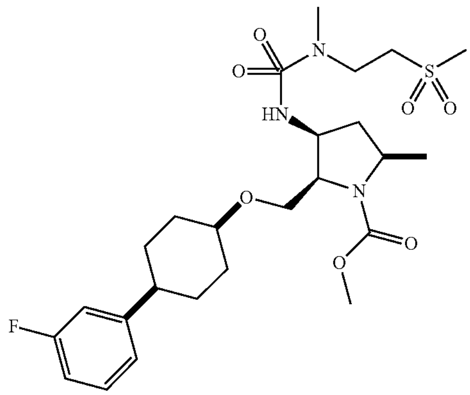 | methyl (2R,3S,5R)-2-((((1s,4S)-4-(3-fluorophenyl)cyclohexyl)oxy)methyl)-5-methyl-3-((N-methyl-N-(2-(methyslulfonyl)ethyl)sulfamoyl)amino)pyrrolidine-1-carboxylate | 564.4 |
| 58 | 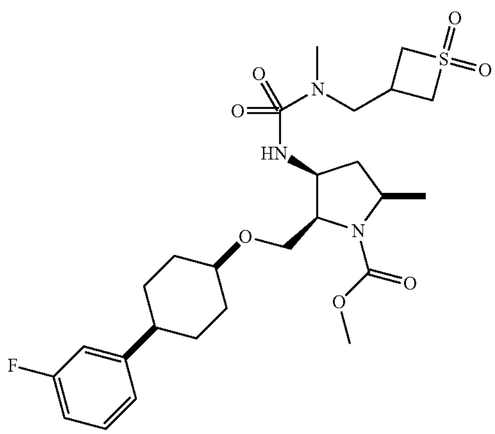 | methyl (2R,3S,5R)-3-((N-((1,1-dioxidothietan-3-yl)methyl)-N-methylsulfamoyl)amino)-2-((((1s,4S)-4-(3-fluorophenyl)cyclohexyl)oxy)methyl)-5-methylpyrrolidine-1-carboxylate | 576.3 |
| 59 | 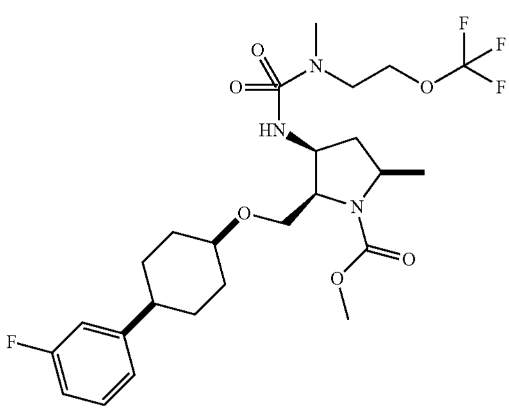 | methyl (2R,3S,5R)-2-((((1s,4S)-4-(3-fluorophenyl)cyclohexyl)oxy)methyl)-5-methyl-3-((N-methyl-N-(2-(trifluoromethoxy)ethyl)sulfamoyl)amino)pyrrolidine-1-carboxylate | 570.4 |

EXAMPLE 60

Methyl (2R,3S,5R)-3-((2,2-difluoroethyl)sulfonamido)-2-((((1s,4S)-4-(3-fluorophenyl)-cyclohexyl)oxy)methyl)-5-methylpyrrolidine-1-carboxylate (60)

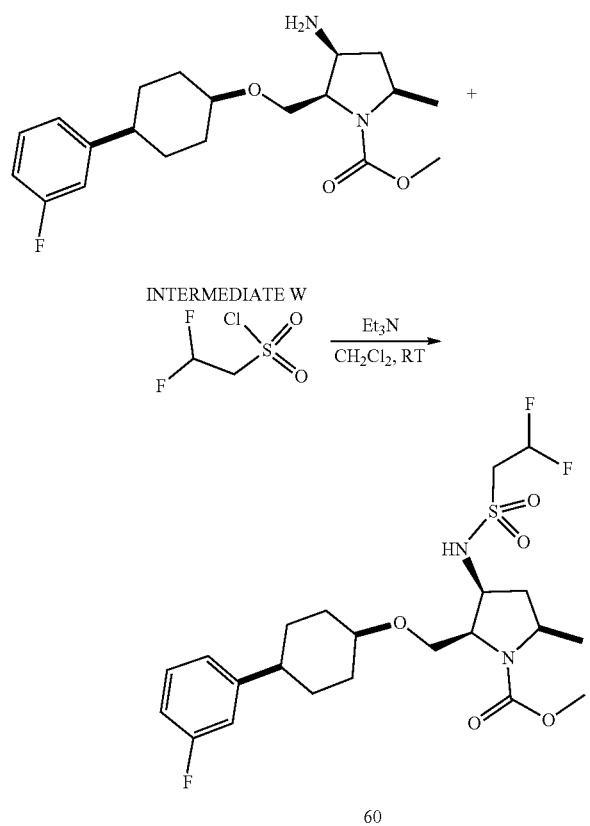

A solution of methyl (2R,3S,5R)-3-amino-2-((((1s,4S)-4-(3-fluorophenyl)cyclohexyl)-oxy)-methyl)-5-methylpyrrolidine-1-carboxylate (W) (15 mg, 0.032 mmol) in dichloromethane (300 μl) was added to 2,2-difluoroethyane-1-sulfonyl chloride (10.67 mg, 0.065 mmol) followed by triethylamine (18.08 μl, 0.130 mmol). The mixture was stirred at RT overnight. After removing the solvent under reduced pressure, the residue was purified by preparative reverse phase HPLC, eluting with 10 to 100% water in acetonitrile with 0.05% TFA. The desired fractions were combined and concentrated to the title compound. MS: 492.0 (M+H). $^1$H NMR (500 MHz, Methanol-d4): δ7.27 (q, J=7.9, 7.2 Hz, 1H), 6.96 (d, J=10.6 Hz, 1H), 6.88 (t, J=8.3 Hz, 1H), 6.26 (t, J=55.1 Hz, 1H), 4.13 (s, 1H), 4.02 (s, 1H), 3.83 (dd, J=16.3, 12.2 Hz, 3H), 3.70 (d, J=19.7 Hz, 6H), 2.61 (t, J=11.8 Hz, 1H), 2.48-2.40 (m, 1H), 2.19-2.04 (m, 2H), 1.97-1.73 (m, 3H), 1.63 (d, J=8.9 Hz, 4H), 1.40 (d, J=5.6 Hz, 3H).

The following compounds were prepared according to the general procedure provided in Examples 1-60, and procedures herein, by substituting with the appropriate sulfonyl chloride. The starting materials are either prepared as described in the intermediates section, commercially available, or may be prepared from commercially available reagents using conventional reactions well known in the art.

| Example Number | Structure | Name | Exact Mass [M + H]$^+$ |
|---|---|---|---|
| 61 | 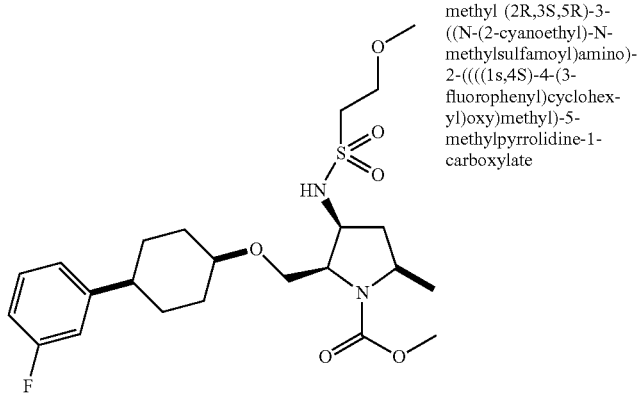 | methyl (2R,3S,5R)-3-((N-(2-cyanoethyl)-N-methylsulfamoyl)amino)-2-((((1s,4S)-4-(3-fluorophenyl)cyclohexyl)oxy)methyl)-5-methylpyrrolidine-1-carboxylate | 487.2 |

-continued

| Example Number | Structure | Name | Exact Mass [M + H]+ |
|---|---|---|---|
| 62 | 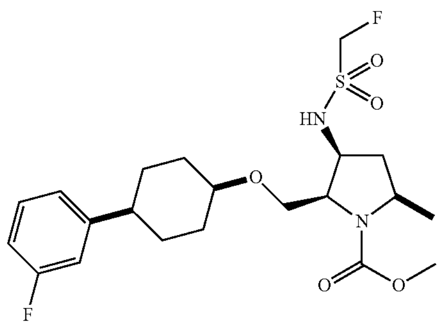 | methyl (2R,3S,5R)-3-((fluoromethyl)sulfonamido)-2-((((1s,4S)-4-(3-fluorophenyl)cyclohexyl)oxy)methyl)-5-methylpyrrolidine-1-carboxylate | 461.2 |

EXAMPLES 63 AND 64

Methyl (2R,3S,5R)-2-((((1s,4S)-4-(4-cyano-3-methylphenyl)cyclohexyl)oxy)methyl)-3-(N,N-dimethylsulfamoyl)amino)-5-methylpyrrolidine-1-carboxylate (63)

Methyl (2R,3S,5R)-2-(((1r,4R)-4-(4-cyano-3-methylphenyl)cyclohexyl)oxy)methyl)-3-((N,N-dimethylsulfamoyl)amino)-5-methylpyrrolidine-1-carboxylate (64)

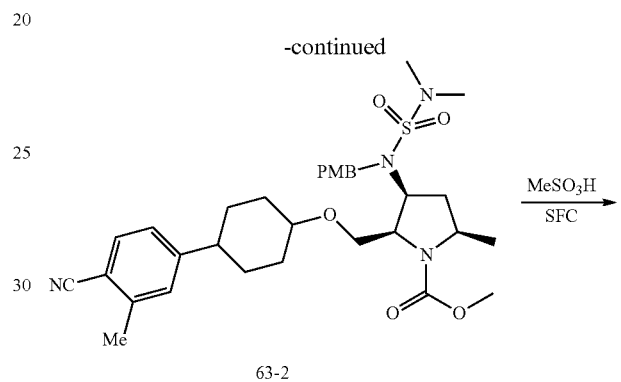

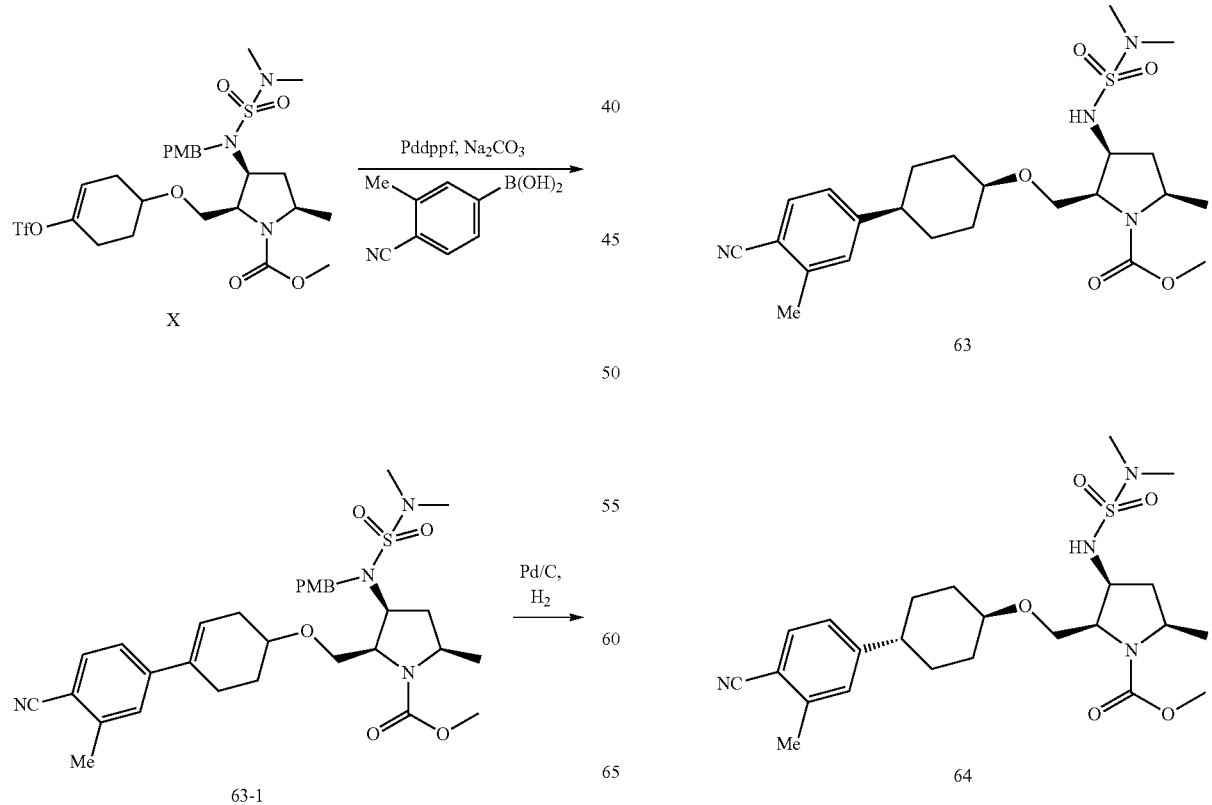

Step 1: Methyl (2R,3S,5R)-2-(((4'-cyano-3'-methyl-2,3,4,5-tetrahydro-[1,1'-biphenyl]-4-yl)oxy)methyl)-3-((N,N-dimethylsulfamoyl)(4-methoxybenzyl)amino)-5-methylpyrrolidine-1-carboxylate (63-1)

A vial containing methyl (2R,3S,5R)-3-((N,N-dimethylsulfamoyl)(4-methoxybenzyl)amino)-5-methyl-2-(((4-(((trifluoromethyl)sulfonyl)oxy)cyclohex-3-en-1-yl)oxy)methyl)pyrrolidine-1-carboxylate (Intermediate X) 100 mg (0.155 mmol), 4-CYANO-3-METHYLPHENYLBORONIC ACID (25.01 mg, 0.155 mmol), SODIUM CARBONATE (49.4 mg, 0.466 mmol) and 1,1'-BIS(DIPHENYLPHOSPHINO)FERROCENE-PALLADIUM(II)-DICHLORIDE DICHLOROMETHANE COMPLEX (19.62 mg, 0.023 mmol) under N₂ was treated with Dioxane (518 µl) and the mixture purged. Water (259 µl) was then added and the mixture purged and stirred under N₂ at 95° C. for 8 h. The mixture was diluted with EtOAc and filtered. The filtrate was washed with water and brine, dried (MsSO₄), filtered and concentrated under reduced pressure to afford the crude. The crude was purified on the CombiFlash NextGEn 300+ on a silica gel 12 g column, eluting with a gradient of ethyl acetate/hexane 0:100% to 60:40% to give the title compound. LC-MS: m/z=611.3 (M+1).

Step 2: Methyl (2R,3S,5R)-2-(((4-(4-cyano-3-methylphenyl)cyclohexyl)oxy)methyl)-3-((N,N-dimethylsulfamoyl)(4-methoxybenzyl)amino)-5-methylpyrrolidine-1-carboxylate (63-2)

A solution of methyl (2R,3S,5R)-2-(((4'-cyano-3'-methyl-2,3,4,5-tetrahydro-[1,1'-biphenyl]-4-yl)oxy)methyl)-3-((N,N-dimethylsulfamoyl)(4-methoxybenzyl)amino)-5-methylpyrrolidine-1-carboxylate (63-1), 42 mg (0.069 mmol) in MeOH (688 µl) and Ethyl acetate (688 µl) was purged and then Pd—C (7.32 mg, 6.88 µmol) was added. The resulting suspension was purged again and backfilled with H2 from a balloon. The mixture was then stirred at 25° C. for 3 h. The mixture was filtered through celite and the filtrate concentrated to afford the crude. The crude was purified on the CombiFlash NextGEn 300+ with ELSD on a silica gel 12 g column, eluting with a gradient of ethyl acetate:ethanol (3:1)/hexane 0:100% to 40:60% to give the title compound as thin film (mixture of Diastereomers). LC-MS: m/z=613.3 (M+1).

Step 3: Methyl (2R,3S,5R)-2-((((1s,4S)-4-(4-cyano-3-methylphenyl)cyclohexyl)oxy)methyl)-3-((N,N-dimethylsulfamoyl)amino)-5-methylpyrrolidine-1-carboxylate (63) and Methyl (2R,3S,5R)-2-((((1r,4R)-4-(4-cyano-3-methylphenyl)cyclohexyl)oxy)methyl)-3-((N,N-dimethylsulfamoyl)amino)-5-methylpyrrolidine-1-carboxylate (64)

A solution of methyl (2R,3S,5R)-2-(((4-(4-cyano-3-methylphenyl)cyclohexyl)-oxy)methyl)-3-((N,N-dimethylsulfamoyl)(4-methoxybenzyl)amino)-5-methylpyrrolidine-1-carboxylate (63-2) 26 mg (0.042 mmol) in DCM (424 µl) was treated with METHANESULFONIC ACID (27.6 µl, 0.424 mmol) and the mixture stirred at 25° C. for 2 h. The mixture was cool to 0° C. and the reaction quenched slowly with Sat. Aq. NaHCO₃. The mixture was extracted with DCM (×2) and the organic layer washed with brine, dried (MgSO₄), filtered and concentrated under reduced pressure to afford the crude product. This was purified on the CombiFlash NextGEn 300+ with ELSD, on a silica gel 12 g column, eluting with a gradient of ethyl acetate:ethanol (3:1)/hexane 0:100% to 30:70% to give 18 mg of a mixture of a mixture of diastereomers. The mixture was separated by SFC on the AD-H column to afford Examples 63 and 64. LC-MS: m/z=494.1 (M+1).

EXAMPLES 65 AND 66

Methyl (2R,3S,5R)-3-((N,N-dimethylsulfamoyl)amino)-2-((((1s,4S)-4-(2-ethylphenyl)cyclohexyl)oxy)methyl)-5-methylpyrrolidine-1-carboxylate (65)

methyl (2R,3S,5R)-3-((N,N-dimethylsulfamoyl)amino)-2-((((1r,4R)-4-(2-ethylphenyl)cyclohexyl)oxy)methyl)-5-methylpyrrolidine-1-carboxylate (66)

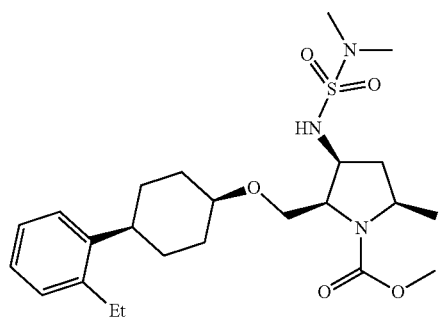

65

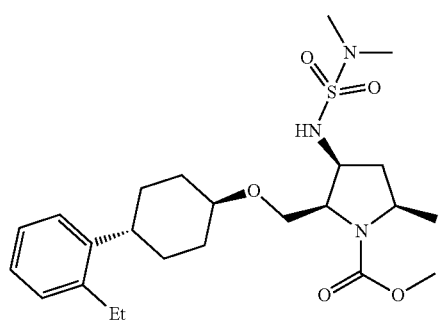

66

The title compound of Example 65 and 66 were prepared by following the general procedure described for Examples 63 and 64, using commercially available (2-ethylphenyl)boronic acid in Step 1.

EXAMPLES 67 AND 68

Methyl (2R,3S,5R)-3-((N,N-dimethylsulfamoyl)amino)-2-((((1S,3R,4R)-4-(3-fluorophenyl)cyclohexyl-3,4-d2)oxy)methyl)-5-methylpyrrolidine-1-carboxylate (67)

Methyl (2R,3S,5R)-3-((N,N-dimethylsulfamoyl)amino)-2-((((1S,3S,4S)-4-(3-fluorophenyl)cyclohexyl-3,4-d2)oxy)methyl)-5-methylpyrrolidine-1-carboxylate (68)

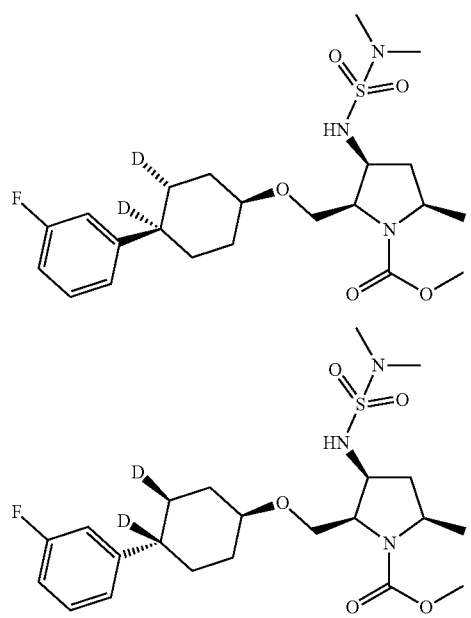

The title compound of Example 67 and 68 were prepared by following the general procedure described for Examples 63 and 64, using commercially available 3-Fluorophenylboronic in Step 1 and D2 in Step 2.

EXAMPLES 69 AND 70

Methyl (2R,3S,5R)-5-methyl-3-(methylsulfonamido)-2-((((1r,4R)-4-(pyrimidin-2-yl)cyclohexyl)oxy)methyl)pyrrolidine-1-carboxylate (69)

Methyl (2R,3S,5R)-5-methyl-3-(methylsulfonamido)-2-((((1s,4S)-4-(pyrimidin-2-yl)cyclohexyl)oxy)methyl)pyrrolidine-1-carboxylate (70)

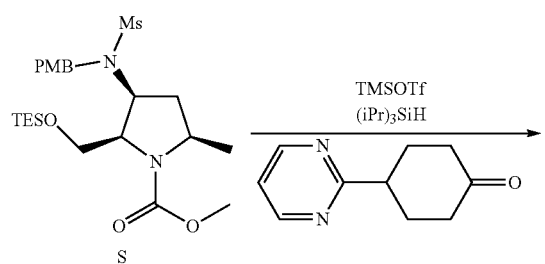

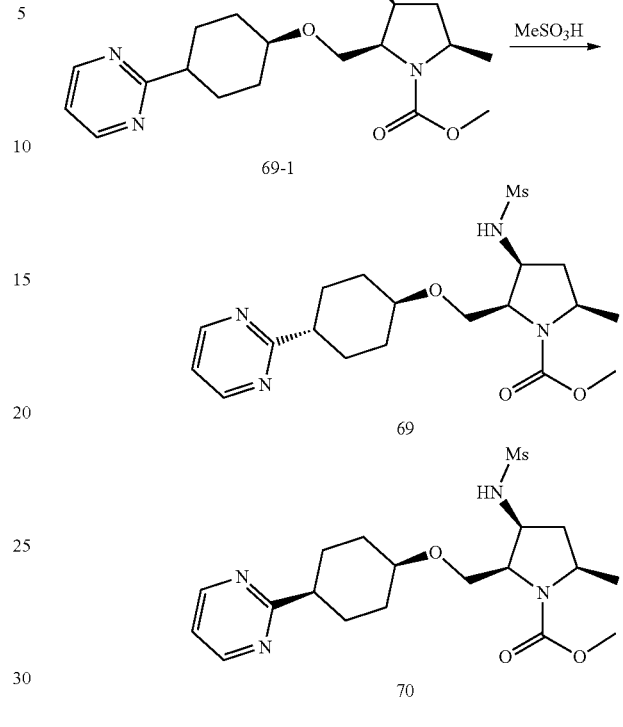

Step 1: methyl (2R,3S,5R)-3-(N-(4-methoxybenzyl)methylsulfonamido)-5-methyl-2-(((4-(pyrimidin-2-yl)cyclohexyl)oxy)methyl)pyrrolidine-1-carboxylate (69-1)

A solution of methyl (2R,3S,5R)-2-(hydroxymethyl)-3-(N-(4-methoxybenzyl)methylsulfonamido)-5-methylpyrrolidine-1-carboxylate (S) 50 mg, (0.129 mmol), 4-(pyrimidin-2-yl)cyclohexan-1-one (29.6 mg, 0.168 mmol) and TRIISOPROPYLSILANE (53.0 μl, 0.259 mmol) at −35° C. under N2 was treated with TRIMETHYLSILYL TRIFLUOROMETHANESULFONATE (23.42 μl, 0.129 mmol) via a syringe and needle and the mixture stirred at −35° C. for 1 h and slowly warm to 0° C. and kept for 2 h. The reaction was quenched with Sat. Aq. NaHCO$_3$ and diluted with EtOAc. After warming up to rt the layers were separated and the Aq layer washed EtOAc. The combined organics was dried (MgSO$_4$), filtered and concentrated under reduced pressure to afford the crude. The crude was purified by silica gel chromatography, on the Combiflash NextGen 300+ with ELSD on a 12 g column, eluting with a gradient of ethyl acetate:ethanol (3:1)/hexanes—0:100 to 40:60 to afford the title compound (mixture of Diastereomers). MS (m/z)=547.4 (M+1).

Step 2: Methyl (2R,3S,5R)-5-methyl-3-(methylsulfonamido)-2-((((1r,4R)-4-(pyrimidin-2-yl)cyclohexyl)oxy)methyl)pyrrolidine-1-carboxylate (69)
Methyl (2R,3S,5R)-5-methyl-3-(methylsulfonamido)-2-((((1s,4S)-4-(pyrimidin-2-yl)cyclohexyl)oxy)methyl)pyrrolidine-1-carboxylate (70)

A solution of methyl (2R,3S,5R)-3-(N-(4-methoxybenzyl)methylsulfonamido)-5-methyl-2-(((4-(pyrimidin-2-yl)

cyclohexyl)oxy)methyl)pyrrolidine-1-carboxylate (69-1), in DCM (284 µl) was treated with METHANESULFONIC ACID (18.41 µl, 0.284 mmol) and the mixture stirred at 25° C. for 2 h. The reaction was diluted with DCM and quenched with Sat. Aq. NaHCO₃.

The layers were separated and the Aq layer washed with DMC. The combined organics was dried (MgSO₄), filtered and concentrated under reduced pressure to afford the crude. The crude was purified by silica gel chromatography, on the Combiflash NextGen 300+ with ELSD on a 4 g column, eluting with a gradient of ethyl acetate:ethanol (3:1)/hexanes—0:100 to 80:20 to afford the title compounds as a mixture of diastereomers. The mixture of diastereomers were separated by SFC to afford 69 (MS=427.3 (M+1)) and 70 (MS=427.3 (M+1)).

EXAMPLES 71 AND 72

Methyl (2R,3S,5R)-2-((((1s,4S)-4-(3,5-difluorophenyl)cyclohexyl)oxy)methyl)-5-methyl-3-(methylsulfonamido)pyrrolidine-1-carboxylate (71)

Methyl (2R,3S,5R)-2-((((1r,4R)-4-(3,5-difluorophenyl)cyclohexyl)oxy)methyl)-5-methyl-3-(methylsulfonamido)pyrrolidine-1-carboxylate (72)

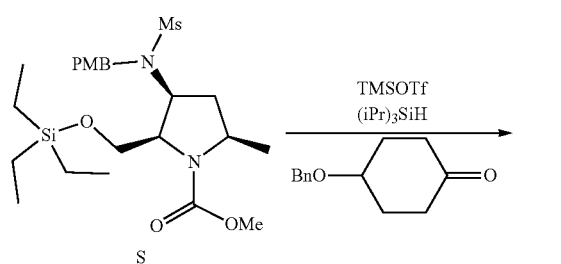

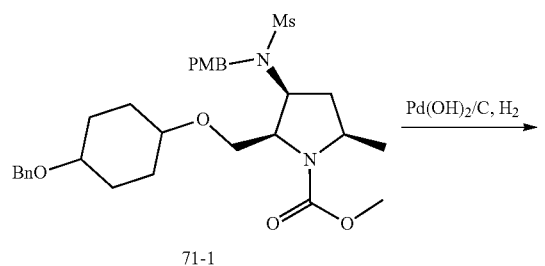

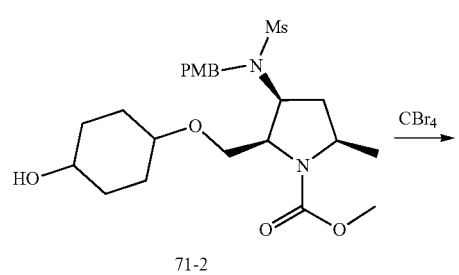

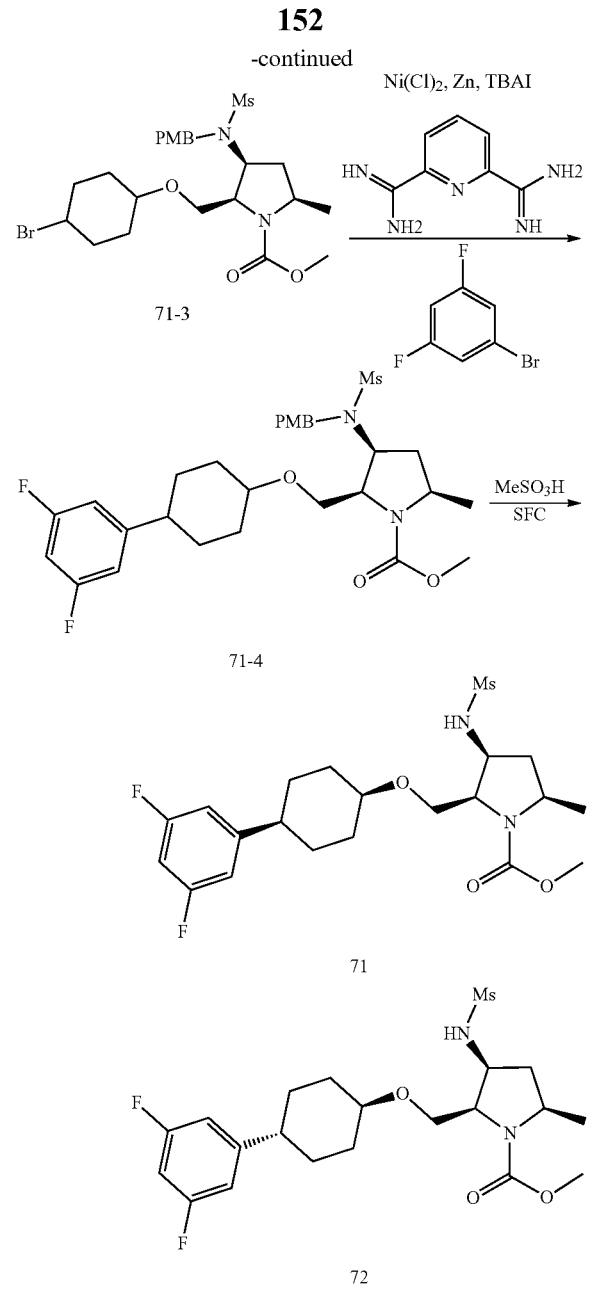

Step 1: Methyl (2R,3S,5R)-2-(((4-(benzyloxy)cyclohexyl)oxy)methyl)-3-(N-(4-methoxybenzyl)methylsulfonamido)-5-methylpyrrolidine-1-carboxylate (71-1)

A solution of methyl (2R,3S,5R)-3-(N-(4-methoxybenzyl)methylsulfonamido)-5-methyl-2-(((triethylsilyl)oxy)methyl)pyrrolidine-1-carboxylate (S) 3.0 g (5.99 mmol), 4-(benzyloxy)cyclohexan-1-one (1.591 g, 7.79 mmol) and TRIISOPROPYLSILANE (2.455 ml, 11.98 mmol) at −40° C. under N2 was treated with TRIMETHYLSILYL TRIFLUORO-METHANESULFONATE (1.084 ml, 5.99 mmol) using a Hamilton syringe and needle and the mixture stirred at −40° C. for 2 h (temp rise to −10 C). The reaction was quenched with Sat. Aq NaHCO₃ and diluted with EtOAc. After warming to rt the layers were separated and the aq layer washed EtOAc. The combined organics was dried (MgSO$_4$), filtered and concentrated under reduced pressure to afford the crude. The crude was purified by silica gel chromatography, on the Combiflash NextGen 300+ with ELSD on an 80 g column, eluting with a gradient of ethyl acetate:ethanol (3:1)/hexanes—0:100 to 30:70 to afford the title compound (cis/trans). MS: m/z=575.4 (M+1).

Step 2: Methyl (2R,3S,5R)-2-(((4-(benzyloxy)cyclohexyl)oxy)methyl)-3-(N-(4-methoxybenzyl)methylsulfonamido)-5-methylpyrrolidine-1-carboxylate (71-2)

In a rb flask containing a solution of methyl (2R,3S,5R)-2-(((4-(benzyloxy)-cyclohexyl)oxy)methyl)-3-(N-(4-methoxybenzyl)methylsulfonamido)-5-methylpyrrolidine-1-carboxylate (71-1), 2.76 g (4.80 mmol) in MeOH (96 ml) was treated with 20% Pd(OH)$_2$ on carbon (0.674 g, 0.960 mmol) and the flask sealed. The flask was purged, and the mixture stirred under a HYDROGEN atmosphere (Balloon) for 10 h. The mixture was diluted with MeOH and filtered through celite. The filtrate was concentrated under reduced pressure to afford the crude as a blackish solid. The crude was purified on the CombiFlash NextGEn 300+ on a silica gel 80 g column, eluting with a gradient of ethyl acetate; ethanol (3:1)/hexane 0 to 100% to give the title compound (mixture of diastereomers). MS: m/z=485.4 (M+1).

Step 3: methyl (2R,3S,5R)-2-(((4-bromocyclohexyl)oxy)methyl)-3-(N-(4-methoxybenzyl)methylsulfonamido)-5-methylpyrrolidine-1-carboxylate (71-3)

A solution of methyl (2R,3S,5R)-2-(((4-hydroxycyclohexyl)oxy)methyl)-3-(N-(4-methoxybenzyl)methylsulfonamido)-5-methylpyrrolidine-1-carboxylate (71-2) 1.5 g (3.10 mmol) and CARBON TETRABROMIDE (1.232 g, 3.71 mmol) at 0° C. under N$_2$, was treated with TRIPHENYLPHOSPHINE (0.974 g, 3.71 mmol) slowly, and the mixture stirred at 0° C. 3 h then at 25° C. for 16. At 0° C., the reaction was quenched with NaHCO$_3$ and then extracted with EtOAc (×2).

The organic layer was dried (MgSO$_4$), filtered and concentrated under reduced pressure to afford the crude. The crude was purified by silica gel chromatography, on the Combiflash Rf on an 80 g column, eluting with a gradient of ethyl acetate/hexanes—0:100 to 40:60 to afford the title compound as a white solid (mixture of diastereomers). MS: m/z=547.4, 549.4 (M, M+2).

Step 4: methyl (2R,3S,5R)-2-(((4-(3,5-difluorophenyl)cyclohexyl)oxy)methyl)-3-(N-(4-methoxybenzyl)methylsulfonamido)-5-methylpyrrolidine-1-carboxylate (71-4)

To a vial containing methyl (2R,3S,5R)-2-(((4-bromocyclohexyl)oxy)methyl)-3-(N-(4-methoxybenzyl)methylsulfonamido)-5-methylpyrrolidine-1-carboxylate (71-3), 75 mg (0.137 mmol), pyridine-2,6-bis(carboximidamide)dihydrochloride (3.23 mg, 0.014 mmol), 1-bromo-3,5-difluorobenzene, 52.9 mg (0.274 mmol) and Tetrabutylammonium Iodide (12.65 mg, 0.034 mmol) in a vial in the glove box was added ZINC (26.9 mg, 0.411 mmol) followed by Nickel (II) Chloride Ethylene Glycol Dimethyl Ether complex (3.01 mg, 0.014 mmol) dissolved in DMA (1370 µl) and the mixture stirred at 60° C. in the glove box for 18 h. Analysis showed lots of SM. Added more ZINC (26.9 mg, 0.411 mmol), NICKEL(II) CHLORIDE ETHYLENE GLYCOL DIMETHYL ETHER COMPLEX (3.01 mg, 0.014 mmol), pyridine-2,6-bis(carboximidamide)dihydrochloride (3.23 mg, 0.014 mmol) and TETRABUTYL-AMMONIUM IODIDE (12.65 mg, 0.034 mmol) and stirred in the Glove box for another 20 h. The mixture was quenched with water and extracted with EtOAc (×2). The organic layer was washed with brine, dried (MgSO$_4$), filtered and concentrated under reduced pressure to afford the crude. The crude was purified on the CombiFlash NextGEn 300+ with ELSD on a silica gel 12 g column, eluting with a gradient of ethyl acetate/hexane 0:100% to 80:20% to give the title compound (as a mixture of diastereomers). LC-MS: m/z=581.4 (M+1).

Step 5: Methyl (2R,3S,5R)-2-(((((1s,4S)-4-(3,5-difluorophenyl)cyclohexyl)oxy)methyl)-5-methyl-3-(methylsulfonamido)pyrrolidine-1-carboxylate (71)

Methyl (2R,3S,5R)-2-(((((1r,4R)-4-(3,5-difluorophenyl)cyclohexyl)oxy)methyl)-5-methyl-3-(methylsulfonamido)pyrrolidine-1-carboxylate (72)

A solution of methyl (2R,3S,5R)-2-(((4-(3,5-difluorophenyl)cyclohexyl)-oxy)methyl)-3-(N-(4-methoxybenzyl)methylsulfonamido)-5-methylpyrrolidine-1-carboxylate (71-4) 33 mg (0.057 mmol) in DCM (568 µl) at 25° C. was treated with Methanesulfonic acid (36.9 µl, 0.568 mmol) and the mixture stirred at 25° C. for 2 h. The reaction mixture was diluted DCM and quenched with Sat. Aq. NaHCO$_3$. The layers were separated, and the organic layer washed with brine, dried (MgSO$_4$), filtered and concentrated under reduced pressure to afford the crude. The crude was purified on the CombiFlash NextGEn 300+ with ELSD on a silica gel 12 g column, eluting with a gradient of ethyl acetate:ethanol (3:1)/hexane 0:100% to 65:35% to give the title compound as a clear sticky oil as a mixture of diastereomers. The Diastereomers were separated by SFC on an AD-H column to afford Examples 71 and 72. LC-MS: m/z=461.4 (M+1).

EXAMPLE 73

Methyl (2R,3S,5R)-2-(((((1s,4S)-4-(3,4-difluorophenyl)cyclohexyl)oxy)methyl)-5-methyl-3-(methylsulfonamido)pyrrolidine-1-carboxylate (73)

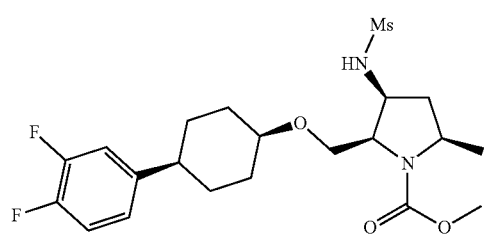

The title compound of Example 73 was provided by following the general procedure described for Examples 71, but using 4-bromo-1,2-difluorobenzene in Step 4.

The following table shows representative data for the compounds of the Examples as orexin receptor agonists as determined by the assays described herein.

| Example | hOX2R_IP IC$_{50}$ (nM) | Emax (%) |
| --- | --- | --- |
| 1 | 15.2 | 101 |
| 2 | 117 | 100 |
| 3 | 19.3 | 98 |
| 4 | 17.7 | 102 |
| 5 | 227 | 101 |
| 6 | 78.5 | 100 |
| 7 | 45.5 | 100 |
| 8 | 9.52 | 101 |
| 9 | 8.57 | 101 |
| 10 | 69.3 | 99 |
| 11 | 264 | 99 |
| 12 | 390 | 99 |
| 13 | 1.9 | 101 |
| 14 | 2.5 | 100 |
| 15 | 3.18 | 101 |
| 16 | 0.5 | 101 |
| 17 | 0.53 | 102 |
| 18 | 0.5 | 101 |
| 19 | 0.5 | 100 |
| 20 | 1.67 | 102 |
| 21 | 0.47 | 101 |
| 22 | 0.66 | 100 |
| 23 | 0.92 | 97 |
| 24 | 1.00 | 102 |
| 25 | 0.27 | 102 |
| 26 | 0.92 | 98 |
| 26 | 0.23 | 102 |
| 27 | 6.82 | 100 |
| 28 | 1.07 | 102 |
| 29 | 0.93 | 102 |
| 30 | 10.8 | 100 |
| 31 | 3.63 | 100 |
| 32 | 0.52 | 101 |
| 33 | 2150 | 92 |
| 34 | 37.5 | 99 |
| 35 | 12.5 | 102 |
| 36 | 0.76 | 99 |
| 37 | 0.23 | 102 |
| 37 | 1027 | 96 |
| 38 | 7.07 | 100 |
| 39 | 1.15 | 101 |
| 40 | 4.56 | 100 |
| 41 | 224 | 99 |
| 42 | 316 | 100 |
| 43 | 8.1 | 103 |
| 44 | 73.5 | 101 |
| 45 | 7331 | 62 |
| 46 | 3.0 | 101 |
| 47 | 34.8 | 101 |
| 48 | 9.4 | 102 |
| 49 | 5.5 | 102 |
| 50 | 17.7 | 101 |
| 51 | 0.7 | 101 |
| 52 | 7.8 | 102 |
| 53 | 0.6 | 102 |
| 54 | 0.7 | 98 |
| 55 | 1.2 | 100 |
| 56 | 0.8 | 101 |
| 57 | 1.6 | 100 |
| 58 | 1.8 | 101 |
| 59 | 1.0 | 99 |
| 60 | 5.2 | 99 |
| 61 | 4.6 | 105 |
| 62 | 1.4 | 98 |
| 63 | 1.1 | 100 |
| 64 | 12.5 | 99 |
| 65 | 2.2 | 101 |
| 66 | 111 | 100 |
| 67 | 0.46 | 101 |
| 68 | 8.3 | 102 |
| 69 | 10420 | 98 |
| 70 | 892 | 99 |
| 71 | 0.76 | 102 |
| 72 | 108 | 100 |
| 73 | 25.5 | 101 |

With respect to other compounds such as those disclosed in US 2017/0226137, WO 2017/135306, WO 2018/164191, WO 2018/164192, WO 2019/027003, WO 2019/027058, U.S. Pat. No. 9,527,807, 10,287,305, 10,428,023, or 10,508,083 it would be desirable that the present compounds exhibit unexpected properties, such as improved Pgp transport properties and brain penetration for compounds wherein X is O, and equipotency among compounds wherein X is O and X is NH. For example, in contrast to compounds of US 2017/0226137, WO 2017/135306, WO 2018/164191, WO 2018/164192, WO 2019/027003, WO 2019/027058, U.S. Pat. No. 9,527,807, 10,287,305, 10,428,023, or 10,508,083, the compounds of the present examples may possess improved Pgp transport properties and brain penetration for the carbamate compounds wherein X is O, and possess essentially equipotency among the carbamate compounds wherein X is O and the urea compounds wherein X is NH.

As indicated by the data herein, the compounds of the present examples provide unexpected potency as orexin receptor agonists. The distinction in potency as orexin receptor agonists provides greater functional activity and potential for enhanced in vivo efficacy and may provide benefits over other orexin receptor agonists that are known in the art.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula Ib''':

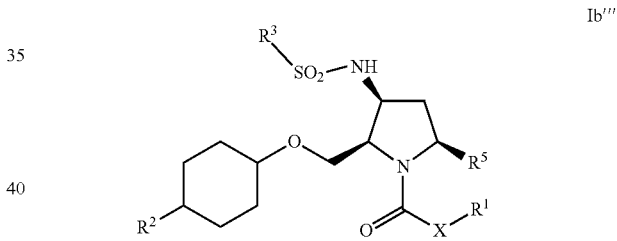

wherein:

X is —O— or —NH—, or X may be a direct bond to R$^1$;

R$^1$ is selected from:
(1) —C$_{1-6}$alkyl, where the alkyl is unsubstituted or substituted with one to six substituents independently selected from R$^4$, and
(2) —C$_{3-6}$cycloalkyl, where the cycloalkyl is unsubstituted or substituted with one to six substituents independently selected from R$^4$;

R$^2$ is selected from:
(1) hydrogen,
(2) —C$_{1-6}$alkyl, where the alkyl is unsubstituted or substituted with one to six substituents independently selected from R$^4$,
(3) —C$_{3-6}$cycloalkyl, where the cycloalkyl is unsubstituted or substituted with one to six substituents independently selected from R$^4$,
(4) -phenyl, where the phenyl is unsubstituted or substituted with one to three substituents independently selected from R$^4$, and
(5) -heteroaryl, where the heteroaryl is selected from: pyridyl, pyrimidinyl, and pyrazinyl, and the heteroaryl is unsubstituted or substituted with one to three substituents independently selected from R$^4$;

R³ is selected from:
 (1) —C₁₋₆alkyl, where the alkyl is unsubstituted or substituted with one to six substituents independently selected from R⁴,
 (2) —C₃₋₆cycloalkyl, where the cycloalkyl is unsubstituted or substituted with one to six substituents independently selected from R⁴,
 (3) -phenyl, where the phenyl is unsubstituted or substituted with one to three substituents independently selected from R⁴,
 (4) —NR¹⁰R¹¹, wherein R¹⁰ and R¹¹ are independently selected from:
  (a) hydrogen, and
  (b) C₁₋₆alkyl, which is unsubstituted or substituted with one to six R⁴;
R⁴ is selected from:
 (1) hydroxyl,
 (2) halogen,
 (3) C₁₋₆alkyl, which is unsubstituted or substituted with one to six fluoro,
 (4) C₂₋₄alkenyl,
 (5) C₂₋₄alkynyl,
 (6) —C₃₋₆cycloalkyl,
 (7) —O—C₁₋₆alkyl,
 (8) —O(C=O)—C₁₋₆alkyl,
 (9) —NH₂,
 (10) —NH—C₁₋₆alkyl,
 (11) —NO₂,
 (12) phenyl,
 (13) —CO₂H,
 (14) —SO₂—C₁₋₆alkyl,
 (15) —C₃₋₅cycloalkyl(SO₂), and
 (16) —CN;
R⁵ is:
 (1) C₁₋₆alkyl, where the alkyl is unsubstituted or substituted with one to six substituents independently selected from R⁴, and
 (2) —C₃₋₆cycloalkyl, where the cycloalkyl is unsubstituted or substituted with one to six substituents independently selected from R⁴;
or a pharmaceutically acceptable salt thereof.

2. The compound of claim 1 or a pharmaceutically acceptable salt thereof wherein X is —O—.

3. The compound of claim 1 or a pharmaceutically acceptable salt thereof wherein X is —NH—.

4. The compound of claim 1 or a pharmaceutically acceptable salt thereof wherein R¹ is selected from:
 (1) methyl,
 (2) ethyl,
 (3) —CH₂OH,
 (4) —CH₂CF₃,
 (5) —CH₂CHF₂,
 (6) —CH(CH₃)₂,
 (7) —CH₂CH₂CH₂F,
 (8) cyclopropyl,
 (9) —CH₂-cyclopropyl,
 (10) —CH₂-cyclobutyl, and
 (11) —CH₂O(C=O)CH₃.

5. The compound of claim 1 or a pharmaceutically acceptable salt thereof wherein R² is selected from:
 (1) hydrogen,
 (2) —CH₂(CH₃)₂,
 (3) —CF₃,
 (4) —CH₂CHF₂,
 (5) —CH₂CF₃, and
 (6) phenyl, which is unsubstituted or substituted with —CF₃, —CH₂CF₃, or one to three fluoro.

6. The compound of claim 1 or a pharmaceutically acceptable salt thereof wherein R³ is selected from:
 (1) —C₁₋₆alkyl, where the alkyl is unsubstituted or substituted with one to three fluoro,
 (2) —C₃₋₆cycloalkyl,
 (3) —NH₂,
 (4) —NH(C₁₋₆alkyl),
 (5) —N(C₁₋₆alkyl)(C₁₋₆alkyl), and
 (6) -phenyl.

7. The compound of claim 1 or a pharmaceutically acceptable salt thereof wherein R⁵ is selected from:
 (1) al methyl,
 (2) ethyl,
 (3) —CHF₂,
 (4) —CF₃,
 (5) —CH₂OH,
 (6) —CH₂OCH₃, and
 (7)₀ cyclopropyl.

8. The compound of claim 1 or a pharmaceutically acceptable salt thereof wherein R⁵ is methyl.

9. A compound which is selected from:
 (2R,3S,5R)-N-ethyl-2-(((4-isopropylcyclohexyl)oxy)methyl)-5-methyl-3-(methylsulfonamido)-pyrrolidine-1-carboxamide;
 (2R,3S,5R)-N-ethyl-5-methyl-3-(methylsulfonamido)-2-(((4-(trifluoromethyl)-cyclohexyl)oxy)methyl)pyrrolidine-1-carboxamide;
 methyl (2R,3S,5R)-2-(((4-isopropylcyclohexyl)oxy)methyl)-5-methyl-3-(methylsulfonamido)-pyrrolidine-1-carboxylate;
 methyl (2R,3S,5R)-2-((((1s,4S)-4-isopropylcyclohexyl)oxy)-methyl)-5-methyl-3-(methylsulfonamido)pyrrolidine-1-carboxylate;
 isopropyl (2R,3S,5R)-2-(((4-isopropylcyclohexyl)oxy)methyl)-5-methyl-3-(methylsulfonamido)pyrrolidine-1-carboxylate;
 isopropyl (2R,3S,5R)-2-(((4-isopropylcyclohexyl)oxy)methyl)-5-methyl-3-((N-methylsulfamoyl)amino)pyrrolidine-1-carboxylate;
 ethyl (2R,3S,5R)-2-(((4-isopropylcyclohexyl)oxy)methyl)-5-methyl-3-(methylsulfonamido)pyrrolidine-1-carboxylate;
 ethyl (2R,3S,5R)-3-((N,N-dimethylsulfamoyl)amino)-2-(((4-isopropylcyclohexyl)-oxy)methyl)-5-methylpyrrolidine-1-carboxylate;
 2,2-difluoroethyl (2R,3S,5R)-2-(((4-isopropylcyclohexyl)oxy)methyl)-5-methyl-3-(methylsulfonamido)pyrrolidine-1-carboxylate;
 2-fluoroethyl (2R,3S,5R)-2-(((4-isopropylcyclohexyl)oxy)methyl)-5-methyl-3-(methylsulfonamido)pyrrolidine-1-carboxylate;
 methyl (2R,3S,5R)-3-((N,N-dimethylsulfamoyl)amino)-5-methyl-2-((4-(trifluoromethyl)cyclohexyl)oxy)methyl)pyrrolidine-1-carboxylate;
 methyl (2R,3S,5R)-5-methyl-3-(methylsulfonamido)-2-((4-(2,2,2-trifluoroethyl)-cyclohexyl)oxy)methyl)pyrrolidine-1-carboxylate;
 2,2-difluoroethyl (2R,3S,5R)-2-(((4-isopropylcyclohexyl)oxy)methyl)-5-methyl-3-((N-methylsulfamoyl)amino)pyrrolidine-1-carboxylate;
 2,2-difluoroethyl (2R,3S,5R)-3-((N,N-dimethylsulfamoyl)amino)-2-((4-isopropylcyclohexyl)oxy)methyl)-5-methylpyrrolidine-1-carboxylate;
 methyl (2R,3S,5R)-5-methyl-3-(methylsulfonamido)-2-(((((1s,4S)-4-phenylcyclohexyl)oxy)-methyl)pyrrolidine-1-carboxylate;

2,2-difluoroethyl (2R,3S,5R)-5-methyl-3-((N-methylsulfamoyl)amino)-2-((((1s,4S)-4-phenylcyclohexyl)oxy)methyl)pyrrolidine-1-carboxylate;
2,2-difluoroethyl (2R,3S,5R)-3-((N,N-dimethylsulfamoyl)amino)-5-methyl-2-((((1s,4S)-4-phenylcyclohexyl)oxy)methyl)pyrrolidine-1-carboxylate;
methyl (2R,3S,5R)-5-methyl-3-((N-methylsulfamoyl)amino)-2-((((1s,4S)-4-phenylcyclohexyl)-oxy)methyl)pyrrolidine-1-carboxylate;
methyl (2R,3S,5R)-5-methyl-3-((N-methylsulfamoyl)amino)-2-((((1s,4S)-4-phenylcyclohexyl)-oxy)methyl)pyrrolidine-1-carboxylate;
methyl (2R,3S,5R)-3-((N,N-dimethylsulfamoyl)amino)-5-methyl-2-((((1s,4S)-4-phenylcyclohexyl)-oxy)methyl)pyrrolidine-1-carboxylate;
methyl (2R,3S,5R)-2-((((1r,4R)-4-(2,5-difluorophenyl)cyclohexyl)oxy)methyl)-5-methyl-3-(methylsulfonamido)pyrrolidine-1-carboxylate;
methyl (2R,3S,5R)-2-((((1r,4R)-4-(2,5-difluorophenyl)cyclohexyl)oxy)methyl)-3-((N,N-dimethylsulfamoyl)amino)-5-methylpyrrolidine-1-carboxylate;
2,2-difluoroethyl (2R,3S,5R)-2-((((1r,4R)-4-(2,5-difluorophenyl)-cyclohexyl)oxy)-methyl)-3-((N,N-dimethylsulfamoyl)amino)-5-methylpyrrolidine-1-carboxylate;
methyl (2R,3S,5R)-3-((N,N-dimethylsulfamoyl)amino)-2-((((1s,4S)-4-(2-fluorophenyl)cyclohexyl)oxy)methyl)-5-methylpyrrolidine-1-carboxylate;
methyl (2R,3S,5R)-2-((((1s,4S)-4-(3-fluorophenyl)cyclohexyl)oxy)methyl)-5-methyl-3-(methylsulfonamido)pyrrolidine-1-carboxylate;
methyl (2R,3S,5R)-2-((((1s,4S)-4-(3-fluorophenyl)cyclohexyl)oxy)methyl)-5-methyl-3-((N-methylsulfamoyl)amino)pyrrolidine-1-carboxylate;
methyl (2R,3S,5R)-3-((fluoromethyl)sulfonamido)-2-((((1s,4S)-4-(3-fluorophenyl)cyclohexyl)oxy)methyl)-5-methylpyrrolidine-1-carboxylate;
methyl (2R,3S,5R)-5-methyl-3-(methylsulfonamido)-2-((((1r,4R)-4-(2-(trifluoromethyl)phenyl)cyclohexyl)oxy)methyl)pyrrolidine-1-carboxylate;
methyl (2R,3S,5R)-5-methyl-3-(methylsulfonamido)-2-((((1r,4R)-4-(2,3,6-trifluorophenyl)cyclohexyl)oxy)methyl)pyrrolidine-1-carboxylate;
methyl (2R,3S,5R)-3-((fluoromethyl)sulfonamido)-5-methyl-2-((((1r,4R)-4-phenylcyclohexyl)oxy)methyl)pyrrolidine-1-carboxylate;
methyl (2R,3S,5R)-3-((N,N-dimethylsulfamoyl)amino)-2-((((1R,4S)-2-fluoro-4-phenylcyclohexyl)oxy)methyl)-5-methylpyrrolidine-1-carboxylate;
methyl (2R,3S,5R)-3-((N,N-dimethylsulfamoyl)amino)-2-((((1R,4S)-2-fluoro-4-(3-fluorophenyl)cyclohexyl)oxy)methyl)-5-methylpyrrolidine-1-carboxylate;
methyl (2R,3S,5R)-2-((((1s,4S)-4-(3,5-difluorophenyl)cyclohexyl)oxy)methyl)-3-((N,N-dimethylsulfamoyl)amino)-5-methylpyrrolidine-1-carboxylate;
methyl (2R,3S,5R)-3-((N,N-dimethylsulfamoyl)amino)-2-((((1s,4S)-4-(3-fluorophenyl)cyclohexyl)-oxy)methyl)-5-methylpyrrolidine-1-carboxylate;
isopropyl (2R,3S,5R)-5-methyl-3-((N-methylsulfamoyl)amino)-2-((1-(pyrimidin-2-yl)piperidin-4-yl)oxy)methyl)pyrrolidine-1-carboxylate;
isopropyl (2R,3S,5R)-3-((N,N-dimethylsulfamoyl)amino)-2-(((1-(5-fluoropyrimidin-2-yl)piperidin-4-yl)oxy)methyl)-5-methylpyrrolidine-1-carboxylate;
methyl (CIS)-5-ethyl-3-(methylsulfonamido)-2-((((CIS)-4-phenylcyclohexyl)-oxy)methyl)-pyrrolidine-1-carboxylate;
methyl (2R,3S,5R)-5-ethyl-3-(methylsulfonamido)-2-(((((CIS)-4-phenylcyclohexyl)-oxy)methyl)-pyrrolidine-1-carboxylate;
methyl (CIS)-5-cyclopropyl-3-(methylsulfonamido)-2-(((((CIS)-4-phenylcyclohexyl)oxy)methyl)pyrrolidine-1-carboxylate;
methyl (2S,3R,5S)-5-ethyl-3-(methylsulfonamido)-2-(((((CIS)-4-phenylcyclohexyl)oxy)methyl)-pyrrolidine-1-carboxylate;
methyl (2R,3S,5R)-5-ethyl-3-(methylsulfonamido)-2-(((((CIS)-4-phenylcyclohexyl)oxy)methyl)pyrrolidine-1-carboxylate;
methyl (CIS)-5-ethynyl-3-(methylsulfonamido)-2-(((((CIS)-4-phenylcyclohexyl)oxy)methyl)-pyrrolidine-1-carboxylate;
methyl (CIS)-3-(methylsulfonamido)-2-(((((CIS)-4-phenylcyclohexyl)oxy)methyl)-5-vinylpyrrolidine-1-carboxylate;
methyl (CIS)-5-(2-hydroxyethyl)-3-(methylsulfonamido)-2-(((((CIS)-4-phenylcyclohexyl)oxy)methyl)pyrrolidine-1-carboxylate;
methyl (CIS)-5-(hydroxymethyl)-3-(methylsulfonamido)-2-(((((CIS)-4-phenylcyclohexyl)oxy)-methyl)pyrrolidine-1-carboxylate;
methyl (2R,3S,5S)-3-((N,N-dimethylsulfamoyl)amino)-2-((((CIS)-4-(3-fluorophenyl)cyclohexyl)oxy)methyl)-5-(methoxymethyl)pyrrolidine-1-carboxylate;
methyl (2R,3S,5S)-5-(cyanomethyl)-3-((N,N-dimethylsulfamoyl)amino)-2-((((CIS)-4-(3-fluorophenyl)cyclohexyl)oxy)methyl)pyrrolidine-1-carboxylate;
methyl (2R,3S,5R)-3-((N-(cyanomethyl)-N-methylsulfamoyl)amino)-2-((((1s,4S)-4-(3-fluorophenyl)cyclohexyl)oxy)methyl)-5-methylpyrrolidine-1-carboxylate;
methyl (2R,3S,5R)-3-((N-(2-cyanoethyl)-N-methylsulfamoyl)amino)-2-((((1s,4S)-4-(3-fluorophenyl)cyclohexyl)oxy)methyl)-5-methylpyrrolidine-1-carboxylate;
methyl (2R,3S,5R)-2-((((1s,4S)-4-(3-fluorophenyl)cyclohexyl)oxy)methyl)-3-((N-(2-methoxyethyl)-N-methylsulfamoyl)amino)-5-methylpyrrolidine-1-carboxylate;
methyl (2R,3S,5R)-2-((((1s,4S)-4-(3-fluorophenyl)cyclohexyl)oxy)methyl)-3-((N-(2-hydroxyethyl)-N-methylsulfamoyl)amino)-5-methylpyrrolidine-1-carboxylate;
methyl (2R,3S,5R)-2-((((1s,4S)-4-(3-fluorophenyl)cyclohexyl)oxy)methyl)-5-methyl-3-((N-methyl-N-(2-(methylsulfonyl)ethyl)sulfamoyl)amino)pyrrolidine-1-carboxylate;
methyl (2R,3S,5R)-3-((N-((1,1-dioxidothietan-3-yl)methyl)-N-methylsulfamoyl)-amino)-2-((((1s,4S)-4-(3-fluorophenyl)cyclohexyl)oxy)methyl)-5-methylpyrrolidine-1-carboxylate;
methyl (2R,3S,5R)-2-((((1s,4S)-4-(3-fluorophenyl)cyclohexyl)oxy)methyl)-5-methyl-3-((N-methyl-N-(2-(trifluoromethoxy)ethyl)sulfamoyl)amino)pyrrolidine-1-carboxylate;
methyl (2R,3S,5R)-3-((2,2-difluoroethyl)sulfonamido)-2-((((1s,4S)-4-(3-fluorophenyl)cyclohexyl)oxy)methyl)-5-methylpyrrolidine-1-carboxylate;
methyl (2R,3S,5R)-3-((N-(2-cyanoethyl)-N-methylsulfamoyl)amino)-2-((((1s,4S)-4-(3-fluorophenyl)cyclohexyl)oxy)methyl)-5-methylpyrrolidine-1-carboxylate;
methyl (2R,3S,5R)-3-((fluoromethyl)sulfonamido)-2-((((1s,4S)-4-(3-fluorophenyl)cyclohexyl)oxy)methyl)-5-methylpyrrolidine-1-carboxylate;
methyl (2R,3S,5R)-2-((((1s,4S)-4-(4-cyano-3-methylphenyl)cyclohexyl)oxy)-methyl)-3-((N,N-dimethylsulfamoyl)amino)-5-methylpyrrolidine-1-carboxylate;

methyl (2R,3S,5R)-2-((((1r,4R)-4-(4-cyano-3-methylphenyl)cyclohexyl)oxymethyl)-3-((N,N-dimethylsulfamoyl)amino)-5-methylpyrrolidine-1-carboxylate;

methyl (2R,3S,5R)-3-((N,N-dimethylsulfamoyl)amino)-2-((((1s,4S)-4-(2-ethylphenyl)cyclohexyl)oxy)methyl)-5-methylpyrrolidine-1-carboxylate;

methyl (2R,3S,5R)-3-((N,N-dimethylsulfamoyl)amino)-2-((((1r,4R)-4-(2-ethylphenyl)cyclohexyl)oxy)methyl)-5-methylpyrrolidine-1-carboxylate;

methyl (2R,3S,5R)-3-((N,N-dimethylsulfamoyl)amino)-2-((((1S,3R,4R)-4-(3-fluorophenyl)cyclohexyl-3,4-d2)oxy)methyl)-5-methylpyrrolidine-1-carboxylate;

methyl (2R,3S,5R)-3-((N,N-dimethylsulfamoyl)amino)-2-((((1S,3S,4S)-4-(3-fluorophenyl)cyclohexyl-3,4-d2)oxy)methyl)-5-methylpyrrolidine-1-carboxylate;

methyl (2R,3S,5R)-5-methyl-3-(methylsulfonamido)-2-((((1r,4R)-4-(pyrimidin-2-yl)cyclohexyl)oxy)methyl)pyrrolidine-1-carboxylate;

methyl (2R,3S,5R)-5-methyl-3-(methylsulfonamido)-2-((((1s,4S)-4-(pyrimidin-2-yl)cyclohexyl)oxy)methyl)pyrrolidine-1-carboxylate;

methyl (2R,3S,5R)-2-((((1s,4S)-4-(3,5-difluorophenyl)cyclohexyl)oxy)methyl)-5-methyl-3-(methylsulfonamido)pyrrolidine-1-carboxylate;

methyl (2R,3S,5R)-2-((((1r,4R)-4-(3,5-difluorophenyl)cyclohexyl)oxy)methyl)-5-methyl-3-(methylsulfonamido)pyrrolidine-1-carboxylate; and methyl (2R,3S,5R)-2-((((1s,4S)-4-(3,4-difluorophenyl)cyclohexyl)oxy)methyl)-5-methyl-3-(methylsulfonamido)pyrrolidine-1-carboxylate;

or a pharmaceutically acceptable salt thereof.

10. A pharmaceutical composition which comprises an inert carrier and a compound of claim 1 or a pharmaceutically acceptable salt thereof.

11. A method for treating narcolepsy in a mammalian subject which comprises administering to the patient an effective amount of the compound of claim 1 or a pharmaceutically acceptable salt thereof.

12. A method for treating hypersomnia in a mammalian subject which comprises administering to the patient an effective amount of the compound of claim 1 or a pharmaceutically acceptable salt thereof.

* * * * *